(12) United States Patent
Poirier et al.

(10) Patent No.: US 11,072,632 B2
(45) Date of Patent: Jul. 27, 2021

(54) INHIBITORS OF 17β-HSD1, 17β-HSD3 AND 17β-HSD10

(75) Inventors: Donald Poirier, L'Ancienne-Lorette (CA); Jenny Roy, Saint-Jean-Chrysostome (CA); Rene Maltais, Quebec (CA)

(73) Assignee: UNIVERSITÉ LAVAL, Québec (CA)

( * ) Notice: Subject to any disclaimer, the term of this patent is extended or adjusted under 35 U.S.C. 154(b) by 381 days.

(21) Appl. No.: 14/007,577

(22) PCT Filed: Mar. 26, 2012

(86) PCT No.: PCT/CA2012/000316
§ 371 (c)(1),
(2), (4) Date: Dec. 6, 2013

(87) PCT Pub. No.: WO2012/129673
PCT Pub. Date: Oct. 4, 2012

(65) Prior Publication Data
US 2014/0088053 A1     Mar. 27, 2014

Related U.S. Application Data

(60) Provisional application No. 61/467,764, filed on Mar. 25, 2011.

(51) Int. Cl.
| | | |
|---|---|---|
| *C07J 41/00* | (2006.01) | |
| *A61K 31/567* | (2006.01) | |
| *A61K 31/58* | (2006.01) | |
| *A61K 51/04* | (2006.01) | |
| *A61K 31/566* | (2006.01) | |
| *A61K 31/69* | (2006.01) | |
| *A61K 31/675* | (2006.01) | |
| *C07J 51/00* | (2006.01) | |
| *C07J 1/00* | (2006.01) | |
| *A61K 31/5685* | (2006.01) | |
| *A61K 45/06* | (2006.01) | |
| *C07J 43/00* | (2006.01) | |
| *C07J 21/00* | (2006.01) | |
| *C07J 31/00* | (2006.01) | |

(52) U.S. Cl.
CPC ......... *C07J 41/0005* (2013.01); *A61K 31/566* (2013.01); *A61K 31/567* (2013.01); *A61K 31/5685* (2013.01); *A61K 31/58* (2013.01); *A61K 31/675* (2013.01); *A61K 31/69* (2013.01); *A61K 45/06* (2013.01); *A61K 51/04* (2013.01); *C07J 1/0007* (2013.01); *C07J 1/0062* (2013.01); *C07J 41/0011* (2013.01); *C07J 41/0038* (2013.01); *C07J 41/0072* (2013.01); *C07J 43/003* (2013.01); *C07J 43/006* (2013.01); *C07J 51/00* (2013.01); *C12Y 101/01051* (2013.01); *C07J 21/00* (2013.01); *C07J 21/008* (2013.01); *C07J 31/006* (2013.01)

(58) Field of Classification Search
CPC .. C07J 41/0005; C07J 41/0072; A61K 31/567
See application file for complete search history.

(56) References Cited

U.S. PATENT DOCUMENTS

| | | | | |
|---|---|---|---|---|
| 5,232,917 A * | 8/1993 | Bolger | ................. | A61K 31/565 |
| | | | | 514/169 |
| 5,512,570 A * | 4/1996 | Dorn | .................... | C07D 265/30 |
| | | | | 514/235.5 |
| 5,952,319 A * | 9/1999 | Cook | .......................... | C07J 1/00 |
| | | | | 514/179 |
| 6,933,312 B2 * | 8/2005 | Price | .................... | C07D 403/06 |
| | | | | 514/406 |
| 2009/0029957 A1 * | 1/2009 | Peters | ...................... | C07J 1/007 |
| | | | | 514/171 |
| 2010/0130463 A1 * | 5/2010 | Yarger | ................. | C12N 5/0693 |
| | | | | 514/182 |

FOREIGN PATENT DOCUMENTS

| | | |
|---|---|---|
| JP | H01-132523 | 5/1989 |
| WO | WO 2005/047303 | 5/2005 |
| WO | WO 2006/125800 | 11/2006 |
| WO | WO 2008/034796 | 3/2008 |
| WO | WO 2008/065100 | 6/2008 |
| WO | WO 2008/089093 A2 | 7/2008 |

OTHER PUBLICATIONS

Dhareshwar S.S., Stella V.J., Prodrugs of Alcohols and Phenols. In: Stella V.J., Borchardt R.T., Hageman M.J., Oliyai R., Maag H., Tilley J.W. (eds) Prodrugs. Biotechnology: Pharmaceutical Aspects, vol. V. Springer, New York, NY, (Year: 2007).*

Bundgaard, "Design and Application of Prodrugs". Textbook of Drug Design and Development (Year: 1991).*

Ferriz et al., "Prodrug Design of Phenolic Drugs". Current Pharmaceutical Design, vol. 16(18), pp. 2033-2052 (Year: 2010).*

Ayan et al., "Impact of estradiol structural modifications (18-methyl and/or 17-hydroxy inversion of configuration) on the in vitro and in vivo estrogenic activity", Journal of Steroid Biochemistry and Molecular Biology, 127, 324-330, 2011.

Berube et al., "Chemical synthesis and in vitro biological evaluation of a phosphorylated bisubstrate inhibitor of type 3 17β-hydroxysteroid dehydrogenase", Journal of Enzyme Inhibition and Medicinal Chemistry, 22, 201-211, 2007.

Berube et al., "Design, synthesis and in vitro evaluation of 4-androstene-3,17-dione/adenosine hybrid compounds as bisubstrate inhibitors of type 3 17β-hydroxysteroid dehydrogenase", Medicinal Chemistry, 2, 329-347, 2006.

(Continued)

*Primary Examiner* — Barbara P Badio
(74) *Attorney, Agent, or Firm* — Parker Highlander PLLC

(57) ABSTRACT

The present application discloses 17β hydroxy steroid dehydrogenase (17β HSD) type 1, 3, 10 inhibitors and use thereof (alone and in combination) in the treatment of cancer and other afflictions. 17β HSD1 inhibitors include estradiol derivatives with a nieta-carbamoylbenzyl substituent at C 16. 17β HSD3/HSD10 inhibitors include androsterone derivatives substituted at the C3 position with a sulfonamide piperazine. Also disclosed are compounds that are inhibitors of both 17β HSD1 and 17β HSD3 that have a spiromorpholine substituent at C20.

6 Claims, 17 Drawing Sheets

(56) References Cited

OTHER PUBLICATIONS

Day et al., "Design and validation of specific inhibitors of 17b-hydroxysteroid dehydrogenases for therapeutic application in breast and prostate cancer, and in endometriosis", Endocrine-Related Cancer, 15, 665-692, 2008.
Degtyar, "Reductase activity of 17β-hydroxysteroid oxidoreductase in prostatic tumors of different histological structure", Bulletin of Experimental Biology and Medicine, 139, 715-717, 2005.
Dizerega et al., "Endometriosis: role of ovarian steroids in initiation, maintenance, and suppression", Fertility and Sterility, 33, 649-653, 1980.
Fang et al., "Structure-activity relationships for a large diverse set of natural, synthetic, and environmental estrogens", Chem. Res. Toxicol., 14, 280-294, 2001.
Group. VACUR, "Treatment and survival of patients with cancer of the prostate", Surgery, Gynecology & Obstetrics, 124, 1011-1017, 1967.
He et al., "Abundant type 10 17β-hydroxysteroid dehydrogenase in the hippocampus of mouse Alzheimer's disease model", Molecular Brain Research, 99, 46-53, 2002.
He et al., "Characterization and localization of human type10 17β-hydroxysteroid dehydrogenase", Eur. J. Biochem., 268, 4899-4907, 2001.
He et al., "Intracellular oxidation of allopregnanolone by human brain type 10 17beta-hydroxysteroid dehydrogenase", Brain Research, 1040, 29-35, 2005.
He et al., "Oxidative 3α-hydroxysteroid dehydrogenase activity of human type 10 17βhydroxysteroid dehydrogenase" Journal of Steroid Biochemistry & Molecular Biology, 87, 191-198, 2003.
He et al., "Roles of type 10 17beta-hydroxysteroid dehydrogenase in intracrinology and metabolism of isoleucine and fatty acids", Endocrine, Metabolic & Immune Disorders—Drug Targets, 6, 95-102, 2006.
Hedlund, "Side effects of endocrine treatment and their mechanisms: castration, antiandrogens and estrogens", Prostate Supplement, 10, 32-37, 2000.
Inano et al., "Testicular 17β-hydroxysteroid dehydrogenase: molecular properties and reaction mechanism", Steroids 48, 1-26, 1986.
Ittner et al., "Amyloid-β and tau—a toxic pas de deux in Alzheimer's disease", Nat. Rev. Neurosci., 12, 67-72, 2011.
Kissinger et al., "Crystal structure of human ABAD/HSD10 with a bound inhibitor: implications for design of Alzheimer's disease therapeutics", J. Mol. Biol., 342, 943-952, 2004.
Koh et al., "Differential expression of 17β-hydroxysteroid dehydrogenase isozyme genes in prostate cancer and noncancer tissues", The Prostate, 53, 154-159, 2002.
Labrie, "Intracrinology", Molecular and Cellular Endocrinology, 78, C113-C118, 1991.
Laplante et al., "Estradiol and Estrone C-16 derivatives as inhibitors of type 1 17β-hydroxysteroid dehydrogenase: Blocking of ER+ breast cancer cell proliferation induced by estrone", Bioorganic & Medicinal Chemistry, 16, 1849-1860, 2008.
Laplante, "Proliferative effect of androst-4-ene-3,17-dione and its metabolites in the androgen-sensitive LNCaP cell line", Steroids, 73, 266-271, 2008.
Leibowitz et al., "Treatment of localized prostate cancer with intermittent triple androgen blockade: preliminary results in 110 consecutive patients", The Oncologist, 6, 177-182, 2001.
Locke et al., "Androgen levels increase by intratumoral De novo steroidogenesis during progression of castration-resistant prostate cancer", Cancer Res., 68, 6407-6415, 2008.
Luu-The et al., "Androgen biosynthetic pathways in the human prostate", Best Practice & Research Clinical Endocrinology & Metabolism, 22, 207-221, 2008.
Luu-The et al., "Characteristics of human types 1, 2 and 3 17β-hydroxysteroid dehydrogenase activities: oxidation/reduction and inhibition", J. Steroid Biochem. Mol. Biol., 55, 581-587, 1995.
Maltais et al., "A Solution-phase combinatorial parallel synthesis of 3β-amido-3α-hydroxy-5α-androstane-17-ones", Tetrahedron Letters, 39, 4151-4154, 1998.
Maltais et al., "Development of 3-substituted androsterone derivatives as potent inhibitors of 17β-hydroxysteroid dehydrogenase type 3", Bioorganic & Medicinal Chemistry, 19, 4652-4668, 2011.
Maltais et al., "Parallel solid-phase synthesis of 3β-peptido-3α-hydroxy-5α-androstan-17-one derivatives for inhibition of type 3 17β-hydroxysteroid dehydrogenase", Bioorganic & Medicinal Chemistry, 9, 3101-3111, 2001.
Maltais et al., "Solid-phase synthesis of hydroxysteroid derivatives using the diethylsilyloxy linker", Journal of Combinatorial Chemistry, 2, 604-614, 2000.
Maltais et al., "Synthesis and optimization of a new family of type 3 17β-hydroxysteroid dehydrogenase inhibitors by parallel liquid-phase chemistry", Journal of Medicinal Chemistry, 45, 640-653, 2002.
Mazumdar et al., "Binary and ternary crystal structure analyses of a novel inhibitor with 17β-HSD type 1: a lead compound for breast cancer therapy", Biochem. J., 10, 357-366, 2009.
Moeller et al., "Integrated view on 17β-hydroxysteroid dehydrogenase", Molecular and Cellular Endocrinology, 301, 7-19, 2009.
Mohler et al., "Hydroxysteroid dehydrogenase (17β-HSD3, 17β-HSD5, and 3α -HSD3) inhibitors: extragonadal regulation of intracellular sex steroid hormone levels", Recent Patents on Endocrine, Metabolic & Immune Drug Discovery, 1, 103-118, 2007.
Montgomery et al., "Maintenance of intratumoral androgens in metastatic prostate cancer: mechanism for castration-resistant tumor growth", Cancer Res., 68, 4447-4454, 2008.
Mostaghel et al., "Intraprostatic androgens and androgen-regulated gene expression persist after testosterone suppression: therapeutic implications for castration-resistant prostate cancer", Cancer Res., 67, 5033-5041, 2007.
Nakamura et al., "Steroid sulfatase and estrogen sulfotransferase in human prostate cancer", The Prostate, 66, 1005-1012, 2006.
Nordling et al., "Human type 10 17β-hydroxysteroid dehydrogenase: molecular modelling and substrate docking", Journal of Molecular Graphics and Modelling, 19, 514-520, 2001.
Page et al., "Persistent intrapostatic androgen concentration after medical castration in healthy men", The Journal of Clinical Endocrinology and Metabolism, 91, 3850-3856, 2006.
Penning et al., "17β-hydroxysteroid dehydrogenase: inhibitors and inhibitor design", Endocrine-Related Cancer, 3, 41-56, 1996.
Poirier et al., "Estrone and estradiol C-16 derivatives as inhibitors of type 1 17β-hydroxysteroid dehydrogenase", Molecular and Cellular Endocrinology, 248, 236-238, 2006.
Poirier, "17β-Hydroxysteroid dehydrogenase inhibitors: a patent review", Expert Opinion Ther. Patents, 20, 1123-1145, 2010.
Poirier, "Advances in Development of Inhibitors of 17β-Hydroxysteroid Dehydrogenases", Anti-cancer Agents in Medicinal Chemistry, 9, 642-660, 2009.
Poirier, "Contribution to the development of inhibitors of 17β-hydroxysteroid dehydrogenase type 1 and 7: Key tools for studying and treating estrogen-dependent diseases", Journal of Steroid Biochemistry and Molecular Biology, 125, 83-94, 2011.
Poirier, "Inhibitors of 17β-hydroxysteroid dehydrogenase", Current Medicinal Chemistry, 10, 453-477, 2003.
Poirier, "New cancer drugs targeting the biosynthesis of estrogens and androgens", Drug Development Research, 69, 304-318, 2008.
Roy et al., "Chemical synthesis and biological activities of 16α-derivatives of 5α-androstane-3α,17β-diol as antiandrogens", Bioorganic & Medicinal Chemistry, 15, 3003-3018, 2007.
Santen, "Endocrine treatment of prostate cancer", Clinical Review 37, Journal of Clinical Endocrinology & Metabolism, 75, 685-689, 1992.
Seidenfeld et al., "Single-therapy androgen suppression in men with advanced prostate cancer: a systematic review and meta-analysis", Ann. Intern. Med., 132, 566-577, 2000.
Shahinian et al., "Risk of fracture after androgen deprivation for prostate cancer", the New England Journal of Medicine, 352, 154-164, 2005.

(56) References Cited

OTHER PUBLICATIONS

Sharifi et al., "Microwave-promoted transformation of nitriles to amides with aqueous sodium perborate", Synthetic Communications, 31, 431-434, 2001.
Simard et al., "Full oestrogenic activity of $C_{19\text{-}}\Delta^5$ adrenal steroids in rat pituitary lactotrophs and somatotrophs", Mol. Cell. Endocrinol., 55, 233-242, 1988.
Skoda-Földes et al., "Direct and carbonylative vinylation of steroid triflates in the presence of homogeneous palladium catalysts", Steroids, 59, 691-695, 1994.
Tammela, "Endocrine treatment of prostate cancer," Journal of Steroid Biochemistry & Molecular Biology, 92, 287-295, 2004.
Tchedam-Nagtcha et al., "3-β-alkyl-androsterones as inhibitors of type 3 17β-hydroxysteroid dehydrogenase: inhibitory potency in intact cells, selectivity towards isoforms 1, 2, 5 and 7, binding affinity for steroid receptors, and proliferative/antiproliferative activities on AR+ and ER+ cell lines", Molecular and Cellular Endocrinology, 248, 225-232, 2006.
Tchedam-Nagtcha et al., "Androsterone 3-α-ether-3β-substituted and androsterone 3β-substituted derivatives as inhibitors of type 3 17β-hydroxysteroid dehydrogenase: chemical synthesis and structure-activity relationship", Journal of Medicinal Chemistry, 48, 5257-5268, 2005.
Theobald et al., "Management of advanced breast cancer with endocrine therapy: the role of the primary healthcare team", Int. J. Clin. Pract., 54, 665-669, 2000.
Tian et al., "Asymmetric synthesis of (-) Swainsonine", J. Org. Chem., 74, 3962-3965, 2009.
Tremblay et al., "Overview of a rational approach to design type I 17β-hydroxysteroid dehydrogenase inhibitors without estrogenic activity: chemical synthesis and biological evaluation", J. Steroid Biochem. Mol. Biol, 66, 179-191, 1998.
Wang et al., "The biological basis for the use of an anti-androgen and a 5-α-reductase inhibitor in the treatment of recurrent prostate cancer: case report and review", Oncology Reports, 11, 1325-1329, 2004.
Wysowski et al., "Fatal and nonfatal hepatotoxicity associated with flutamide", Annals of Internal Medicine, 118, 860-864, 1993.
Xu et al., "Estrogen reduces neuronal generation of Alzheimer β-amyloid peptides", Nature Medicine, 4, 447-451, 1998.
Yang et al., "Multiple functions of type 10 17β-hydroxysteroid dehydrogenase", Trends in Endocrinology and Metabolism, 16, 167-175, 2005.

Berube et al., "Preparation of 6β-estradiol derivative libraries as bisubstrate inhibitors of 7beta-hydroxysteroid dehydrogenase type using the multidetachable sulfamate linker," Molecules, 15, 1590-1631, 2010.
Farhane et al., "Chemical synthesis, characterisation and biological evaluation of furanic-estradiol derivatives as inhibitors of 17β-hydroxysteroid dehydrogenase type 1," Med. Chem., 72(2), 80-91, 2011.
Maltais et al., "Crucial role of 3-Bromoethyl in removing the estrogenic activity of 17β-HSD1 inhibitor 16β-(m-Carbamoylbenzyl)estradiol," ACS Med. Chem. Lett., 2, 678-681, 2011.
PCT International Search Report and Written Opinion issued in International Patent Application No. PCT/CA2012/003 16, dated Jul. 17, 2012.
Supplemental European Search Report issued in European application No. EP 12765822, dated Nov. 7, 2014.
English translation of Office Communication issued in Japanese Patent Application No. 2014-500216, dated Mar. 7, 2016.
Office Communication issued in Australian Patent Application No. 2012234682, dated Apr. 18, 2016.
Smirnov, "Estrophilic 3 alpha,3 beta,17 beta,20 alpha-hydroxysteroid dehydrogenase from rabbit liver-II. Mechanisms of enzyme-steroid interaction," *J. Steroid Biochem.*, 36(6):617-629, 1990.
Annual Reports in Medicinal Chemistry, Ed. John E. Macor. Wallingford: Bristol-Myers Squibb R&D, vol. 46, pp. 491 and 495, 2011.
Annual Reports in Medicinal Chemistry, Ed. Manoj C. Desai, Foster City: Gilead Sciences, Inc., vol. 48, pp. 489 and 491, 2013.
Annual Reports in Medicinal Chemistry, Ed. Manoj C. Desai. Foster City: Gilead Sciences, Inc., vol. 47, p. 555, 2012.
Maltais et al., "Discovery of a Non-Estrogenic Irreversible Inhibitor of 17β-Hydroxysteroid Dehydrogenase Type 1 from 3-Substituted-16β-(m-carbamoylbenzyl)-estradiol Derivatives" *Journal of Medicinal Chemistry*, 57204-222, 2014.
Rautio et al., "The expanding role of prodrugs in contemporary drug design and development," *Nature Reviews Drug Discovery*, 17(8):559-58, 2018.
Huttunen et al., "Prodrugs—from Serendipity to Rational Design," *Pharmacological Reviews*, 63:750-7111, 2011.
Office Communication issued in corresponding Japanese Application No. 2017-253315, dated Feb. 25, 2019. (English translation).

\* cited by examiner

INHIBITORS OF 17β-HSD1, 17β-HSD3 AND 17β-HSD10

This application is a national phase application under 35 U.S.C. § 371 of International Application No. PCT/CA2012/000316, filed Mar. 26, 2012, which claims the benefit of United States Provisional Patent Application No. 61/467,764, filed Mar. 25, 2011.

FIELD

The present description broadly relates to inhibitors of at least one of 17β-HSD1, 17β-HSD3 and 17β-HSD10.

BACKGROUND

17β-Hydroxysteroid dehydrogenase type 1 (17β-HSD1) transforms estrone (E1) into estradiol (E2), the most potent natural ligand for the estrogen receptor (ER). This enzyme also catalyzes the reduction of dehydroepiandrosterone (DHEA) into 5-androstene-3β,17β-diol (Δ$^5$-diol), a weaker estrogen but especially important after menopausis.[1,2] Inhibitors of 17β-HSD1 are thus interesting therapeutic agents for the control of estrogen-dependent diseases such as breast cancers and endometriosis.[3,4] During the last thirty years, intense efforts were deployed with the goal of designing potent inhibitors of this key steroidogenic enzyme[5-8] but, it is only recently that lead candidates have been reported with very good inhibitory activities.[9-10] The presence of a residual estrogenic activity associated with steroidal inhibitors, which are often built around an estrane scaffold,[11] represented a major drawback in their development.

16β-(m-carbamoylbenzyl)estradiol (I) has been reported as a potent inhibitor of 17β-HSD1.[12] Despite of its good inhibitory potency, I was found to stimulate in vitro both the MCF-7 and T-47D estrogen-sensitive breast cancer cell lines, thus greatly reducing its therapeutic potential.

In order to eliminate its undesirable residual estrogenic activity, the impact on both 17β-HSD1 inhibition and estrogenicity by positioning small chains differently functionalized in substitution of the phenol group at position C3 has been previously explored. The choice of replacing the phenolic group of I by a 3-alkyl chain was guided from X-ray analysis of the crystallized complex of inhibitor I with 17β-HSD1, which shows key interactions for the inhibitory activity (Scheme 1).[13] In fact, three major interactions were identified in the binary complex of 17β-HSD1 and inhibitor I): the 17β-OH forms a hydrogen bond with the Ser142; the CONH$_2$ group forms a hydrogen bond with Phe192; and the phenyl ring at C16 forms a π-π interaction with Tyr155. However, contrary to E1, the natural substrate of the enzyme, the 3-OH of I does not form hydrogen bonding with either Glu282 or His221.

Scheme 1: Key Interactions for the Inhibitory Activity of 17β-HSD1

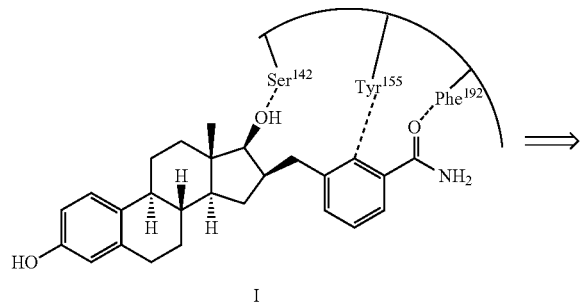

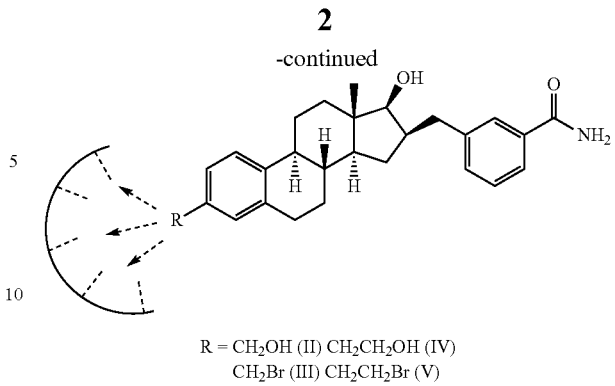

R = CH$_2$OH (II) CH$_2$CH$_2$OH (IV)
CH$_2$Br (III) CH$_2$CH$_2$Br (V)

Prostate cancer is the most common cancer among United States men with an estimated 217730 new diagnosed cases in 2010 and with 32050 associated deaths.[14] Endocrine therapy has been recognized as one of the most efficient treatments for prostate cancer with a positive response in cancer regression in nearly of 80% of the cases following a first treatment.[15] Different endocrine treatments are now available to block either the testicular source of androgens (medical or surgical castration) or to block the effect of androgen testosterone (T) and dihydrotestosterone (DHT) on the androgen receptor (antiandrogens).[16,17] Although it improves survival, these androgen deprivation treatments are associated with important side effects and are not curative in cases of advanced prostate cancer.[18-20] Thus, the development of new therapeutic options are strongly needed to improve survival as well as the life quality of treated patients.[21]

17β-hydroxysteroid dehydrogenase type 3 (17β-HSD3), also named testicular 17β-hydroxysteroid dehydrogenase, is a steroidogenic enzyme that catalyzes the reduction of non-androgenic 4-androstene-3,17-one (Δ$^4$-dione)[22] to potent androgen T using NADPH as cofactor.[9,23-25] This enzyme is found primarily in the Leydig cells in the microtubule part of the testis and contributes to the production of approximately 60% of total active androgens in men.[26] The other 40% of active androgens would be directly synthesized in the prostate from the inactive adrenal precursors dehydroepiandrosterone (DHEA) and Δ$^4$-dione by the action of 3β-hydroxysteroid dehydrogenases, 5α-reductases and other 17β-HSDs such as type 5 or type 15.[27,28] However, although the 17β-HSD3 expression level is very low in normal prostate tissue, it has been reported that 17β-HSD3 is suspected to play an important role in the conversion of adrenal steroids into potential androgens in prostate cancer tissue.[29,30] In fact, the expression level of 17β-HSD3 mRNA in prostatic tissue with malignancy is significantly higher (31 times) than those in prostatic tissue without malignancy. Furthermore, it was recently shown that 17β-HSD3 is overexpressed (8 times) in the LuCaP 23 and LuCAP 35 cell lines isolated from metastatic tissue obtained from patients resistant to castration therapy.[31-34] Importantly, despite a castrated level of T in the bloodstream, the level of T within the metastatic tumors was found to be sufficiently high to stimulate the proliferation of cancer cells.

17β-hydroxysteroid dehydrogenase type 10 (17β-HSD10) is a mitochondrial enzyme involved in estrogen inactivation, androgen activation, β-oxidation of fatty acids and isomerisation of bile acids. Since this enzyme uses estradiol (E2) as a substrate, there is evidence that the enzyme contributes to Alzheimer's disease pathogenesis by reducing neuroprotective estrogen levels. Moreover, this enzyme plays a significant role in a non-classical androgen synthesis pathway and its expression is up-regulated in certain prostate cancer cells, thus conferring an advantage upon these cells for surviving androgen ablation therapy.[6,35-37] Consequently, the inhibition of 17β-HSD10 provides a new approach to the treatment of these diseases.

The present specification refers to a number of documents, the content of which is herein incorporated in their entirety.

SUMMARY

The present disclosure relates to inhibitors of 17β-HSD1, 17β-HSD3 and 17β-HSD10. In an embodiment, the present disclosure relates to inhibitors of at least one of 17β-HSD1, 17β-HSD3 and 17β-HSD10. In an embodiment, the present disclosure relates to selective inhibitors of 17β-HSD1, 17β-HSD3 or 17β-HSD10. In an embodiment of the present disclosure, the inhibitors exhibit a non-estrogenic (17β-HSD1) or non-androgenic profile (17β-HSD3).

DETAILED DESCRIPTION

Figure 1:
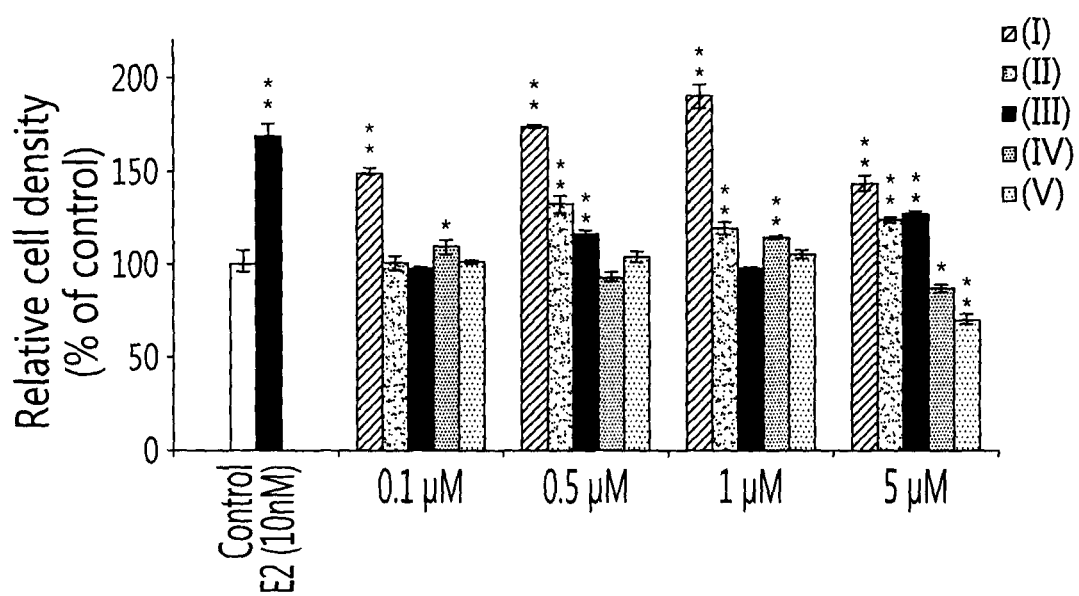
FIG. 1 is an illustration of the effect of inhibitors I-V on the growth of estrogen-starved estrogen sensitive MCF-7 cells after 7 days of treatment at different concentrations. The proliferation of control cells is fixed at 100%. Results are expressed as means±SEM of triplicate. *P≤0.05 versus control. **P≤0.01 versus control.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this disclosure pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The terms "acyl" or "alkanoyl," as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups comprise from 2 to 10 carbons.

The term "alkyl" or "alk" as used herein, represents a monovalent group derived from a straight or branched chain saturated hydrocarbon comprising, unless otherwise specified, from 1 to 15 carbon atoms and is exemplified by methyl, ethyl, n- and iso-propyl, n-, sec-, iso- and tert-butyl, neopentyl and the like and may be optionally substituted with one, two, three or, in the case of alkyl groups comprising two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) $OC(O)R^A$, where $R^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) $C(O)R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) $C(O)NR^CR^D$, where each of $R^C$ and $R^D$ is independently selected from the group consisting of (a) hydrogen, (b) alkyl, (c) aryl and (d) arylalkyl, where the alkylene group comprises one to six carbon atoms; (28) $S(O)R^E$, where $R^E$ is selected from the group consisting of (a) alkyl, (b) aryl, (c) arylalkyl, where the alkylene group comprises one to six carbon atoms, and (d) hydroxyl; (29) $S(O)_2R^E$, where $R^E$ is selected from the group consisting of (a) alkyl, (b) aryl, (c) arylalkyl, where the alkylene group comprises one to six carbon atoms, and (d) hydroxyl; (30) $S(O)_2NR^FR^G$, where each of $R^F$ and $R^G$ is independently selected from the group consisting of (a) hydrogen, (b) alkyl, (c) aryl and (d) arylalkyl, where the alkylene group comprises one to six carbon atoms; and (31) $-NR^HR^I$, where each of $R^H$ and $R^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The terms "alkoxy" or "alkyloxy," as used interchangeably herein, represent an alkyl group attached to the parent molecular group through an oxygen atom.

The term "alkylsulfinyl" as used herein, represents an alkyl group attached to the parent molecular group through an S(O) group.

The term "alkylsulfonyl," as used herein, represents an alkyl group attached to the parent molecular group through a $S(O)_2$ group.

The term "alkylthio" as used herein, represents an alkyl group attached to the parent molecular group through a sulfur atom.

The term "alkylene" as used herein, represents a saturated divalent hydrocarbon group derived from a straight or branched chain saturated hydrocarbon by the removal of two hydrogen atoms, and is exemplified by methylene, ethylene, isopropylene and the like.

The term "alkenyl," as used herein, represents monovalent straight or branched chain groups of, unless otherwise specified, from 2 to 15 carbons, such as, for example, 2 to 6 carbon atoms or 2 to 4 carbon atoms, containing one or more carbon-carbon double bonds and is exemplified by ethenyl, 1-propenyl, 2-propenyl, 2-methyl-1-propenyl, 1-butenyl, 2-butenyl and the like and may be optionally substituted with one, two, three or four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) $OC(O)R^A$, where $R^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) $C(O)R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) $C(O)NR^CR^D$, where each of $R^C$ and $R^D$ is independently selected from the group consisting of (a) hydrogen, (b) alkyl, (c) aryl and (d) arylalkyl, where the alkylene group comprises one to six carbon atoms; (28) $S(O)R^E$, where $R^E$ is selected from the group consisting of (a) alkyl, (b) aryl, (c) arylalkyl, where the alkylene group comprises one to six carbon atoms, and (d) hydroxyl; (29) $S(O)_2R^E$, where $R^E$ is selected from the group consisting of (a) alkyl, (b) aryl, (c) arylalkyl, where the alkylene group comprises one to six carbon atoms, and (d) hydroxyl; (30) $S(O)_2NR^FR^G$, where each of $R^F$ and $R^G$ is independently selected from the group consisting of (a) hydrogen, (b) alkyl, (c) aryl and (d) arylalkyl, where the alkylene group comprises one to six carbon atoms; and (31) —$NR^HR^I$, where each of $R^H$ and $R^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms; (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The term "alkynyl" as used herein, represents monovalent straight or branched chain groups of from two to six carbon atoms comprising a carbon-carbon triple bond and is exemplified by ethynyl, 1-propynyl, and the like and may be optionally substituted with one, two, three or four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) $OC(O)R^A$, where $R^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) $C(O)R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) $C(O)NR^CR^D$, where each of $R^C$ and $R^D$ is independently selected from the group consisting of (a) hydrogen, (b) alkyl, (c) aryl and (d) arylalkyl, where the alkylene group comprises one to six carbon atoms; (28) $S(O)R^E$, where $R^E$ is selected from the group consisting of (a) alkyl, (b) aryl, (c) arylalkyl, where the alkylene group comprises one to six carbon atoms, and (d) hydroxyl; (29) $S(O)_2R^E$, where $R^E$ is selected from the group consisting of (a) alkyl, (b) aryl, (c) arylalkyl, where the alkylene group comprises one to six carbon atoms, and (d) hydroxyl; (30) $S(O)_2NR^FR^G$, where each of $R^F$ and $R^G$ is independently selected from the group consisting of (a) hydrogen, (b) alkyl, (c) aryl and (d) arylalkyl, where the alkylene group comprises one to six carbon atoms; and (31) —$NR^HR^I$, where each of $R^H$ and $R^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The term "aryl" as used herein, represents mono- and/or bicyclic carbocyclic ring systems and/or multiple rings fused together and is exemplified by phenyl, naphthyl, 1,2-dihydronaphthyl, 1,2,3,4-tetrahydronaphthyl, fluorenyl, indanyl, indenyl and the like and may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups are independently comprised of one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde)alkyl, where the alkylene group comprises one to six carbon atoms; (20) cycloalkyl of three to eight carbon atoms; (21) alkcycloalkyl, where the cycloalkyl group comprises three to eight carbon atoms and the alkylene group comprises one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises one to six carbon atoms; (33) oxo; (34) thioalkoxy of one to six carbon atoms; (35) thioalkoxyalkyl, where the alkyl and alkylene groups independently comprise from one to six carbon atoms; (36) $(CH_2)_qCO_2R^A$, where q is an integer ranging from zero to four and $R^A$ is selected from the group consisting of (a) alkyl, (b) aryl, and (c) arylalkyl, where the alkylene group comprises one to six carbon atoms; (37) $(CH_2)_qC(O)NR^BR^C$, where $R^B$ and $R^C$ are independently selected from the group consisting of (a) hydrogen, (b) alkyl, (c) aryl, and (d) arylalkyl, where the alkylene group comprises one to six carbon atoms; (38) $(CH_2)_qS(O)_2R^D$, where $R^D$ is selected from the group consisting of (a) alkyl, (b) aryl, and (c) arylalkyl, where the alkylene group comprises one to six carbon atoms; (39) $(CH_2)_qS(O)_2NR^ER^F$, where each of $R^E$ and $R^F$ is independently selected from the group consisting of (a) hydrogen, (b) alkyl, (c) aryl, and (d) arylalkyl, where the alkylene group comprises one to six carbon atoms; (40) $(CH_2)_qNR^GR^H$, where each of $R^G$ and $R^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, and (i) alkcycloalkyl, where the cycloalkyl group comprises three to eight carbon atoms, and the alkylene group comprises one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; (48) arylalkoxy and (49) thiohaloalkyl The term "aralkyl" represents an aryl group attached to the parent molecular group through an alkyl group.

The term "alkheterocyclyl" represents a heterocyclic group attached to the parent molecular group through an alkyl group.

The term "aryloxy" as used herein, represents an aryl group that is attached to the parent molecular group through an oxygen atom.

The term "alkoxyalkyl" as used herein means alkyl-O-alkyl-, wherein alkyl is defined above.

The term "alkoxyaryl" as used herein means alkyl-O-aryl-, wherein alkyl is defined above.

The term "thioalkyl" as used herein means alkyl-S—, wherein alkyl is defined above.

The term "alkthioalkyl" as used herein means alkyl-S-alkyl-, wherein alkyl is defined above.

The term "alkthioaryl" as used herein means alkyl-S-aryl-, wherein alkyl is defined above.

The terms "aryloyl" or "aroyl" as used interchangeably herein, represent an aryl group that is attached to the parent molecular group through a carbonyl group.

The term "carbonyl" as used herein, represents a C(O) group, which can also be represented as C=O.

The terms "carboxy" or "carboxyl," as used interchangeably herein, represents a $CO_2H$ group.

The term "cycloalkyl" as used herein, represents a monovalent saturated or unsaturated non-aromatic cyclic hydrocarbon group of three to eight carbon atoms, unless otherwise specified, and is exemplified by cyclopropyl, cyclobutyl, cyclopentyl, cyclohexyl, cycloheptyl, bicyclo[2.2.1.]heptyl and the like. The cycloalkyl groups of the present disclosure can be optionally substituted with: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups independently comprise from one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde)alkyl, where the alkylene group comprises one to six carbon atoms; 20) cycloalkyl of three to eight carbon atoms; (21) alkcycloalkyl, where the cycloalkyl group comprises three to eight carbon atoms and the alkylene group comprises one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises one to six carbon atoms; (33) oxo; (34) thioalkoxy of one to six carbon atoms; (35) thioalkoxyalkyl, where the alkyl and alkylene groups independently comprise from one to six carbon atoms; (36) $(CH_2)_qCO_2R^A$, where q is an integer ranging from zero to four and $R^A$ is selected from the group consisting of (a) alkyl, (b) aryl, and (c) arylalkyl, where the alkylene group comprises one to six carbon atoms; (37) $(CH_2)_qC(O)NR^BR^C$, where each of $R^B$ and $R^C$ is independently selected from the group consisting of (a) hydrogen, (b) alkyl, (c) aryl, and (d) arylalkyl, where the alkylene group comprises one to six carbon atoms; (38) $(CH_2)_qS(O)_2R^D$, where $R^D$ is selected from the group consisting of (a) alkyl, (b) aryl, and (c) arylalkyl, where the alkylene group comprises one to six carbon atoms; (39) $(CH_2)_qS(O)_2NR^ER^F$, where each of $R^E$ and $R^F$ is independently, selected from the group consisting of (a) hydrogen, (b) alkyl, (c) aryl, and (d) arylalkyl, where the alkylene group comprises one to six carbon atoms; (40) $(CH_2)_qNR^GR^H$, where each of $R^G$ and $R^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms and (i)

alkcycloalkyl, where the cycloalkyl group comprises three to eight carbon atoms, and the alkylene group comprises one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "halogen" or "halo" as used interchangeably herein, represents F, Cl, Br and I.

The term "heteroaryl" as used herein, represents that subset of heterocycles, as defined herein, which is aromatic: (i.e., containing 4n+2 pi electrons within a mono- or multicyclic ring system).

The terms "heterocycle" or "heterocyclyl" as used interchangeably herein represent a 5-, 6- or 7-membered ring, unless otherwise specified, comprising one, two, three, or four heteroatoms independently selected from the group consisting of nitrogen, oxygen, and sulfur. The 5-membered ring has from zero to two double bonds and the 6- and 7-membered rings have from zero to three double bonds. The term "heterocycle" also includes bicyclic, tricyclic, and tetracyclic groups in which any of the above heterocyclic rings is fused to one or two rings independently selected from the group consisting of an aryl ring, a cyclohexane ring, a cyclohexene ring, a cyclopentane ring, a cyclopentene ring and another monocyclic heterocyclic ring such as indolyl, quinolyl, isoquinolyl, tetrahydroquinolyl, benzofuryl, benzothienyl and the like. Heterocycles include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroinidolyl, tetrahydroquinolyl, tetrahydroisoquinolyl, pyranyl, dihydropyranyl, dithiazolyl, benzofuranyl, benzothienyl and the like. Heterocyclic groups also include compounds of the formula

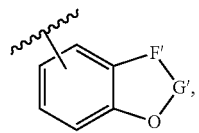

where F' is selected from the group consisting of CH$_2$, CH$_2$O and O, and G' is selected from the group consisting of C(O) and (C(R')(R"))$_v$, where each of R' and R" is independently selected from the group consisting of hydrogen and alkyl of one to four carbon atoms, and v is an integer ranging from one to three, and includes groups such as 1,3-benzodioxolyl, 1,4-benzodioxanyl and the like. Any of the heterocyclic groups mentioned herein may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups independently comprise from one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde)alkyl, where the alkylene group comprises one to six carbon atoms; (20) cycloalkyl of three to eight carbon atoms; (21) alkcycloalkyl, where the cycloalkyl group comprises from three to eight carbon atoms and the alkylene group comprises from one to ten carbon atoms; (22) halo; (23) haloalkyl of one to six carbon atoms; (24) heterocycle; (25) (heterocycle)oxy; (26) (heterocycle)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises from one to six carbon atoms; (33) oxo; (34) thioalkoxy of one to six carbon atoms; (35) thioalkoxyalkyl, where the alkyl and alkylene groups independently comprise from one to six carbon atoms; (36) (CH$_2$)$_q$CO$_2$R$^A$, where q is an integer ranging from zero to four and R$^A$ is selected from the group consisting of (a) alkyl, (b) aryl, and (c) arylalkyl, where the alkylene group comprises from one to six carbon atoms; (37) (CH$_2$)$_q$C(O)NR$^B$R$^C$, where each of R$^B$ and R$^C$ is independently selected from the group consisting of (a) hydrogen, (b) alkyl, (c) aryl, and (d) arylalkyl, where the alkylene group comprises from one to six carbon atoms; (38) (CH$_2$)$_q$S(O)$_2$R$^D$, where R$^D$ is selected from the group consisting of (a) alkyl, (b) aryl, and (c) arylalkyl, where the alkylene group comprises from one to six carbon atoms; (39) (CH$_2$)$_q$S(O)$_2$NR$^E$R$^F$, where each of R$^E$ and R$^F$ is independently selected from the group consisting of (a) hydrogen, (b) alkyl, (c) aryl, and (d) arylalkyl, where the alkylene group comprises from one to six carbon atoms; (40) (CH$_2$)$_q$NR$^G$R$^H$, where each of R$^G$ and R$^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises from one to six carbon atoms; (h) cycloalkyl of three to eight carbon atoms, and (i) alkcycloalkyl, where the cycloalkyl group comprises from three to eight carbon atoms, and the alkylene group comprises from one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The terms "heterocyclyloxy" or "(heterocycle)oxy" as used interchangeably herein, represents a heterocyclic group, as defined herein, attached to the parent molecular group through an oxygen atom.

The term "heterocyclyloyl" or "(heterocycle)oyl" as used interchangeably herein, represents a heterocyclic group, as defined herein, attached to the parent molecular group through a carbonyl group.

The term "amino acid", as used herein, is understood as including both the L and D isomers of the naturally occurring amino acids, as well as other non-proteinaceous amino acids used in peptide chemistry to prepare synthetic analogs of peptides. Examples of naturally-occurring amino acids include, but are not limited to glycine, alanine, valine, leucine, isoleucine, serine, and threonine. Examples of non-proteinaceous amino acids include, but are not limited to norleucine, norvaline, cyclohexyl alanine, biphenyl alanine, homophenyl alanine, naphthyl alanine, pyridyl alanine, and substituted phenyl alanines (substituted with a or more substituents including but not limited to alkoxy, halogen and nitro groups). Beta and gamma amino acids are also within the scope of the term "amino acid". Amino acids protected by standard protecting groups commonly used in peptide synthesis are also within the scope of the term "amino acid". These compounds are known to persons skilled in the art of peptide chemistry.

The term "oxo" as used herein, represents =O.

The term "perfluoroalkyl" as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "heteroatom", as used herein, is understood as being oxygen, sulfur or nitrogen.

The term "sulfonyl" as used herein, represents an $S(O)_2$ group.

The term "thioalkoxy" as used herein, represents an alkyl group attached to the parent molecular group through a sulfur atom. Exemplary unsubstituted thioalkoxy groups comprise from 1 to 6 carbon atoms.

The term "thiocarbonyl" as used herein, represents a C(S) group, which can also be represented as C=S.

The term "pharmaceutically acceptable salt," as used herein, refers to those salts which are, within the scope of sound medical judgment, suitable for use in contact with the tissues of humans without undue toxicity, irritation, allergic response and the like, and are commensurate with a reasonable benefit/risk ratio. Pharmaceutically acceptable salts are well-known in the art. The salts can be prepared in situ during the final isolation of the compounds, or separately by reacting the free base or acid function with a suitable organic acid or base, respectively. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Basic addition salts can be prepared during the final isolation and purification of the compounds by reacting a carboxy group (or other acidic moiety) with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine and piperazine.

17β-HSD1

To obtain a further interaction (H-bonding or hydrophobic interaction) in the binding pocket in proximity of position 3 of I, and therefore improve its binding with 17β-HSD1, various functional groups as well as various changes in the length of the side chain were explored (Scheme 1). Moreover, it is widely surmised that replacing the OH at position C3 could remove the undesirable estrogenic activity by disturbing the binding to ER. In fact, a phenolic OH appears to be a crucial requirement for ER binding.[38] Based on SAR (Structure Activity Relationship) studies, numerous C3 derivatives of I were prepared and tested, examples of which include compounds II-V (Scheme 1). It was surmised that this modification at C3 would result in compounds having an additional interaction in the binding pocket of 17β-HSD1 and hence improve their binding while concomitantly eliminating the undesirable estrogenic activity observed for I.

Compounds II and III were synthesized from 3-carboxyestrone.[39] The benzylcarbamide side chain was introduced at position C16 by means of an aldol condensation reaction with 3-formyl benzamide.[40,41] The C17 ketone was then reduced using sodium borohydride and the 16-exo double bound was subsequently reduced using hydrogenation with Pd (10%) on charcoal (10%). The 3-carboxylic acid was then activated using BOP to promote reduction using sodium borohydride to provide the corresponding alcohol II. Alcohol II was subsequently brominated using triphenylphosphine and carbon tetrabromide to provide the bromomethyl bromide derivative III (Scheme 2).

Compounds IV and V were synthesized from 3-vinyl-17-dioxolane-estrone (1) which is readily obtained from carbonylative vinylation of estrone triflate followed by C17 dioxolane protection.[42] The vinyl group was first converted into the primary alcohol 2 by oxidative hydroboration using $BH_3$-DMS.[43] Alcohol 2 was subsequently protected as the benzyl ether followed by dioxolane deprotection in acidic conditions to provide 3. The benzylcarbamide side chain was introduced at position C16 by means of an aldol condensation reaction with 3-formyl benzamide. The C17 ketone was then reduced using sodium borohydride and the 16-exo double bound was subsequently reduced using hydrogenation with Pd (10%) on charcoal (10%). The hydrogenation reaction concomitantly cleaved 3-O-benzylether to provide the m-16β-carbamoylbenzyl derivative IV. Alcohol IV was subsequently brominated using triphenylphosphine and carbon tetrabromide to provide the bromoethyl derivative V (Scheme 2).

Scheme 2:
Part A:

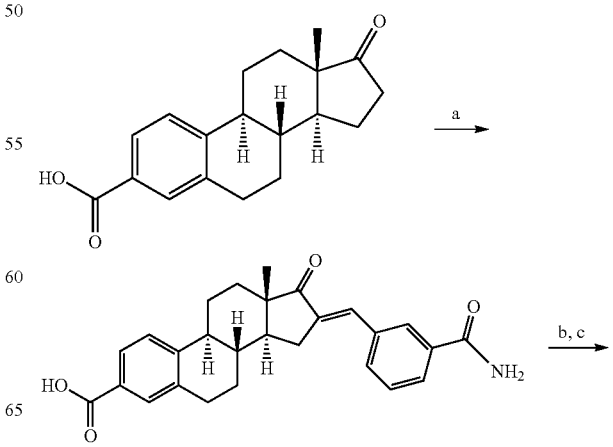

15
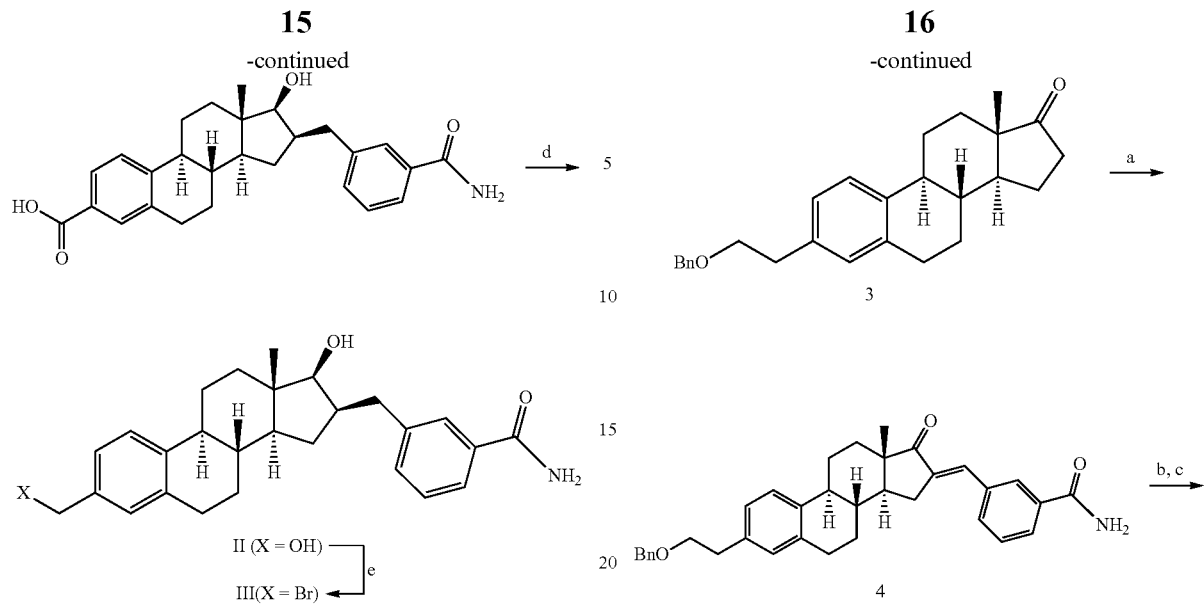
16
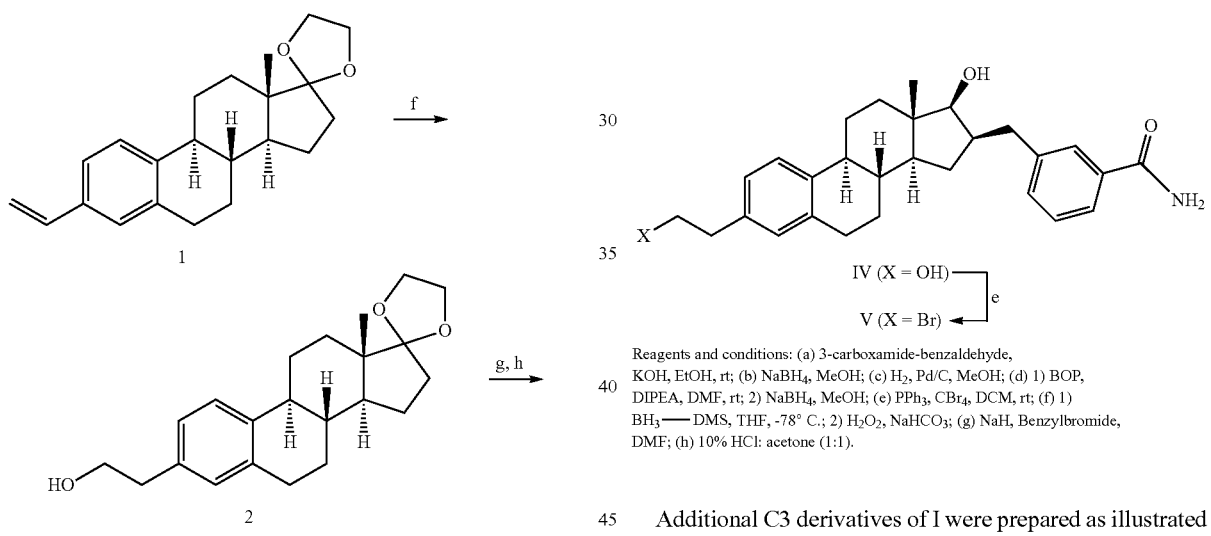
Reagents and conditions: (a) 3-carboxamide-benzaldehyde, KOH, EtOH, rt; (b) NaBH$_4$, MeOH; (c) H$_2$, Pd/C, MeOH; (d) 1) BOP, DIPEA, DMF, rt; 2) NaBH$_4$, MeOH; (e) PPh$_3$, CBr$_4$, DCM, rt; (f) 1) BH$_3$—DMS, THF, -78° C.; 2) H$_2$O$_2$, NaHCO$_3$; (g) NaH, Benzylbromide, DMF; (h) 10% HCl: acetone (1:1).
Additional C3 derivatives of I were prepared as illustrated herein below in Schemes 3-14.
Scheme 3
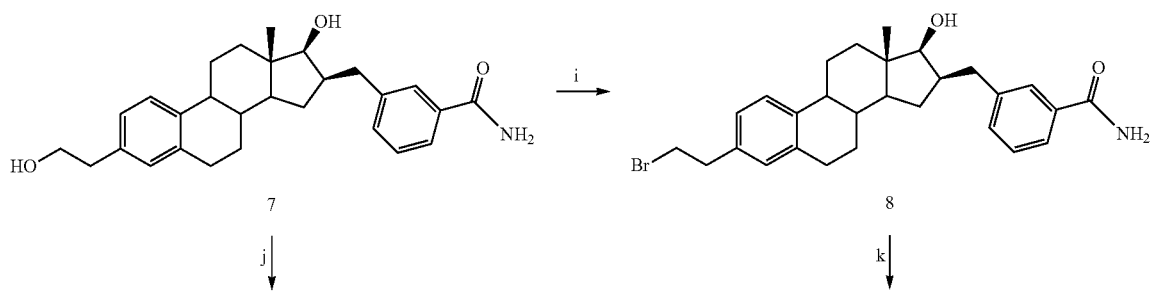

17
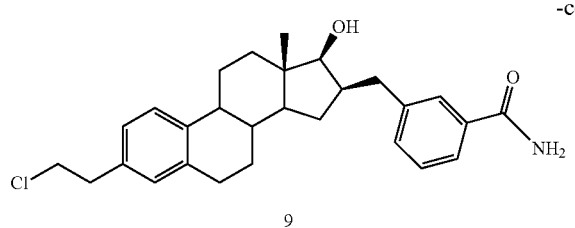
18
-continued
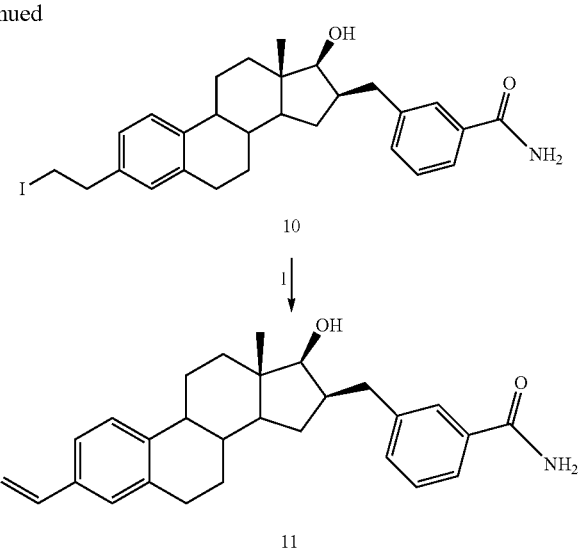
Reagents and conditions: (i) PPh₃, CBr₄, DCM, rt; (j) CPMA, DCM
Scheme 4
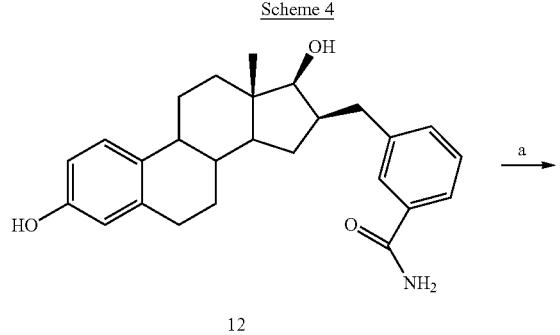
-continued
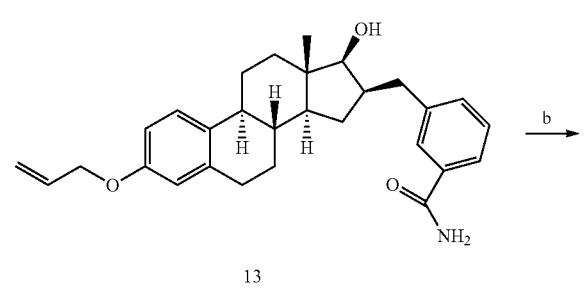
Reagents and conditions: (a) allylbromide, NaOH, acetone, rc; (b) i) NaIO₄, RuCl₃ x H₂O, EtOAc/ACN; ii) NaBH₄, H₂O; (c) PPh₃, CBr₄, DCM, 0 to rt.
Scheme 5
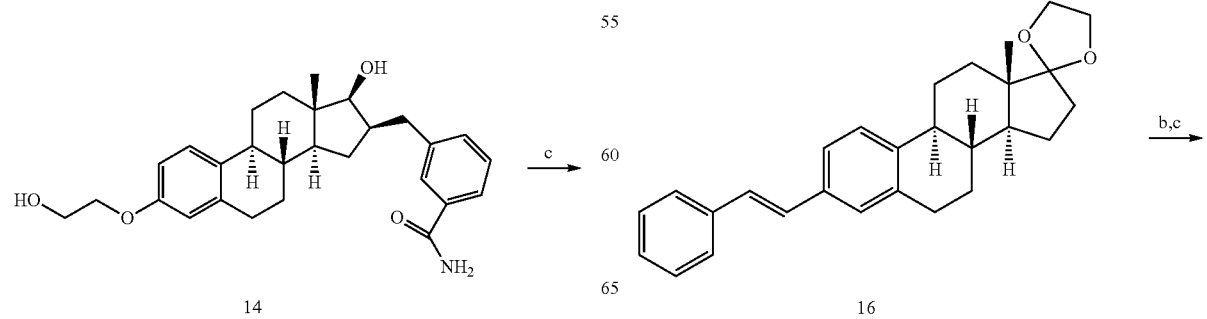

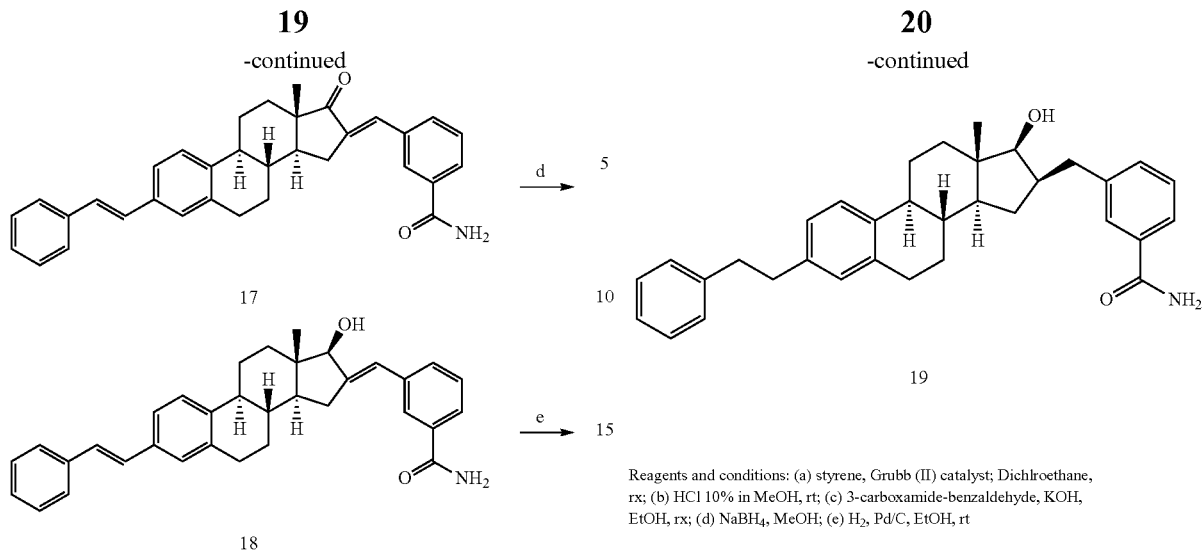
Reagents and conditions: (a) styrene, Grubb (II) catalyst; Dichlroethane, rx; (b) HCl 10% in MeOH, rt; (c) 3-carboxamide-benzaldehyde, KOH, EtOH, rx; (d) NaBH₄, MeOH; (e) H₂, Pd/C, EtOH, rt
Scheme 6
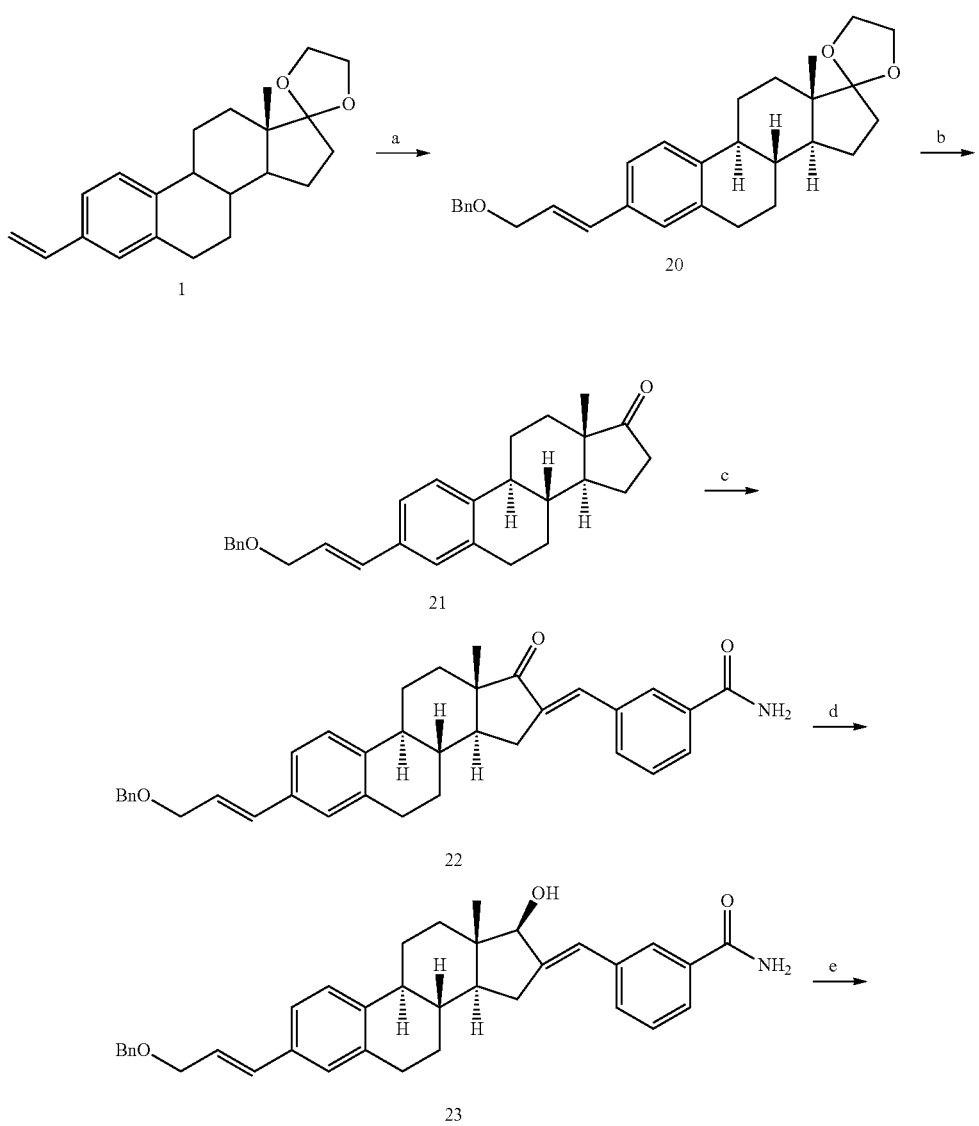

-continued
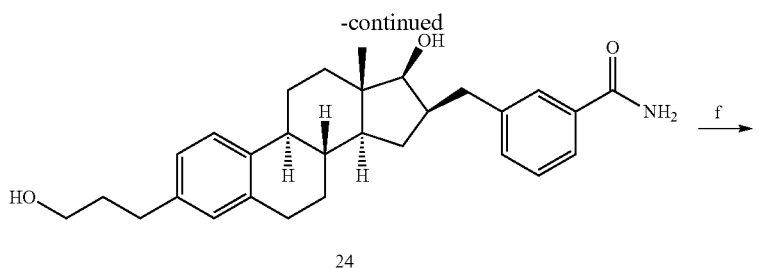
Reagents and conditions: (a) Grubb II catalyst, allyloxymethyl-benzene; (b) HCl, MeOH; (c) 3-carboxamide-benzaldehyde, KOH, EtOH, rx; (d) NaBH₄, MeOH; (e) H₂, Pd/C, MeOH; (f) PPh₃, CBr₄, DCM, rt.
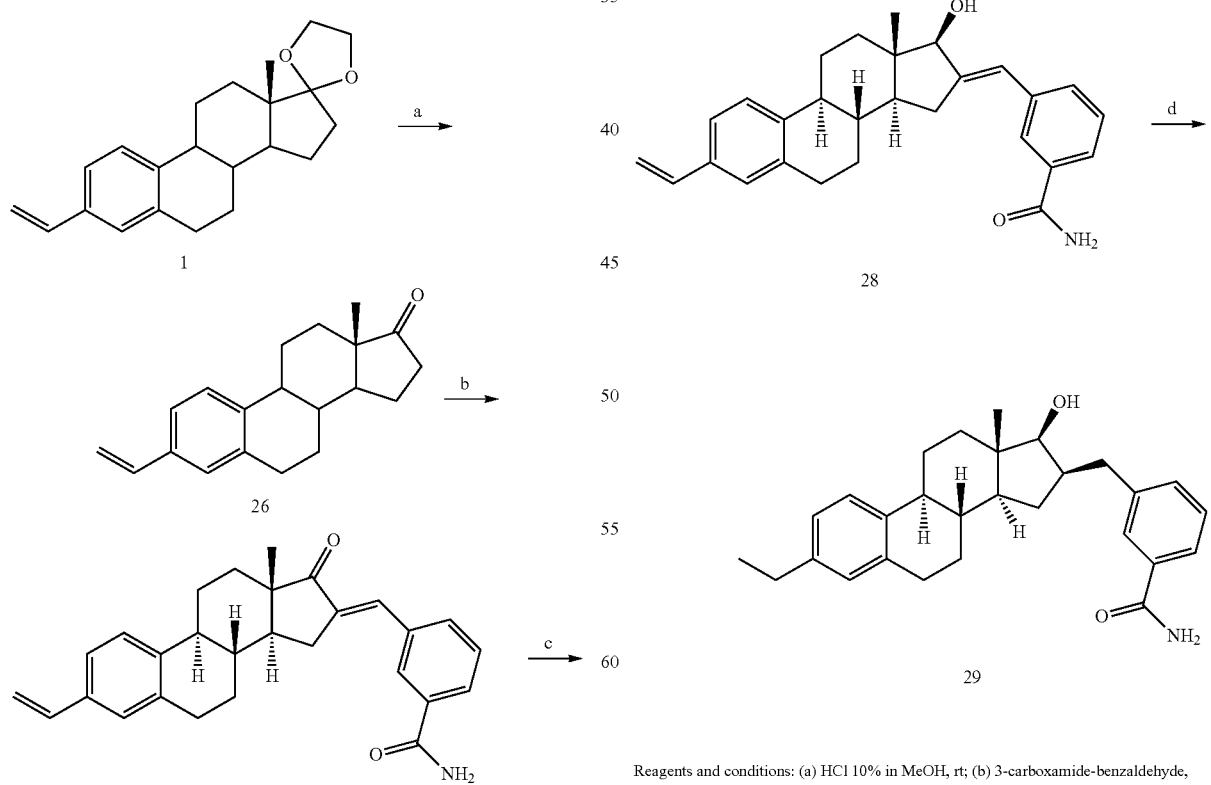
Reagents and conditions: (a) HCl 10% in MeOH, rt; (b) 3-carboxamide-benzaldehyde, KOH, EtOH, rx; (d) NaBH₄, MeOH; (e) H₂, Pd/C, EtOH, rt Scheme 8
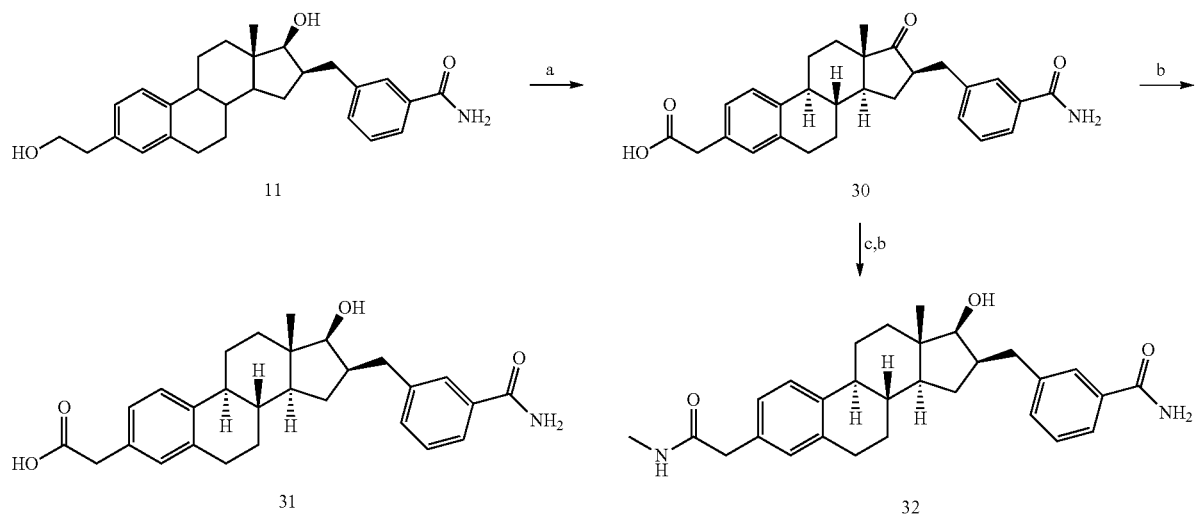
Reagents and conditions: (a) Dess-Martin, NaOCl₂, t-BuOH, 2-methyl-butene, KH₂PO₄ (b) NaBH₄, MeOH; (c) BOP, DIPEA, Methylamine in THF.
Scheme 9
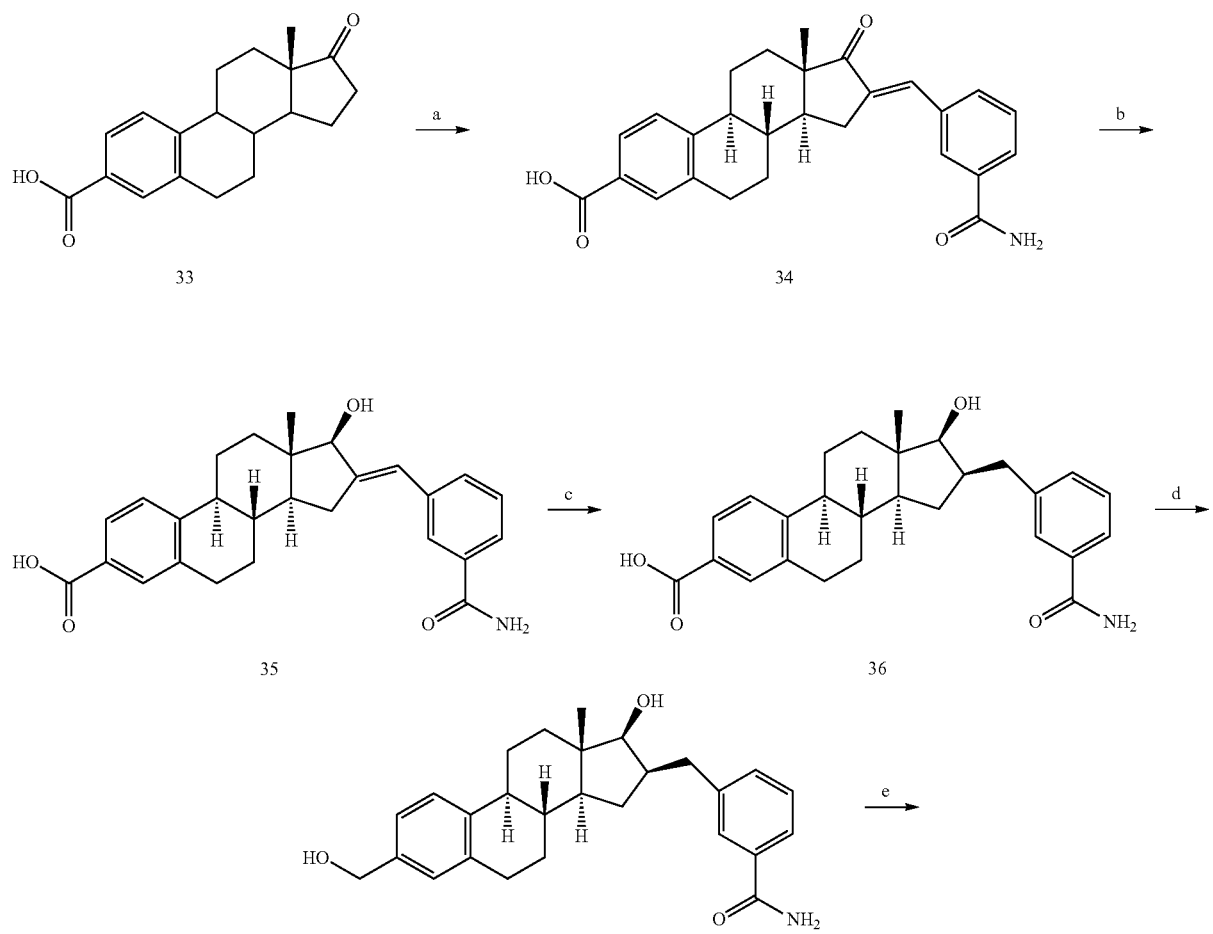

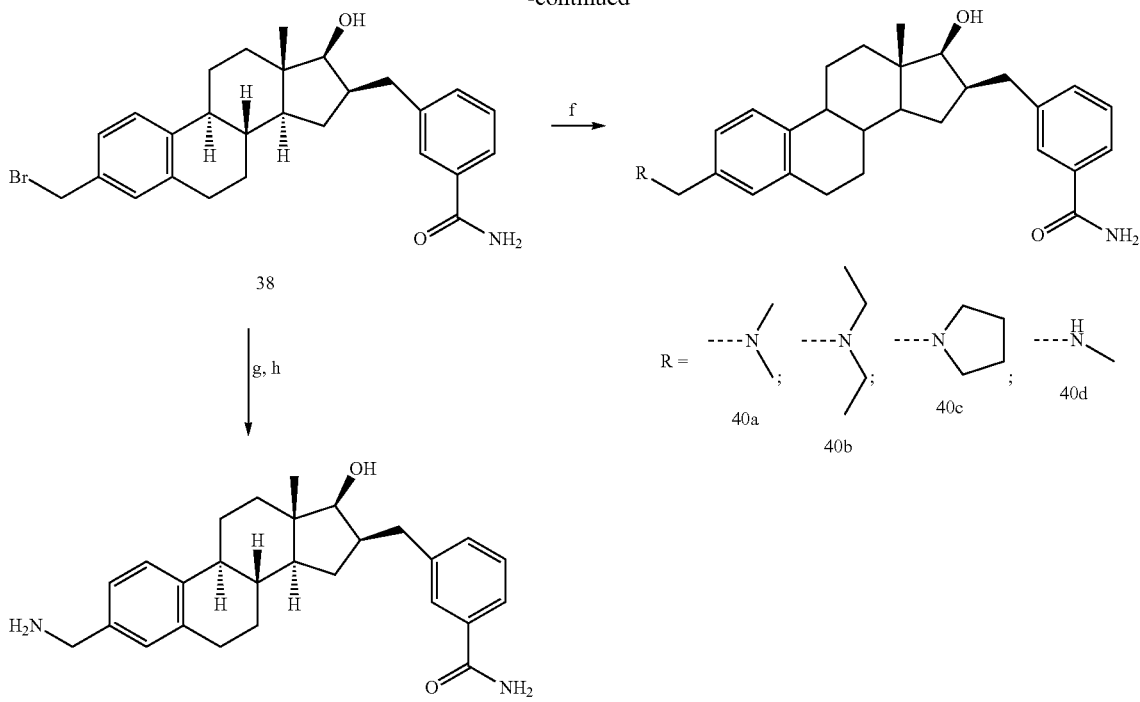
38
39
Reagents and conditions: (a) 3-carboxamide benzaldehyde, KOH, EtOH, rx; (b) NaBH$_4$, MeOH/DCM (1:1); (c) H$_2$, Pd/C (10%), EtOH; (d) i) BOP, DIPEA, THF; ii) NaBH$_4$, rt; (e) PPh$_3$, CBr$_4$, DCM, 0 to rt; (f) NHR$_1$R$_2$, Et$_3$N, DCM, rt; (g) NaN$_3$, DMF, 60 C.; (h) H$_2$, Pd/C (10%), EtOH;
Scheme 10
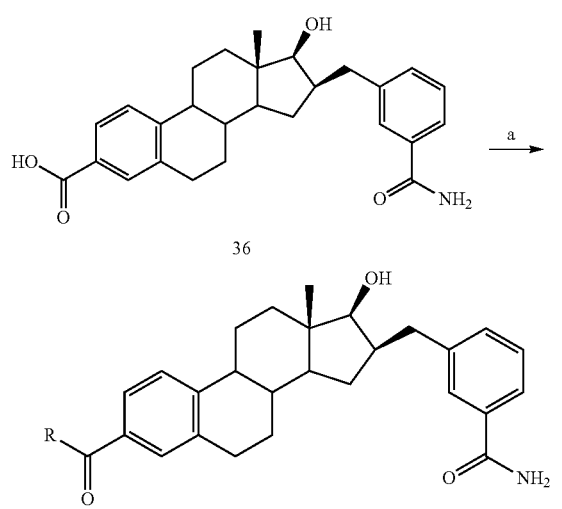
36
Reagents and conditions: (a) R$_1$R$_2$NH, BOP, DIPEA, DMF
Scheme 11
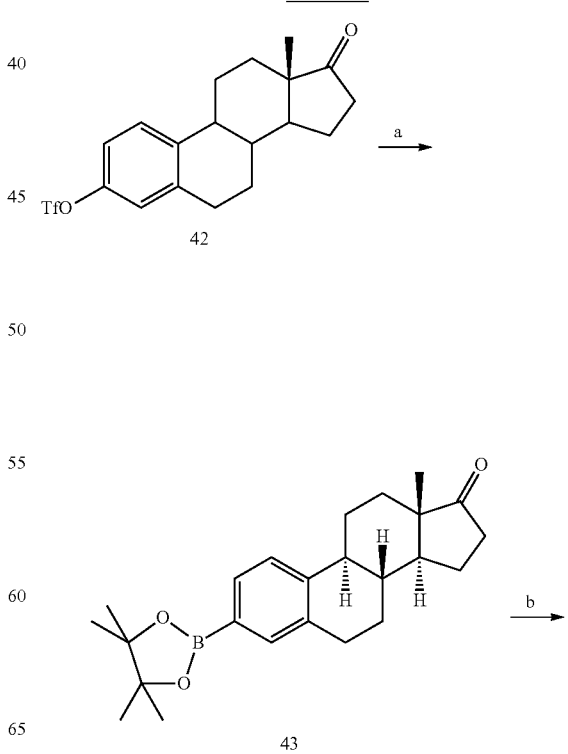

27
-continued
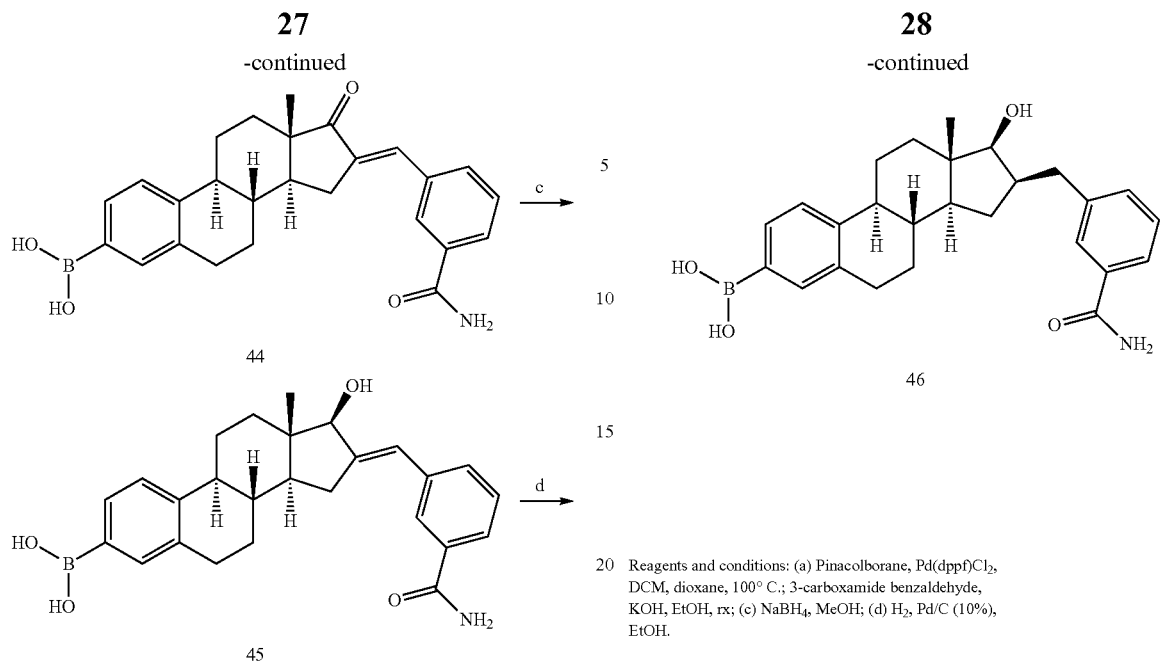
Reagents and conditions: (a) Pinacolborane, Pd(dppf)Cl₂, DCM, dioxane, 100° C.; 3-carboxamide benzaldehyde, KOH, EtOH, rx; (c) NaBH₄, MeOH; (d) H₂, Pd/C (10%), EtOH.
Scheme 12
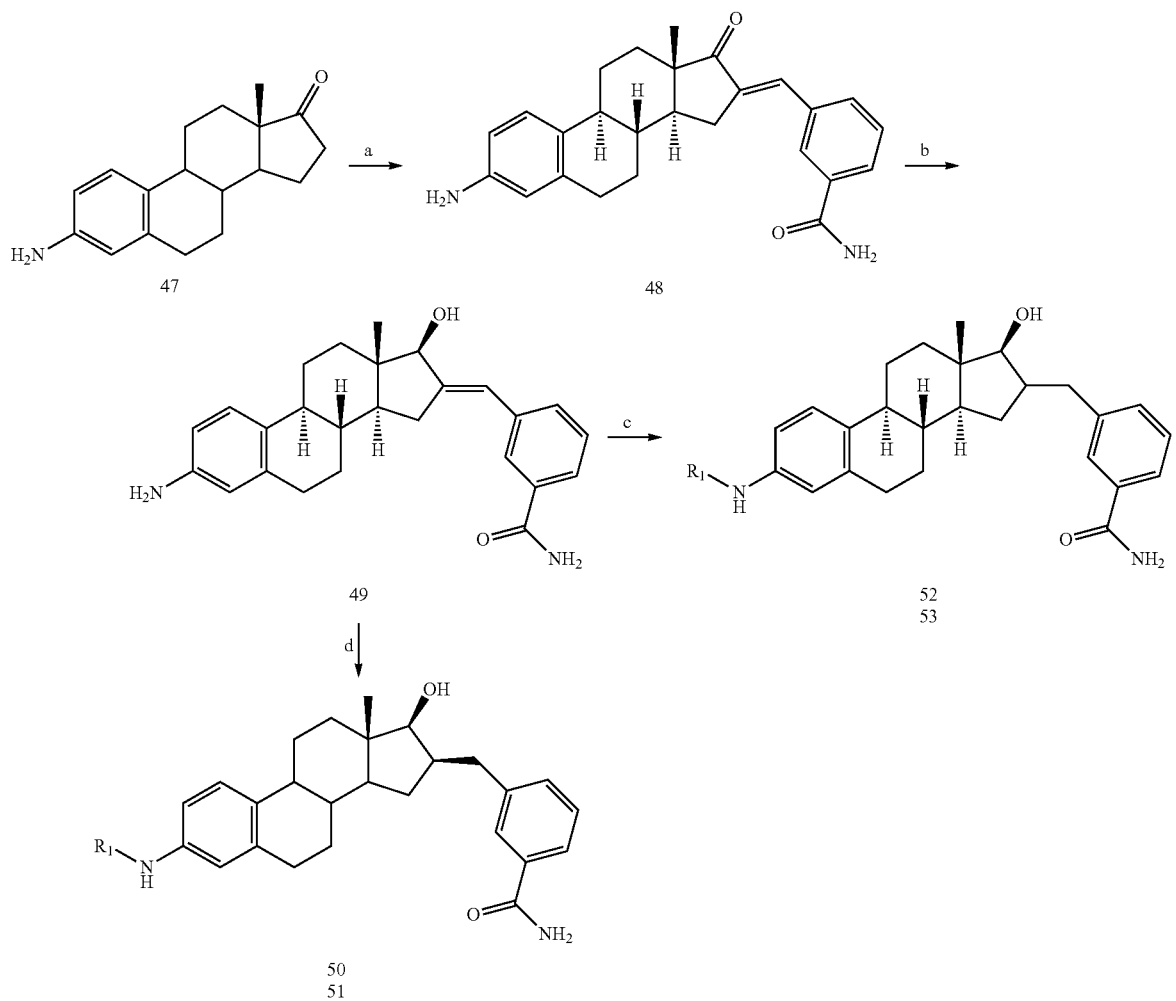
Reagents and conditions: (a) 3-carboxamide- benzaldehyde,KOH, EtOH, rx; (b) NaBH₄, MeOH, rt; (c) Pd/C (10%), MeOH; (d) Pd/C (10%), EtOH, rt.

Scheme 13

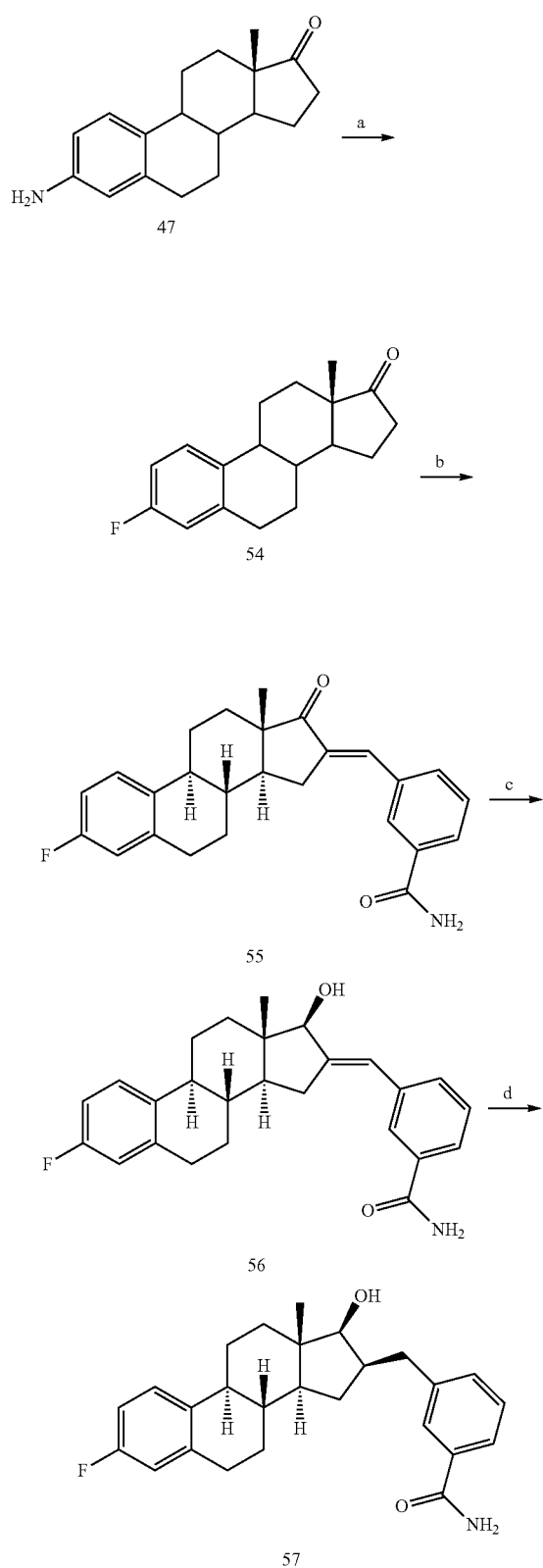

Reagents and conditions: (a) t-butyl nitrite, BF₃O(Et)₂, DCM; (b) 3-carboxamide-benzaldehyde, KOH, EtOH, rx; (c) NaBH₄, MeOH; (d) H₂, Pd/C (10%), EtOH Scheme 14

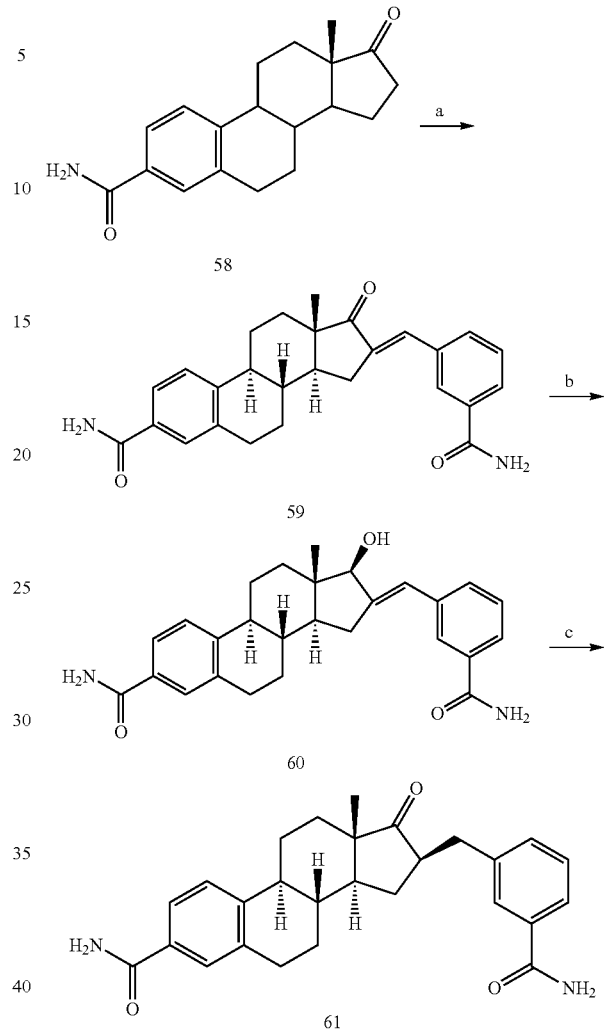

Reagents and conditions: (a) 3-carboxamide-benzaldehyde, KOH, EtOH, rx; (b) NaBH₄, MeOH/DCM (9:1), rt; (c) Pd/C (10%), EtOH, rt.

In one embodiment of the present disclosure, there are included inhibitors of 17β-HSD1, in which the inhibitor has the structure:

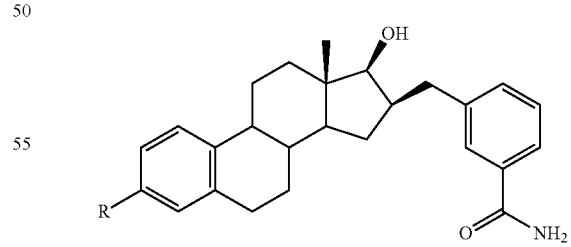

wherein R is —OH, halo, —NH₂, alkyl, alkenyl, alkoxy, aralkyl, carboxy, —CH₂-heterocyclyl, heterocyclyloyl, —C(O)N(R')(R'') or —B(OH)₂, wherein R' and R'' are independently or simultaneously H or alkyl, or R' and R'' are joined together, along with the nitrogen atom to which they are attached, to form a heterocyclic ring, or a pharmaceutically acceptable salt or tautomer thereof.

In one embodiment, the 17β-HSD1 inhibitor is the compound V, or a pharmaceutically acceptable salt thereof. In one embodiment, the inhibitor is the corresponding hydrochloride (HCl) salt of compound V, or other acid addition salt on the carboxamide moiety of compound V.

In another embodiment, the 17β-HSD1 inhibitor is a radiolabelled derivative of compound V having the structure

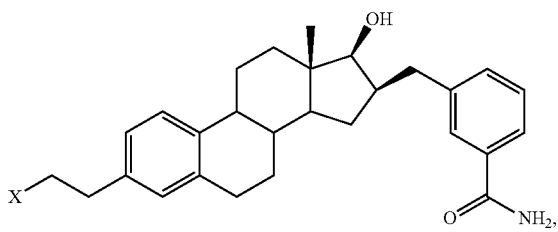

wherein X is $I^{123}$, $I^{125}$, $I^{131}$ or $Br^{76}$.

In another embodiment, the 17β-HSD1 inhibitor is a radiolabelled derivative of compound V having the structure

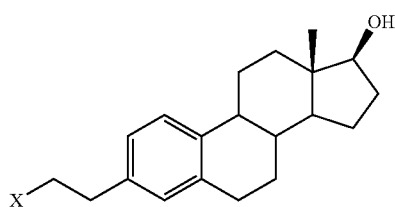

wherein X is $I^{123}$, $I^{125}$, $I^{131}$ or $Br^{76}$.

In another embodiment, the radiolabel is located (e.g. $I^{123}$, $I^{125}$, $I^{131}$ or $Br^{76}$) in a suitable positions on the steroid core of compound V providing for additional radiolabelled derivatives.

The radiolabelled derivatives of the compound V as shown above are useful for the radioimaging and radiotherapeutic treatment of breast cancer and prostate cancer, as such cancers are known to express 17β-HSD, in addition to any other cancers which express 17β-HSD such as endometrial cancer.

In another embodiment, the 17β-HSD1 inhibitor is the alpha-acetylenic derivative of the compound V having the following structure

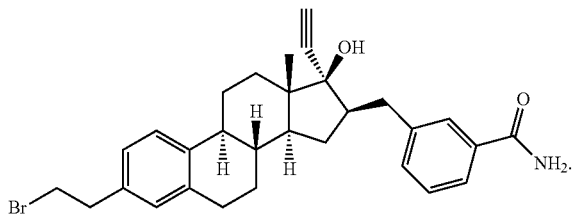

Biological Activity

Compounds I-V were tested for their ability to inhibit the transformation of E1 into E2 by 17β-HSD1 in T-47D cells (Table 1), a cell line well known to express endogenous 17β-HSD1. The effect of the inhibitors on the growth of estrogen-starved estrogen sensitive MCF-7 cells was also evaluated (Table 1). In the alcohol series, it was observed that extending the hydroxyl away from ring A of the steroid structure resulted in a negative effect on the inhibition potency, with values dropping from 66% for phenol I to 37% for methyl alcohol II and 17% for ethyl alcohol IV when tested at 0.1 μM. These results, and those obtained at lower concentrations (0.01 μM), highlight the fact that no additional interaction was obtained in the binding pocket of 17β-HSD1. The bromoalkyl derivatives III and V proved more promising. In fact, the inhibitory activity of V ($IC_{50}$=68 nM) was just two times lower than that of reference inhibitor I ($IC_{50}$=27 nM). More importantly, the estrogenic activity was greatly modulated by the presence of the C3-side chain (FIG. 1). Compound I, bearing a hydroxyl at position C3, strongly stimulated the estrogen sensitive MCF-7 cells at concentration ranging from 0.1 μM to 5 μM. Extending the hydroxyl away from ring A of the steroid structure (compound II) greatly decreased the estrogenicity of the compound while maintaining significant estrogenic activity at doses ranging from 0.5 mM to 5 μM. Extending the hydroxyl by a further methylene unit (compound IV) completely removed any estrogenic activity. The same observations were made with the corresponding bromide (compound V) showing no estrogenicity at any of concentrations ranging from 0.5 μM to 5 μM.

TABLE 1

Inhibition Values and Estrogenic Activities for Compounds I-V

| Compound | R | Inhibition % (0.01 μM)[a] | Inhibition % (0.1 μM)[a] | $IC_{50}$ (nM)[b] |
|---|---|---|---|---|
| I | OH | 35 | 66 | 27 ± 4 |
| II | $CH_2OH$ | 14 | 37 | N/A |
| III | $CH_2Br$ | 20 | 36 | N/A |
| IV | $CH_2CH_2OH$ | 7 | 17 | N/A |
| V | $CH_2CH_2Br$ | 23 | 49 | 68 ± 6 |

[a]Inhibition of the transformation of [$^{14}C$]-E1 (60 nM) into [$^{14}C$]-E2 by 17β-HSD1 in T-47D intact cells. The experiments were performed in triplicate (SD < ± 5%).
[b]Mean ± SD of an experiment performed in triplicate.

Compound V proved to be the most active inhibitor, demonstrating the tolerance of 17β-HSD1 for a hydrophobic chain introduced at position C3. Most importantly, the substitution of the hydroxyl group of I with the hydrophobic chain of V, proved to be very efficient for removing any residual estrogenic activity while undergoing only a slight drop in inhibitory activity. In view of the very good inhibitory activity of V ($IC_{50}$=68 nM) and more importantly in view of the absence of any estrogenic effect observed on estrogen-sensitive breast cancer cells, V represents an excellent candidate for in vivo studies targeting 17β-HSD1.

Figure 2:
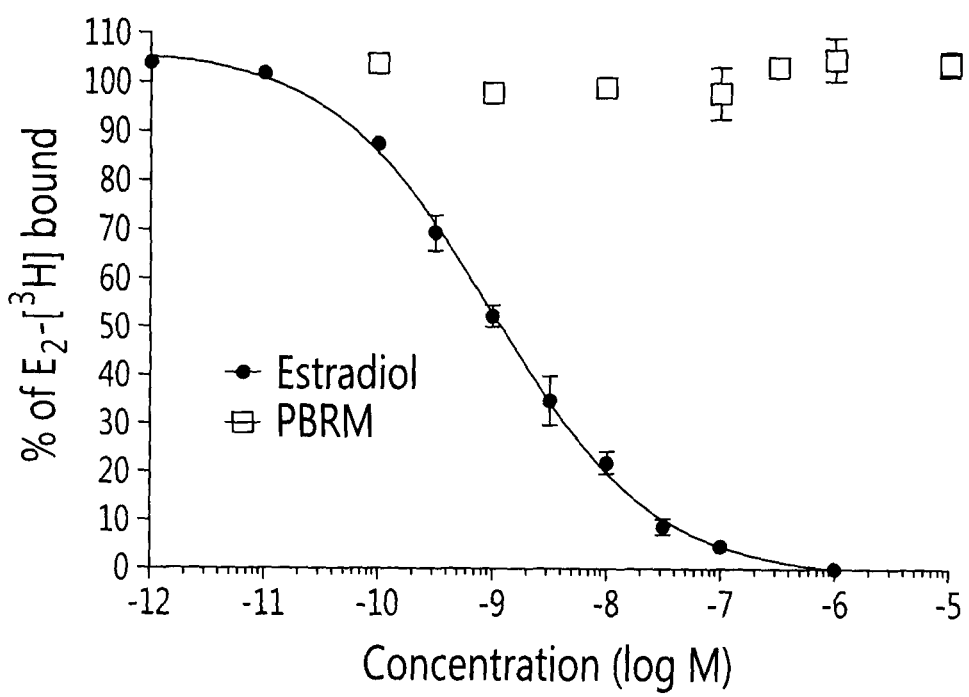
FIG. 2 is an illustration of a competitive binding assay of Compound V and estradiol in a human estrogen receptor assay.

Compound V was also tested with estradiol in a competitive binding assay on a human estrogen receptor alpha. FIG. 2. shows the competitive binding in which Compound V binds to the receptor at all concentrations.

Compound V was also tested on the 17β-HSD2 enzyme for the conversion of E2 to E1 at the tested concentrations varying from 5 nM to 20 μM, and demonstrated no inhibition for this enzyme.

Compound V was also tested on CYP3A4 and demonstrated an $IC_{50}$ of 4.06±0.57 µM, compared to 1.52±0.29 µM for compound I.

Compounds 7-10, 15, 19, 24, 25, 29, 31, 32, 36-41, 46, 50, 57 and 61 were tested for their ability to inhibit the transformation of E1 into E2 by 17β-HSD1 in T-47D cells (Table 2), a cell line well known to express endogenous 17β-HSD1. The effect of the inhibitors on the growth of estrogen-starved estrogen sensitive MCF-7 cells was also evaluated (Table 2).

TABLE 2

Inhibition Values and Estrogenic Activities for Compounds 7-10, 15, 19, 24, 25, 29, 31, 32, 36-41, 46, 50, 57 and 61.

| Compound # | R | Inhibition[a] (0.1 µM) | Inhibition[a] (1 µM) | Estrogenicity[b] (0.1 µM) | Estrogenicity[b] (1.0 µM) |
|---|---|---|---|---|---|
| DP-156 | ----OH | 75 | 90 | ++ | ++ |
| 7 | ~~~~OH | 19 | 57 | + | ++ |
| 8 | ~~~~Br | 56 | 89 | — | — |
| 9 | ~~~~I | 55 | N/A | N/A | N/A |
| 10 | ~~~~Cl | 7 | N/A | N/A | N/A |
| 15 | ~~~~O~~~~Br | 39 | 81 | N/A | N/A |
| 19 | ~~~~Ph | 13 | N/A | N/A | N/A |
| 24 | ~~~~OH | 16 | N/A | N/A | N/A |
| 25 | ~~~~Br | 37 | 82 | N/A | N/A |
| 29 | ~~~~H | 12 | N/A | N/A | N/A |
| 31 | ~~~~C(O)OH | 12 | 29 | — | + |
| 32 | ~~~~C(O)NHMe | 5 | 15 | — | — |
| 36 | ~~~~OC(O)OH | 5 | 8 | — | ++ |
| 37 | ~~~~OH | 56 | 73 | — | + |
| 38 | ~~~~Br | 19 | 66 | — | — |
| 39 | ~~~~NH$_2$ | 35 | 73 | ++ | ++ |
| 40a | ~~~~N(Me)$_2$ | 12 | 49 | — | — |
| 40b | ~~~~N(Et)$_2$ | 5 | 27 | — | — |
| 40c | ~~~~N-pyrrolidinyl | 1 | 28 | — | — |
| 40d | ~~~~NHMe | 26 | 65 | — | — |
| 41d | ~~~~C(O)NHMe | 3 | 5 | — | + |
| 41a | ~~~~C(O)N(Me)$_2$ | 2 | 16 | + | + |
| 41b | ~~~~C(O)N(Et)$_2$ | 1 | 14 | — | — |
| 41c | ~~~~C(O)N-pyrrolidinyl | 0 | 13 | — | — |
| 46 | ----B(OH)$_2$ | 39 | N/A | ++ | ++ |
| 50 | ----NH$_2$ | 35 | 43 | — | + |

TABLE 2-continued

Inhibition Values and Estrogenic Activities for
Compounds 7-10, 15, 19, 24, 25, 29, 31, 32, 36-41, 46, 50, 57 and 61.

[Structure: steroid core with OH at 17β, R substituent on A-ring, and 16β-CH2-phenyl-C(O)NH2 side chain]

| Compound # | R | Inhibition$^a$ (0.1 µM) | Inhibition$^a$ (1 µM) | Estrogenicity$^b$ (0.1 µM) | Estrogenicity$^b$ (1.0 µM) |
|---|---|---|---|---|---|
| 57 | ----F | 48 | 50 | — | + |
| 61 | -C(O)NH2 | 3 | 23 | — | ++ |

$^a$Inhibition of the transformation of [$^{14}$C]-E1 (60 nM) into [$^{14}$C]-E2) by 17β-HSD1 in T-47D intact cells. The experiment was performed in triplicate (SD < ± 5%). The inhibitors were tested at two concentrations of 0.1 and 1 µM.
$^b$Effect of inhibitors on the growth of estrogen-starved estrogen sensitive MCF-7 cells after 7 days of treatment at different concentrations.
Legend: — = no; + = weak ++ = medium to strong.

EXPERIMENTAL

Materials, Methods, Synthesis and Characterization

Chemical reagents were purchased from Sigma-Aldrich Canada Ltd. (Oakville, ON, Canada). The usual solvents were obtained from Fisher Scientific (Montréal, QC, Canada) and were used as received. Anhydrous dichloromethane (DCM), dimethylformamide (DMF) and tetrahydrofuran (THF) were obtained from Sigma-Aldrich. Thin-layer chromatography (TLC) and flash-column chromatography were performed on 0.20-mm silica gel 60 F254 plates and with 230-400 mesh ASTM silica gel 60, respectively (E. Merck; Darmstadt, Germany). Infrared spectra (IR) were recorded using a Horizon MB 3000 ABB FT-IR spectrometer and the significant bands reported in $cm^{-1}$. Nuclear magnetic resonance (NMR) spectra were recorded at 400 MHz for $^1$H and 100.6 MHz for $^{13}$C using a Bruker Avance 400 digital spectrometer (Billerica, Mass., USA). The chemical shifts (δ) were expressed in ppm and referenced to chloroform (7.26 and 77.0 ppm), acetone (2.06 and 29.24 ppm) or methanol (3.31 ppm and 49.0) for $^1$H and $^{13}$C NMR respectively. Low-resolution mass spectra (LRMS) were recorded using a PE Sciex API-150ex apparatus (Foster City, Calif., USA) equipped with a turbo ion-spray source and expressed in m/z. High-resolution mass spectra (HRMS) were provided by Pierre Audet at the Département de Chimie de l'Université Laval (Québec, QC, Canada). The purity of the compounds was determined by high-performance liquid chromatography (HPLC) (Waters Associates Milford, Mass., USA) using a Luna phenyl hexyl column (75×4.6 mm id, 3 µm, serial N°: 338048-2, 60 Å) or a Nova Pak C18 reverse-phase column (150 mm×3.0 mm id, 4 µm, 60 Å).

Cell Culture

The ER-positive breast cancer cell lines T-47D and MCF-7 cells were obtained from the American Type Culture Collection (ATCC) and maintained in 175 $cm^2$ culture flasks at 37° C. in a humidified atmosphere at 5% $CO_2$. The T-47D cells were grown in RPMI medium supplemented with 10% (v/v) fetal bovine serum (FBS), L-glutamine (2 nM), penicillin (100 IU/mL), streptomycin (100/g/mL) and estradiol (1 nM). The MCF-7 cells were propagated in Dubelcco's Modified Eagle Medium: Nutrient Mixture F-12 Ham (DMEM-F12) medium supplemented with 5% FBS, glutamine (2 nM), penicillin (100 IU/mL), streptomycin (100 µg/mL) and estradiol (1 nM).

Inhibition of 17β-HSD1 in T-47D Cells

T-47D cells were seeded in a 24-well plate (3000 cells/well) in medium supplemented with insulin (50 ng/mL) and 5% dextran-coated charcoal treated FBS rather than 10% FBS to remove remaining hormones. After 24 h, the cells were incubated with 60 nM of [$^{14}$C]-Estrone (American Radiolabeled Chemicals, Inc., St. Louis, Mo., U.S.A). An ethanolic solution of inhibitors (0.5% v/v) at concentrations of 0.01 µM and 0.1 µM for all inhibitors were added to freshly changed cultured medium and the cells were incubated over a period of 24 h. For the most active inhibitors, concentrations ranging from 0.01 µM to 10 µM were tested to determinate their $IC_{50}$ values. Each inhibitor was assessed in triplicate. After incubation, the culture medium was removed and labelled steroids (E1 and E2) extracted with 1 mL of diethyl ether. The organic phases were separated and evaporated to dryness using nitrogen. Residues were dissolved in dichloromethane and dropped on silica gel thin layer chromatography plates (EMD Chemicals Inc., Gibbstown, N.J., USA) and eluted with a toluene/acetone (4:1) solvent system. Substrate [$^{14}$C]-E1 and metabolite [$^{14}$C]-E2 were identified by comparison with reference steroids and quantified using a Storm 860 system (Molecular Dynamics, Sunnyvale, Calif., USA). The percentage of transformation and inhibition were calculated as follows: % transformation=100×[$^{14}$C]-E2/([$^{14}$C]-E1+[$^{14}$C]-E2) and % of inhibition=100×(% transformation without inhibitor−% transformation with inhibitor)/% transformation without inhibitor.

Estrogenic Activity in MCF-7 Cells

MCF-7 cells were seeded with medium supplemented with insulin (50 ng/mL) and 5% dextran-coated charcoal treated FBS rather than 10% FBS to remove remaining hormones. Aliquots (100 µL) of the cell suspension were seeded in 96-well plates (3000 cells/well). After 48 h, the medium was replaced with a fresh one containing an appropriate concentration of products to be tested and was replaced every 2 days. Cells were grown either in the absence or presence of the compounds over a period of 7 days. Quantification of cell growth was determined by using the CellTiter 96®Aqueous Solution Cell Proliferation Assay (Promega, Nepean, ON, Canada) following the manufacturer's instructions. To determine the proliferative (estrogenic) activity, the cells were grown in the absence (control fixed as 100%) or presence of the tested compounds at the indicated concentrations.

ER Alpha Binding Assay with Compound V

A competitive binding assay using a purified full-length recombinant human ERa (Life Technologies, Grand Island, N.Y.) was done as previously described (Davis et al. *J. Steroid Biochem. Mol. Biol.*, 2008, 108, 23-31; Arcaro et al. *J. Cell. Biochem.* 1999, 72, 94-102). Briefly, each reaction consisted of 1.2 nM rhERa and 2.5 nM [$^3$H]-estradiol in assay buffer (10 mM Tris, 1.5 mM EDTA, 1 mM dithiothreitol, 10% glycerol, 1 mg/mL BSA, pH 7.5) with different concentrations of the compounds or cold estradiol in a total reaction volume of 100 µL. Non-specific binding was determined by incubation with an excess of cold estradiol (1 µM).

After an overnight incubation at 4° C., 100 μl of cold 50% hydroxyapatite slurry was added to bind the receptor/ligand complex. After 15 minutes, 1 mL of wash buffer (40 mM Tris, 1 mM EDTA, 1 mM EGTA, 100 mM KCl, pH 7.4) was added and the tubes were centrifuged at 4500 rpm for 5 minutes at 4° C. The washing step was repeated twice. The radioactivity of the pellet was extracted by incubation with 1 mL of ethanol for 1 h at room temperature. The suspension was then put into 10 mL of Biodegradable Counting Scintillant and the radioactivity counted with a Wallac 1411 Liquid Scintillation Counter. $IC_{50}$ values were obtained using GraphPad Prism 5 and RBA values were obtained by using the following equation: ($IC_{50}$ of 17β-estradiol/$IC_{50}$ of compound)×100.

|  | $IC_{50}$ | RBA |
| --- | --- | --- |
| Estradiol | 1.02 nM ± 0.09 nM | 100 |
| Compound V | — | — |

Inhibition of 17β-HSD2 with Compound V

Inhibition assays were performed using stable 17β-HSD2 HEK-293 transfected intact cells with 5000 cells per well using 24 well plates (Poirier et al. *Mol. Cell. Endocrinol.*, 2001, 171, 119-128). The cells were incubated for 1 h at 37° C. in 1 mL of MEM medium steroid free with 60 nM $C^{14}$ estradiol. The steroids were then extracted, quantified and separated as previously described for 17β-HSD1 enzymatic activity and the % inhibition calculated (Tremblay et al *J. Enzyme Inhib. Med. Chem.*, 2005, 20, 153-163). Compound V did not show any inhibition on the 17β-HSD2 enzyme for the conversion of E2 to E1 at the tested concentrations varying from 5 nM to 20 μM.

Inhibition of CYP3A4 with Compound V

The P450 Inhibition Kit CYP3A4/DBF purchased from BD Biosciences was used as suggested by the company, with the exception that the compound V was dissolved in a mixture of 5% DMSO/95% acetonitrile Compound V demonstrated a lower inhibition of CYP3A4 with a $IC_{50}$ of 4.06±0.57 μM, compared to 1.52±0.29 μM for compound I.

17β-HSD1 Inhibition in Breast Cancer Cell Lines with Compound V

In Vitro Studies-Cell Culture

Breast cancer cell line T-47D was obtained from the American Type Culture Collection (ATCC) and maintained in a 175 $cm^2$ culture flask at 37° C. in a humidified atmosphere at 5% $CO_2$. Cells were grown in RPMI medium supplemented with 10% (v/v) fetal bovine serum (FBS), L-glutamine (2 nM), penicillin (100 IU/mL), streptomycin (100 μg/mL) and estradiol (1 nM).

17β-HSD1 Inhibition Assay

T-47D cells were seeded in a 24-well plate (3000 cells/well) in 990 μL of medium supplemented with insulin (50 ng/mL) and 5% dextran-coated charcoal-treated FBS, which was used rather than untreated 10% FBS, to remove the remaining steroid hormones. Stock solutions of inhibitors Compounds I and V were previously prepared in ethanol and diluted with culture medium to achieve appropriate concentrations prior to use. After 24 h of incubation, 5 μL of the diluted solution were added to the cells to obtain a final concentration ranging from 1 nM to 10 μM to determine the $IC_{50}$ value. The final concentration of ethanol in the well was adjusted to 0.1%. Additionally, 5 μL of a solution of [$^{14}$C]-estrone (American Radiolabeled Chemicals, Inc., St. Louis, Mo., USA) was added to obtain a final concentration of 60 nM. Cells were incubated for 24 h and each inhibitor was assessed in triplicate. After incubation, the culture medium was removed and labeled steroids (E1 and E2) were extracted with 1 mL of diethyl ether. The organic phases were evaporated to dryness with nitrogen. Residues were dissolved in dichloromethane and dropped on silica gel thin layer chromatography plates (EMD Chemicals Inc., Gibbstown, N.J., USA) and eluted with toluene/acetone (4:1) as solvent system. Substrate [$^{14}$C]-E1 and metabolite [$^{14}$C]-E2 were identified by comparison with reference steroids (E1 and E2) and quantified using the Storm 860 system (Molecular Dynamics, Sunnyvale, Calif., USA). The percentage of transformation and the percentage of inhibition were calculated as follow: % transformation=100×[$^{14}$C]-E2/([$^{14}$C]-E1+[$^{14}$C]-E2) and % of inhibition=100×(% transformation without inhibitor−% transformation with inhibitor)/% transformation without inhibitor (Tremblay M R, Boivin R P, Luu-The V, Poirier D. Inhibitors of type 1 17beta-hydroxysteroid dehydrogenase with reduced estrogenic activity: modifications of the positions 3 and 6 of estradiol. J Enzyme Inhib Med Chem 2005; 20:153-63; Cadot C, Laplante Y, Kamal F, Luu-The V, Poirier D. C6-(N,N-butyl-methyl-heptanamide) derivatives of estrone and estradiol as inhibitors of type 1 17beta-hydroxysteroid dehydrogenase: Chemical synthesis and biological evaluation. Bioorg Med Chem 2007; 15:714-2).

Cell Proliferation Assays (17β-HSD1 Inhibitory, Estrogenic and Antiestrogenic Activities)

Quantification of cell growth was determined by using CellTiter 96®Aqueous Solution Cell Proliferation Assay (Promega, Nepean, ON, Canada) following the manufacturer's instructions. T-47D cells were resuspended with the medium supplemented with insulin (50 ng/mL) and 5% dextran-coated charcoal treated FBS rather than 10% FBS to remove remaining hormones. Aliquots (100 μL) of the cell suspension were seeded in 96-well plates (3000 cells/well). After 48 h, the medium was changed with a new one containing an appropriate concentration of products to be tested and was replaced every 2 days. Cells have grown either in absence or presence of the compounds for 7 days. To determine the proliferative (estrogenic) activity, the estrogen-sensitive T-47D cells were grown in absence (basal cell proliferation was fixed as 100%) or presence of compounds to be tested at 0.5 to 10 μM. The potent estrogen E2 was used as a reference control. To determine the inhibition of E1-induced cell proliferation, the T-47D cells were grown in the presence of E1 (0.1 nM) without (control) or with the inhibitor at a concentration of 0.5, 1, 2.5, and 5 μM. The cell proliferation without E1±inhibitor (control) was fixed as 100%. To determine the potential antiestrogenic activity of inhibitor Compound V, the T-47D (ER⁺) cells were grown in the presence of estrogen E2 (0.1 nM) and pure antiestrogen EM-139 (0.5 μM) [34] or inhibitor Compound V (0.5 μM). The cell proliferation without E2 and tested compounds (control) were fixed as 100%.

ERα Binding Assay

A competitive binding assay using a purified full-length recombinant human ERα (Life Technologies, Grand Island, N.Y.). Briefly, each reaction consisted of 1.2 nM rhERα and 2.5 nM [$^3$H]-estradiol in assay buffer (10 mM Tris, 1.5 mM EDTA, 1 mM dithiothreitol, 10% glycerol, 1 mg/mL BSA, pH 7.5) with different concentrations of the compounds or untritiated estradiol (E2) in a total reaction volume of 100 μL. Non-specific binding was determined by incubation with an excess of E2 (1 μM). After an overnight incubation at 4° C., 100 μL of cold 50% hydroxyapatite slurry was added to bind the receptor/ligand complex. After 15 minutes, 1 mL of wash buffer (40 mM Tris, 1 mM EDTA, 1 mM EGTA, 100 mM KCl, pH 7.4) was added and the tubes were centrifuged at 4500 rpm for 5 minutes at 4° C. The washing step was repeated twice. The radioactivity of the pellet was extracted by incubation with 1 mL of ethanol for 1 h at room temperature. The suspension was then put into 10 mL of Biodegradable Counting Scintillant and the radioactivity counted with a Wallac 1411 Liquid Scintillation Counter. $IC_{50}$ values were obtained using GraphPad Prism 5 and RBA values were obtained by using the following equation: ($IC_{50}$ of 17β-E2/$IC_{50}$ of tested compound)×100.

In Vivo Studies—Animals

All animals were acclimatized to environmental conditions (temperature: 22±3° C.; humidity: 50±20%; 12-h light/12-h dark cycles, lights on at 07:15 h) for at least 3 days before starting the experiment. The animals were allowed free access to water and a certified commercial rodent food (Rodent Diet #T.2018.15, Harlan Teklad, Madison, Wis., USA) and randomized according to their body weight. The experiments with animals were conducted in an animal facility approved by the Canadian Council on Animal Care (CCAC) and the Association for Assessment and Accreditation of Laboratory Animal Care. The study was performed in accordance with the CCAC Guide for Care and Use of Experimental Animals. Institutional approval was obtained.

Plasmatic Concentration of Inhibitor after a Single Subcutaneous Injection

Six week-old male Sprague-Dawley rats weighing approximately 220 g were obtained from Charles-River, Inc. (St-Constant, Qc., Canada). The animals were housed 3 per cage. A pharmacokinetic study was carried out following one subcutaneous (s.c.) injection of the inhibitor at one concentration (2.3 mg/kg of body weight in 0.5 mL of vehicle fluid). The inhibitor was first dissolved in ethanol (EtOH) and thereafter we added propylene glycol (PG) to obtain a final concentration of EtOH of 8%. During this experiment, the rats were housed individually and were fasted for 8 h before inhibitor injection but allowed free access to water. Blood samples for determination of inhibitor plasma concentration were collected at the jugular vein (0.4 mL by animal) at target intervals of 3, 7, 12 and 24 h post-dose for Compound V and 3 and 12 h for CC-156, from three rats per time point. After the collection at 7 h, a replacement fluid (0.9% sodium chloride injection USP) was injected in the rat. Blood samples were collected into Microvette potassium-EDTA (ethylenediamine tetraacetic acid)-coated tube (Sarstedt, Aktiegesellchaft & Co, Germany) and centrifuged at 3200 rpm for 10 minutes at 4° C. The plasma was collected and stored at −80° C. until analyzed by liquid chromatography/mass spectrometry/mass spectrometry (LC/MS/MS) analysis.

Measurement of Plasma Concentrations

The concentration of the inhibitors (Compounds I and V) was determined by LC/MS/MS analysis using a procedure developed at CHUQ (CHUL)-Research Center (Québec, Qc, Canada). Briefly, for extraction from serum, 100 µL of serum sample is transferred to individual tubes and 600 µL of ammonium acetate (1 mM) is added. A methanolic solution (50 µL) containing a steroidal internal standard is then added to each tube. Samples are transferred on Strata-X SPE columns (Phenomenex, Torrance, Calif., USA), which have been conditioned with 2 mL of methanol and 2 mL of water. Each column is washed with 2 mL of methanol:water (10:90, v/v). The inhibitor is then eluted with 5 mL of methanol containing 5 mM ammonium acetate. Methanol is evaporated at 45° C. under inert atmosphere and the residue dissolved in 100 µL of methanol:water (85:15, v/v). For the steroid analysis, the HPLC system uses a 75×4.6-mm, 3 µm reversed-phase Luna Phenyl-Hexyl column (Phenomenex, Torrance, Calif., USA) at a flow rate of 0.8 mL/min. The inhibitor is detected using an API 3000 mass spectrometer, equipped with TurbolonSpray (Applied Biosystems, Canada). ESI in positive ion mode was used. The area under the curve (AUC) was calculated using the linear trapezoidal rule.

In Vivo Estrogenicity Assay

Female ovariectomized (OVX) BALB/c mice weighing approximately 20 g were obtained from Charles-River, Inc. (St-Constant, Qc., Canada). The animals were housed 5 per cage. Groups of 5 mice were treated with E1 (0.02 µg in 8% EtOH/92% PG) or 17β-HSD1 inhibitor at 10, 50 and 250 µg (0.1 mL s.c.) daily for 7 days. Animals were killed 24 h after administration of the last dose of compound and uteri and vagina were removed, excised of fat and weighed. Total body weights of mice were also recorded.

Inhibition of E1-Stimulated T-47D Tumor Growth in Nude OVX Mice (Xenograft Model)

Female OVX BALB/c athymic nude mice weighing approximately 20 g were obtained from Charles-River, Inc. (St-Constant, Qc., Canada). The animals were housed 5 per cage. For the inhibition of T-47D tumor growth, 24 h after a pre-dose of E1 (0.1 µg) s.c. per mouse, mice were inoculated s.c. with $1 \times 10^7$ T-47D cells in 50 µL Matrigel (BD Biosciences, Bedford, Mass.) into both flanks of each mouse. T-47D tumor growth was stimulated using 0.1 µg of E1 s.c. per mouse per day for 15 days. From day 16, animals with tumors were randomized in function of tumor volume and separated into three groups. Group 1 (control mice) was treated s.c. with 100 µL of vehicle alone (8% EtOH/92% PG) per mouse per day. Group 2 (E1 0.1 µg) was treated with E1 (0.1 µg/day, s.c. per mouse) during 32 days. Group 3 (E1 0.1 µg+Compound V 250 µg) was treated with E1 (0.1 µg/day) and Compound V (250 µg/day) per mouse in a combined s.c. injection for 32 days. The mice were weighed at start and volumes of tumors were determined by external caliper twice a week and the greatest longitudinal diameter (length) and the greatest transverse diameter (width) were determined. Tumor volume based on caliper measurements was calculated by the modified ellipsoidal formula: Tumor volume=½(length×width$^2$) (Jensen M M, Jorgensen J T, Binderup T, Kjaer A. Tumor volume in subcutaneous mouse xenografts measured by microCT is more accurate and reproducible than determined by 18F-FDG-microPET or external caliper. BMC Med Imaging 2008; 8:16). At the end of the studies the mice were terminally anaesthetized, final body weights and tumor sizes were determined. Uteri and vagina were removed, excised of fat and weighed (Day J M, Foster P A, Tutill H J, Parsons M F, Newman S P, Chander S K, et al. 17beta-hydroxysteroid dehydrogenase type 1, and not type 12, is a target for endocrine therapy of hormone-dependent breast cancer. Int J Cancer 2008; 122:1931-40; Husen B, Huhtinen K, Poutanen M, Kangas L, Messinger J, Thole H. Evaluation of inhibitors for 17beta-hydroxysteroid dehydrogenase type 1 in vivo in immunodeficient mice inoculated with MCF-7 cells stably expressing the recombinant human enzyme. Mol Cell Endocrinol 2006; 248:109-13; Husen B, Huhtinen K, Saloniemi T, Messinger J, Thole H H, Poutanen M: Human hydroxysteroid (17-beta) dehydrogenase 1 expression enhances estrogen sensitivity of MCF-7 breast cancer cell xenografts. Endocrinology 2006; 147:5333-9; Messinger J, Hirvela L, Husen B, Kangas L, Koskimies P, Pentikainen O, et al. New inhibitors of 17beta-hydroxysteroid dehydrogenase type 1. Mol Cell Endocrinol 2006; 248:192-8).

Statistical Analysis

Statistical significance was determined according to the multiple-range test of Duncan-Kramer (Kramer C. Extension of multiple range tests to group with unique numbers of replications. Biometrics 1956; 12:307-10). P values which were less than 0.05 were considered as statistically significant.

17β-HSD1 Inhibitory Activity

Figure 3:
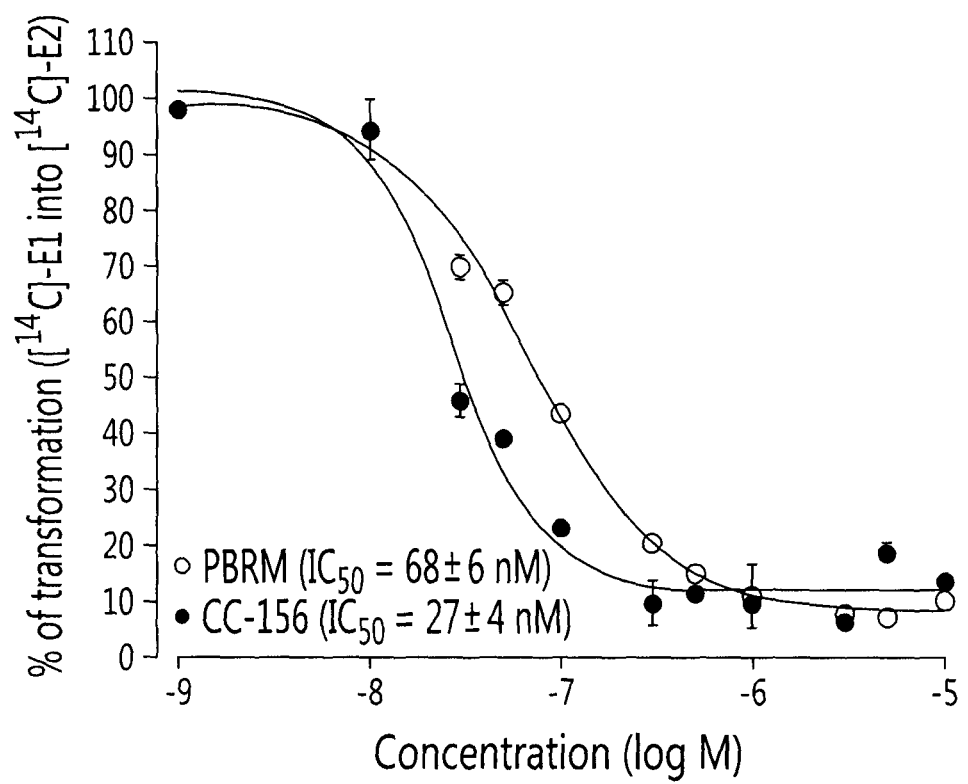
FIG. 3 shows the inhibitory potency of Compound V and I in T-47D intact cells. Results are the means (±SEM) of a triplicate.

The $IC_{50}$ values of Compound V and Compound I were determined using breast cancer T-47D cell line (FIG. 3), which exerts strong endogenous expression of 17β-HSD1 (Day J M, Foster P A, Tutill H J, Parsons M F, Newman S P, Chander S K, et al. 17beta-hydroxysteroid dehydrogenase type 1, and not type 12, is a target for endocrine therapy of hormone-dependent breast cancer. Int J Cancer 2008; 122: 1931-40). Compound V has a good inhibitory effect on 17β-HSD1 with $IC_{50}$ value of 68 nM. As a reference, inhibitor compound I inhibited the enzyme with an $IC_{50}$ of 27 nM. This $IC_{50}$ value is in agreement with the previous value of 44 M obtained using the same cell line but a different lot of cells and also with a different number of passages (Laplante Y, Cadot C, Fournier M A, Poirier D. Estradiol and estrone C-16 derivatives as inhibitors of type 1 17beta-hydroxysteroid dehydrogenase: blocking of $ER^+$ breast cancer cell proliferation induced by estrone. Bioorg Med Chem 2008; 16:1849-60).

Inhibition of E1-Stimulated Cell Proliferation

Figure 4A:
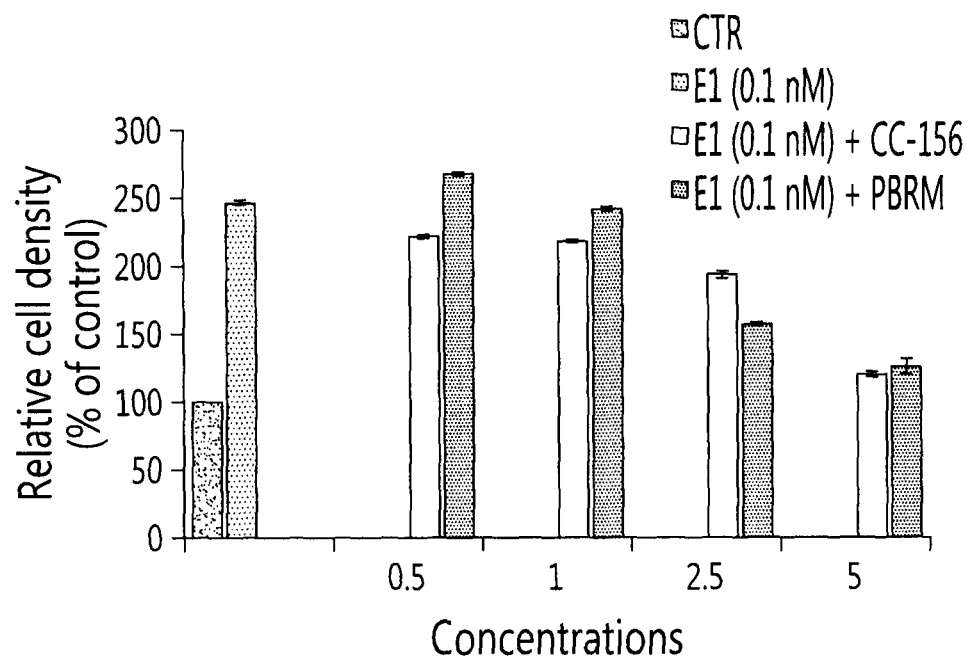
FIG. 4. A shows the cell growth of T-47D cells induced by a physiologic concentration of E1 (0.1 nM) in the presence or absence of inhibitors Compounds I and V at various concentrations. Results are expressed as means (±SEM) of triplicate. B: Effect of inhibitor Compound V and the pure antiestrogen EM-139 on the inhibition of E2 (0.1 nM)-induced proliferation (antiestrogenic activity) of estrogen-sensitive (ER$^+$) human breast cancer T-47D cells. Results are expressed as means (±SEM) of triplicate.

The effectiveness of Compounds V and I to block the proliferative effect induced by E1 in estrogen-sensitive breast cancer cell line T-47D was investigated. The ability of these 17β-HSD1 inhibitors to inhibit the cell growth induced by the transformation of E1 (0.1 nM) into potent estrogen E2 was investigated. This concentration of E1 is close to the intracellular concentration in breast cancer cells (Pasqualini J R, Cortes-Prieto J, Chemite G, Talbi M, Ruiz A. Concentrations of estrone, estradiol and their sulfates, and evaluation of sulfatase and aromatase activities in patients with breast fibroadenoma. Int J Cancer 1997; 70:639-43). Compound V was able to inhibit the proliferative effect induced by E1 in a concentration-dependent manner (FIG. 4A). Compound V reduced the cell growth from 250% to 156 and 125%, at 2.5 and 5 μM respectively.

Figure 4B:
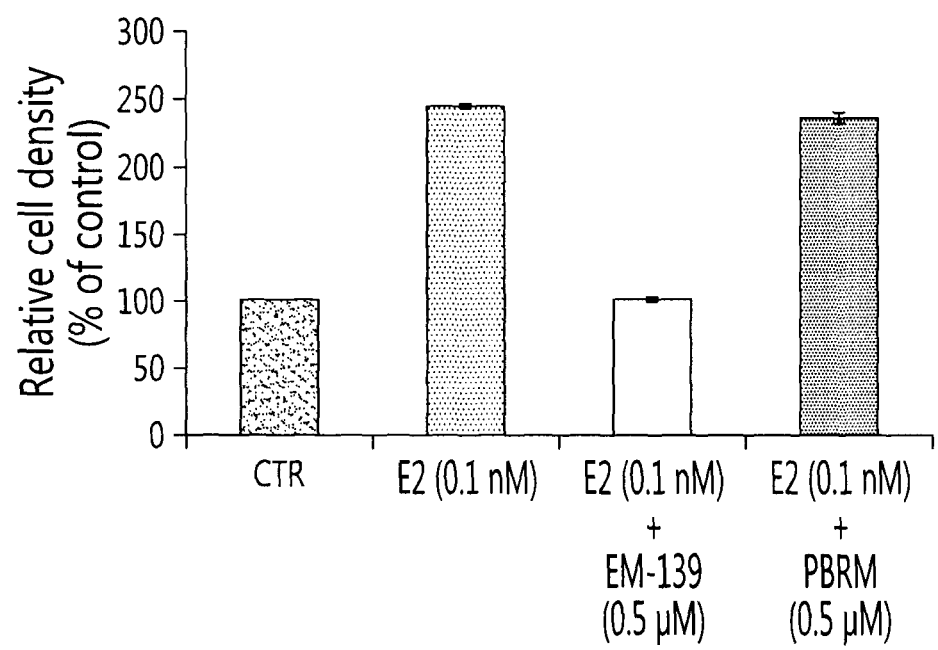

The reduction of E1-induced cell proliferation obtained when using inhibitor Compound V could also be the result of an antiestrogenic activity of this E2 derivative. Indeed, an antiestrogenic compound will block the proliferative (estrogenic) effect of E2 mediated by its action on the estrogen receptor (ER). As illustrated in FIG. 4B, the enzyme inhibitor Compound V does not reverse the proliferative effect on $ER^+$ cells of E2 (0.1 nM) like the pure antiestrogen EM-139 (Levesque C, Merand Y, Dufour J M, Labrie C, Labrie F. Synthesis and biological activity of new halo-steroidal antiestrogens. J Med Chem 1991; 34:1624-30) does. This result indicates that Compound V does not work as an antiestrogenic compound, but acts instead as an inhibitor of E1 into E2 transformation catalyzed by 17β-HSD1.

Estrogenic Activity on T-47D ($ER^+$) Cell Line and ERα Binding Affinity

Figure 5A:
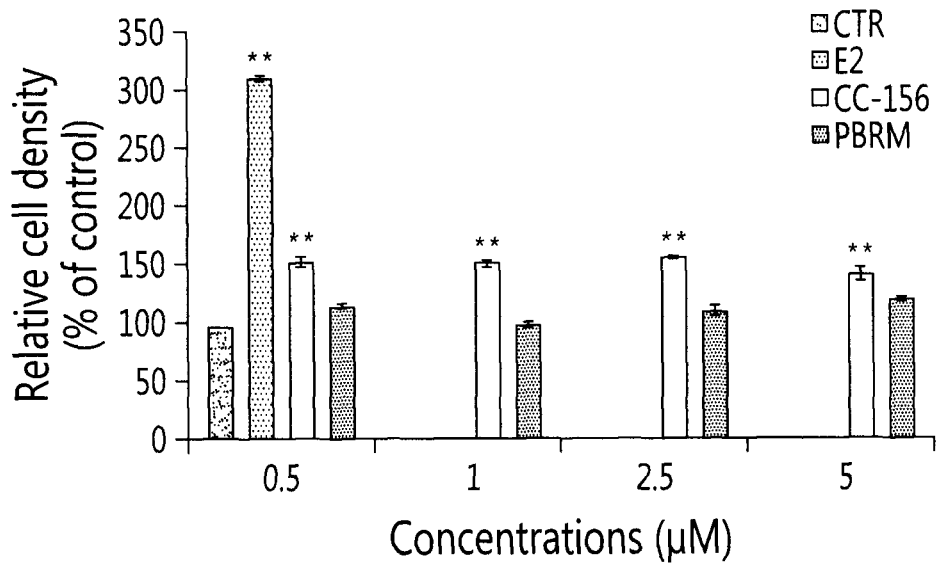
FIG. 5 A shows the effects of inhibitors Compounds I and V on the growth of estrogen-starved T-47D (ER$^+$) human breast cancer cells after 7 days of treatment. Results are expressed as means (±SEM) of triplicate (*P<0.05 and **P<0.01). B: Effects of increasing concentrations of Compounds I and V in displacing [$^3$H]-E2 binding to the human ERα.

In order to detect any undesirable estrogenic activity of 17β-HSD1 inhibitors, cell proliferative assays were carried out on the T-47D cell line which is known to express the estrogen receptor ($ER^+$) (Keydar I, Chen L, Karby S, Weiss F R, Delarea J, Radu M, et al. Establishment and characterization of a cell line of human breast carcinoma origin. Eur J Cancer 1979; 15:659-70). Proliferative activity of compounds V and I was evaluated at 0.5, 1, 2.5 and 5 μM (FIG. 5A). It is clear that Compound V was not estrogenic at any concentration tested, which underlines the importance of the 3-bromoethyl chain to remove the undesired estrogenicity.

Figure 5B:
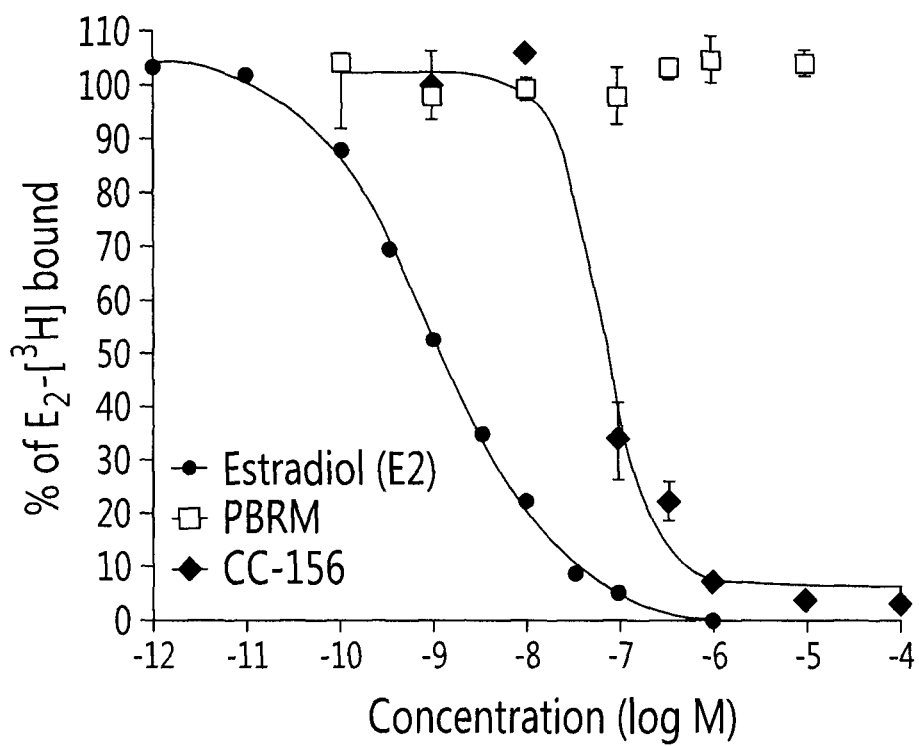

Having assessed the in vitro estrogenic activity of Compound V and I on $ER^+$ cell proliferation, their affinity for ERα (FIG. 5B), the predominant receptor isoform involved in estrogenic effect was investigated. The concentration at which the unlabeled natural ligand (E2) displaces half the specific binding of [$^3$H]-17β-E2 on ERα ($IC_{50}$) was determined by computer fitting of the data using non-linear regression analysis and the relative binding affinity (RBA) then calculated. The RBA of E2 was established as 100% whereas the RBA for inhibitor Compound I was 1.5%. Although low, this binding affinity for ERα can explain the proliferative (estrogenic) activity we have measured in the T-47D estrogen-sensitive cell line. No binding affinity was detected for Compound V.

Estrogenic Activity of Inhibitors in Mice

Figure 6A:
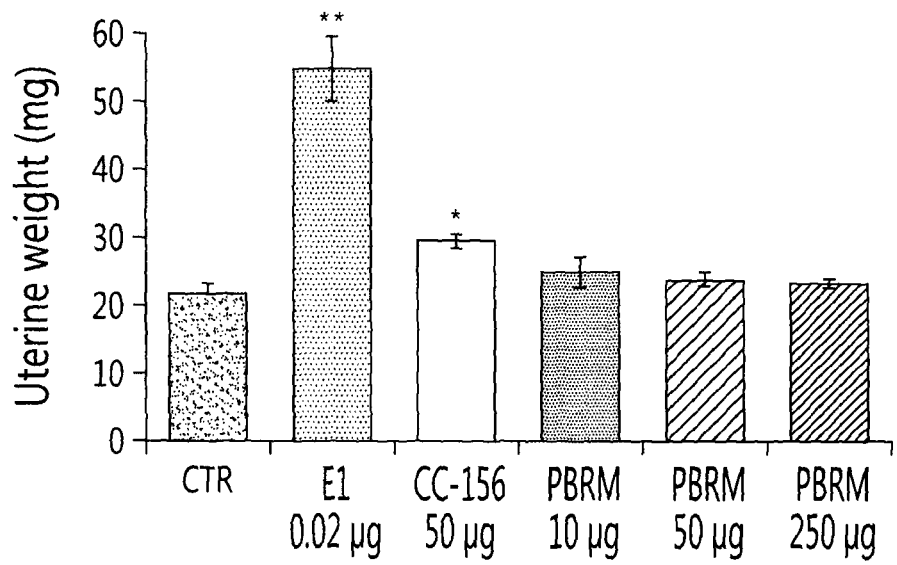
FIG. 6. shows the effect of inhibitors Compounds I and V on uterine (A) and vagina (B) weight of ovariectomized (OVX) mice treated for 7 days (*P<0.05 and **P<0.01, experimental versus OVX control animals (CTR)).
Figure 6B:
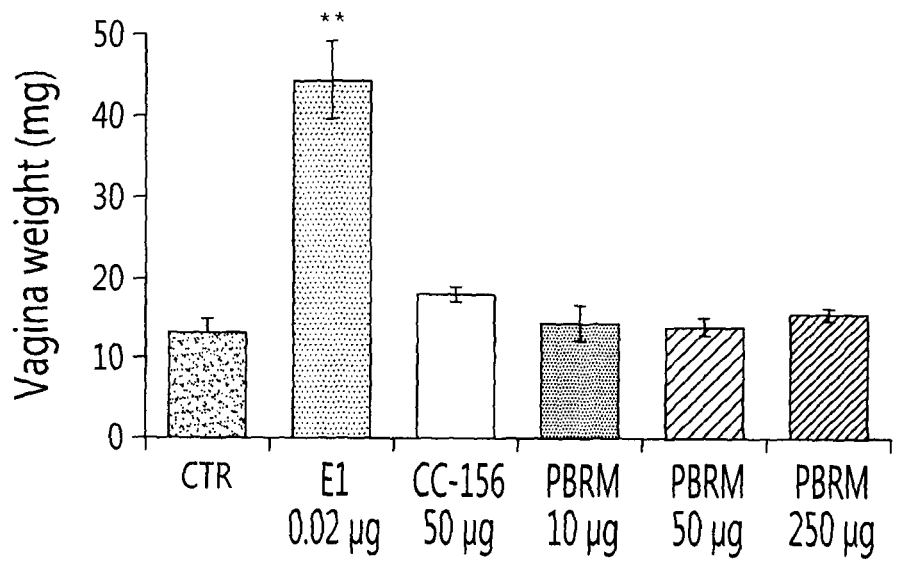

To verify that the lack of estrogenicity of Compound V observed in vitro in the T-47D cell proliferation assay translates into the in vivo setting, the estrogenicity of Compound V was investigated using the OVX mouse model by measuring the weight of the uterus (FIG. 6A) and vagina (FIG. 6B), two estrogen-sensitive ($ER^+$) tissues. For the OVX mice control group (OVX-CTR) a low weight of 22 mg was observed for the uterus. However, when administrated s.c. to OVX mice, E1 (0.02 μg/mouse/day) is converted into E2 by 17β-HSD1 and we observed a 2.5-time increase in uterine weight compared to OVX-CTR (22 mg vs 55 mg; P<0.01). Weights of the uterus from all Compound V dose groups (10, 50 and 250 μg/mouse/day), were not significantly different to those of the OVX-CTR group after seven days of treatment (25, 24 and 23 mg, respectively). Thus, these results confirmed that Compound V is non-estrogenic in vivo. The measurement of vagina weights clearly demonstrated the same tendency for Compound V as previously observed with the uterus.

Plasma Concentration of Inhibitors

Figure 7:
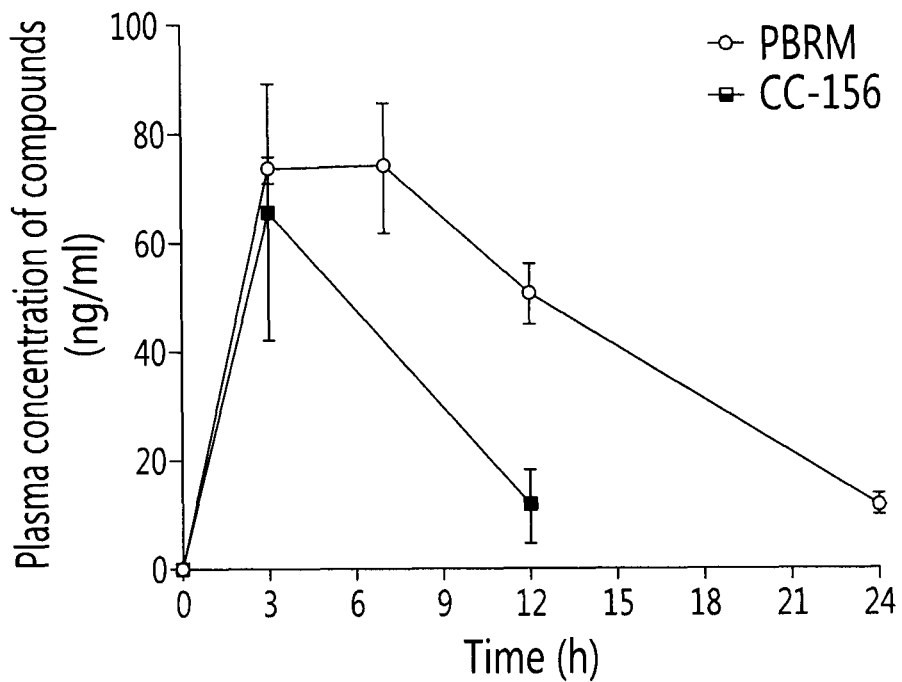
FIG. 7 shows the plasma concentration of Compounds I and V as a function of time following subcutaneous (s.c.) injection of 2.3 mg/kg in Sprague-Dawley rats.

A single subcutaneous injection (2.3 mg/kg) of inhibitors Compounds V and I was given to two different groups of rats in order to determine the inhibitor bioavailability. The mean plasma concentrations of inhibitors Compounds V and I at different times and the corresponding area under the curve (AUC) are presented in FIG. 7. The plasma concentrations at each sampling time were compared to determine the times at which significant differences occurred. At first, it was found that the maximum plasma concentration ($C_{max}$) was attained at 3 h following injection for both inhibitors. For Compound V, values of 73.8 and 50.7 ng/mL were found after 7 and 12 h of injection respectively. After 24 h, a plasma concentration of 11.7 ng/mL was measured for Compound V, thus an $AUC_{0-24\ h}$ of 1146 ng*h/mL was obtained for it.

Inhibition of E1-Stimulated T-47D Tumor Growth in OVX Nude Mice

Figure 8:
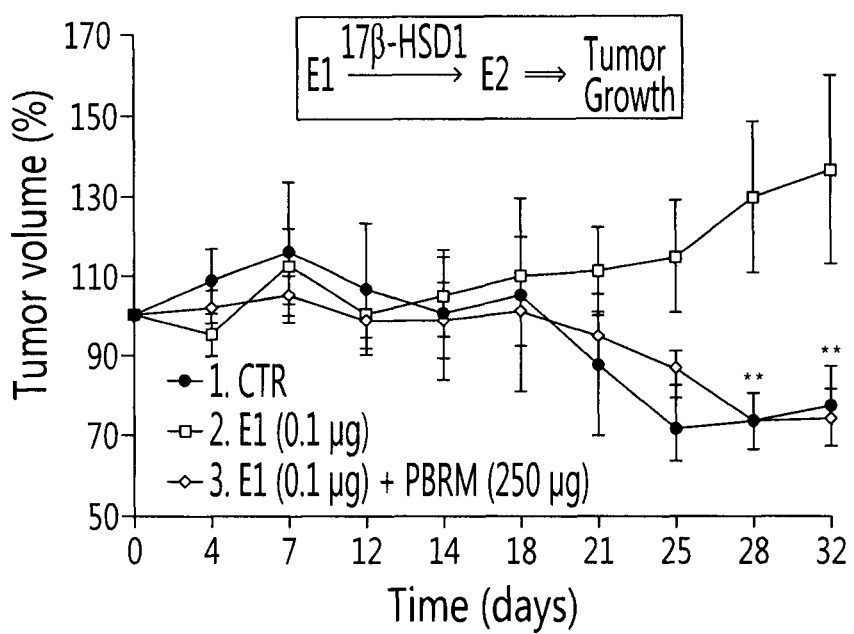
FIG. 8 shows the effect of Compound V on the growth of E1 (s.c.)-stimulated T-47D tumors (xenograft) in ovariectomized (OVX) nude mice. (*P<0.05 and **P<0.01, E1-Compound V and OVX control animals (CTR) versus E1).

After it was established that Compound V was found in plasma after a one-day single s.c. injection, the efficacy of Compound V in vivo was investigated. Female OVX Balb/c nude mice were inoculated with $1 \times 10^7$ T-47D ($ER^+$) cells in Matrigel, as in the procedure described by Day et al (Day J M, Foster P A, Tutill H J, Parsons M F, Newman S P, Chander S K, et al. 17beta-hydroxysteroid dehydrogenase type 1, and not type 12, is a target for endocrine therapy of hormone-dependent breast cancer. Int J Cancer 2008; 122: 1931-40), except that inoculation was made into both flanks of mouse. The mice received E1 (0.1 μg/day), which after its transformation to E2 by 17β-HSD1, stimulates tumor growth. Only mice with tumors which were well established after 15 days of treatment with 0.1 µg E1/mouse s.c. were selected to continue the study. We used the dose of 250 µg/mouse of Compound V because this was the highest dose tested in the in vivo estrogenicity assay that proved to be non estrogenic. FIG. 8 shows the effect of Compound V on the growth of tumors stimulated with 0.1 µg E1/mouse/day. In the first 18 days of treatment, the tumors were not actively growing and maintained their initial size at the beginning of treatment. From day 19, the volume of tumors in the control (CTR) group began to decrease until they reached approximately the 74% of the initial volume after 28 days and continued at the same level until day 32 (77%). In the E1 treated group however, tumors grew reaching 136% of their initial size, whereas in the mice treated E1-Compound V the growth of the tumors was inhibited (74%), decreasing to the level of the CTR group at the end of treatment (P<0.01 at days 28 and 32, E1-Compound V vs E1). Clearly, Compound V blocks the formation of E2 in the tumor through the inhibition of 17β-HSD1 and thus the tumor growth.

Figures 9A, 9B, 9C:
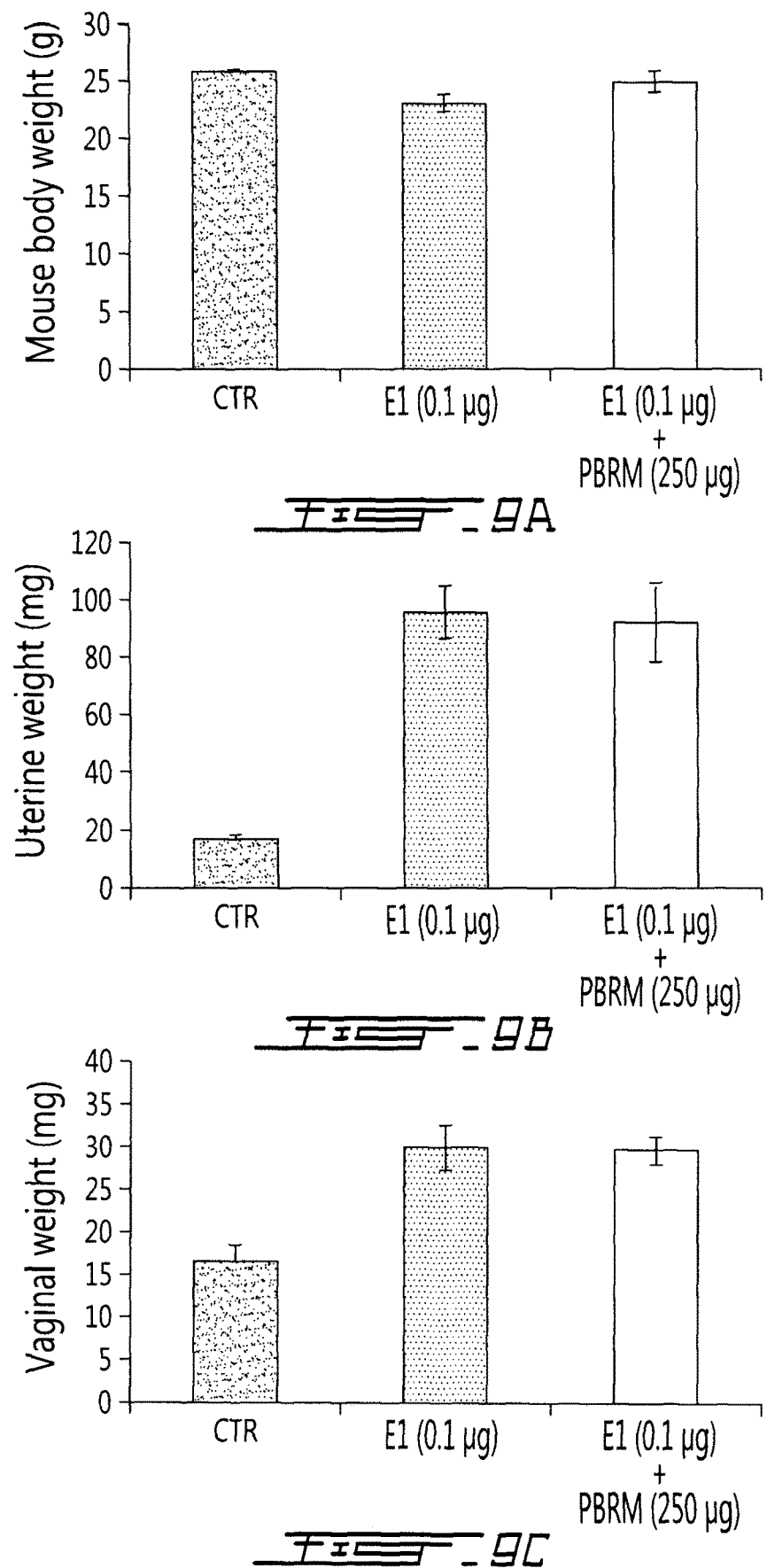
FIG. 9. shows the effect of inhibitor of Compound V and estrone (E1) on the body (A), uterine (B) and vaginal (C) weight of ovariectomized nude mice after 32 days of treatment. CTR: control.

At the end of the study, the body weights of the mice were recorded and the estrogen-sensitive tissues (uterus and vagina) were taken for analysis. There was no effect of either E1 or Compound V on mouse weight over the 32-day treatment period (FIG. 9), indicating that there is no apparent toxicity of Compound V at 250 µg/day/mouse (s.c.). Although uterine and vagina weights were increased significantly in both of the E1-treated groups (P<0.01, E1 and E1-Compound V vs. CTR), treatment with Compound V had no effect on the E1-stimulated uterine and vaginal weight increase (FIGS. 9B and 9C).

Synthesis of 3-(2-hydroxyethyl) estra-1(10), 2,4-trien-17-dioxolane (2)

To a solution of $BH_3$-dimethylsulfide (2.0 M in THF, 10.4 mL) in anhydrous THF (70 mL) at −78° C. was added dropwise 3-vinyl-estra-1(10),2,4-trien-17-dioxolane (1) (2.25 g, 6.93 mmol) in THF (5 mL) under an argon atmosphere. The resulting solution was stirred at ambient temperature over a period of 16 h. The solution was then cooled to 0° C. and aqueous $NaHCO_3$ (1 M, 27.7 mL) was added, immediately followed by the addition of 30% $H_2O_2$ (11.7 mL). The solution was vigorously stirred over a period of 3 h at room temperature and then diluted with EtOAc (50 mL). The resulting solution was poured into water (200 mL) and extracted with EtOAc (5×75 mL). The organic layers were combined, washed with brine, dried with $MgSO_4$ and evaporated under reduced pressure. The crude compound was purified by flash chromatography (EtOAc/Hexanes: 4:6) to provide 1.18 g (50% yield) of compound 2. $^1H$ NMR (400 MHz, Acetone-$d_6$): 0.88 (s, 18-$CH_3$), 1.27-2.38 (unassigned CH and $CH_2$), 2.73 (t, J=7.1 Hz, C$\underline{H}_2$CH$_2$OH), 2.82 (m, 6-$CH_2$), 3.62 (br t, OH), 3.71 (m, CH$_2$C$\underline{H}_2$OH), 3.87 (m, 2×$CH_2$ of dioxolane), 6.92 (s, 4-CH), 6.97 (d, J=8.0 Hz, 2-CH), 7.19 (d, J=7.9 Hz, 1-CH); $^{13}C$ NMR (100.6 Hz, Acetone $d_6$): 13.9, 22.1, 25.9, 27.0, 28.4, 28.6, 30.7, 33.9, 39.0, 39.1, 44.1, 45.9, 49.3, 63.1, 64.3, 64.9, 118.8, 125.1, 126.2, 129.4, 136.1, 136.5, 137.7. LRMS for $C_{22}H_{31}O_3$ $[M+H]^+$ 343.4 m/z.

Synthesis of 3-[2-(benzyloxy)ethyl]estra-1(10),2,4-trien-17-one (3)

To a solution of compound 2 (1.1 g, 3.5 mmol) in anhydrous DMF (50 mL), was added NaH (60% in oil) (168 mg, 4.2 mmol) at 0° C. under an argon atmosphere. The solution was stirred over a period of 1 h at 0° C. and benzyl bromide (898 mg, 627 µL, 5.3 mmol) was added in one portion. The solution was subsequently allowed to warm to room temperature and was subsequently stirred overnight, poured into water (300 mL) and extracted with EtOAc (3×75 mL). The organic layers were combined, washed with brine, dried with $MgSO_4$ and evaporated under reduced pressure. The crude compound was then treated with an aqueous solution of HCl (10%) in acetone (1:1) (50 mL) and stirred over a period of 5 h at room temperature. The resulting solution was neutralized using an aqueous $NaHCO_3$ (10%) solution and extracted with EtOAc (2×75 mL). The organic layers were combined, washed with brine, dried with $MgSO_4$ and evaporated under reduced pressure. The crude compound was purified by flash chromatography (EtOAc/Hexanes: 1:9) to provide 1.04 g (73% yield, 2 steps) of compound 3. $^1H$ NMR (400 MHz, $CDCl_3$): 0.91 (s, 18-$CH_3$), 1.20-2.40 (unassigned CH and $CH_2$), 2.51 (dd, $J_1$=8.5 Hz, $J_2$=18.9 Hz, 16β-CH), 2.88 (m, 6-$CH_2$ and C$\underline{H}_2$CH$_2$O), 3.68 (t, J=7.3 Hz, CH$_2$C$\underline{H}_2$O), 4.54 (s, OC$\underline{H}_2$Ph), 6.97 (s, 4-CH), 7.02 (d, J=8.0 Hz, 2-CH), 7.22 (d, J=7.9 Hz, 1-CH), 7.23-7.38 (m, 5H, OCH$_2$Ph); $^{13}C$ NMR (100.6 Hz, $CDCl_3$): 13.8, 21.6, 25.7, 26.5, 29.4, 31.6, 35.8, 35.9, 38.2, 44.3, 48.0, 50.5, 71.3, 72.9, 125.3, 126.3, 127.5, 127.6, 128.3, 129.6, 136.3 (2×), 136.4 (2×), 137.6, 138.4, 232.5. LRMS for $C_{27}H_{33}O_2$ $[M+H]^+$ 389.4 m/z.

Synthesis of 3-{(E)-[(16E)-3-[2-(benzyloxy)ethyl]-17-oxoestra-1(10),2,4-trien-16-ylidene]methyl}benzamide (4)

To a solution of compound 3 (400 mg, 1.03 mmol) in EtOH (25 mL) was added 3-formyl-benzamide (344 mg, 2.05 mmol) and an aqueous KOH (10%) solution (4.5 mL). The resulting reaction mixture was heated at reflux over a period of 30 min. The resulting solution was diluted with water (200 mL), neutralized with aqueous HCl (10%), and extracted with EtOAc (3×50 mL). The organic layers were combined, washed with brine, dried with $MgSO_4$ and evaporated under reduced pressure to provide 400 mg (76% yield) of compound 4. $^1H$ NMR (400 MHz, $CDCl_3$): 1.00 (s, 18-$CH_3$), 1.25-2.65 (unassigned CH and $CH_2$), 2.89 (t, J=7.3 Hz, C$\underline{H}_2$CH$_2$O), 2.93 (m, 6-$CH_2$), 3.00 (m, 15-H) 3.69 (t, J=7.3 Hz, CH$_2$C$\underline{H}_2$O), 4.54 (s, OC$\underline{H}_2$Ph), 5.82 and 6.17 (2 broad s, $NH_2$), 6.99 (s, 4-CH), 7.03 (d, J=8.0 Hz, 2-CH), 7.22-7.38 (m, 5H, 4H of OCH$_2$Ph and 1H of 1-CH), 7.49 (d, 1H, J=3.7 Hz, 1'-CH), 7.52 (t, J=7.7 Hz, 1H of OCH$_2$Ph), 7.71 (d, J=7.8 Hz, 6"-CH), 7.77 (d, J=7.8 Hz, 4"-CH), 8.04 (s, 2"-CH); $^{13}C$ NMR (100.6 Hz, $CDCl_3$): 14.5, 25.7, 26.9, 29.1, 29.3, 31.7, 35.8, 37.8, 44.3, 47.9, 48.6, 71.2, 72.9, 125.3, 126.4, 126.9, 127.5, 127.6, 127.7, 128.4 (2×), 129.0, 129.2, 129.6, 131.9, 133.5, 133.8, 136.2, 136.3, 136.4, 137.4, 137.5, 138.4, 168.9, 209.4. LRMS for $C_{35}H_{37}NO_3Na$ $[M+Na]^+$ 542.4 m/z.

Synthesis of 3-{[(17β)-17-hydroxy-3-(2-hydroxyethyl)estra-1(10),2,4-trien-16-yl]methyl}benzamide (IV)

To a solution of compound 4 (390 mg, 0.69 mmol) in a mixture of MeOH and DCM (4:1) was added $NaBH_4$ (85 mg, 2.23 mmol). The solution was stirred at room temperature over a period of 1 h. The resulting solution was concentrated under vacuo, diluted with DCM (30 mL), washed with water, dried with $MgSO_4$ and evaporated under reduced pressure to provide 375 mg of the crude 17β-alcohol. The crude 17β-alcohol was subsequently dissolved in EtOH (100 mL) under an argon atmosphere followed by the addition of Pd on charcoal (10%) (80 mg). The reaction vessel was flushed three times with $H_2$ and stirred over a period of 36 h, then filtered on celite and evaporated under reduced pressure. The crude compound was purified by flash chromatography (EtOAc/Hexanes: 4:6) to provide 255 mg (84% yield, 2 steps) of compound IV. $^1$H NMR (400 MHz, $CD_3OD$): 0.90 (s, 18-$CH_3$), 1.10-2.55 (unassigned CH and $CH_2$), 2.74 (t, J=7.2 Hz, $CH_2CH_2OH$), 2.79 (m, 6-$CH_2$), 3.17 (dd, $J_1$=2.7 Hz, $J_2$=12.5 Hz, 1H), 3.71 (t, J=7.2 Hz, $CH_2CH_2OH$), 3.83 (d, J=9.4 Hz, 17α-H), 6.89 (s, 1H, 4-CH), 6.96 (d, J=8.0 Hz, 2-CH), 7.19 (d, J=8.0 Hz, 1-CH), 7.35-7.45 (m, 5"-CH and 6"-CH), 7.70 (d, J=7.0 Hz, 4"-CH), 7.75 (s, 2"-CH); $^{13}$C NMR (100.6 Hz, $CD_3OD$): 13.3, 27.4, 28.6, 30.5, 33.0, 38.9, 39.0, 39.7, 39.8, 43.3, 45.4, 50.0, 64.4, 83.0, 126.0, 126.2, 127.2, 129.1, 129.2, 129.4, 130.4, 133.5, 134.8, 137.2, 137.5, 139.3, 144.3, 172.0. LRMS for $C_{28}H_{36}NO_3$ $[M+H]^+$ 434.4.

Synthesis of 3-{[(16β,17β)-3-(2-bromoethyl)-17-hydroxyestra-1(10),2,4-trien-16-yl]methyl}benzamide (V)

To a solution of compound IV (175 mg, 0.40 mmol) in DCM (15 mL) was added at 0° C. triphenylphosphine (200 mg, 0.76 mmol) and carbon tetrabromide (252 mg, 0.76 mmol). The solution was stirred at 0° C. over a period of 40 min followed by a further addition of triphenylphosphine (100 mg, 0.38 mmol) and carbon tetrabromide (126 mg, 0.38 mmol). The solution was stirred for an addition hour while at 0° C. The resulting mixture was poured into water (150 mL), extracted with DCM (50 mL), dried with $MgSO_4$ and evaporated under reduced pressure. The crude compound was purified by flash chromatography (DCM/MeOH: 97:3) to provide 168 mg (84% yield) of compound V. $^1$H NMR (400 MHz, $CD_3OD$): 0.91 (s, 18-$CH_3$), 1.10-2.55 (unassigned CH and $CH_2$), 2.82 (m, 6-$CH_2$), 3.06 (t, J=7.3 Hz, C$\underline{H}_2CH_2Br$), 3.17 (dd, $J_1$=2.7 Hz, $J_2$=12.5 Hz, 1H), 3.55 (t, J=7.2 Hz, $CH_2C\underline{H}_2Br$), 3.84 (d, J=9.4 Hz, 17α-H), 6.91 (s, 4-CH), 6.97 (d, J=8.0 Hz, 2-CH), 7.22 (d, J=8.0 Hz, 1-CH), 7.36-7.44 (m, 5"-CH and 6"-CH), 7.69 (d, J=7.0 Hz 4"-CH), 7.75 (s, 2"-CH); $^{13}$C NMR (100.6 Hz, $CD_3OD$): 13.3, 27.3, 28.5, 30.5, 33.0, 34.0, 38.8, 38.9, 39.6, 40.1, 43.3, 45.4, 45.7, 50.0, 83.0, 126.0, 126.4, 127.0, 129.1, 129.4, 130.1, 133.5, 134.8, 137.4, 137.8, 140.0, 144.3, 175.1. LRMS for $C_{28}H_{34}NO_2$ $[M+H-Br]^+$ 496.0 and 498.1; HPLC (MeOH/$H_2O$: 70:30): 98.5% purity.

Synthesis of 3-{[(16β,17β)-3-(2-chloroethyl)-17-hydroxyestra-1(10),2,4-trien-16-yl]methyl}benzamide (9)

To a solution of compound 7 (20 mg, 0.05 mmol) in DCM (1.0 mL) was added chlorodimethyl(phenylthio)-chloride methanaminium (CPMA) (45 mg, 0.19 mmol) at 0° C. under an argon atmosphere. The solution was then allowed to return to room temperature and stirred for an additional 3 h. The crude compound was directly purified by flash chromatography (DCM/MeOH: 97:3) to provide 12 mg (57%) of compound 9. $^1$H NMR (MeOD): 0.91 (s, 3H, 18-$CH_3$), 1.14-2.48 (residual CH and $CH_2$), 2.82 (m, 2H, 6-$CH_2$), 2.96 (t, 2H, J=7.3 Hz, 3-$CH_2CH_2Cl$), 3.19 (m, 1H), 3.69 (t, 2H, J=7.40 Hz, 3-$CH_2CH_2Cl$), 3.84 (d, 1H, J=9.4 Hz, 17α-H), 6.92 (s, 1H, 4-CHar), 6.98 (d, 1H, CHar, J=8.0 Hz), 7.22 (d, 1H, CHar, J=8.0 Hz), 7.36-7.44 (m, 2H, CHar-benzamide), 7.69 (d, 1H, CHar-benzamide, J=7.0 Hz), 7.75 (s, 1H, CHar-benzamide); $^{13}$C NMR (MeOD): 13.3, 27.3, 28.6, 30.5, 33.0, 38.8, 39.0, 39.6, 39.8, 43.4, 45.4, 45.7, 46.0, 50.0, 83.0, 126.0, 126.4, 127.1, 129.1, 129.4, 130.3, 133.6, 134.8, 136.7, 137.8, 140.0, 144.4, 172.7.

Synthesis of 3-{[(16β,17β)-17-hydroxy-3-(2-iodoethyl)estra-1(10),2,4-trien-16-yl]methyl}benzamide (10)

To a solution of compound 8 (35 mg, 0.07 mmol) in acetone (5 mL) was added sodium iodide (15 mg, 0.1 mmol). The solution was stirred at room temperature under an argon atmosphere over a period of 24 h followed by the addition of another portion of sodium iodide (52 mg, mmol). The solution was the stirred for an additional 24 h. The reaction mixture was subsequently poured into water (100 mL), and extracted three times with EtOAc (3×25 mL). The combined organic layer were washed with brine, dried with $MgSO_4$ and concentrated. The crude compound was purified by flash chromatography (DCM/MeOH: 95:5) to provide 18 mg (47%) of compound 10. $^1$H NMR (MeOD): 0.91 (s, 3H, 18-$CH_3$), 1.14-2.03 (residual CH and $CH_2$), 2.81 (m, 2H, 6-$CH_2$), 3.07 (t, 2H, J=7.7 Hz, 3-$CH_2CH_2I$), 3.19 (m, 1H), 3.35 under the MeOD peak (t, 2H, 3-$CH_2CH_2I$), 3.84 (d, 1H, J=9.4 Hz, 17α-H), 6.92 (s, 1H, 4-CHar), 6.95 (d, 1H, CHar, J=8.0 Hz), 7.21 (d, 1H, CHar, J=8.0 Hz), 7.37-7.42 (m, 2H, CHar-benzamide), 7.69 (d, 1H, CHar-benzamide, J=7.0 Hz), 7.76 (s, 1H, CHar-benzamide); $^{13}$C NMR (MeOD): 4.8, 11.9, 25.9, 27.2, 29.1, 31.6, 37.4, 37.6, 38.2, 39.7, 42.0, 44.0, 44.3, 48.6, 81.6, 124.6, 125.1, 125.2, 127.7, 128.0, 128.4, 132.1, 133.4, 136.5, 137.8, 138.6, 143.0, 171.3.

Synthesis of 3-{[(16β,17β)-3-ethenyl-17-hydroxyestra-1(10),2,4-trien-16-yl]methyl}benzamide (11)

To a solution of compound 10 (20 mg) in anhydrous dioxane (1.5 mL) was added TBAF (1.0 M in THF, 37 mg) at room temperature under an argon atmosphere. The solution was then stirred at room temperature over a period of 3 h. The resulting solution was then poured into water (100 mL) and extracted three times with EtOAc (3×25 mL). The combined organic layers were washed with brine, dried with $MgSO_4$ and concentrated. The crude compound was purified by flash chromatography (DCM/MeOH: 95:5) to provide 8 mg (53%) of compound 11. $^1$H NMR ($CDCl_3$): 0.88 (s, 3H, 18-$CH_3$), 1.11-2.49 (residual CH and $CH_2$), 2.83 (m, 2H, 6-$CH_2$), 3.18 (m, 1H), 3.87 (d, 1H, J=9.5 Hz, 17α-H), 5.18 (d, 1H, $CH_2$=CH—, J=10.9 Hz), 5.69 (d, 1H, $CH_2$=CH—, J=17.5 Hz), (5.7 and 6.2, 2 br s, 2H, $CONH_2$), 6.66 (dd, 1H, $CH_2$=CH, $J_1$=Hz, $J_2$ Hz), 7.11 (s, 1H, CHar), 7.20 (d, 1H, CHar, J=8.2 Hz), 7.26 (d, under solvent peak, 1H, CHar), 7.38 (m, 2H, CHar), 7.40 (d, 1H, J=7.2 Hz, CHar), 7.71 (s, 1H, CHar); $^{13}$C NMR (MeOD): 13.3, 27.3, 28.6, 30.5, 33.0, 38.9, 39.0, 39.6, 43.4, 45.4, 45.9, 50.0, 83.0, 112.8, 124.4, 126.0, 126.4, 127.8, 129.1, 129.4, 133.5, 134.8, 136.2, 137.8, 138.2, 141.4, 144.4, 170.0.

Synthesis of 3-{[(16β,17β)-17-hydroxy-3-(prop-2-en-1-yloxy)estra-1(10),2,4-trien-16-yl]methyl}benzamide (13)

To a solution of compound 12 (150 mg, 0.37 mmol) in acetone (3 mL) was added NaOH (50 mg, 1.25 mmol) and allyl bromide (40 µL, 0.46 mmol). The resulting solution was then stirred at 60° C. over a period of 5 h. The reaction mixture was then diluted with EtOAc and washed with a saturated solution of ammonium chloride. The organic layer was washed with brine, dried with $MgSO_4$ and concentrated to provide 165 mg (99%) of compound 13. Crude compound 13 was found to be sufficiently pure to be used in the next step without further purification. $^1$H NMR (Acetone-$d_6$): 0.87 (s, 3H, 18-CH3), 1.07-2.47 (residual CH and CH$_2$), 2.79 (m, 2H, 6-CH$_2$), 3.15 (m, 1H), 3.83 (d, 1H, J=10.2 Hz, 17α-H), 4.49 (d, 2H, OCH$_2$CH=CH$_2$, J=5.3 Hz), 5.26 (d, 1H, J=10.4 Hz, CH$_2$=CH), 5.39 (d, 1H, J=17.3 Hz, CH$_2$=CH), 6.04 (m, 1H, CH$_2$=CH), 6.12 and 6.33 (2 br s, CONH$_2$), 6.62 (s, 1H, CHar), 6.71 (dd, 1H, J$_1$=2.4 Hz, J$_2$=8.6 Hz), 7.18 (d, 1H, CHar, J=8.6 Hz), 7.33 (m, 2H, CHar), 7.60 (d, 1H, CHar, J=7.3 Hz), 7.71 (s, 1H, CHar).

Synthesis of 3-{[(16β,17β)-17-hydroxy-3-(2-hydroxyethoxy)estra-1(10),2,4-trien-16]-yl}methyl benzamide (14)

Sodium periodate (108 mg, 0.50 mmol) was added to water (0.5 mL) and stirred at 0° C. over a period of 5 min, followed by subsequent addition of RuCl$_3$—H$_2$O (4 mg, 0.02 mmol), EtOAc (1 mL) and acetonitrile (1 mL). Compound 13 (150 mg, 0.33 mmol) was then added to the solution and the reaction mixture stirred for about 2 minutes. The reaction mixture was then quenched by the addition of a saturated aqueous solution of Na$_2$S$_2$O$_3$ (2 mL). The phases were separated and the aqueous layer extracted with EtOAc (3×3 mL). The combined organic layers were dried with Na$_2$SO$_4$ and concentrated. The residue was then dissolved in a mixture of THF (1 mL) and water (1 mL), followed by the addition of NaBH$_4$ (13 mg, 0.34 mmol). The reaction mixture was stirred at room temperature over a period of 20 min followed by the subsequent addition of water (10 mL). The reaction mixture was then extracted with DCM (3×15 mL), the combined organic layers washed with a saturated bicarbonate solution, dried with Na$_2$SO$_4$, and concentrated. The residue was dissolved in THF (1 mL) and water (1 mL) at 0° C. followed by the addition of sodium periodate (144 mg, 0.67 mmol) in small portions. The solution was subsequently stirred over a period of 20 min at room temperature. Ethylene glycol (50 µL) was then added and the reaction mixture diluted with water (3 mL). The reaction mixture was extracted with EtOAc (3×5 mL) and the combined organic layers dried with Na$_2$SO$_4$ and concentrated. The residue was redissolved in a mixture of THF (1 mL) and water (1 mL) followed by the addition NaBH$_4$ (13 mg, 0.34 mmol). The resulting reaction mixture was stirred at room temperature over a period of 1 h followed by the addition of water (1 mL). The reaction mixture was extracted with DCM (3×5 mL) and the combined organic layers washed with a saturated bicarbonate solution, dried with Na$_2$SO$_4$, and concentrated. The crude compound was purified by flash chromatography (EtOAc/Hexanes: 9:1) to provide 25 mg (15%) of compound 14. $^1$H NMR (MeOD): 0.91 (s, 3H, 18-CH3), 0.96-2.48 (residual CH and CH$_2$), 2.79 (m, 2H, 6-CH$_2$), 3.18 (m, 1H), 3.84 (m, 3H, OCH$_2$CH$_2$OH and 17α-H), 3.99 (m, 2H, OCH$_2$CH$_2$OH), 6.69 (d, 1H, 4-CHar, J=2.8 Hz), 6.72 (d, 1H, CHar, J=2.7 Hz), 7.17 (d, 1H, CHar, J=8.0 Hz), 7.38-7.42 (m, 2H, CHar-benzamide), 7.69 (d, 1H, CHar-benzamide, J=7.4 Hz), 7.76 (s, 1H, CHar-benzamide).

Synthesis of 3-{[(16β,17β)-3-(2-bromoethoxy)-17-hydroxyestra-1(10),2,4-trien-16-yl]methyl}benzamide (15)

To a solution of compound 14 (20 mg, 0.46 mmol) in a mixture of anhydrous DCM (2 mL) and anhydrous THF (1 mL) was added at 0° C. triphenylphosphine (23 mg, 0.87 mmol) and carbon tetrabromide (29 mg, 0.87 mmol). The reaction mixture was stirred at 0° C. over a period of 40 min followed by a further addition of triphenylphosphine (20 mg, 0.46 mmol) and carbon tetrabromide (23 mg, 0.87 mmol). The reaction mixture was stirred at 0° C. for an additional 40 min followed by the further addition of triphenylphosphine (20 mg, 0.46 mmol) and carbon tetrabromide (23 mg, 0.87 mmol). The reaction mixture was then stirred for an additional hour at 0° C. The reaction mixture was subsequently poured into water (100 mL) and extracted with DCM (2×25 mL). The combined organic layers were dried with MgSO$_4$ and concentrated. The crude compound was purified by flash chromatography (DCM/ether/MeOH: 75:20:5) to provide 12 mg (52%) of compound 15. $^1$H NMR (MeOD): 0.91 (s, 3H, 18-CH$_3$), 1.13-2.48 (residual CH and CH$_2$), 2.78 (m, 2H, 6-CH$_2$), 3.17 (m, 1H), 3.67 (t, 2H, J=7.2 Hz, 3-OCH$_2$CH$_2$Br, J=Hz), 3.84 (d, 1H, J=9.4 Hz, 17α-H), 4.25 (t, 2H, 3-OCH$_2$CH$_2$Br, J=5.7 Hz), 6.62 (s, 1H, 4-CHar), 6.69 (d, 1H, CHar, J=8.7 Hz), 7.19 (d, 1H, CHar, J=8.6 Hz), 7.38-7.42 (m, 2H, CHar-benzamide), 7.69 (d, 1H, CHar-benzamide, J=7.4 Hz), 7.76 (s, 1H, CHar-benzamide); $^{13}$C NMR (CDCl$_3$): 13.3, 27.5, 28.6, 30.7 (2×), 33.0, 38.8, 39.0, 39.8, 43.3, 45.4 (2×), 49.9, 69.2, 83.0, 113.3, 115.6, 126.0, 127.4, 129.1, 129.4, 133.6, 134.5, 134.8, 139.1, 144.4, 157.5, 172.4.

Synthesis of (8R,9S,13S,14S)-13-methyl-3-[(E)-2-phenylethenyl]-6,7,8,9,11,12,13,14,15,16-decahydrospiro[cyclopenta[α]phenanthrene-17,2'-[1,3]dioxolane] (16)

To a solution of compound 1 (350 mg, 1.07 mmol) in DCM (75 mL) under an argon atmosphere was added styrene (257 µL, 233 mg, 2.24 mmol). The solution was purged by argon bubbling over a period of 5 min followed by the addition of Grubb (II) catalyst (48 mg, 0.056 mmol). The reaction mixture was subsequently refluxed over a period of 24 h under an argon atmosphere. The reaction mixture was then poured into water, extracted twice with DCM (2×50 mL), filtered using a phase separator device (Biotage) and concentrated. The crude compound was purified by flash chromatography (EtOAc/Hexanes: 95:5) to provide 50 mg (11%) of compound 16. $^1$H NMR (CDCl$_3$): 0.89 (s, 3H, 18-CH$_3$), 1.34-2.39 (residual CH and CH$_2$), 2.90 (m, 2H, 6-CH$_2$), 3.89 (m, 4H, 2×CH$_2$ of dioxolane), 7.19 (s, 2H), 7.23-7.38 (m, 6H, CHar and CH=CH), 7.58 (d, 2H, CHar, J=8.2 Hz).

Synthesis of 3-{(E)-[(16E)-17-oxo-3-[(E)-2-phenylethenyl]estra-1(10),2,4-trien-16-ylidene]methyl}benzamide (17)

To a solution of compound 16 (42 mg, 0.105 mmol) in methanol (3 mL) was added an aqueous solution of HCl 10% (1 mL). The reaction mixture was then stirred at room temperature over a period of 2 h. The reaction mixture was then poured into a sodium bicarbonate solution (50 mL) and extracted twice with EtOAc (2×20 mL). The combined organic layers were washed with brine, dried with MgSO$_4$ and concentrated to provide 40 mg of deprotected ketone product. $^1$H NMR (CDCl$_3$): 0.92 (s, 3H, 18-CH$_3$), 1.25-2.53 (residual CH and CH$_2$), 2.95 (m, 2H, 6-CH$_2$), 7.08 (s, 2H), 7.23-7.38 (m, 6H, CHar+CH=CH), 7.51 (d, 2H, J=8.4 Hz). The crude ketone compound (38 mg) was then dissolved in ethanol (5 mL) followed by the addition of 3-formylbenzamide (34 mg, 0.227 mmol) and an aqueous KOH solution (10%, 0.6 mL). The reaction mixture was then heated at reflux over a period of 60 min. The resulting reaction mixture was then diluted with water (50 mL), neutralized with an aqueous HCl solution (10%), and extracted with EtOAc (3×20 mL). The combined organic layers were washed with brine, dried with MgSO$_4$ and concentrated to provide 40 mg (72%) of compound 17. $^1$H NMR (CDCl$_3$): 1.03 (s, 3H, CH$_3$-18), 1.25-2.67 (residual CH and CH$_2$), 2.99 (m, 2H, 6-CH$_2$), 5.7 and 6.1 (br s, 2H, CONH$_2$), 7.08 (s, 1H), 7.23-7.52 (m, 8H, CHar and PhCH=CHPh), 7.71 (d, 1H, CHar, J=Hz), 7.77 (d, 1H, CHar, J=Hz), 8.04 (s, 1H, CHar).

Synthesis of 3-{(E)-[(16E,17β)-17-hydroxy-3-[(E)-2-phenylethenyl]estra-1(10),2,4-trien-16-ylidene]methyl}benzamide (18)

To a solution of compound 17 (40 mg, 0.082 mmol) in MeOH (3 mL) was added NaBH$_4$ (10 mg, 0.26 mmol). The reaction mixture was then stirred at room temperature over a period of 1 h and subsequently poured into water and extracted twice with EtOAc (20 mL). The combined organic layers were washed with brine, dried with MgSO$_4$ and concentrated. The crude compound was purified by flash chromatography (EtOAc/Hexanes: 95:5) to provide 24 mg (60%) of compound 18. $^1$H NMR (CDCl$_3$): 0.76 (s, 3H, 18-CH$_3$), 0.79-2.46 (residual CH and CH$_2$), 2.80 (m, 2H, 6-CH$_2$), 4.18 (d, 1H, 17α-H, J=9.0 Hz), 5.7 and 6.1 (br s, 2H, CONH$_2$), 6.60 (s, 1H, C=CH-benzamide), 7.08 (s, 2H, CHar), 7.23-7.62 (m, 8H, CHar and PhCH=CHPh), 7.71 (d, 1H, CHar, J=7.8 Hz), 7.77 (d, 1H, CHar, J=7.8 Hz), 8.04 (s, 1H).

Synthesis of 3-{[(16β,17β)-17-hydroxy-3-(2-phenylethyl)estra-1(10),2,4-trien-16-yl]methyl}benzamide (19)

To a solution of compound 18 (20 mg, 0.041 mmol) in a mixture of EtOH/DCM (1:1) (3 mL) at room temperature and under an argon atmosphere was added palladium on charcoal (10%) (5 mg). The reaction vessel was then flushed three times with hydrogen and stirred over a period of 24 h. The resulting reaction mixture was filtered on celite and then concentrated. The crude compound was purified by flash chromatography (EtOAc/Hexanes: 7:3) to provide 6 mg (32%) of compound 19. $^1$H NMR (CDCl$_3$): 0.88 (s, 3H, 18-CH$_3$), 0.91-2.50 (residual CH and CH$_2$), 2.77-2.93 (m, 6H, 6-CH$_2$ and 2×CH$_2$Ph), 3.17 (m, 1H), 3.87 (m, 1H), 5.7 and 6.1 (br s, 2H, CONH$_2$), 6.94 (s, 1H), 7.19 (dd, 1H, J$_1$=7.9 Hz, J$_2$=1.3 Hz), 7.22-7.53 (m, 7H, CHar), 7.60 (d, 1H, J=5.9 Hz), 7.72 (s, 1H); $^{13}$C NMR (MeOD): 13.3, 27.4, 28.7, 30.5, 33.0, 38.7, 38.8, 39.0, 39.2, 39.7, 43.4, 45.4, 45.7, 50.0, 83.0, 126.0, 126.1, 126.8 (2×), 129.1, 129.2 (2×), 129.4, 129.5 (2×), 129.9, 133.5, 134.8, 137.4, 139.0, 140.1, 143.3, 144.4, 167.6.

Synthesis of (8R,9S,13S,14S)-3-[(1E)-3-(benzyloxy)prop-1-en-1-yl]-13-methyl-6,7,8,9,11,12,13,14,15,16-decahydrospiro[cyclopenta[a]phenanthrene-17,2'-[1,3]dioxolane] (20)

To a solution of compound 1 (1.5 g, 4.82 mmol) in DCM (400 mL) under an argon atmosphere was added [(prop-2-en-1-yloxy)methyl]benzenebenzyl prop-2-en-1-yl ether (1.3 g, 9.55 mmol). The reaction mixture was subsequently stirred over a period of 5 min followed by the addition of Grubb (II) catalyst (204 mg, 0.24 mmol). The resulting solution was then stirred at 60° C. while under an argon atmosphere over a period of 48 h. The reaction mixture was then concentrated and purified by flash chromatography using EtOAc/Hexanes (5:95) as eluant to provide 130 mg (6%) of compound 20. $^1$H NMR (CDCl$_3$): 0.91 (s, 3H, 18-CH$_3$), 1.25-2.42 (residual CH and CH$_2$), 2.78 (m, 2H, 6-CH$_2$), 3.74-4.06 (m, 4H, 2×CH$_2$ of dioxolane), 4.18 (d, 2H, J=6.1 Hz, CH$_2$OCH$_2$Ph), 4.56 (s, 2H, CH$_2$OCH$_2$Ph), 6.24-6.31 (m, 1H, CH=CHCH$_2$O), 6.57 (d, 1H, J=16.2 Hz, CH=CHCH$_2$O), 7.11 (s, 1H, CH ar), 7.18 (d, 1H, J=8.2 Hz, CHar), 7.25-7.39 (m, 6H, CHar).

Synthesis of 3-[(1E)-3-(benzyloxy)prop-1-en-1-yl]estra-1(10),2,4-trien-17-one (21)

To a solution of compound 20 (120 mg, 0.28 mmol) in acetone (3 mL) was added an aqueous solution of HCl (10%, 3 mL). The reaction mixture was then stirred at room temperature over a period of 6 h. The reaction mixture was then diluted with water (60 mL), neutralized with bicarbonate solution and extracted three times with EtOAc (3×20 mL). The combined organic layers washed with brine, dried with MgSO$_4$, and concentrated. The crude compound was purified by flash chromatography (EtOAc/Hexanes: 5:95) to provide 80 mg (69%) of compound 21. $^1$H NMR (CDCl$_3$): 0.91 (s, 3H, 18-CH$_3$), 1.22-2.32 (residual CH and CH$_2$), 2.52 (dd, 1H, J$_1$=19.1 Hz, J$_2$=8.9 Hz, 16β-CH), 2.92 (m, 2H, CH$_2$-6), 4.19 (d, 2H, J=6.1 Hz, OCH$_2$CH=CH), 4.57 (s, 2H, OCH$_2$Ph), 6.26-6.33 (m, 1H, CH=CHCH$_2$O), 6.58 (d, 1H, J=16.0 Hz, CH=CHCH$_2$O), 7.14 (s, 1H, CH ar), 7.19 (d, 1H, J=8.2 Hz, CHar), 7.25-7.39 (m, 6H, CHar).

Synthesis of 3-{(E)-[(16E)-3-[(1E)-3-(benzyloxy)prop-1-en-1-yl]-17-oxoestra-1(10),2,4-trien-16-ylidene]methyl}benzamide (22)

To a solution of compound 21 (80 mg) in EtOH (10 mL) was added 3-formyl-benzamide (62 mg) and an aqueous KOH solution (10%, 1.7 mL). The reaction mixture was then heated at reflux over a period of 30 min. The resulting reaction mixture was then diluted with water (100 mL), neutralized with an aqueous HCl solution (10%), and extracted with EtOAc (3×25 mL). The combined organic layers were washed with brine, dried with MgSO$_4$ and concentrated. The crude compound was purified by flash chromatography (EtOAc/Hexanes: 1:1) to provide 65 mg (61%) of compound 22. $^1$H NMR (MeOD): 1.05 (s, 3H, 18-CH$_3$), 0.89-3.24 (residual CH and CH$_2$), 4.20 (d, 2H, J=6.1 Hz, OCH$_2$CH=CH), 4.58 (s, 2H, OCH$_2$Ph), 6.26-6.33 (m, 1H, CH=CHCH$_2$O), 6.58 (d, 1H, J=16.0 Hz, CH=CHCH$_2$O), 7.16 (s, 1H, CH ar), 7.21 (d, 1H, J=8.1 Hz, CHar), 7.25-7.39 (m, 6H, CHar) 7.49 (s, 1H, CHar-benzamide), 7.59 (t, 2H, OCH$_2$Ph, J=7.7 Hz), 7.81 (d, 1H, CHar of benzamide, J=7.7 Hz), 7.91 (d, 1H, CHar-benzamide, J=8.2 Hz), 8.14 (s, H, CHar-benzamide).

Synthesis of 3-{(E)-[(16E,17β)-3-[(1E)-3-(benzyloxy)prop-1-en-1-yl]-17-hydroxyestra-1(10),2,4-trien-16-ylidene]methyl}benzamide (23)

To a solution of compound 22 (55 mg, 0.11 mmol) in a mixture of MeOH and DCM (4:1) was added NaBH$_4$ (12 mg, 0.32 mmol). The reaction mixture was stirred at room temperature over a period of 2 h and concentrated. The residue was diluted with DCM (15 mL) and washed with water. The organic layer was then dried with MgSO$_4$ and concentrated to provide 50 mg (91%) of compound 23 (without further purification). $^1$H NMR (MeOD): 0.77 (s, 3H, 18-CH$_3$), 0.80-2.84 (residual CH and CH$_2$), 2.89 (m, 2H, CH$_2$-6), 4.14 (br s, 1H, 17α-H), 4.19 (d, 2H, J=6.2 Hz, OCH$_2$CH=CH), 4.57 (s, 2H, OCH$_2$Ph), 6.27-6.34 (m, 1H, CH=CHCH$_2$O), 6.56 (m, 2H, CH=CHCH$_2$O and C=CHPhCONH$_2$), 7.13 (s, 1H, CH ar), 7.20 (d, 1H, J=8.1 Hz, CHar), 7.27-7.42 (m, 6H, CHar) 7.46 (t, 1H, J=7.7 Hz, CHar-benzamide), 7.60 (d, 1H, CHar of benzamide, J=7.7 Hz), 7.70 (d, 1H, CHar-benzamide, J=8.2 Hz), 7.94 (s, 1H, CHar-benzamide).

Synthesis of 3-{[(16β,17β)-17-hydroxy-3-(3-hydroxypropyl)estra-1(10),2,4-trien-16-yl]methyl}benzamide (24)

To a solution of compound 23 (45 mg, 0.086 mmol) in a mixture of EtOH/DCM (4:1) (5 mL) at room temperature and under an argon atmosphere was added palladium on charcoal (10%) (20 mg). The reaction vessel was then flushed three times with hydrogen and stirred over a period of 36 h. The resulting reaction mixture was filtered on celite and then concentrated. The crude compound was purified by flash chromatography (EtOAc) to provide 38 mg (99%) of compound 24. $^1$H NMR (MeOD): 0.91 (s, 3H, 18-CH$_3$), 1.22-2.48 (residual CH and CH$_2$), 2.59 (t, 2H, J=7.4 Hz, CH$_2$CH$_2$OH), 2.78 (m, 2H, 6-CH$_2$), 3.16 (m, 1H), 3.56 (t, 2H, J=6.6 Hz, CH$_2$CH$_2$OH), 3.84 (d, 1H, J=9.4 Hz, 17α-H), 6.87 (s, 1H, 4-CHar), 6.93 (d, 1H, CHar, J=8.0 Hz), 7.18 (d, 1H, CHar, J=8.0 Hz), 7.38-7.44 (m, 2H, CHar-benzamide), 7.41 (d, 1H, CHar-benzamide, J=7.0 Hz), 7.76 (s, 1H, CHar-benzamide); $^{13}$C NMR (MeOD): 13.3, 27.4, 28.7, 30.5, 32.6, 33.0, 35.5, 38.9, 39.0, 39.8, 43.4, 45.4, 45.7, 50.0, 62.3, 83.0, 126.0, 126.2, 126.7, 129.1, 129.4, 129.9, 133.5, 134.8, 137.5, 138.9, 140.3, 144.4, 172.7.

Synthesis of 3-{[(16β,17β)-3-(3-bromopropyl)-17-hydroxyestra-1(10),2,4-trien-16-yl]methyl}benzamide (25)

To a solution of compound 24 (28 mg, 0.063 mmol) in DCM (3 mL) at 0° C. was added triphenylphosphine (33 mg, 0.13 mmol) and carbon tetrabromide (42 mg, 0.13 mmol). The reaction mixture was then stirred at 0° C. over a period of 40 min followed by the addition of a second portion of triphenylphosphine (13 mg, 0.05 mmol) and carbon tetrabromide (17 mg, 0.05 mmol). The reaction mixture was then stirred for an additional hour while at 0° C. The reaction mixture was subsequently poured into water (50 mL) and extracted with DCM (2×25 mL). The combined organic layers were then dried with MgSO$_4$ and concentrated. The crude compound was purified by flash chromatography (DCM/MeOH: 97:3) to provide 8 mg (25%) of compound 25. $^1$H NMR (CDCl$_3$): 0.88 (s, 3H, 18-CH$_3$), 1.11-2.55 (residual CH and CH$_2$), 2.70 (t, 2H, J=7.2 Hz, CH$_2$CH$_2$Br), 2.78 (m, 2H, 6-CH$_2$), 3.16 (m, 1H), 3.41 (t, 2H, J=6.6 Hz, CH$_2$CH$_2$Br), 3.88 (m, 1H, 17α-H), 5.6 and 6.2 (2 br s, CONH$_2$), 6.91 (s, 1H, 4-CHar), 6.97 (d, 1H, CHar, J=8.0 Hz), 7.22 (d, 1H, CHar, J=8.0 Hz), 7.35-7.42 (m, 2H, CHar-benzamide), 7.40 (d, 1H, CHar-benzamide, J=7.0 Hz), 7.72 (s, 1H, CHar-benzamide); $^{13}$C NMR (MeOD): 13.3, 27.4, 28.6, 30.5, 33.0, 33.7, 34.4, 35.7, 38.8, 39.0, 39.7, 43.4, 45.4, 45.7, 50.0, 83.0, 126.0, 126.4, 126.8, 129.1, 129.4, 130.0, 133.8, 134.8, 137.7, 139.0, 139.3, 144.4, 172.7.

Synthesis of 3-ethenylestra-1(10),2,4-trien-17-one (26)

To a solution of compound 1 (180 mg, 0. mmol) in acetone (18 mL) was added an aqueous solution of HCl (10%, 2 mL). The reaction mixture was then stirred at room temperature over a period of 2 h. The solution was then poured into a sodium bicarbonate solution (50 mL) and extracted twice with EtOAc (2×20 mL). The combined organic layers were washed with brine, dried with MgSO$_4$ and concentrated to provide 140 mg of deprotected ketone product. $^1$H NMR (Acetone-d$_6$): 0.90 (s, 3H, 18-CH$_3$), 1.38-2.48 (residual CH and CH$_2$), 2.86 (m, 2H, 6-CH$_2$), 5.16 (d, 1H, PhCH=CH$_2$, J=10.9 Hz), 5.74 (d, 1H, PhCH=CH$_2$, J=Hz), 6.69 (m, 1H, PhCH=CH$_2$), 7.16 (s, 1H, CHar), 7.26 (m, 2H, CHar).

Synthesis of 3-{(E)-[(16E,17β)-3-ethenyl-17-hydroxyestra-1(10),2,4-trien-16-ylidene]methyl}benzamide (27)

To a solution of compound 26 (115 mg, 0.40 mmol) in EtOH (10 mL) was added 3-formyl-benzamide (125 mg, 0.84 mmol) and an aqueous KOH solution (10%, 1.7 mL). The reaction mixture was then heated at reflux over a period of 40 min. The resulting reaction mixture was then diluted with water (100 mL), neutralized with an aqueous HCl solution (10%), and extracted with EtOAc (3×25 mL). The combined organic layers were washed with brine, dried with MgSO$_4$ and concentrated. The crude compound was purified by flash chromatography (EtOAc/Hexanes: 7:3) to provide 80 mg (47%) of compound 27. $^1$H NMR (CDCl$_3$): 0.90 (s, 3H, 18-CH$_3$), 1.28-2.65 (residual CH and CH$_2$), 2.98 (m, 3H, 6-CH$_2$ and 15-CH), 5.20 (d, 1H, PhCH=CH$_2$, J=10.9 Hz), 5.72 (d, 1H, PhCH=CH$_2$, J=17.5 Hz), 5.9 and 6.2 (2 br s, CONH$_2$), 6.67 (m, 1H, PhCH=CH$_2$), 7.16 (s, CHar), 7.24 (m, 2H, CHar), 7.49 (s, 1H, CHar), 7.51 (tapp, 1H, CHar, J=7.7 Hz), 7.71 (d, 1H, CHar, J=7.8 Hz), 7.77 (d, 1H, CHar, J=7.8 Hz), 7.79 (s, 1H).

Synthesis of 3-{(E)-[(16E,17β)-3-ethenyl-17-hydroxyestra-1(10),2,4-trien-16-ylidene]methyl}benzamide (28)

To a solution of compound 27 (80 mg, 0.19 mmol) in a mixture of MeOH and DCM (9:1) was added NaBH$_4$ (22 mg, 0.58 mmol). The reaction mixture was stirred at room temperature over a period of 2 h and concentrated. The residue was diluted with DCM (25 mL) and washed with water. The organic layer was then dried with MgSO$_4$ and concentrated. The crude compound was purified by flash chromatography (DCM/MeOH: 95:5) to provide 74 mg (92%) of compound 27. $^1$H NMR (MeOD): 0.74 (s, 3H, 18-CH$_3$), 1.26-2.78 (residual CH and CH$_2$), 2.88 (m, 2H, 6-CH$_2$), 4.17 (br d, 1H, 17α-H, J=8.6 Hz), 5.17 (d, 1H, PhCH=CH$_2$, J=11.5 Hz), 5.71 (d, 1H, PhCH=CH$_2$, J=17.5 Hz), 5.7 and 6.2 (2 br s, CONH$_2$), 6.60 (s, 1H, 16-CH=Ph), 6.67 (m, 1H, PhCH=CH$_2$), 7.15 (s, CHar), 7.21 (d, 2H, CHar, J=8.1 Hz), 7.28 (d (under solvent peak), 1H, CHar, J=10.7 Hz), 7.43 (t, 1H, CHar, J=7.7 Hz), 7.56 (d, 1H, CHar, J=7.8 Hz), 7.61 (d, 1H, CHar, J=7.8 Hz), 7.87 (s, 1H).

Synthesis of 3-{[(16β,17β)-3-ethyl-17-hydroxyestra-1(10),2,4-trien-16-yl]methyl}benzamide (29)

To a solution of compound 28 (74 mg, 0.18 mmol) in EtOH (5 mL) at room temperature and under an argon atmosphere was added palladium on charcoal (10%) (15 mg). The reaction vessel was then flushed three times with hydrogen and stirred over a period of 48 h. The resulting reaction mixture was filtered on celite and then concentrated. The crude compound was purified by flash chromatography (EtOAc) to provide 40 mg (54%) of compound 29. $^1$H NMR (CDCl$_3$): 0.87 (s, 3H, 18-CH$_3$), 1.10-2.60 (residual CH and CH$_2$), 1.22 (t, 3H, CH$_3$CH$_2$Ph), 2.59 (q, 2H, J=7.4 Hz, CH$_3$CH$_2$Ph), 2.82 (m, 2H, 6-CH$_2$), 3.16 (m, 1H), 3.56 (t, 2H, J=6.6 Hz, CH$_2$CH$_2$OH), 3.88 (m, 1H, 17α-H), 5.7 and 6.2 (2 br s, CONH$_2$), 6.92 (s, 1H, 4-CHar), 6.99 (d, 1H, CHar, J=8.0 Hz), 7.22 (d, 1H, CHar, J=8.0 Hz), 7.37 (m, 2H, CHar-benzamide), 7.60 (d, 1H, CHar-benzamide, J=7.0 Hz), 7.72 (s, 1H, CHar-benzamide); $^{13}$C NMR (MeOD): 13.3, 16.3, 27.4, 28.7, 29.4, 30.5, 33.0, 38.9, 39.0, 39.7, 43.3, 45.4, 45.6, 50.0, 83.0, 126.0, 126.1, 126.2, 129.1, 129.2, 129.4, 133.5, 134.8, 137.4, 138.6, 142.4, 144.3, 172.7.

Synthesis of [(16β)-16-(3-carbamoylbenzyl)-17-oxoestra-1(10),2,4-trien-3-yl]acetic acid (30)

Dess Martin periodane (67 mg, 0.16 mmol) was added in one portion to a solution of alcohol 11 (50 mg, 0.12 mmol) in DCM (4 mL) at room temperature. The reaction mixture was stirred at room temperature over a period of 1 h and subsequently treated with a saturated aqueous solution of NaHSO$_3$ (0.25 mL) followed by treatment with NaHCO$_3$ (5 mL). The aqueous layer was then extracted with EtOAc (2×5 mL) and the combined organic layers dried with MgSO$_4$, filtered and concentrated. The crude product (49 mg) was subsequently taken up in t-BuOH (2.2 mL) and water (0.2 mL) followed by the addition of 2-methyl-2-butene (64 μL, 0.76 mmol), NaClO$_2$ (13 mg, 0.14 mmol) and KH$_2$PO$_4$ (19 mg, 0.14 mmol). The suspension was subsequently stirred over a period of 12 h at room temperature. The organic phase was then concentrated and the aqueous phase acidified with an aqueous solution of HCl (1N, 1 mL). The aqueous phase was then extracted with EtOAc (3×10 mL). The combined organic layers were then washed with brine, dried over MgSO$_4$ and concentrated. The crude product was purified by trituration from MeOH to provide 30 mg (59%) of compound 30. $^1$H NMR (Acetone-d6): 0.68 (s, 3H, 18-CH$_3$), 1.33-2.73 (residual CH and CH$_2$), 2.78 (m, 2H, 6-CH$_2$), 3.09 (m, 1H), 3.46 (s, 2H, CH$_2$COOH), 6.92 (s, 1H, CHar), 6.98 (d, 1H, CHar, J=8.2 Hz), 7.20 (d, 1H, CHar, J=8.0 Hz), 7.36 (m, 2H, CHar), 7.71 (m, 2H, CHar), 12.1 (br, s, COOH).

Synthesis of [(16β,17β)-16-(3-carbamoylbenzyl)-17-hydroxyestra-1(10),2,4-trien-3-yl]acetic acid (31)

To a solution of compound 30 (30 mg, 0.067 mmol) in MeOH (5 mL) was added NaBH$_4$ (7 mg, 0.18 mmol). The reaction mixture was then stirred at room temperature over a period of 2 h followed by the addition of two further portions (7 mg, 0.18 mg) of NaBH$_4$ sequentially added over a period of 2 h. The reaction mixture was then concentrated, diluted with DCM (25 mL) and washed with water. The organic layer was dried with MgSO$_4$ and concentrated. The crude product was purified by flash chromatography (DCM/MeOH: 9:1) to provide 15 mg (50%) of compound 31. $^1$H NMR (MeOD): 0.91 (s, 3H, 18-CH$_3$), 1.13-2.49 (residual CH and CH$_2$), 2.81 (m, 2H, 6-CH$_2$), 3.17 (m, 1H), 3.52 (s, 2H, CH$_2$COOH), 3.84 (d, 1H, 17α-H, J=9.4 Hz), 6.96 (s, 1H, CHar), 7.01 (d, 1H, CHar, J=8.0 Hz), 7.23 (d, 1H, CHar, J=8.0 Hz), 7.40 (m, 2H, CHar), 7.69 (d, 2H, CHar, J=6.0 Hz), 7.75 (s, 1H, CHar); $^{13}$C NMR (MeOD): 13.3, 27.3, 28.6, 30.5, 33.0, 38.8, 39.0, 39.6, 43.4, 45.4, 45.7, 50.0, 83.0, 126.0, 126.4, 127.6, 129.1, 129.4, 130.8, 133.3, 133.6, 134.8, 137.8, 140.1, 144.4, 172.7.

Synthesis of 3-{[(16β,17β)-17-hydroxy-3-[2-(methylamino)-2-oxoethyl]estra-1(10),2,4-trien-16-yl]methyl}benzamide (32)

To a solution of compound 30 (37 mg, 0.08 mmol) in anhydrous DMF (3 mL), under an argon atmosphere, was added BOP (40 mg, 0.09 mmol), methyl amine (115 μL, 0.03 mmol; 2.0 M in THF) and DIPEA (18 μL, 0.11 mmol). The reaction mixture was stirred at room temperature over a period of 3 h, subsequently poured into water and extracted twice with EtOAc (2×10 mL). The combined organic layers were washed with brine, dried with MgSO$_4$ and concentrated to provide 41 mg of crude product. The crude product was taken up into a mixture of methanol/DCM (9:1) followed by the addition of NaBH$_4$ (15 mg, 0.40 mmol). The reaction mixture was then stirred at room temperature over a period of 30 min and poured into water. The reaction mixture was extracted twice with EtOAc (2×10 mL) and the combined organic layers washed with brine, dried with MgSO$_4$ and concentrated. The crude compound was purified by flash chromatography (DCM/MeOH: 95:5) to provide 6 mg (15%) of compound 32. $^1$H NMR (MeOD): 0.91 (s, 3H, 18-CH$_3$), 1.14-2.49 (residual CH and CH$_2$), 2.71 (s, 3H, CH$_2$CONHCH$_3$), 2.80 (m, 2H, 6-CH$_2$), 3.16 (m, 1H), 3.41 (s, 2H, CH$_2$CONHCH$_3$), 3.84 (d, 1H, 17α-H, J=9.4 Hz), 6.96 (s, 1H, CHar), 7.01 (d, 1H, CHar, J=8.0 Hz), 7.23 (d, 1H, CHar, J=8.0 Hz), 7.42 (m, 2H, CHar), 7.69 (d, 2H, CHar, J=6.0 Hz), 7.76 (s, 1H, CHar); $^{13}$C NMR (MeOD): 13.3, 26.5, 27.3, 28.6, 30.5, 33.0, 38.9, 39.0, 39.7, 43.4 (2×), 45.4, 45.7, 50.0, 83.0, 125.4, 126.0, 126.5, 127.3, 129.1, 129.4, 130.5, 133.5, 134.8, 138.0, 140.2, 144.4, 175.1.

Synthesis of (16E)-16-(3-carbamoylbenzylidene)-17-oxoestra-1,3,5(10)-triene-3-carboxylic acid (34)

To a solution of compound 33 (250 mg, 0.84 mmol) in EtOH (10 mL) was added 3-formyl-benzamide (250 mg, 1.67 mmol) and an aqueous KOH solution (10%, 1.7 mL). The reaction mixture was then heated at reflux over a period of 30 min. The resulting reaction mixture was then diluted with water (200 mL), neutralized with an aqueous HCl solution (10%), and extracted with EtOAc (3×50 mL). The combined organic layers were washed with brine, dried with MgSO$_4$ and concentrated. The crude compound was purified by flash chromatography (DCM/MeOH: 95:5) to provide 143 mg (40%) of compound 34. $^1$H NMR (MeOD): 1.06 (s, 3H, 18-CH$_3$), 1.31-2.77 (residual CH and CH$_2$), 3.40 (m, 2H, 6-CH$_2$), 7.42 (d, 1H, CHar, J=Hz), 7.50 (s, 1H, CH=CH), 7.59 (t, 1H, CHar, J=7.8 Hz), 7.77 (d, 1H, CHar, J=10.2 Hz), 7.83 (d, 1H, CHar, J=7.7 Hz), 7.91 (d, 1H, CHar, J=7.8 Hz), 8.14 (s, 1H, CHar).

Synthesis of (16E,17β)-16-(3-carbamoylbenzylidene)-17-hydroxyestra-1,3,5(10)-triene-3-carboxylic acid (35)

To a solution of compound 34 (140 mg, 0.33 mmol) in a mixture of MeOH and DCM (1:1) was added NaBH$_4$ (21 mg, 0.55 mmol). The reaction mixture was stirred at room temperature over a period of 2 h and concentrated. The residue was diluted with DCM (25 mL) and washed with water. The organic layer was then dried with MgSO$_4$ and concentrated. The crude compound was purified by flash chromatography (DCM/MeOH: 95:5) to provide 68 mg (48%) of compound 35. $^1$H NMR (MeOD): 0.79 (s, 3H, 18-CH$_3$), 1.31-2.41 (residual CH and CH$_2$), 2.97 (m, 2H, 6-CH$_2$), 4.16 (br s, 1H, 17α-H), 6.59 (br s, 1H, CH=CH), 7.38 (d, 1H, CHar, J=8.1 Hz), 7.46 (t, 1H, CHar, J=7.7 Hz), 7.62 (d, 1H, CHar, J=7.8 Hz), 7.72 (m, 2H, CHar), 7.94 (s, 1H, CHar).

Synthesis of (16β,17β)-16-(3-carbamoylbenzyl)-17-hydroxyestra-1,3,5(10)-triene-3-carboxylic acid (36)

To a solution of compound 35 (68 mg, 0.158 mmol) in EtOH (5 mL) at room temperature and under an argon atmosphere was added palladium on charcoal (10%) (10 mg). The reaction vessel was then flushed three times with hydrogen and stirred over a period of 48 h. The resulting reaction mixture was filtered on celite and then concentrated. The crude compound was purified by flash chromatography using DCM/MeOH (95:5) as the eluent system to provide 10 mg (15%) of compound 36. $^1$H NMR (MeOD): 0.92 (s, 3H, 18-CH$_3$), 1.16-2.49 (residual CH and CH$_2$), 2.88 (m, 2H, 6-CH$_2$), 3.17 (m, 1H), 3.85 (br d, 1H, 17α-H, J=9.5 Hz), 7.41 (m, 3H, CHar), 7.71 (m, 3H), 7.76 (s, 1H, CHar); $^{13}$C NMR (MeOD): 13.3, 27.2, 28.3, 30.4, 33.0, 38.8, 38.9, 39.3, 43.3, 45.4, 50.0, 83.0, 126.0, 126.4, 128.0, 129.1, 129.2, 129.4, 131.3, 133.5, 134.8, 138.0, 144.3, 143.6, 146.8, 171.0, 172.7.

Synthesis of 3-{[(16β,17β)-17-hydroxy-3-(hydroxymethyl)estra-1,3,5(10)-trien-16-yl]methyl}benzamide (37)

To a solution of compound 36 (300 mg, 0.70 mmol) in anhydrous THF (20 mL), under an argon atmosphere, was successively added BOP (338 mg, 0.76 mmol) and DIPEA (145 μL, 0.84 mmol) at room temperature. The reaction mixture was stirred over a period of 10 min followed by the addition NaBH$_4$ (30 mg, 0.79 mmol). The reaction mixture was then stirred for an additional hour, poured into water and extracted twice with EtOAc (2×30 mL). The combined organic layers were then washed with brine, dried with MgSO$_4$ and concentrated. The crude compound was subjected to consecutive purifications by flash chromatography using DCM/MeOH (95:5) as the eluent in the first purification and acetone/hexanes (1:1) as the eluant in the second purification to provide 88 mg (30%) of compound 37. $^1$H NMR (MeOD): 0.92 (s, 3H, 18-CH$_3$), 1.15-2.49 (residual CH and CH$_2$), 2.83 (m, 2H, 6-CH$_2$), 3.17 (m, 1H), 3.85 (br d, 1H, 17α-H, J=9.5 Hz), 4.89 (s, 2H, CH$_2$OH), 7.03 (s, 1H, CHar), 7.08 (d, 1H, CHar, J=8.1 Hz), 7.27 (d, 1H, CHar, J=8.0 Hz), 7.41 (m, 2H, CHar), 7.69 (d, 1H, CHar, J=7.8 Hz), 7.76 (s, 1H, CHar); $^{13}$C NMR (MeOD): 13.3, 27.4, 28.6, 30.5, 33.0, 38.8, 39.0, 39.7, 43.4, 45.4, 45.8, 50.0, 65.1, 83.0, 125.5, 126.0, 126.3, 128.6, 129.1, 129.4, 133.5, 134.8, 137.6, 139.6, 140.6, 144.4, 172.7.

Synthesis of 3-{[(16β,17β)-3-(bromomethyl)-17-hydroxyestra-1,3,5(10)-trien-16-yl]methyl}benzamide (38)

To a solution of compound 37 (65 mg, 0.15 mmol) in DCM (7 mL) at 0° C. was added triphenylphosphine (61 mg, 0.23 mmol) and carbon tetrabromide (77 mg, 0.23 mmol). The reaction mixture was then stirred at 0° C. over a period of 5 h. The reaction mixture was subsequently poured into water and extracted with DCM (2×20 mL). The combined organic layers were then dried with MgSO$_4$ and concentrated. The crude compound was purified by flash chromatography (DCM/MeOH: 97:3) to provide 45 mg (60%) of compound 38. $^1$H NMR (Acetone-d$_6$): 0.92 (s, 3H, 18-CH$_3$), 1.14-2.48 (residual CH and CH$_2$), 2.82 (m, 2H, 6-CH$_2$), 3.22 (m, 1H), 3.85 (m, 2H, 17α-H and OH), 4.58 (s, 2H, CH$_2$Br), 6.6 (br s, 1H, CONH$_2$), 7.12 (s, 1H, CHar), 7.19 (d, 1H, CHar, J=Hz), 7.29 (d, 1H, CHar, J=Hz), 7.35 (t, 1H, J=Hz), 7.41 (d and br s under peak, 1H of CHar and 1H of CONH$_2$, J=Hz), 7.74 (d, 1H, CHar, J=Hz), 7.84 (s, 1H, CHar).

Synthesis of 3-{[(16β,17β)-3-(aminomethyl)-17-hydroxyestra-1,3,5(10)-trien-16-yl]methyl}benzamide (39)

To a solution of compound 38 (30 mg, 0.06 mmol) in anhydrous DMF (3 mL) was added sodium azide (12 mg, 0.18 mmol). The solution was then stirred at 60° C. over a period of 3 h while under an argon atmosphere. The reaction mixture was subsequently poured into water and extracted twice with EtOAc. The combined organic layers were washed with brine, dried with MgSO$_4$ and concentrated. The crude compound (25 mg) was then dissolved in ethanol (3 mL). Palladium on charcoal (10%) (10 mg) was then added while under an argon atmosphere. The reaction vessel was then flushed three times with hydrogen and stirred over a period of 24 h. The resulting reaction mixture was filtered on celite and then concentrated. The crude compound was purified by flash chromatography using DCM/MeOH (95:5) as the eluent system to provide 15 mg (58%) of compound 39. $^1$H NMR (MeOD): 0.91 (s, 3H, 18-CH$_3$), 1.13-2.49 (residual CH and CH$_2$), 2.82 (m, 2H, 6-CH$_2$), 3.17 (m, 1H), 3.84 (d, 1H, 17α-H, J=9.4 Hz), 4.41 (s, 2H, CH$_2$NH$_2$), 7.01 (s, 1H, CHar), 7.25 (d, 1H, CHar, J=8.1 Hz), 7.33 (m, 2H, CHar), 7.69 (d, 1H, CHar, J=7.5 Hz), 7.76 (s, 1H, CHar); $^{13}$C NMR (MeOD): 13.3, 27.4, 28.5, 30.5, 33.0, 38.8, 39.0, 39.7, 43.4, 45.4, 45.7, 45.9, 50.0, 83.0, 126.0, 126.2, 126.7, 129.1, 129.2, 129.4, 133.5, 134.8, 138.0, 138.8, 140.7, 144.4, 172.7.

General Procedure for N-alkylation of 3-{[(16β,17β)-3-(bromomethyl)-17-hydroxyestra-1,3,5(10)-trien-16-yl]methyl}benzamide (Compounds 40a-d)

To a solution of compound 38 (25 mg, 0.06 mmol) in DCM (3 mL) was added triethylamine (43 μL, 3.0 mmol) and the appropriate amine (3.0 mmol). The resulting reaction mixture was stirred at room temperature over a period of 3 h. The reaction mixture was then poured into water, extracted twice with DCM, filtered using a phase separator device (Biotage) and concentrated. The desired N-alkylamine derivatives were isolated following purification by flash chromatography (DCM/MeOH 95:5 to 9:1).

3-{[(16β,17β)-3-[(dimethylamino)methyl]-17-hydroxyestra-1,3,5(10)-trien-16-yl]methyl}benzamide (40a)

Yield (10 mg, 43%); $^1$H NMR (MeOD): 0.91 (s, 3H, 18-CH$_3$), 1.14-2.49 (residual CH and CH$_2$), 2.24 (s, 6H, CH$_2$N(CH$_3$)$_2$), 2.82 (m, 2H, 6-CH$_2$), 3.17 (m, 1H), 3.41 (s, 3H, CH$_2$N), 3.84 (d, 1H, 17α-H, J=9.4 Hz), 4.41 (s, 2H, CH$_2$N), 7.00 (s, 1H, CHar), 7.05 (d, 1H, CHar, J=8.1 Hz), 7.26 (d, 1H, CHar, J=8.1 Hz), 7.41 (m, 2H, CHar), 7.69 (d, 1H, CHar, J=7.5 Hz), 7.76 (s, 1H, CHar); $^{13}$C NMR (MeOD): 13.3, 27.3, 28.6, 30.5, 33.0, 38.8, 39.0, 39.6, 43.4, 45.1 (2×), 45.4, 45.8, 50.0, 64.6, 83.0, 126.0, 126.3, 128.0, 129.1, 129.4, 131.3, 133.5, 134.8, 135.4, 137.7, 140.9, 144.4, 172.7.

3-{[(16β,17β)-3-[(dipropylamino)methyl]-17-hydroxyestra-1,3,5(10)-trien-16-yl]methyl}benzamide (40b)

Yield (5 mg, 21%); $^1$H NMR (MeOD): 0.88 (t, 3H, CH$_3$CH$_2$CH$_2$N), J=7.4 Hz), 0.92 (s, 3H, 18-CH$_3$), 1.27 (t, 3H, CH$_3$CH$_2$N, J=7.2 Hz), 1.15-2.65 (residual CH and CH$_2$), 2.82 (m, 2H, 6-CH$_2$), 3.17 (m, 1H), 3.41 (s, 3H, CH$_2$N), 3.58 (s, 2H, PhCH$_2$N), 3.84 (d, 1H, 17α-H, J=9.4 Hz), 4.41 (s, 2H, CH$_2$NH$_2$), 7.01 (s, 1H, CHar), 7.07 (d, 1H, CHar, J=8.1 Hz), 7.26 (d, 1H, CHar, J=8.1 Hz), 7.41 (m, 2H, CHar), 7.70 (d, 1H, CHar, J=7.5 Hz), 7.76 (s, 1H, CHar); $^{13}$C NMR (MeOD): 11.3, 12.1, 13.3, 20.1, 27.3, 28.6, 30.5, 33.0, 38.8, 39.0, 39.6, 43.4, 45.4, 45.8, 48.1, 50.0, 55.8, 58.8, 58.4, 83.0, 126.0, 126.3, 128.1, 129.1, 129.4, 131.3, 133.5, 134.8, 137.7, 140.8, 144.4, 172.7.

3-{[(16β,17β)-17-hydroxy-3-(pyrrolidin-1-ylmethyl) estra-1,3,5(10)-trien-16-yl]methyl}benzamide (40c)

Yield (7 mg, 28%); $^1$H NMR (MeOD): 0.91 (s, 3H, 18-CH$_3$), 1.15-2.65 (residual CH and CH$_2$), 2.82 (m, 2H, 6-CH$_2$), 3.17 (m, 1H), 3.57 (s, 3H, CH$_2$N), 3.84 (d, 1H, 17α-H, J=9.4 Hz), 7.02 (s, 1H, CHar), 7.07 (d, 1H, CHar, J=8.1 Hz), 7.25 (d, 1H, CHar, J=8.1 Hz), 7.41 (m, 2H, CHar), 7.71 (d, 1H, CHar, J=7.5 Hz), 7.76 (s, 1H, CHar); $^{13}$C NMR (MeOD): 11.9, 22.6, 25.9, 27.2, 29.1, 31.6, 37.4, 37.6, 38.2, 42.0, 44.0, 44.4, 47.0, 48.2, 48.6, 53.4, 59.7, 81.6, 124.6, 124.9, 126.4, 127.7, 128.0, 129.6, 132.1, 133.4, 134.6, 136.3, 139.4, 143.0, 171.3.

3-{[(16β,17β)-17-hydroxy-3-[(methylamino)methyl] estra-1,3,5(10)-trien-16-yl]methyl}benzamide (40d)

Yield (2 mg, 8%); $^1$H NMR (MeOD): 0.91 (s, 3H, 18-CH$_3$), 1.14-2.49 (residual CH and CH$_2$), 2.51 (s, 3H, NHCH$_3$), 2.82 (m, 2H, 6-CH$_2$), 3.17 (m, 1H), 3.84 (m, 2H, 17α-H and CH$_2$NH), 7.07 (s, 1H, CHar), 7.13 (d, 1H, CHar, J=8.3 Hz), 7.33 (d, 1H, CHar, J=8.0 Hz), 7.40 (m, 2H, CHar), 7.69 (d, 1H, CHar, J=7.5 Hz), 7.76 (s, 1H, CHar).

General Procedure for N-acylation of (16E,17β)-16-(3-carbamoylbenzylidene)-17-hydroxyestra-1,3,5(10)-triene-3-carboxylic acid (35) (Compounds 41a-d)

To a solution of compound 36 (50 mg, 0.12 mmol) in DMF (3 mL) was added BOP (43 μL, 0.14 mmol) the appropriate amine (0.36 mmol) and DIPEA (28 μL, 0.17 mmol). The resulting reaction mixture was stirred at room temperature over a period of 2 h. The reaction mixture was then poured into water and extracted twice with EtOAc. The combined organic layers were washed with water, brine, dried with MgSO$_4$ and concentrated. The desired N-acylated derivatives were isolated following purification by flash chromatography (DCM/MeOH 95:5 to 9:1).

(16β,17β)-16-(3-carbamoylbenzyl)-17-hydroxy-N,N-dimethylestra-1,3,5(10)-triene-3-carboxamide (41a)

Yield (7 mg, 13%); $^1$H NMR (MeOD): 0.92 (s, 3H, 18-CH$_3$), 1.16-2.49 (residual CH and CH$_2$), 2.51 (s, 3H, NHCH$_3$), 2.86 (m, 2H, 6-CH$_2$), 3.10 and 3.32 (2s, 6H, (CH$_3$)$_2$NCO), 3.17 (m, 1H), 3.85 (m, 2H, 17α-H), 7.11 (s, 1H, CHar), 7.17 (d, 1H, CHar, J=8.1 Hz), 7.33 (d, 1H, CHar, J=8.0 Hz), 7.41 (m, 2H, CHar), 7.70 (d, 1H, CHar, J=8.1 Hz), 7.76 (s, 1H, CHar); $^{13}$C NMR (MeOD): 13.3, 30.4, 33.0, 35.6, 38.0, 38.8, 38.9, 39.4, 41.9, 43.4, 45.0, 45.4, 45.8 (d), 50.0, 83.0, 88.2, 125.3, (126.0 and 126.2 (d)), 126.5, 128.5, 129.1 and 129.2 (d), (129.4 and 129.5 (d)), (133.5 and 133.6 (d)), (134.3, 134.8 and 134.9 (t)), 138.3, (143.6, 143.7 and 143.8 (t)), 144.3, 172.6, 174.2.

(16β,17β)-16-(3-carbamoylbenzyl)-N-ethyl-17-hydroxy-N-propylestra-1,3,5(10)-triene-3-carboxamide (41b)

Yield (17 mg, 30%); $^1$H NMR (MeOD): 0.92 (s, 3H, 18-CH$_3$), 1.16-2.49 (residual CH and CH$_2$), 2.51 (s, 3H, NHCH$_3$), 2.86 (m, 2H, 6-CH$_2$), 3.10 and 3.32 (2s, 6H, (CH$_3$)$_2$NCO), 3.17 (m, 1H), 3.85 (m, 2H, 17α-H), 7.11 (s, 1H, CHar), 7.17 (d, 1H, CHar, J=8.1 Hz), 7.33 (d, 1H, CHar, J=8.0 Hz), 7.41 (m, 2H, CHar), 7.70 (d, 1H, CHar, J=8.1 Hz), 7.76 (s, 1H, CHar); $^{13}$C NMR (MeOD): 13.3, 21.8, 23.0, 27.2, 28.3, 30.4, 33.0, 38.8, 38.9, 45.4, 45.8, 50.0, 82.9, 88.2, 124.4 and 124.6 (d), 126.5, 127.7 and 127.9 (d), 129.1, 129.4, 133.5, 134.8, 135.2, 138.3, 143.3, 144.3, 172.6, 174.2.

3-{[(16β,17β)-17-hydroxy-3-(pyrrolidin-1-ylcarbonyl)estra-1,3,5(10)-trien-16-yl]methyl}benzamide (41c)

Yield (17 mg, 30%); $^1$H NMR (MeOD): 0.91 (s, 3H, 18-CH$_3$), 1.15-2.49 (residual CH and CH$_2$), 2.66 (d, 2H, CH$_2$PhCONH$_2$, J=9.4 Hz), 2.85 (m, 2H, 6-CH$_2$), 3.17 (m, 1H), 3.47 (t, 2H, CH$_2$N of pyrrolidine, J=6.6 Hz), 3.58 (t, 2H, CH$_2$N of pyrrolidine, J=6.9 Hz), 3.84 (d, 2H, 17α-H, J=9.4 Hz), 7.21 (s, 1H, CHar), 7.26 (d, 1H, CHar, J=8.2 Hz), 7.40 (m, 2H, CHar), 7.69 (d, 1H, CHar, J=8.1 Hz), 7.76 (s, 1H, CHar); $^{13}$C NMR (MeOD): 13.3, 25.3, 27.2 (2×), 28.3, 30.4, 33.0, 38.9, 39.4, 43.3, 45.4, 45.8, 50.0, 50.9, 82.0, 88.2, 125.3, 126.0, 126.4, 128.6, 129.4, 133.5, 134.8, 135.1, 138.2, 144.1, 144.3, 172.1, 172.6.

(16β,17β)-16-(3-carbamoylbenzyl)-17-hydroxy-N-methylestra-1,3,5(10)-triene-3-carboxamide (41d)

Yield (22 mg, 42%); $^1$H NMR (MeOD): 0.92 (s, 3H, 18-CH$_3$), 1.15-2.49 (residual CH and CH$_2$), 2.51 (s, 3H, NHCH$_3$), 2.9 (m, 5H, 6-CH$_2$ and CH$_3$NH), 3.17 (m, 1H), 3.85 (m, 2H, 17α-H), 7.51 (s, 1H, CHar), 7.55 (d, 1H, CHar, J=8.2 Hz), 7.69 (d, 1H, CHar, J=7.5 Hz), 7.76 (s, 1H, CHar); $^{13}$C NMR (MeOD): 13.3, 27.2, 28.3, 30.5, 33.0, 38.8, 38.9, 39.3, 43.3, 45.3, 45.9, 50.0, 82.9, 88.2, 125.4, 126.0, 126.5, 128.7, 129.1, 129.4, 132.6, 133.5, 134.8, 138.2, 144.3, 145.6, 170.9, 172.7.

Synthesis of 3-(4,4,5,5-tetramethyl-1,3,2-dioxaborolan-2-yl)estra-1(10),2,4-trien-17-one (43)

To a solution of estrone triflate (42) (455 mg, 1.12 mmol) in anhydrous dioxane (5 mL) at room temperature was added pinacolborane, Pd(dppf)Cl$_2$ and triethylamine (923 μL, 6.62 mmol) under an argon atmosphere. The reaction mixture was bubbled with argon over a period of 5 min and then heated at 100° C. over a period of 24 h. The dioxane was removed under reduce pressure followed by the addition of EtOAc (50 mL). The organic layer was washed successively with water and brine, dried with MgSO$_4$ and concentrated. The crude compound was purified by flash chromatography (EtOAc/Hexanes: 95:5 to 8:2) to provide 275 mg (64%) of compound 43. $^1$H NMR (CDCl$_3$): 0.91 (s, 3H, 18-CH$_3$), 1.34 (12H, 4×CH$_3$ of borolan), 1.39-2.54 (residual CH and CH$_2$), 2.93 (m, 2H, 6-CH$_2$), 7.32 (d, 1H, CHar, J=7.8 Hz), 7.57 (s, 1H, CHar), 7.60 (d, 1H, CHar, J=7.9 Hz).

Synthesis of [(16E)-16-(3-carbamoylbenzylidene)-17-oxoestra-1(10),2,4-trien-3-yl]boronic acid (44)

To a solution of compound 43 (150 mg, 0.39 mmol) in EtOH (10 mL) was added 3-formyl-benzamide (118 mg, 0.79 mmol) and aqueous KOH solution (10%, 1.5 mL). The reaction mixture was then heated at reflux over a period of 30 min. The resulting reaction mixture was then diluted with water (200 mL), neutralized with an aqueous HCl solution (10%), and extracted with EtOAc (3×50 mL). The combined organic layers were washed with brine, dried with MgSO$_4$ and concentrated to provide 80 mg of compound 44. $^1$H NMR (DMSO-d$_6$): 0.94 (s, 3H, 18-CH$_3$), 1.24-2.97 (residual CH and CH$_2$), 4.05 (s, 2H, B(OH)$_2$, 7.27 (d, 1H, CHar, J=7.8 Hz), 7.37 (s, 1H, CHar), 7.49-7.58 (m, 3H, CHar), 7.81 (d, 1H, CHar, J=7.7 Hz), 7.90 (d, 1H, CHar, J=7.8 Hz), 8.1 (s, 1H, CHar).

Synthesis of [(16E,17β)-16-(3-carbamoylbenzylidene)-17-hydroxyestra-1(10),2,4-trien-3-yl]boronic acid (45)

To a solution of compound 44 (70 mg, 0.16 mmol) in MeOH (6 mL) was added NaBH$_4$ (10 mg, 0.26 mmol). The reaction mixture was stirred at room temperature over a period of 1 h and concentrated. The residue was diluted with EtOAc (25 mL) and washed with water. The organic layer was then washed with brine, dried with MgSO$_4$ and concentrated. The crude compound was purified by flash chromatography (DCM/MeOH: 9:1) to provide 54 mg (77%) of compound 45. $^1$H NMR (MeOD): 0.77 (s, 3H, 18-CH$_3$), 1.24-2.97 (residual CH and CH$_2$), 4.05 (s, 2H, B(OH)$_2$, 7.27 (d, 1H, CHar, J=7.8 Hz), 7.37 (s, 1H, CHar), 7.49-7.58 (m, 3H, CHar), 7.81 (d, 1H, CHar, J=7.7 Hz), 7.90 (d, 1H, CHar, J=7.8 Hz), 8.1 (s, 1H, CHar).

Synthesis of [(16β,17β)-16-(3-carbamoylbenzyl)-17-hydroxyestra-1(10),2,4-trien-3-yl]boronic acid (46)

To a solution of compound 45 (47 mg, 0.11 mmol) in EtOH (4 mL) at room temperature and under an argon atmosphere was added palladium on charcoal (10%) (8 mg). The reaction vessel was then flushed three times with hydrogen and stirred over a period of 24 h. The resulting reaction mixture was filtered on celite and then concentrated. The crude compound was purified by flash chromatography using DCM/MeOH (95:5) as the eluent system to provide 13 mg (28%) of compound 46. $^1$H NMR (MeOD): 0.91 (s, 3H, 18-CH$_3$), 1.14-2.49 (residual CH and CH$_2$), 2.82 (m, 2H, 6-CH$_2$), 3.17 (m, 1H), 3.84 (d, 1H, 17α-H, J=9.4 Hz), 7.291 (m, 2H, CHar), 7.35-7.43 (m, 1H, CHar), 7.70 (d, 1H, CHar, J=7.4 Hz), 7.76 (s, 1H, CHar); $^{13}$C NMR (MeOD): 13.3, 27.2, 28.6, 30.5, 33.0, 38.8, 39.0, 39.6, 43.4, 46.0, 50.0, 83.0, 125.4 and 125.5 (d), 126.0, 129.1, 129.4, 131.9 and 132.2 (d), 133.5, 134.8, 135.4 and 135.7 (d), 143.0 and 143.7, 144.4, 172.7.

Synthesis of 3-{(E)-[(16E)-3-amino-17-oxoestra-1,3,5(10)-trien-16-ylidene]methyl}benzamide (48)

To a solution of 3-amino-estrone (47) (68 mg, 0.25 mmol) in EtOH (3.5 mL) was added 3-formyl-benzamide (75 mg, 0.50 mmol) and aqueous KOH solution (10%, 0.5 mL). The reaction mixture was then heated at reflux over a period of 1 h. The resulting reaction mixture was then diluted with water (50 mL), neutralized with an aqueous HCl solution (10%), and extracted with EtOAc (3×15 mL). The combined organic layers were washed with brine, dried with MgSO$_4$ and concentrated. The crude compound was purified by flash chromatography using DCM/MeOH (95:5) as the eluent system to provide 40 mg (40%) of compound 48. $^1$H NMR (Acetone-d$_6$): 1.00 (s, 3H, 18-CH$_3$), 1.29-3.06 (residual CH and CH$_2$), 4.33 (br s, 2H, PhNH$_2$), 6.40 (s, 1H, CHar), 6.47 (d, 1H, CHar, J=8.3 Hz), 7.00 (d, 1H, CHar, J=8.3 Hz), 7.40 (s, 1H, CHar), 7.57 (t, 1H, CHar, J=7.7 Hz), 7.83 (d, 1H, CHar, J=7.8 Hz), 7.96 (d, 1H, J=7.8 Hz), 8.20 (s, 1H, CHar).

Synthesis of 3-{(E)-[(16E,17β)-3-amino-17-hydroxyestra-1,3,5(10)-trien-16-ylidene]methyl}benzamide (49)

To a solution of compound 48 (40 mg, 0.10 mmol) in MeOH (6 mL) was added NaBH$_4$ (19 mg, 0.50 mmol). The reaction mixture was stirred at room temperature over a period of 1 h and concentrated. The residue was diluted with EtOAc (25 mL) and washed with water. The organic layer was then washed with brine, dried with Na$_2$SO$_4$ and concentrated. The crude compound was purified by flash chromatography (DCM/MeOH: 95:5) to provide 26 mg (65%) of compound 49. $^1$H NMR (MeOD): 0.77 (s, 3H, 18-CH$_3$), 1.29-2.82 (residual CH and CH$_2$), 4.13 (s. 1H, 17α-H), 6.50 (s, 1H, CHar), 6.56 (m, 2H, CHar), 7.07 (d, 1H, CHar, J=8.0 Hz), 7.46 (t, 1H, CHar, J=7.7 Hz), 7.60 (d 1H, CHar, J=7.8 Hz), 7.69 (d, 1H, CHar, J=7.9 Hz), 7.94 (s, 1H).

Synthesis of 3-{[(16β,17β)-3-amino-17-hydroxyestra-1,3,5(10)-trien-16-yl]methyl}benzamide (50) and 3-{[(16β,17β)-3-(ethylamino)-17-hydroxyestra-1,3,5(10)-trien-16-yl]methyl}benzamide (51)

To a solution of compound 49 (15 mg, 0.04 mmol) in EtOH (2 mL) at room temperature and under an argon atmosphere was added palladium on charcoal (10%) (5 mg). The reaction vessel was then flushed three times with hydrogen and stirred over a period of 24 h. The resulting reaction mixture was filtered on celite and then concentrated. The crude compound was purified by flash chromatography using Acetone/Hexanes (1:1) as the eluent system to provide 4 mg (27%) of compound 50 and 5 mg (33%) of compound 51.

Compound 50:
$^1$H NMR (MeOD): 0.91 (s, 3H, 18-CH$_3$), 1.14-2.85 (residual CH and CH$_2$), 3.83 (d, 1H, 17α-H, J=9.4 Hz), 6.46 (s, 1H, CHar), 6.55 (d, 1H, CHar, J=8.3 Hz), 7.04 (d, 1H, CHar, J=8.5 Hz), 7.41 (m, 2H, CHar), 7.69 (d, 1H, CHar, J=7.4 Hz), 7.75 (s, 1H); $^{13}$C NMR (MeOD): 13.3, 27.5, 28.7, 30.7, 33.0, 38.9, 39.0, 40.0, 43.4, 45.5, 50.0, 83.1, 88.4, 114.9, 117.2, 126.0, 126.8, 129.1, 129.4, 132.0, 133.5, 134.8, 138.2, 144.4, 145.5, 172.7.

Compound 51:
$^1$H NMR (MeOD): 0.91 (s, 3H, 18-CH$_3$), 1.22 (t, 3H, CH$_3$CH$_2$NH, J=7.1 Hz), 1.12-2.48 (residual CH and CH$_2$), 2.74 (2H, 6-CH$_2$), 3.08 (q, 2H, CH$_3$CH$_2$NH, J=7.1 Hz), 3.17 (m, 1H), 3.83 (d, 1H, 17α-H, J=9.4 Hz), 6.39 (s, 1H, CHar), 6.49 (d, 1H, CHar, J=8.3 Hz), 7.06 (d, 1H, CHar, J=8.5 Hz), 7.41 (m, 2H, CHar), 7.69 (d, 1H, CHar, J=7.4 Hz), 7.76 (s, 1H); $^{13}$C NMR (MeOD): 13.4, 14.9, 27.6, 28.8, 30.9, 33.0, 38.9, 39.0, 40.0, 40.1, 43.4, 45.5, 50.0, 51.7, 83.1, 113.0, 115.0, 126.0, 126.2, 129.1, 129.4, 131.1, 133.5, 134.8, 138.2, 144.4, 147.8, 167.7.

Synthesis of 3-{[(16β,17β)-17-hydroxy-3-(methylamino)estra-1,3,5(10)-trien-16-yl]methyl}benzamide (53)

To a solution of compound 49 (22 mg, 0.05 mmol) in EtOH (3 mL) at room temperature and under an argon atmosphere was added palladium on charcoal (10%) (5 mg). The reaction vessel was then flushed three times with hydrogen and stirred over a period of 24 h. The resulting reaction mixture was filtered on celite and then concentrated.

The crude compound was purified by preparative chromatography using EtOAc/Hexanes (1:1) as the eluent system to provide 3 mg (14%) of compound 50 and 6 mg (27%) of compound 53.

Compound 53:
$^1$H NMR (MeOD): 0.91 (s, 3H, 18-CH$_3$), 1.13-2.48 (residual CH and CH$_2$), 2.74 (5H, 6-CH$_2$ and CH$_3$NH), 3.17 (m, 1H), 3.83 (d, 1H, 17α-H, J=9.4 Hz), 6.39 (s, 1H, CHar), 6.47 (d, 1H, CHar, J=8.3 Hz), 7.07 (d, 1H, CHar, J=8.5 Hz), 7.41 (m, 2H, CHar), 7.69 (d, 1H, CHar, J=7.4 Hz), 7.76 (s, 1H); $^{13}$C NMR (MeOD): 13.4, 27.6, 28.8, 30.9, 31.3, 33.0, 35.2, 38.9, 39.0, 40.1, 43.4, 45.5, 50.0, 83.1, 112.4, 114.2, 126.0, 126.8, 129.1, 129.4, 130.9, 133.5, 134.8, 138.1, 144.4, 148.9, 151.1, 167.7.

Synthesis of 3-{(E)-[(16E)-3-fluoro-17-oxoestra-1(10),2,4-trien-16-ylidene]methyl}benzamide (55)

To a solution of 3-fluoro-estrone (54) (169 mg, 0.62 mmol) in EtOH (10 mL) was added 3-formyl-benzamide (175 mg, 1.17 mmol) and aqueous KOH solution (10%, 1.7 mL). The reaction mixture was then heated at reflux over a period of 1 h. The resulting reaction mixture was then diluted with water (100 mL), neutralized with an aqueous HCl solution (10%), and extracted with EtOAc (3×30 mL). The combined organic layers were washed with brine, dried with MgSO$_4$ and concentrated. The crude compound was purified by flash chromatography using EtOAc/Hexanes (1:1) as the eluent system to provide 146 mg (62%) of compound 55. $^1$H NMR (MeOD): 1.05 (s, 3H, 18-CH$_3$), 1.23-2.76 (residual CH and CH$_2$), 6.84 (m, 2H, CHar), 7.32 (t, 1H, CHar, J=7.7 Hz), 7.49 (s, 1H, CHar), 7.59 (t, 1H, CHar, J=7.8 Hz), 7.82 (d, 1H, CHar, J=7.8 Hz), 7.92 (d, 1H, J=7.7 Hz), 8.14 (s, 1H, CHar).

Synthesis of 3-{(E)-[(16E,17β)-3-fluoro-17-hydroxyestra-1(10),2,4-trien-16-ylidene]methyl}benzamide (56)

To a solution of compound 55 (140 mg, 0.35 mmol) in a mixture of MeOH/DCM (2:1) (15 mL) was added NaBH$_4$ (26 mg, 0.68 mmol). The reaction mixture was stirred at room temperature over a period of 30 min and concentrated. The residue was diluted with DCM (50 mL) and washed with water. The organic layer was then washed with brine, dried with Na$_2$SO$_4$ and concentrated. The crude compound was triturated with diethyl ether and filtered to provide 140 mg (99%) of compound 56. $^1$H NMR (MeOD): 0.77 (s, 3H, 18-CH$_3$), 1.30-2.82 (residual CH and CH$_2$), 2.92 (m, 2H, 6-CH$_2$), 4.13 (s, 1H, 17α-H), 6.58 (s, 1H, CHar), 6.82 (m, 2H, CHar), 7.30 (m, 1H, CHar), 7.45 (t, 1H, CHar, J=7.7 Hz), 7.58 (d, 1H, CHar, J=7.9 Hz), 7.69 (d, 1H, CHar, J=7.8 Hz), 7.94 (s, 1H, CHar).

Synthesis of 3-{[(16β,17β)-3-fluoro-17-hydroxyestra-1(10),2,4-trien-16-yl]methyl}benzamide (57)

To a solution of compound 56 (140 mg, 0.35 mmol) in EtOH (5 mL) at room temperature and under an argon atmosphere was added palladium on charcoal (10%) (28 mg). The reaction vessel was then flushed three times with hydrogen and stirred over a period of 48 h. The resulting reaction mixture was filtered on celite and then concentrated. The crude compound was purified by flash chromatography using Acetone/Hexanes (6:4) as the eluent system to provide 59 mg (42%) of compound 57. $^1$H NMR (MeOD): 0.91 (s, 3H, 18-CH$_3$), 1.14-2.62 (residual CH and CH$_2$), 2.82 (m, 2H, 6-CH$_2$), 3.17 (m, 1H), 3.84 (d, 1H, 17α-H, J=9.4 Hz), 6.78 (m, 2H, CHar), 7.07 (d, 1H, CHar, J=8.5 Hz), 7.30 (m, 1H, CHar), 7.41 (m, 2H, CHar), 7.69 (d, 1H, CHar, J=7.4 Hz), 7.76 (s, 1H); $^{13}$C NMR (MeOD): 13.3, 27.4, 28.3, 30.5, 33.0, 38.8, 39.4, 43.3, 45.3, 49.8, 82.9, 88.2, 113.0 and 113.2 (d), 115.6 and 115.8 (d), 125.9, 127.9 (d), 129.1, 129.4, 133.5, 134.7, 137.3, 140.1 (d), 144.3, 161.0 and 163.4 (d), 172.6.

Synthesis of (16E)-16-(3-carbamoylbenzylidene)-17-oxoestra-1,3,5(10)-triene-3-carboxamide (59)

To a solution of 3-carboxamide-estrone (58) (250 mg, 0.84 mmol) in EtOH (10 mL) was added 3-formyl-benzamide (250 mg, 1.67 mmol) and aqueous KOH solution (10%, 1.7 mL). The reaction mixture was then heated at reflux over a period of 40 min. The resulting reaction mixture was then diluted with water (150 mL), neutralized with an aqueous HCl solution (10%), and extracted with EtOAc (3×35 mL). The combined organic layers were washed with brine, dried with MgSO$_4$ and concentrated. The crude compound was purified by flash chromatography using DCM/MeOH (95:5) as the eluent system to provide 70 mg (19%) of compound 59. $^1$H NMR (DMSO): 0.95 (s, 3H, 18-CH$_3$), 1.43-2.74 (residual CH and CH$_2$), 2.95 (m, 3H), 7.24 and 7.50 (2s, 2H, CONH$_2$), 7.37 (d, 2H, CHar, J=7.6 Hz), 7.57 (t, 1H, CHar, J=7.7 Hz), 7.63 (d, 2H, CHar, J=9.7 Hz), 7.82 (d, 1H, CHar, J=7.9 Hz), 7.87 and 8.07 (2s, 2H, CONH$_2$), 7.90 (d, 1H, J=7.8 Hz), 8.10 (s, 1H, CHar).

Synthesis of (16E,17β)-16-(3-carbamoylbenzylidene)-17-hydroxyestra-1,3,5(10)-triene-3-carboxamide (60)

To a solution of compound 59 (68 mg, 0.16 mmol) in a mixture of MeOH/DCM (1:1) (30 mL) was added NaBH$_4$ (10 mg, 0.26 mmol). The reaction mixture was stirred at room temperature over a period of 1 h and concentrated. The residue was diluted with DCM (50 mL) and washed with water. The organic layer was then washed with brine, dried with Na$_2$SO$_4$ and concentrated. The crude compound was triturated with diethyl ether and filtered to provide 68 mg (99%) of compound 60. $^1$H NMR (MeOD): 0.78 (s, 3H, 18-CH$_3$), 1.43-2.86 (residual CH and CH$_2$), 3.01 (m, 2H, 6-CH$_2$), 4.15 (s, 1H, 17α-H), 6.59 (s, 1H, CHar), 7.47 (m, 2H, CHar), 7.62 (m, 3H, CHar), 7.69 (d, 1H, CHar, J=7.8 Hz), 7.95 (s, 1H, CHar).

Synthesis of (16β,17β)-16-(3-carbamoylbenzyl)-17-hydroxyestra-1,3,5(10)-triene-3-carboxamide (61)

To a solution of compound 60 (64 mg, 0.148 mmol) in EtOH (5 mL) at room temperature and under an argon atmosphere was added palladium on charcoal (10%) (11 mg). The reaction vessel was then flushed three times with hydrogen and stirred over a period of 16 h. The resulting reaction mixture was filtered on celite and then concentrated. The crude compound was purified by flash chromatography using DCM/MeOD (95:5) as the eluent system to provide 21 mg (32%) of compound 61. $^1$H NMR (MeOD): 0.93 (s, 3H, 18-CH$_3$), 1.17-2.49 (residual CH and CH$_2$), 2.89 (m, 2H, 6-CH$_2$), 3.18 (m, 1H), 3.86 (d, 1H, 17α-H, J=9.5 Hz), 7.40 (m, 3H, CHar), 7.58 (s, 1H, CHar), 7.62 (d, 1H, CHar, J=8.2 Hz), 7.69 (d, 1H, CHar, J=6.1 Hz), 7.76 (s, 1H). $^{13}$C NMR (MeOD): 11.9, 25.8, 26.9, 29.0, 31.6, 37.4, 37.5, 37.9, 41.9, 43.9, 44.5, 48.6, 81.5, 124.5, 124.6, 125.1, 127.7, 127.8, 128.0, 130.5, 132.1, 133.4, 136.7, 142.9, 144.6, 171.2.

17β-HSD3

Figure 10:
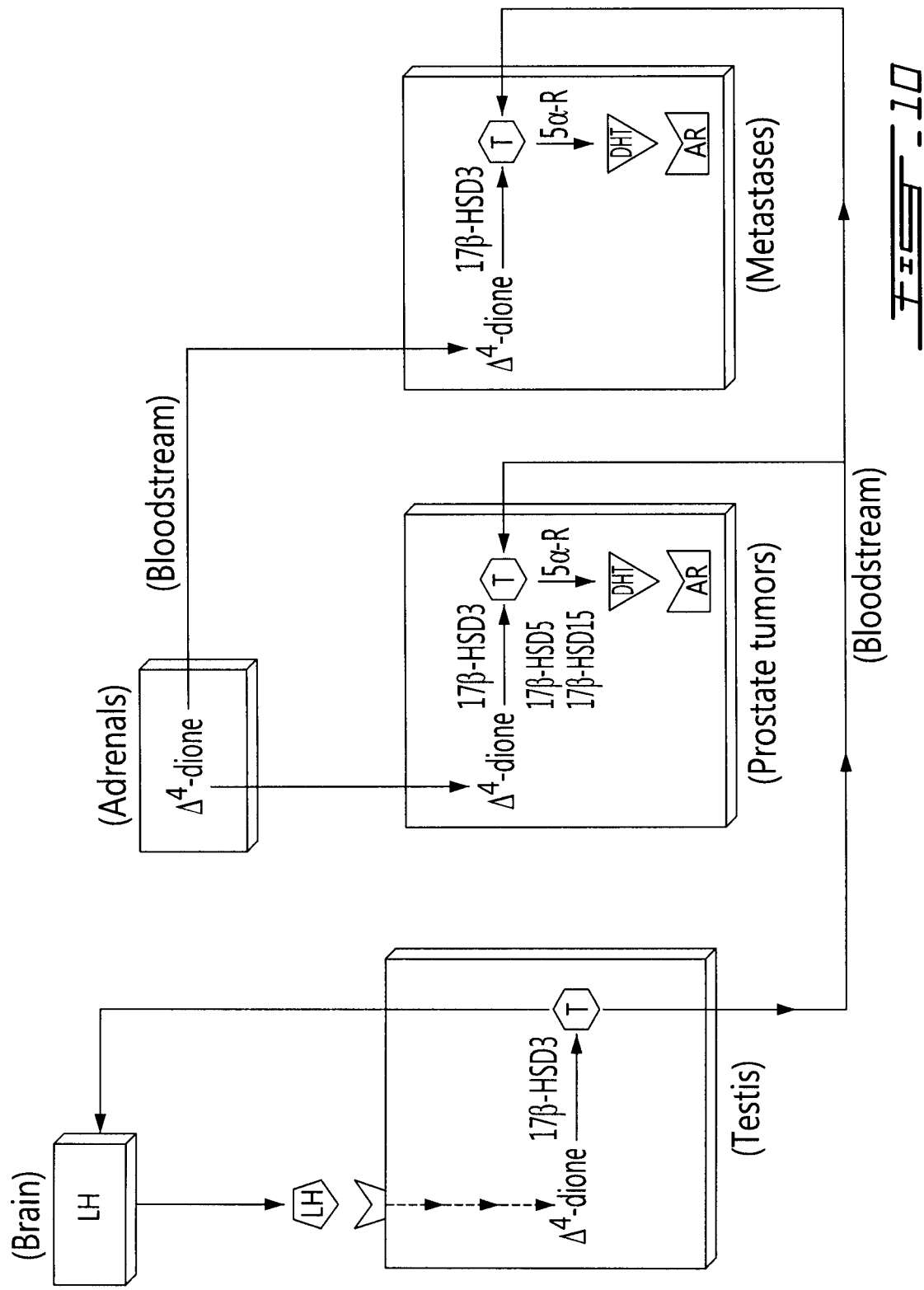
FIG. 10 illustrates a schematic view of the contribution of 17β-HSD3 in androgen testostosterone (T) biosynthesis from the non-androgenic 4-androstene-3,17-dione (Δ$^4$-dione) in different sources including the testis (endocrine), the adrenals (endocrine), and intratumoral tissues (intracrine). LH: Luteinizing hormone, 5α-R: 5α-reductase, AR: androgen receptor, DHT: dihydrotestosterone, 17β-HSD5 and 17β-HSD15: types 5 and 15 of 17β-hydroxysteroid dehydrogenase.

The 17β-HSD3 enzyme represents a promising target for the treatment of advanced prostate cancer by blocking the different sources of active androgen T from the testis (endocrine), adrenals (intracrine) and intratumoral tissues (intracrine) (FIG. 10). Furthermore, it is believed that the use of 17β-HSD3 inhibitors complementary to actual endocrine therapy could increase the efficiency of the antiandrogens, LHRH agonists, and inhibitors of androgen biosynthesis enzymes (5α-reductase and 17α-lyase) by providing a synergistic effect.[44,45] This more complete inactivation of the androgen receptor (AR) could also limit its ability to mutate, and/or diminish the ability of androgen-independent clones to evolve toward androgen independence.

Previous structure-activity relationship (SAR) studies on the inhibition of 17β-HSD3 have identified important criteria for inhibitory activity (FIG. 11A).[46-52] Despite of their good efficiency in homogenated HEK-293 cells overexpressing 17β-HSD3, these inhibitors were however not optimal. The first generation inhibitors of the 3β-alkyl-androsterone series showed an androgenic profile on Shionogi (AR+) cells which is undesirable in the context of a treatment for an androgen-sensitive disease. The inhibitory potency of these inhibitors was also lower in intact than in homogenated HEK-293 cells overexpressing 17β-HSD3, thus suggesting low cell permeability.

Figures 11A, 11B:
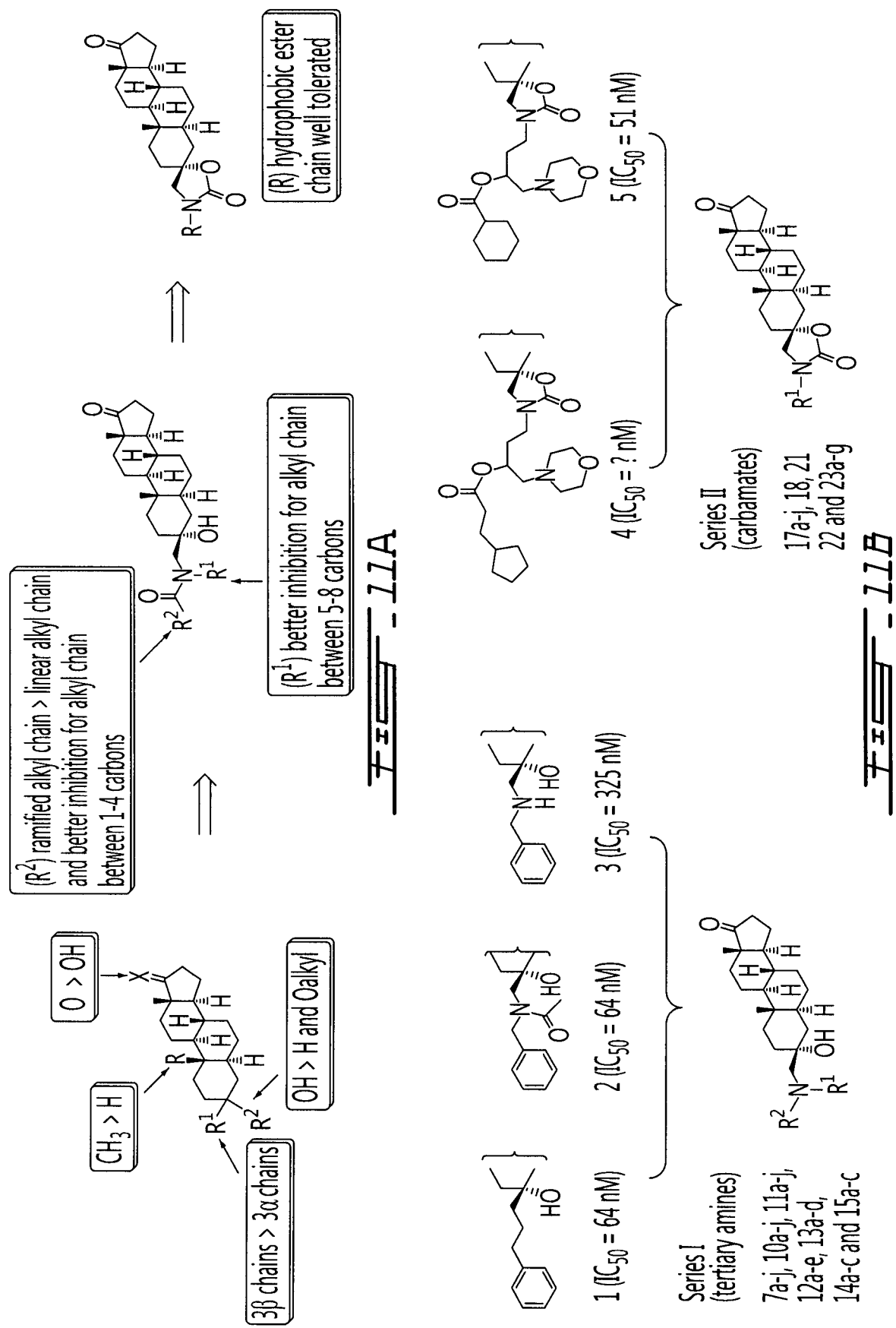
FIG. 11A is an illustration of the relative importance of different chemical groups (i.e. alkyl, alkylamide and carbamate derivatives) attached to position 3β of the androsterone steroid scaffold and their effect on 17β-HSD3 inhibition as established by SAR studies.
FIG. 11B is an illustration of representative inhibitors of 17β-HSD3.

To provide 17β-HSD3 inhibitors with a non-androgenic profile, the enzyme's tolerance for new diversified substituents introduced at position 3 of androsterone (ADT) nucleus was explored. More specifically, two series of ADT derivatives (tertiary amines and carbamates) were designed, synthesized and tested as new inhibitors of 17β-HSD3 (FIG. 11B).

The ADT derivatives 7a-j were readily obtained in acceptable yields (35% to 70%) from the ring opening of oxirane 6 in refluxing ethanol using a series of commercially available secondary amines (Scheme 15). Similarly, oxirane 6 was also opened with piperazine or trans-2,5-dimethylpiperazine to provide intermediates 8 and 9. The free NH of 8 and 9 was subsequently submitted to a series of addition reactions using a variety of building blocks (e.g. benzyl bromide, acyl chloride and sulfonyl chloride) to obtain the corresponding piperazine derivatives 10a-j and 11a-j (amines); 12a-e and 13a-d (amides); and 14a-c and 15a-c (sulfonamides).

Scheme 15: Reagents and conditions: (a) R¹R²NH, ethanol 60° c.; (b) piperazine or 2,5-dimethylpiperazine, ethaol, 60° C.; (c) R¹CH₂Br; TEA, DCM, rt; (d) R¹COCl, TEA, DCM, rt; (e) R¹SO₂Cl, TEA, DCM.

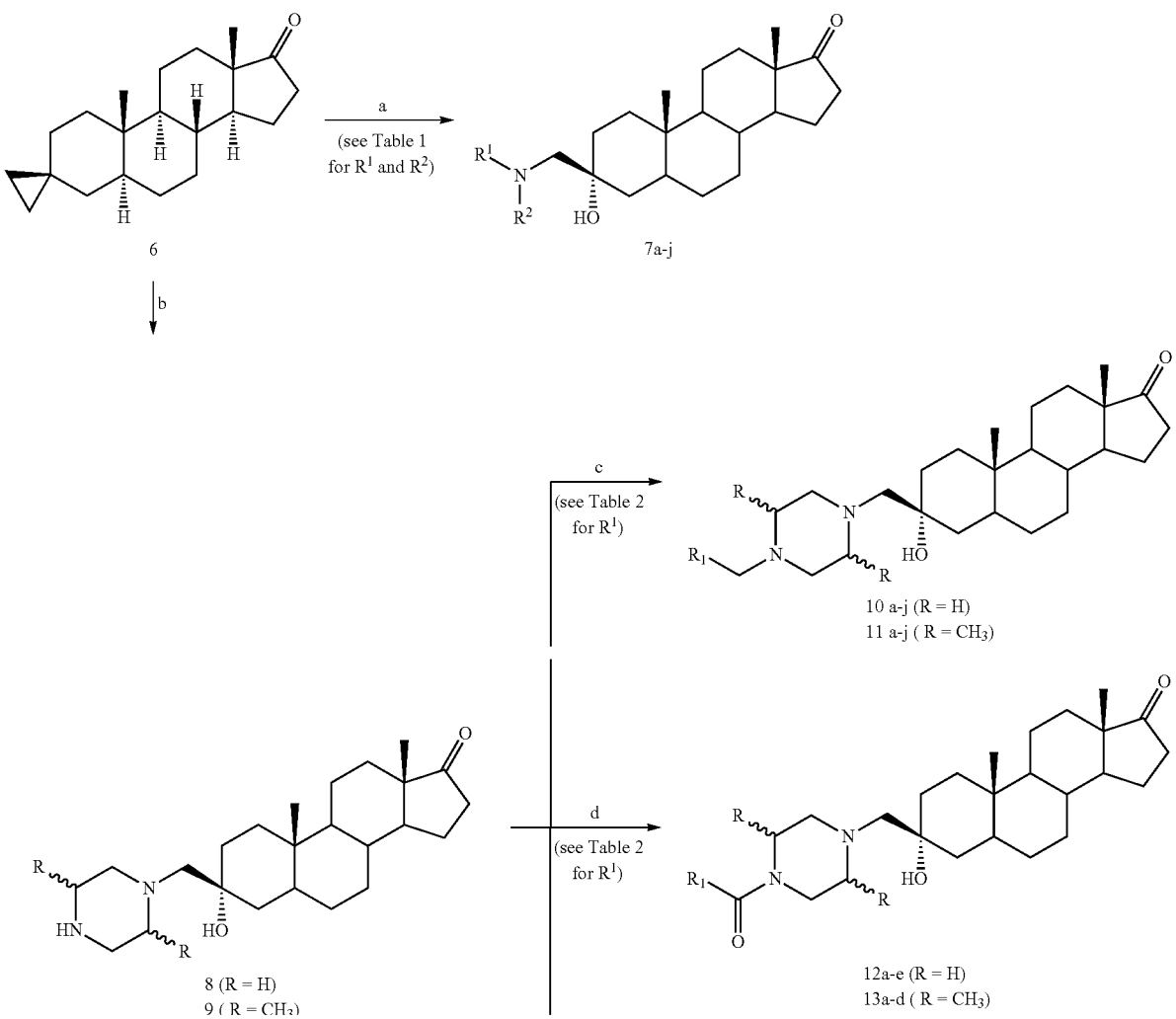

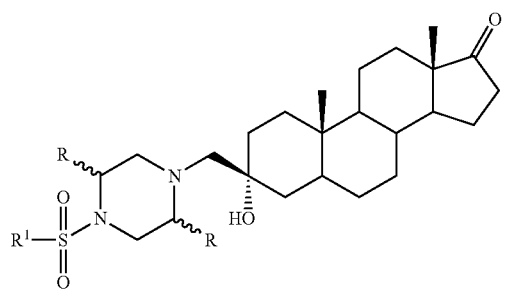

14a-c (R = H)
15a-c (R = CH₃)

The carbamate derivatives 17a-i, 18, 21, 22 and 23a-g were prepared as illustrated hereinbelow in Schemes 16 and 17. Carbamates 17a-i and 18 were prepared from the ring opening of oxirane 6 in refluxing ethanol using a series of commercially available primary amines followed by a cyclization reaction converting the amino-alcohol into a carbamate. Finally, C16 di-methylation of 17b provided 18 (Scheme 16).

Scheme 16: Reagents and conditions: (a) R—NH₂, ethanol, 60° C.; (b) triphosgene, DIPEA, DCM; (c) NaH, MeI, DMF.

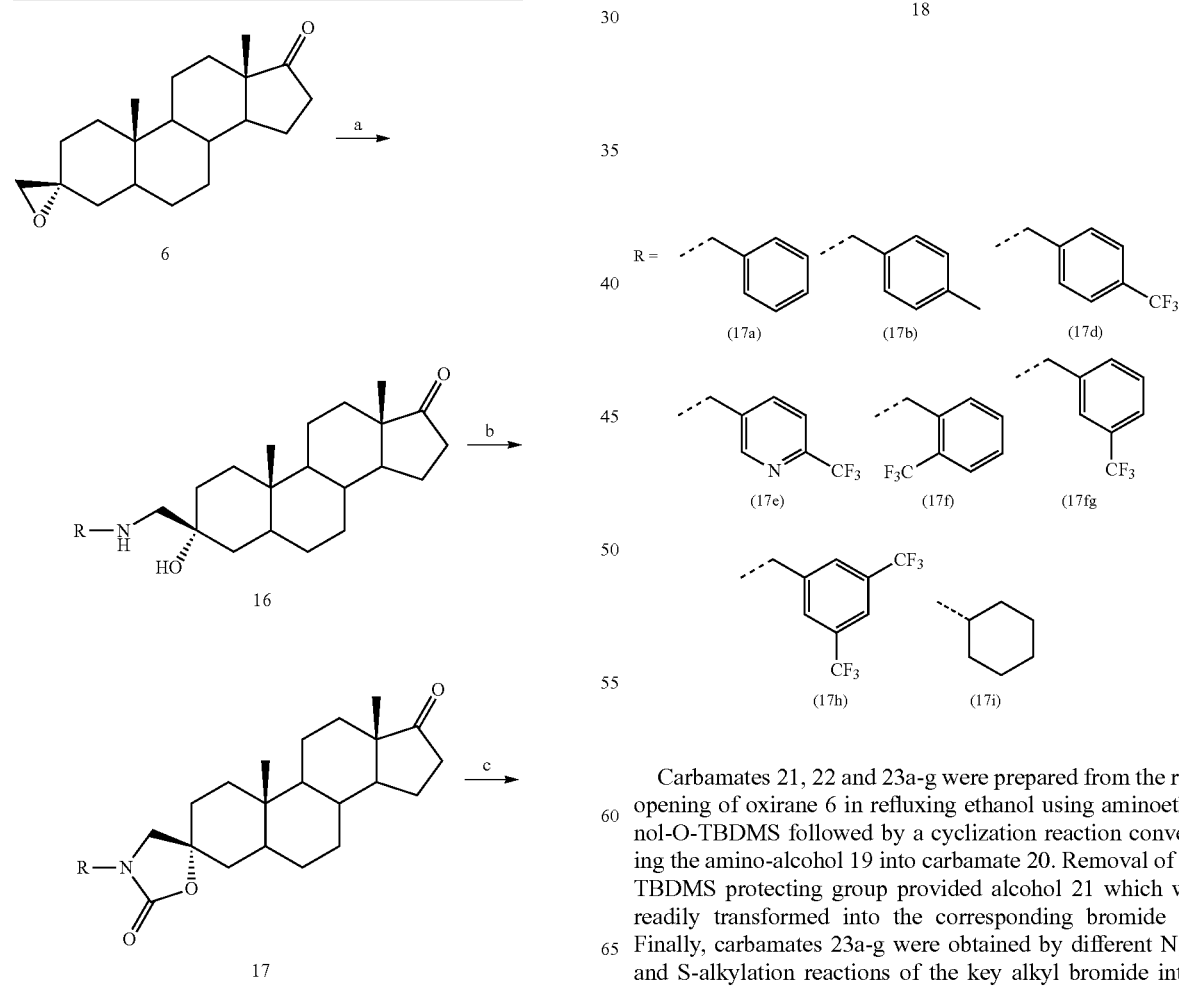

Carbamates 21, 22 and 23a-g were prepared from the ring opening of oxirane 6 in refluxing ethanol using aminoethanol-O-TBDMS followed by a cyclization reaction converting the amino-alcohol 19 into carbamate 20. Removal of the TBDMS protecting group provided alcohol 21 which was readily transformed into the corresponding bromide 22. Finally, carbamates 23a-g were obtained by different N, O and S-alkylation reactions of the key alkyl bromide intermediate 22 (Scheme 17).

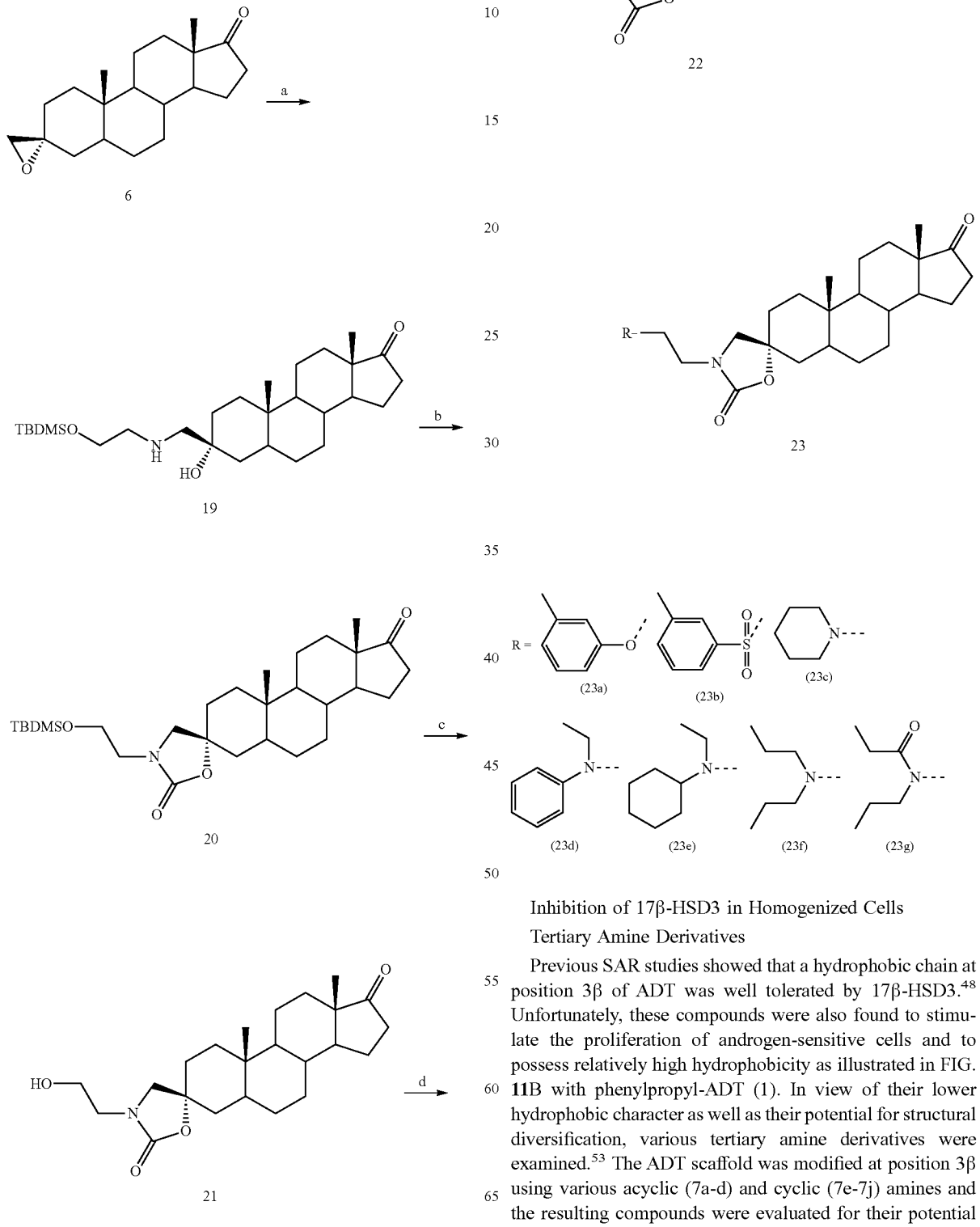

Scheme 17: Reagents and conditions: (a) NH$_2$(CH$_2$)$_2$OTBDMS, ethanol, 60° C.; (b) triphosgene, DIPEA, DCM; (c) TBAF, THF, rt; (d) PPh$_3$, CBr$_4$, DCM, 0° C. to rt; (e) 3-methylphenol (for 23a); (f) i) 3-methylthiophenol, K$_2$CO$_3$, DMF, 80° C.; ii) KHSO$_5$, MeOH/H$_2$O (for 23b); (g) appropriate R$^1$R$^2$NH, ethanol 60° C. (for 23c, 23d, 23e and 23f); (h) i) propylamine, Na$_2$CO$_3$, DMF, 80° C.; ii) propionyl chloride, triethylamine, DCM, rt (for 23g).

Inhibition of 17β-HSD3 in Homogenized Cells

Tertiary Amine Derivatives

Previous SAR studies showed that a hydrophobic chain at position 3β of ADT was well tolerated by 17β-HSD3.[48] Unfortunately, these compounds were also found to stimulate the proliferation of androgen-sensitive cells and to possess relatively high hydrophobicity as illustrated in FIG. 11B with phenylpropyl-ADT (1). In view of their lower hydrophobic character as well as their potential for structural diversification, various tertiary amine derivatives were examined.[53] The ADT scaffold was modified at position 3β using various acyclic (7a-d) and cyclic (7e-7j) amines and the resulting compounds were evaluated for their potential as inhibitors of 17β-HSD3 (Table 2).

TABLE 2

Inhibition of 17β-HSD3 in homogenized and intact cells by various tertiary-amine derivatives of ADT (compounds 7a-j).[a]

| Compound | R | Homo (%) (0.01 μM) | Homo (%) (0.1 μM) | Homo (%) (1 μM) | Intact cells (%) (0.1 μM) | Intact cells (%) (1 μM) |
|---|---|---|---|---|---|---|
| 7a | Ph-CH2-N(Et)- | 42 | 85 | 90 | 86 | 94 |
| 7b | Ph-CH2-N(Me)- | 28 | 79 | 89 | 48 | 92 |
| 7c | Et2N- | 0 | 10 | 60 | N/A | 14 |
| 7d | (n-Bu)2N- | 13 | 70 | 85 | 53 | 90 |
| 7e | piperidin-1-yl | 9 | 19 | 69 | N/A | 23 |
| 7f | 4-benzylpiperidin-1-yl | 40 | 82 | 90 | N/A | 52 |
| 7g | 4-(piperidin-1-yl)piperidin-1-yl | 0 | 4 | 69 | N/A | 20 |
| 7h | 4-methylpiperazin-1-yl | 0 | 0 | 40 | 2 | N/A |
| 7i | 4-phenylpiperazin-1-yl | 13 | 78 | 89 | N/A | 68 |
| 7j | 4-benzylpiperazin-1-yl | 35 | 72 | 90 | 37 | 80 |

[a]For the transformation of [$^{14}$C]-4-androstene-3,17-dione (50 nM) into [$^{14}$C]-testosterone at the indicated concentration of tested compound.

The ability of compounds 7a-7j to inhibit 17β-HSD3 transfected in human embryonic kidney (HEK)-293 cells (homogenized) was determined by measuring the amount of labelled T formed from natural labelled substrate Δ$^4$-dione in the presence of NADPH as cofactor. The results were expressed as the percent of inhibitory activity for a given compound. In the series of acyclic derivatives, compound 7a was the most active inhibitor (42% at 0.01 μM and 85% at 0.1 µM). For the cyclic derivatives, compounds 7f and 7j were the best inhibitors with 40% and 35% inhibition at 0.01 µM, respectively. Piperazine derivative 7j was however considered more interesting considering its lower hydrophobicity (compared to 7f).

Piperazine Derivatives

Various piperazine derivatives were prepared and analyzed (Table 3). The inhibition values remained substantially unchanged for various 3β-piperazine-ADT derivatives comprising a substituted aryl group (Z) attached to the piperazine moiety (compounds 10a-j). Furthermore, the presence of either electron withdrawing groups (e.g. CF₃; Cl) or electron donating groups (e.g. OCH₃) had little or no effect on the inhibition values. Compound 10a demonstrated better inhibition than reference compound 7j. The pyridine ring (compound 10g) appears to have a negative impact on the inhibition of 17β-HSD3, indicative of an apparently poor tolerance for polar substituents. Yet furthermore, modifications to the linker (Y) (e.g. $CH_2$, CO or $SO_2$) had little or no effect on the inhibitory activity (the rest of the compound remaining unchanged). Although the use of a trans-2,5-dimethylpiperazine moiety did not increase the inhibition in the amine (Y=$CH_2$) or amide (Y=CO) series of compounds, when compared to the corresponding compounds comprising a piperazine moiety, it did increase the inhibition in the sulfonamide series. Inhibition values of 55% and 79% at 0.01 µM were recorded for compounds 15b and 15c respectively. Sulfonamide 15c provided a higher percentage of inhibition (79% at 0.01 µM) than its corresponding amide 13d (17%) and its corresponding amine 11c (14%). A strong negative impact on inhibition could also be observed when the C19-steroid nucleus was substituted for the C21-steroid nucleus which is indicative of 17β-HSD3 having a clear preference for the androstane scaffold compared to the pregnane scaffold (84% inhibition at 0.1 µM vs. 12% inhibition respectively when Z=$C_6H_5$; Y=$CH_2$ and X=piperazine). Finally, the presence of an insaturation at positions C4-C5 of the androstane derivative 7j had no significant impact on enzyme inhibition.

TABLE 3

Inhibition of 17β-HSD3 in homogenized and intact cells: optimization of 3β-piperazine ADT series (compounds 10a-j, 11a-j, 12a-e, 13a-d, 14a-c and 15a-c).[a]

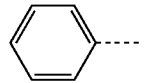

| Compound | Z | Y | X | Homo (%) (0.01 µM) | Homo (%) (0.1 µM) | Intact cells (%) (0.1 µM) |
|---|---|---|---|---|---|---|
| 7j | 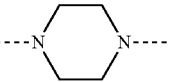 | $CH_2$ | 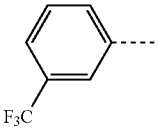 | 36 | 74 | 38 |
| 10a | 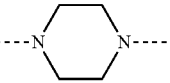 | $CH_2$ | 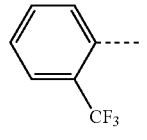 | 51 | 88 | 52 |
| 10b | 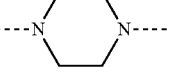 | $CH_2$ | 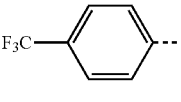 | 18 | 86 | 20 |
| 10c | 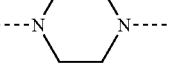 | $CH_2$ | 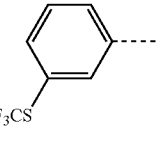 | 14 | 81 | 33 |
| 10d | 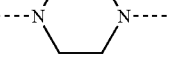 | $CH_2$ | | 3 | 91 | N/A (62)[b] |

TABLE 3-continued

Inhibition of 17β-HSD3 in homogenized and intact cells: optimization of 3β-piperazine ADT series (compounds 10a-j, 11a-j, 12a-e, 13a-d, 14a-c and 15a-c).[a]

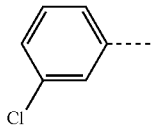

| Compound | Z | Y | X | Homo (%) (0.01 µM) | Homo (%) (0.1 µM) | Intact cells (%) (0.1 µM) |
| --- | --- | --- | --- | --- | --- | --- |
| 10e | 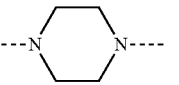 3-Cl-C6H4 | CH2 | 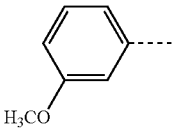 piperazine | 26 | 85 | N/A (75)[b] |
| 10f | 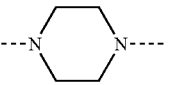 3-MeO-C6H4 | CH2 | 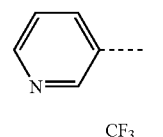 piperazine | 21 | 83 | 47 |
| 10g | 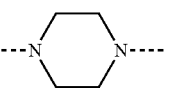 3-pyridyl | CH2 | 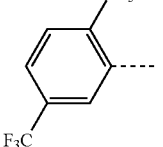 piperazine | 10 | 33 | N/A (63)[b] |
| 10h | 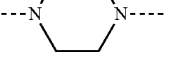 2,4-(CF3)2-C6H3 | CH2 | 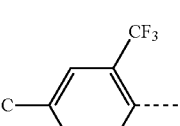 piperazine | 18 | 85 | 12 |
| 10i | 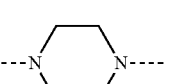 2,4-(CF3)2-C6H3 | CH2 | 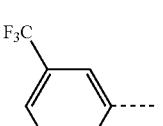 piperazine | 22 | 75 | 16 |
| 10j | 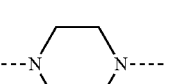 3,5-(CF3)2-C6H3 | CH2 | 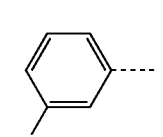 piperazine | 25 | 83 | 25 |
| 11a | 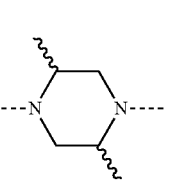 3-CF3-C6H4 | CH2 | 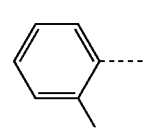 2,5-dimethylpiperazine | 31 | 89 | N/A (78)[b] |
| 11b | 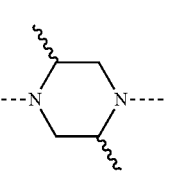 2-CF3-C6H4 | CH2 | 2,5-dimethylpiperazine | 22 | 85 | 36 |

TABLE 3-continued
Inhibition of 17β-HSD3 in homogenized and intact cells: optimization of 3β-piperazine ADT series (compounds 10a-j, 11a-j, 12a-e, 13a-d, 14a-c and 15a-c).[a]
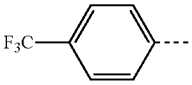
| Compound | Z | Y | X | Homo (%) (0.01 μM) | Homo (%) (0.1 μM) | Intact cells (%) (0.1 μM) |
|---|---|---|---|---|---|---|
| 11c | 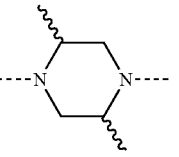 F₃C— | CH₂ | 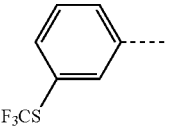 | 14 | 87 | 36 |
| 11d | 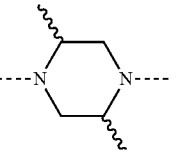 F₃CS— | CH₂ | 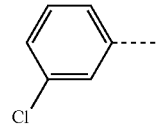 | 18 | 88 | N/A (58)[b] |
| 11e | 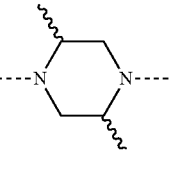 Cl— | CH₂ | 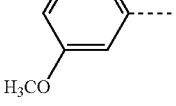 | 26 | 84 | N/A (55)[b] |
| 11f | 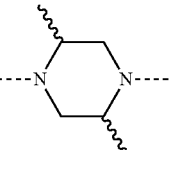 H₃CO— | CH₂ | 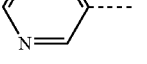 | 19 | 87 | 50 |
| 11g | 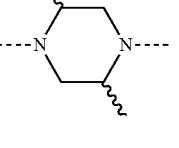 | CH₂ | 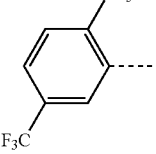 | 17 | 47 | N/A (58)[b] |
| 11h | 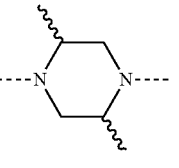 CF₃ / F₃C— | CH₂ | 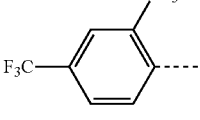 | 16 | 71 | 23 |
| 11i | 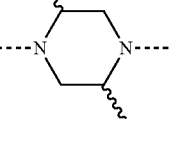 CF₃ / F₃C— | CH₂ |  | 15 | 71 | 21 |

TABLE 3-continued

Inhibition of 17β-HSD3 in homogenized and intact cells: optimization of 3β-piperazine ADT series (compounds 10a-j, 11a-j, 12a-e, 13a-d, 14a-c and 15a-c).[a]

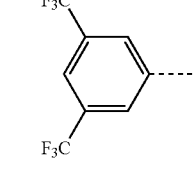

| Compound | Z | Y | X | Homo (%) (0.01 μM) | Homo (%) (0.1 μM) | Intact cells (%) (0.1 μM) |
|---|---|---|---|---|---|---|
| 11j | 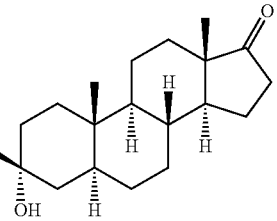 3,5-(F₃C)₂-phenyl | CH₂ | 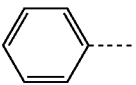 piperazine | 25 | 74 | 16 |
| 12a | 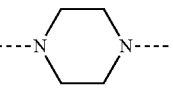 phenyl | CO | 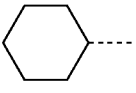 piperazine | 17 | 76 | 50 |
| 12b | 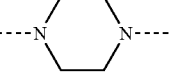 cyclohexyl | CO | piperazine | 19 | 75 | N/A (70)[b] |
| 12c | 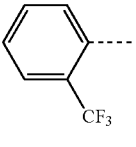 2-CF₃-phenyl | CO | piperazine | 31 | 86 | 62 |
| 12d | 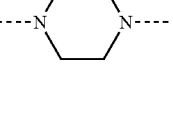 3-CF₃-phenyl | CO | piperazine | 10 | 92 | 91 |
| 12e | 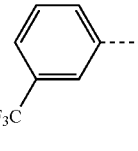 4-CF₃-phenyl | CO | piperazine | 22 | 84 | 56 |
| 13a | 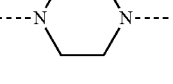 phenyl | CO | 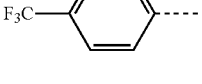 2,5-dimethylpiperazine | 24 | 87 | 78 |
| 13b |  cyclohexyl | CO | 2,5-dimethylpiperazine | 24 | 90 | 77 |

TABLE 3-continued

Inhibition of 17β-HSD3 in homogenized and intact cells:
optimization of 3β-piperazine ADT series
(compounds 10a-j, 11a-j, 12a-e, 13a-d, 14a-c and 15a-c).[a]

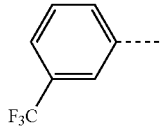

| Compound | Z | Y | X | Homo (%) (0.01 μM) | Homo (%) (0.1 μM) | Intact cells (%) (0.1 μM) |
|---|---|---|---|---|---|---|
| 13c | 3-CF₃-C₆H₄ | CO | piperazine | 28 | 89 | 70 |
| 13d | 4-CF₃-C₆H₄ | CO | piperazine | 17 | 91 | 61 |
| 14a | 3-CF₃-C₆H₄ | SO₂ | piperazine | 21 | 82 | N/A (71)[b] |
| 14b | 2-CF₃-C₆H₄ | SO₂ | piperazine | 45 | 92 | 63 |
| 14c | 4-CF₃-C₆H₄ | SO₂ | piperazine | 21 | 78 | 34 |
| 15a | 3-CF₃-C₆H₄ | SO₂ | 2,5-dimethylpiperazine | 32 | 91 | 77 |
| 15b | 2-CF₃-C₆H₄ | SO₂ | 2,5-dimethylpiperazine | 55 | 92 | 84 |

TABLE 3-continued

Inhibition of 17β-HSD3 in homogenized and intact cells:
optimization of 3β-piperazine ADT series
(compounds 10a-j, 11a-j, 12a-e, 13a-d, 14a-c and 15a-c).[a]

| Compound | Z | Y | X | Homo (%) (0.01 μM) | Homo (%) (0.1 μM) | Intact cells (%) (0.1 μM) |
|---|---|---|---|---|---|---|
| 15c | F₃C-C₆H₄- | SO₂ | piperazine | 79 | 92 | 47 |

[a] For the transformation of [$^{14}$C]-4-androstene-3,17-dione (50 nM) into [$^{14}$C]-testosterone at the indicated concentration of tested compound.
[b] Tested at 1 μM.

Carbamate Derivatives

A small library of 3β-carbamate-ADT derivatives showing promising inhibitory activities on 17β-HSD3 was previously synthesized.[46] Despite the good activities, the compounds possess an ester group (see 4 and 5 in FIG. 11B) vulnerable to in vivo hydrolysis. In order to provide improved inhibitors with a more stable substituent on the carbamate moiety, a further series of new carbamate analogues was prepared (Table 4).

TABLE 4

Inhibition of 17β-HSD3 in homogenized and intact cells:
optimization of 3-carbamate ADT series
(compounds 17a-i, 18, 21, 22 and 23a-g).[a]

| Compound | R¹ | R² | Homo (%) (0.01 μM) | Homo (%) (0.1 μM) | Homo (%) (1.0 μM) | Intact cells (%) (0.1 μM) |
|---|---|---|---|---|---|---|
| 4 | cyclopentyl-propanoate with morpholinomethyl substituent | H | 2 | 79 | 94 | 49 |
| 17a | benzyl | H | 21 | 86 | 93 | 44 |

TABLE 4-continued
Inhibition of 17β-HSD3 in homogenized and intact cells: optimization of 3-carbamate ADT series (compounds 17a-i, 18, 21, 22 and 23a-g).[a]
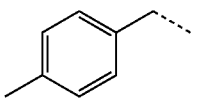
| Compound | R[1] | R[2] | Homo (%) (0.01 μM) | Homo (%) (0.1 μM) | Homo (%) (1.0 μM) | Intact cells (%) (0.1 μM) |
|---|---|---|---|---|---|---|
| 17b | 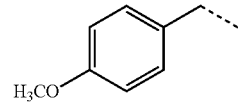 | H | 17 | 81 | 93 | 38 |
| 17c | 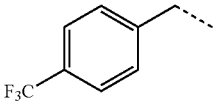 | H | 5 | 84 | 93 | 43 |
| 17d | 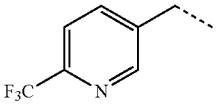 | H | 25 | 80 | nd | 43 |
| 17e | 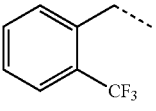 | H | 3 | 65 | nd | 36 |
| 17f | 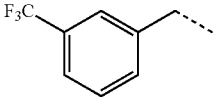 | H | 17 | 81 | nd | 35 |
| 17g | 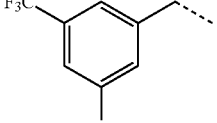 | H | 16 | 80 | nd | 36 |
| 17h | 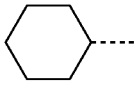 | H | 12 | 66 | nd | 35 |
| 17i | 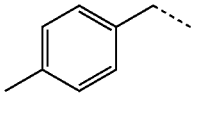 | H | 13 | 75 | 78 | 29 |
| 18 | 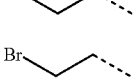 | CH$_3$ | 2 | 22 | 74 | 18 |
| 21 | HO⌒⌒ | H | 0 | 9 | 38 | 16[b] |
| 22 | Br⌒⌒ | H | 17 | 69 | 93 | 31 |

TABLE 4-continued

Inhibition of 17β-HSD3 in homogenized and intact cells:
optimization of 3-carbamate ADT series
(compounds 17a-i, 18, 21, 22 and 23a-g).[a]

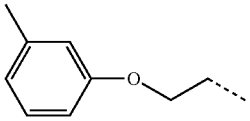

| Compound | R[1] | R[2] | Homo (%) (0.01 μM) | Homo (%) (0.1 μM) | Homo (%) (1.0 μM) | Intact cells (%) (0.1 μM) |
|---|---|---|---|---|---|---|
| 23a | 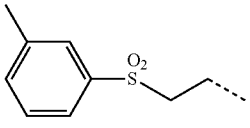 | H | 13 | 85 | 95 | 40 |
| 23b | 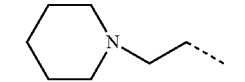 | H | 0 | 52 | 93 | 5 |
| 23c | 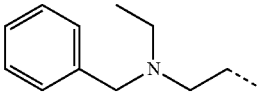 | H | 0 | 0 | 21 | 10[b] |
| 23d | 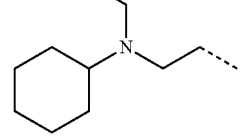 | H | 14 | 71 | 93 | 40 |
| 23e | 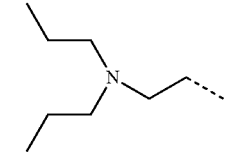 | H | 2 | 21 | 72 | 2 |
| 23f | 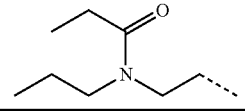 | H | 0 | 10 | 62 | 8[b] |
| 23g |  | H | 0 | 35 | 80 | 25 |

[a]For the transformation of [$^{14}$C]-4-androstene-3,17-dione (50 nM) into [$^{14}$C]-testosterone at the indicated concentration of tested compound.
[b]Tested in another experiment.

The enzyme displayed good tolerance for all carbamates bearing a hydrophobic chain as represented by compounds 17a, 17b, 17d, 17f, 17g, 17h, 17i, 22 and 23a. Weak inhibition results were obtained for the carbamates bearing a hydrophilic chain as represented by compounds 17e, 21, 23b, 23c, 23e, 23f and 23g. This is particularly evident when the inhibitory activity of alcohol 21 is compared with the corresponding bromide 22, and the inhibitory activity of p-CF$_3$-phenyl derivative 17d with p-CF$_3$-pyridine derivative 17e. The sulfone derivative 23b was also less potent than its corresponding ether 23a. The addition of two methyl groups at position C16 of compound 17b was clearly not well tolerated by the enzyme and, consequently, compound 18 displayed only very weak inhibition of 17β-HSD3. A slight improvement of the inhibitory activity was observed for compounds 17a, 17b, 17d, 17f, 17g and 23a relative to reference compound 4.

In one embodiment of the present disclosure, there are included inhibitors of 17β-HSD3, in which the inhibitor has the structure

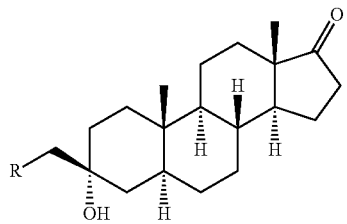

wherein R is heterocyclyl or —NR$_a$R$_b$, wherein R$_a$ and R$_b$ are each independently alkyl or aralkyl, or a pharmaceutically acceptable salt or tautomer thereof.

In another embodiment, there are included further inhibitors of 17β-HSD3, having the structure:

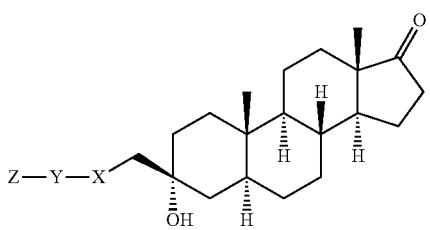

wherein:
X is

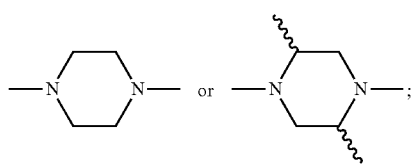

Y is —CH$_2$—, —C(O)— or —S(O)$_2$—; and Z is cycloalkyl, aryl or heterocyclyl, or a pharmaceutically acceptable salt or tautomer thereof.

In one embodiment, the 17β-HSD3 inhibitor has the structure

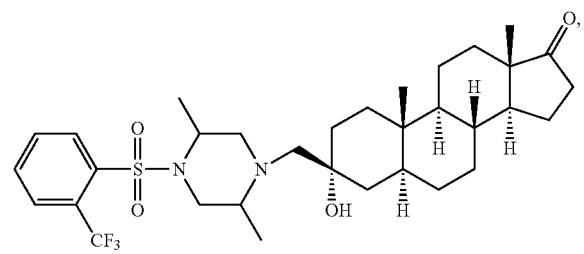

or a pharmaceutically acceptable salt thereof. In one embodiment, the inhibitor is the corresponding hydrochloride (HCl) salt of the above compound, or other acid addition salt on the piperazine moiety of the above compound.

In another embodiment, the 17β-HSD3 inhibitor has the following prodrug structure

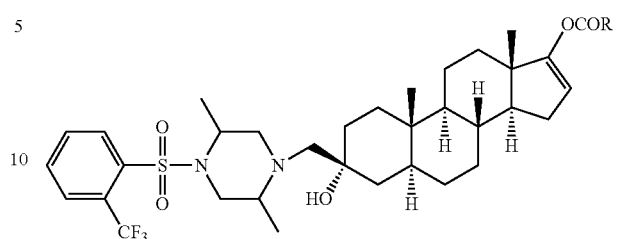

or a pharmaceutically acceptable salt thereof. In one embodiment, the inhibitor is the corresponding hydrochloride (HCl) salt of the above compound, or other acid addition salt on the piperazine moiety of the above compound. R comprises a C1-C4 alkyl group.

In another embodiment, the 17β-HSD3 inhibitor has the following prodrug structure

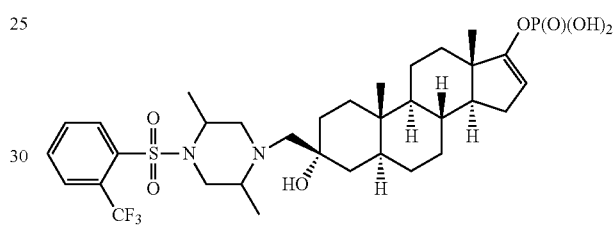

or a pharmaceutically acceptable salt thereof. In one embodiment, the inhibitor is the corresponding hydrochloride (HCl) salt of the above compound, or other acid addition salt on the piperazine moiety of the above compound.

In another embodiment, there are included still further inhibitors of 17β-HSD3, having the structure

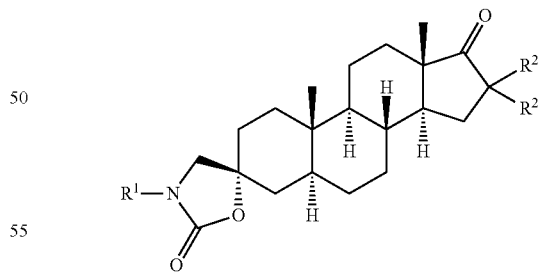

wherein R$^1$ is alkyl, aralkyl, heterocyclyl, cycloalkyl, —CH$_2$CH$_2$S(O)$_2$-aryl, heterocyclyl,
—CH$_2$CH$_2$CH(O-acyl)CH$_2$-heterocyclyl, or
—CH$_2$CH$_2$NR$_a$R$_b$, wherein R$_a$ and R$_b$ are each independently alkyl, cycloalkyl, acyl, or aralkyl; and each R$^2$ is independently hydrogen or alkyl, or a pharmaceutically acceptable salt or tautomer thereof. In another embodiment, the above compound has the structure:

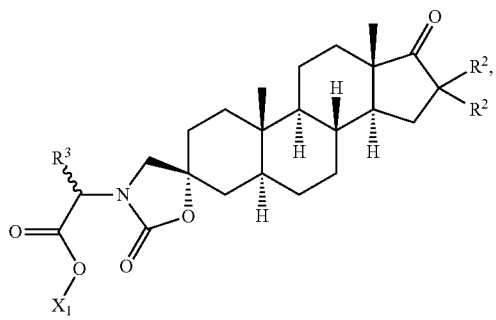

wherein
X$_1$ is alkyl,
R$^2$ is independently hydrogen or alkyl,
R$^3$ is hydrogen, alkyl or aralkyl,
or a pharmaceutically acceptable salt or tautomer thereof.

In another embodiment, there are included still further inhibitors of 17β-HSD3, having the structure

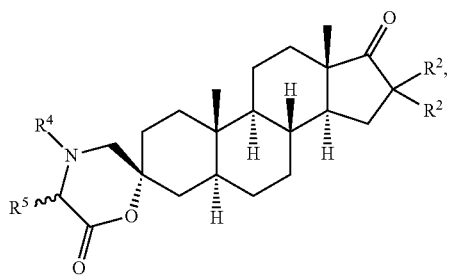

wherein,
R$^2$ is independently hydrogen or alkyl,
R$^4$ is hydrogen or aralkyl,
R$^5$ is hydrogen, alkyl or aralkyl,
or a pharmaceutically acceptable salt or tautomer thereof.

Inhibition of 17β-HSD3 in Intact Cells

After having established the inhibitory activity of the compounds in homogenized HEK-293 cells, the capability of the compounds to exert their inhibitory action in intact cells overexpressing 17β-HSD3 was determined. The results in Table 2 (obtained for intact cells) are indicative of tertiary amine 7a being the best inhibitor. The results in Table 3 indicate that only compounds 10a, 14b, 15b and 15c inhibited over 40% of the activity in homogenized cells (51, 45, 55, 79% inhibition respectively at 0.01 μM. Furthermore, the results in intact cells further illustrated that 15b has the best inhibitory properties. Exhibiting an 84% inhibition at 0.1 μM, compound 15b is a more potent inhibitor in intact cells than 10a, 14b and 15c which exhibited the transformation of 4-dione into T at values of 52, 45 and 47%, respectively. The carbamate-based inhibitors illustrated in Table 4 appear to be less potent inhibitors than either of the series of compounds illustrated in Tables 2 and 3. None of the compounds illustrated in Table 4 provided for an inhibition value exceeding 40% at 0.01 μM in homogenized cells. Moreover, only compounds 17a-i, 22, 23a and 23d exceeded this level of enzyme inhibition at the higher reported concentration of 0.1 μM. Compound 17a was selected as a representative inhibitor of this series of carbamate-ADT derivatives in view of iis inhibition of 44% of 17β-HSD3 activity in intact cells.

Figure 12:
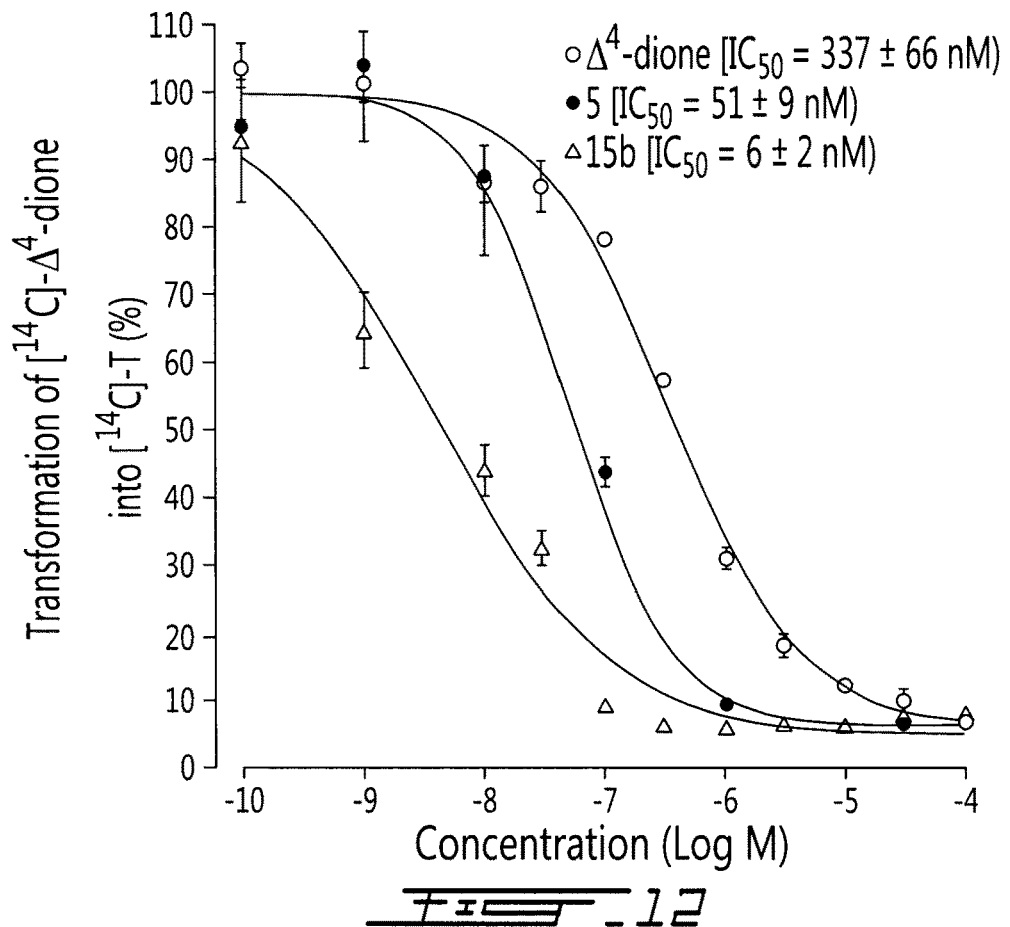
FIG. 12 is an illustration of the inhibition of the transformation of [$^{14}$C]-4-androstene-3,17-dione ([$^{14}$C]-Δ$^4$-dione) (50 nM) into [$^{14}$C]-testosterone ([$^{14}$C]-T) by 17β-HSD3 overexpressed in intact HEK-293 cells.

The IC$_{50}$ value of piperazine derivative 15b, the first generation inhibitor 5 and the natural substrate Δ$^4$-dione were determined. Being less potent in both homogenized and intact cell assays, the carbamate derivative 17a was not selected for IC$_{50}$ determination. Moreover, the tertiary amine derivative 7a was also not selected as it was shown to be an androgenic compound. From the inhibition curve obtained for intact HEK-293 cells overexpressing 17β-HSD3 (FIG. 12), 15b was found to be an 8-fold better inhibitor than reference compound 5 (IC$_{50}$=6 and 51 nM, respectively). Compound 15b was also found to be 56-fold better at inhibiting the transformation of labelled Δ$^4$-dione into T (IC$_{50}$=337 nM) than the unlabelled Δ$^4$-dione used itself as an inhibitor.

Proliferative (Androgenic) Activity on Shionogi Cells

Figure 13:
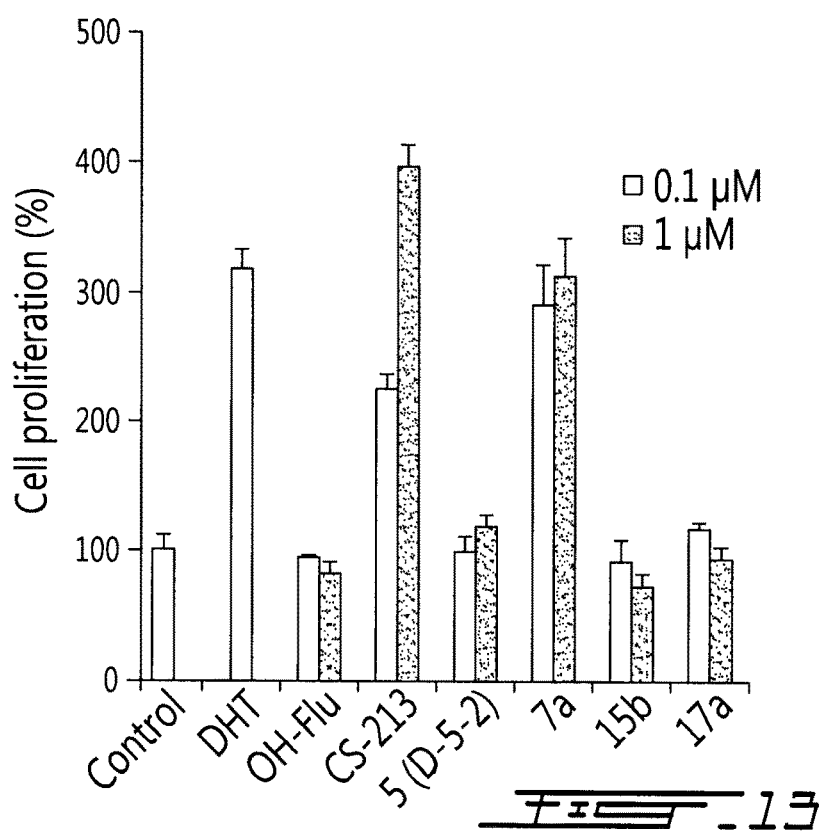
FIG. 13 is an illustration of the proliferative effect (androgenic activity) on androgen sensitive Shionogi cells induced by potent androgen dihydrotestosterone (DHT) and the 17β-HSD3 inhibitors CS-213, 5, 7a, 15b and 17a. The data are expressed as means±SEM of one experiment in triplicate. Significantly different from control (CTL): *(p<0.01).

In the context of the treatment of androgen-dependent diseases, an important criterion for the development of potential 17β-HSD3 candidates is their non-androgenic character or their ability to not activate the androgen receptor (AR). Accordingly, the agonist (proliferative) activity inhibitors 7a, 15b, 17a, 5 and 3β-benzyl-3α-hydroxy-5α-androstan-17-one on androgen-sensitive (AR$^+$) Shionogi cells was evaluated (FIG. 13). In this assay (the basal cell proliferation (control) was set as 100%), the potent androgen dihydrotestosterone (0.1 μM) stimulated cell proliferation to 320% and the antiandrogen (AR antagonist) did not stimulate cell proliferation. Contrary to inhibitor 5, which did not significantly stimulate cell proliferation, the first generation inhibitor CS-213 is fully androgenic, inducing 225% and 396% of basal cell proliferation at 0.1 and 1 μM, respectively. Compound 7a showed a strong proliferative effect (292% and 314% at 0.1 and 1 μM, respectively). At these two concentrations however, compounds 17a and 15b did not stimulate the proliferation of AR$^+$ cells, thus suggesting no androgenic activity. Sulfonamide 15b is thus a non-androgenic inhibitor with strong inhibitory activity (IC$_{50}$=5 nM) for the transformation of 4-dione into T in intact transfected HEK-293 cells overexpressing 17β-HSD3.

Additional 17β-HSD3 inhibitors were prepared as illustrated hereinbelow in Schemes 18-21.

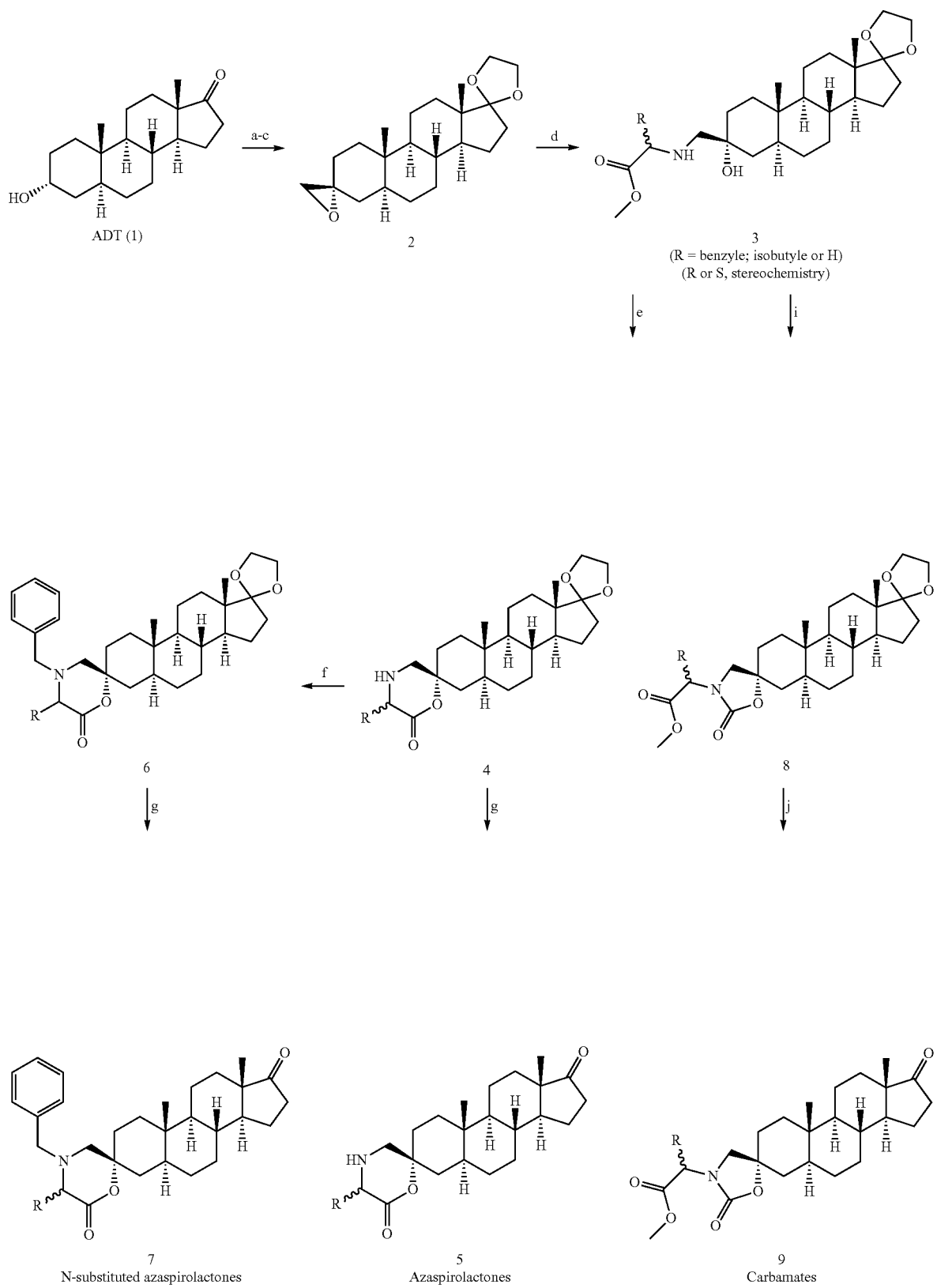

Scheme 19
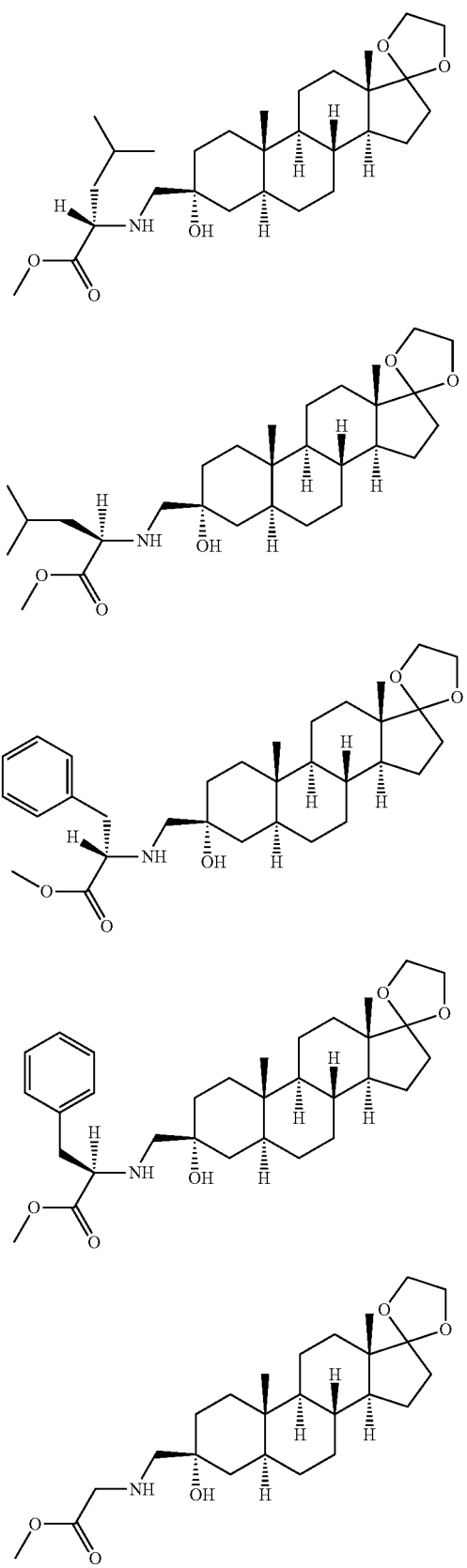
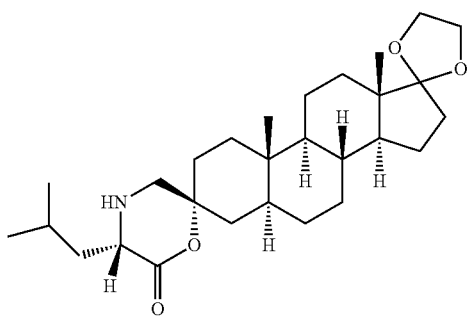
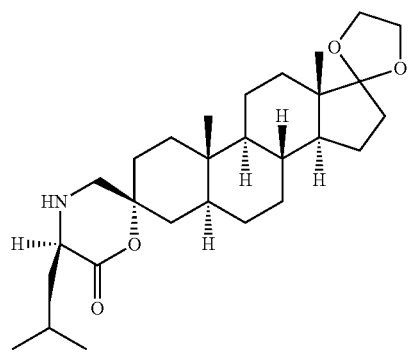
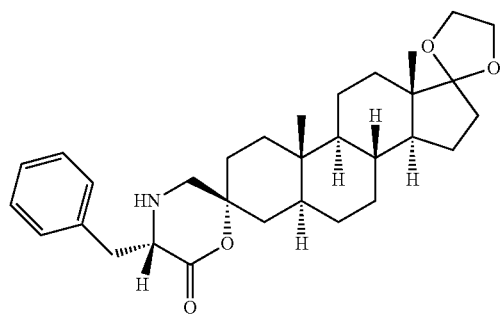
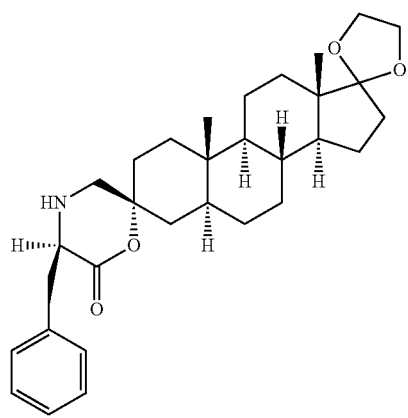

4E 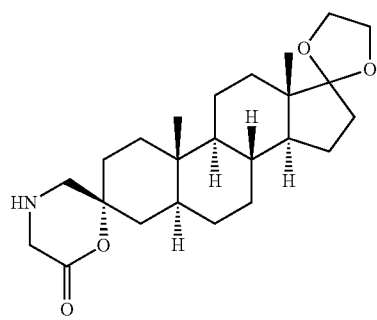
5D 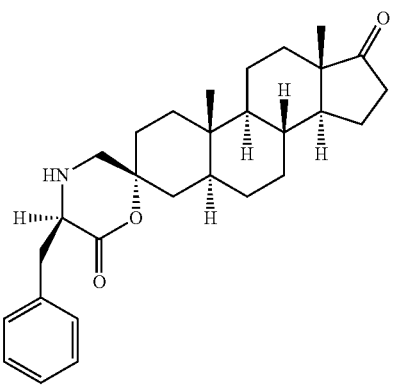
Scheme 20
5A 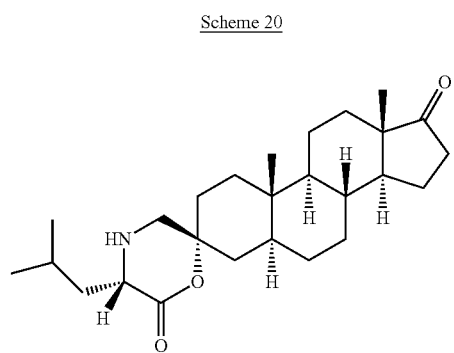
5E 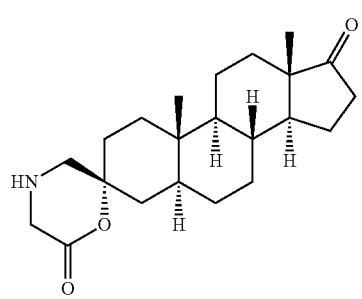
5B 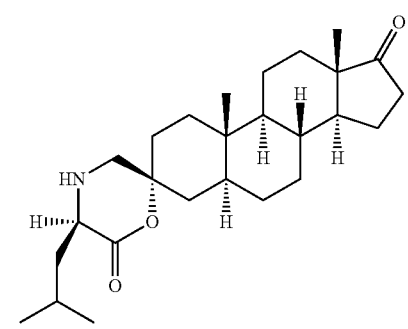
6A 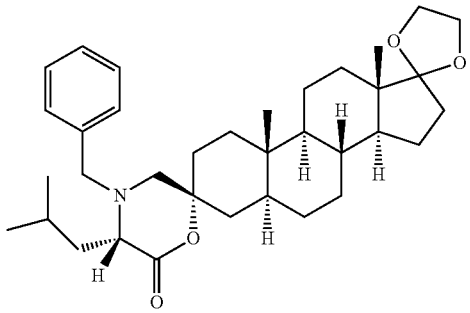
5C 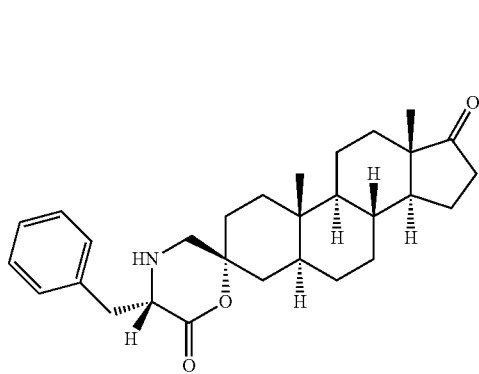
6B 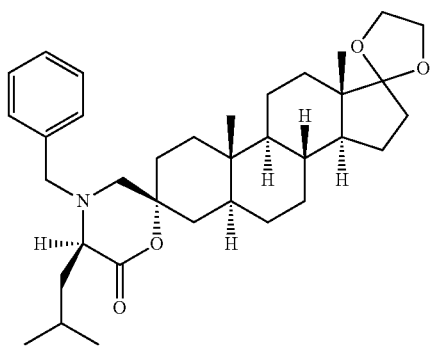

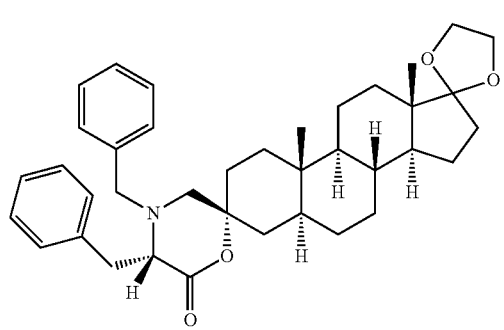
6C
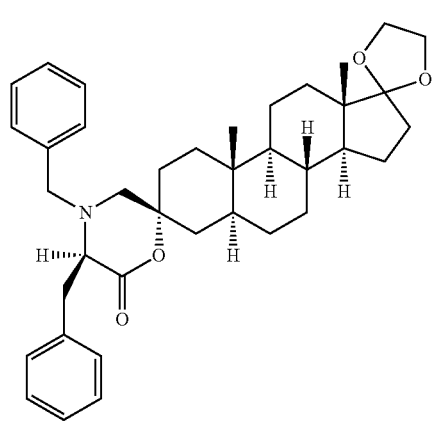
6D
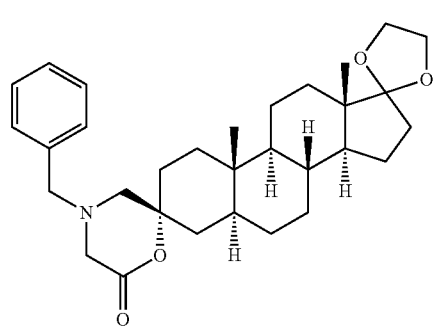
6E
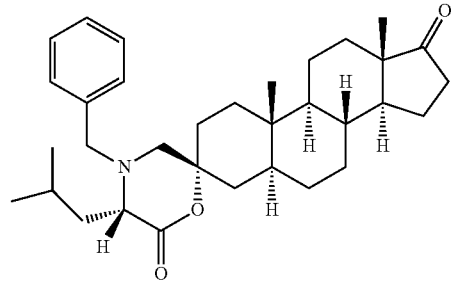
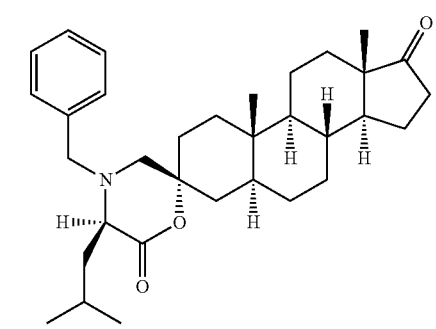
7B
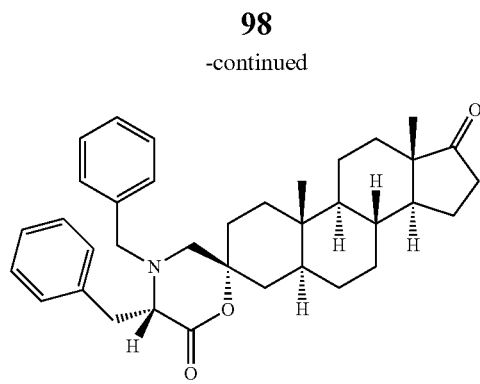
7C
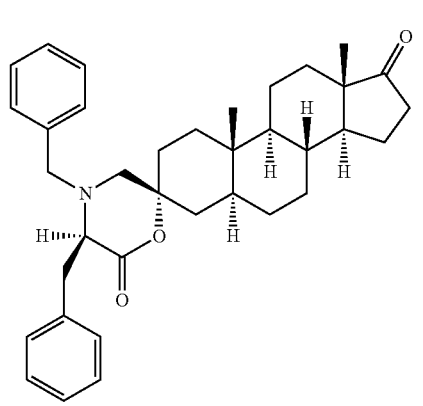
7D
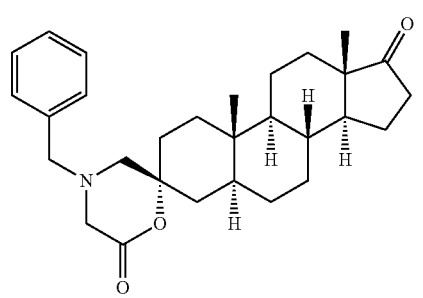
7E
Scheme 21
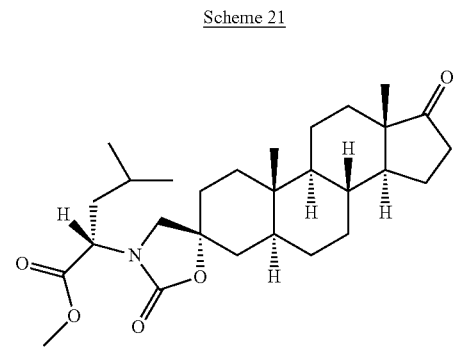
9A -continued

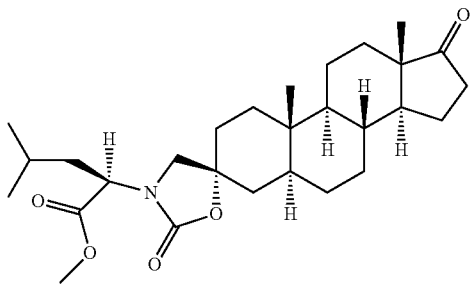

9B

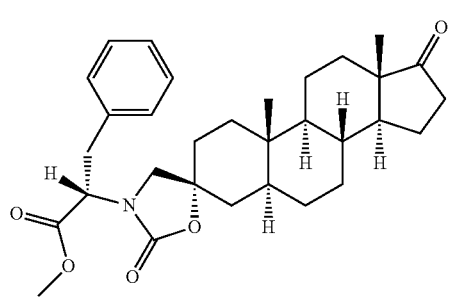

9C

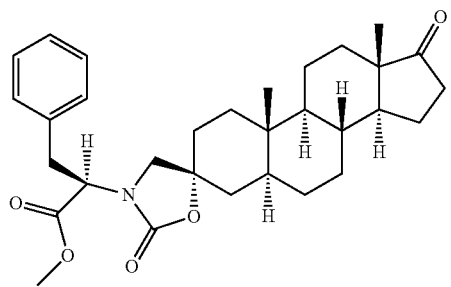

9D

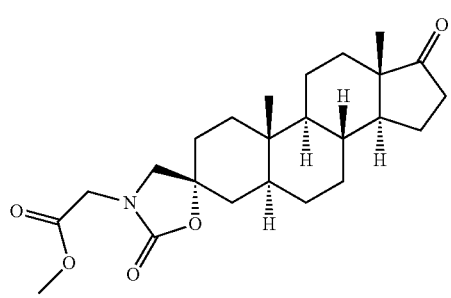

9E

EXPERIMENTAL

Materials, Methods, Synthesis and Characterization

Chemical reagents were purchased from Sigma-Aldrich Canada Ltd. (Oakville, ON, Canada). The usual solvents were obtained from Fisher Scientific (Montréal, QC, Canada) and were used as received. Anhydrous dichloromethane (DCM), dimethylformamide (DMF) and tetrahydrofuran (THF) were obtained from Sigma-Aldrich. Thin-layer chromatography (TLC) and flash-column chromatography were performed on 0.20-mm silica gel 60 F254 plates and with Silicycle R10030B 230-400 mesh silica gel respectively (Québec, QC, Canada). Infrared spectra (IR) were recorded using a Perkin Elmer series 1600 FT-IR spectrometer (Norwalk, Conn.) and the significant bands reported in cm$^{-1}$. Nuclear magnetic resonance (NMR) spectra were recorded at 400 MHz for $^1$H and 100.6 MHz for $^{13}$C using a Bruker Avance 400 digital spectrometer (Billerica, Mass., USA). The chemical shifts (δ) were expressed in ppm and referenced to chloroform (7.26 and 77.0 ppm), acetone (2.06 and 29.24 ppm) or methanol (3.31 ppm and 49.0) for $^1$H and $^{13}$C NMR respectively. Low-resolution mass spectra (LRMS) were recorded using a PE Sciex API-150ex apparatus (Foster City, Calif., USA) equipped with a turbo ion-spray source and expressed in m/z. High-resolution mass spectra (HRMS) were provided by Pierre Audet at the Département de Chimie de l'Université Laval (Québec, QC, Canada). The purity of the compounds was determined by high-performance liquid chromatography (HPLC) (Waters Associates Milford, Mass., USA) equipped with a UV detector (207 nm) using Luna phenyl hexyl column (75×4.6 mm id, 3 μM, serial N°: 228048-2, 60 A°) or a Nova Pack C18 reverse-phase column (150 mm×3.0 mm id, 4 mM, 60A°) and a reverse phase column.

General Procedure for Synthesis of 3β-substituted-3α-hydroxy-androstan-17-one derivatives (7a-j)

To a solution of oxirane 6$^{50}$ (50 mg, 0.17 mmol) in anhydrous ethanol (3 mL) was added the appropriate amine (0.5 mmol) and the solution was stirred over a period of 5 h at 60° C. The solvent was subsequently evaporated and the resulting mixture dissolved in dichloromethane (10 mL) followed by the addition of methylisocyanate resin (300 mg, 1.8 mmol/g). The suspension was stirred over a period of 2 h and filtered to provide the corresponding crude amine product. The crude amine was purified by flash chromatography using EtOAc/hexanes (2:8) as the eluent system to provide the desired amines 7a-j. All compounds were characterized by $^1$H NMR and MS analyses. $^{13}$C NMR, HRMS and HPLC data were also collected for compound 7a.

(3α,5α)-3{[benzyl(ethyl)amino]methyl}3-hydroxy-androstan-17-one (7a)

(15 mg, 20%); $^1$H NMR (Acetone-d$_6$): 0.82 (s, 3H), 0.84 (s, 3H), 1.01 (t, J=7.1 Hz, 3H), 0.80-2.10 (m, 22H), 2.37 (dd, J$_1$=8.7 Hz, J$_2$=18.2 Hz, 1H), 2.45 (s, 2H), 2.52 (q, J=7.1 Hz, 2H), 3.74 (s, 2H), 7.23 (t, J=7.2 Hz, 1H), 7.32 (t, J=7.7 Hz, 2H), 7.39 (d, J=7.5 Hz, 2H); $^{13}$C NMR (CDCl$_3$): 11.3, 12.1, 13.8, 20.2, 21.8, 28.4, 30.8, 31.6, 32.9, 34.0, 35.1, 35.9 (2×), 39.8, 40.8, 47.8, 49.4, 51.4, 54.3, 60.8, 65.3, 70.0, 127.1, 128.4 (2×), 128.6 (2×), 139.5, 221.6; LRMS for C$_{29}$H$_{44}$NO$_2$ [M+H]$^+$ 438.2; HRMS calcd for C$_{29}$H$_{44}$NO$_2$ [M+H]$^+$ 438.3367. found 438.3374; HPLC purity=99.2% (RT=7.2 min; 96:4 MeOH/H$_2$O; isocratic).

(3α,5α)-3-{[benzyl(methyl)amino]methyl}-3-hydroxyandrostan-17-one (7b)

(29 mg, 41%); $^1$H NMR (Acetone-d$_6$): 0.82 (s, 3H), 0.84 (s, 3H), 0.80-2.10 (m, 22), 2.25 (s, 3H), 2.37 (dd, J$_1$=9.0 Hz, J$_2$=18.4 Hz, 1H), 2.41 (s, 2H), 3.63 (s, 2H), 7.24 (t, J=7.2 Hz, 1H), 7.32 (t, J=7.4 Hz, 2H), 7.37 (d, J=7.2 Hz, 2H); LRMS for C$_{28}$H$_{42}$NO$_2$ [M+H]$^+$ 424.2.

(3α,5α)-3-[(diethylamino)methyl]-3-hydroxyandrostan-17-one (7c)

(40 mg, 65%); $^1$H NMR (Acetone-d$_6$): 0.81 (s, 3H), 0.84 (s, 3H), 0.99 (t, J=7.1 Hz, 6H), 0.75-2.08 (m, 22H), 2.37 (s, 2H), 2.30 (dd, $J_1$=8.7 Hz, $J_{2=18.2}$ Hz, 1H), 2.58 (q, J=7.1 Hz, 4H); LRMS for $C_{24}H_{42}NO_2$ [M+H]$^+$ 376.2.

(3α,5α)-3-[(dibutylamino)methyl]-3-hydroxyandrostan-17-one (7d)

(16 mg, 24%); $^1$H NMR (Acetone-d$_6$): 0.81 (s, 3H), 0.84 (s, 3H), 0.91 (t, J=7.1 Hz, 6H), 0.80-2.10 (m, 30H), 2.32 (s, 2H), 2.37 (dd, $J_1$=8.7 Hz, $J_2$=18.1 Hz, 1H), 2.51 (t, J=7.4 Hz, 4H); LRMS for $C_{28}H_{50}NO_2$ [M+H]$^+$ 432.2.

(3α,5α)-3-hydroxy-3-(piperidin-1-ylmethyl)androstan-17-one (7e)

(25 mg, 39%); $^1$H NMR (Acetone-d$_6$): 0.81 (s, 3H), 0.84 (s, 3H), 0.75-2.09 (m, 28H), 2.18 (s, 2H), 2.37 (dd, $J_1$=8.6 Hz, $J_2$=18.2 Hz, 1H), 2.52 (broad s, 4H); LRMS for $C_{25}H_{42}NO_2$ [M+H]$^+$ 388.2.

(3α,5α)-3-[(4-benzylpiperidin-1-yl)methyl]-3-hydroxyandrostan-17-one (7f)

(34 mg, 43%); $^1$H NMR (Acetone-d$_6$): 0.81 (s, 3H), 0.84 (s, 3H), 0.75-2.10 (m, 27H), 2.20 (s and m, 4H), 2.37 (dd, $J_1$=8.7 Hz, $J_2$=18.2 Hz, 1H), 2.53 (d, J=6.9 Hz, 2H), 2.88 (broad d, J=11.4 Hz, 2H), 7.18 (d, J=6.7 Hz, 3H), 7.27 (t, J=7.4 Hz, 2H); LRMS for $C_{32}H_{48}NO_2$ [M+H]$^+$ 478.1.

(3α,5α)-3-(1,4'-bipiperidin-1'-ylmethyl)-3-hydroxyandrostan-17-one (7g)

(28 mg, 44%); $^1$H NMR (Acetone-d$_6$): 0.81 (s, 3H), 0.84 (s, 3H), 0.75-2.15 (m, 33H), 2.21 (s, 2H), 2.25 (m, 2H), 2.38 (dd, $J_1$=8.8 Hz, $J_2$=18.2 Hz, 1H), 2.47 (t, J=4.9 Hz, 4H), 2.93 (d, J=11.5 Hz, 2H); LRMS for $C_{30}H_{51}N_2O_2$ [M+H]$^+$ 471.3.

(3α,5α)-3-hydroxy-3-[(4-methylpiperazin-1-yl)methyl]androstan-17-one (7h)

(29 mg, 43%): $^1$H NMR (Acetone-d$_6$): 0.81 (s, 3H), 0.84 (s, 3H), 0.75-2.10 (m, 22H), 2.16 (s, 3H), 2.23 (s, 2H), 2.34 (broad m, 4H), 2.37 (dd, $J_1$=8.7 Hz, $J_2$=18.2 Hz, 1H), 2.58 (broad s, 4H); LRMS for $C_{25}H_{43}N_2O_2$ [M+H]$^+$ 403.2.

(3α,5α)-3-hydroxy-3-[(4-phenylpiperazin-1-yl)methyl]androstan-17-one (7j)

(54 mg, 70%); $^1$H NMR (Acetone-d$_6$): 0.83 (s, 3H), 0.84 (s, 3H), 0.75-2.10 (m, 21H), 2.32 (s, 2H), 2.37 (dd, $J_1$=8.7 Hz, J=18.2 Hz, 1H), 2.75 (m, 4H), 3.18 (m, 4H), 6.77 (t, J=7.3 Hz, 1H), 6.94 (d, J=8.6 Hz, 2H), 7.21 (d, J=8.7 Hz, 2H); LRMS for $C_{30}H_{45}N_2O_2$ [M+H]$^+$ 465.0.

(3α,5α)-3-[(4-benzylpiperazin-1-yl)methyl]-3-hydroxyandrostan-17-one (7j)

(60 mg, 76%): $^1$H NMR (Acetone-d$_6$): 0.81 (s, 3H), 0.84 (s, 3H), 0.75-2.10 (m, 22H), 2.24 (s, 2H), 2.37 (dd, $J_1$=8.8 Hz, $J_2$=18.3 Hz, 1H), 2.43 (broad m, 4H), 2.61 (s, 4H), 3.47 (s, 2H), 7.23 (m, 1H), 7.32 (m, 4H); LRMS for $C_{31}H_{47}N_2O_2$ [M+H]$^+$ 478.9.

Synthesis of Intermediates 8 and 9

To a solution of oxirane 6$^{50}$ (1.0 g, 3.3 mmol) in anhydrous ethanol (15 mL) was added either piperazine (573 mg, 6.7 mmol) or trans-2,5-dimethylpiperazine (755 mg, 6.7 mmol). The solution was stirred over a period of 5 h at 60° C. The resulting solution was subsequently poured into water and extracted three times with EtOAc. The combined organic layers were washed with brine, dried with MgSO$_4$, filtered and evaporated under reduced pressure to provide either crude compound 8 or 9. Pure compounds were obtained following flash chromatography using EtOAc/hexanes (1:1) as the eluent system.

(3α,5α)-3-hydroxy-3-(piperazin-1-ylmethyl)androstan-17-one (8)

(750 mg, 61%); $^1$H NMR (MeOH-d$_4$): 0.84 (s, 3H), 0.89 (s, 3H), 1.01 (t, J=7.1 Hz, 3H), 0.80-2.15 (m, 20H), 2.25 (s, 2H), 2.45 (dd, $J_1$=8.6 Hz, $J_2$=19.2 Hz, 1H), 2.58 (broad s, 4H), 2.84 (t, J=4.8 Hz, 4H).

(3α,5α)-3-{[(2ξ,5ξ)-2,5-dimethylpiperazin-1-yl]methyl}-3-hydroxyandrostan-17-one (9)

(650 mg, 53%); $^1$H NMR (CDCl$_3$): 0.77 (s, 3H), 0.85 (s, 3H), 0.99 (d, J=6.0 Hz, 3H), 1.00 (d, J=6.1 Hz, 3H), 0.75-1.85 (m, 22H), 1.94 (m, 1H), 2.04 (m, 3H), 2.25 (m, 2H), 2.43 (dd, $J_1$=8.6 Hz, $J_2$=18.9 Hz, 1H), 2.54 (t, 1H), 2.61 (d, J=13.9 Hz, 1H), 2.90 (m, 3H); LRMS for $C_{26}H_{45}N_2O_2$ [M+H]$^+$ 417.3.

General Procedure for the Synthesis of Amines 10a-j and 11a-j

To a solution of compound 8 (25 mg, 0.06 mmol) or compound 9 (30 mg, 0.07 mmol) in anhydrous dichloromethane (5 mL) was added triethylamine (24 mg, 0.24 mmol, 33 µL) and the appropriate benzyl bromide (0.12 mmol). The mixture was stirred overnight and the resulting solution evaporated and purified by flash chromatography using EtOAc/hexanes (3:7) as the eluant system to provide benzylamines 10a-j and 11a-j. All compounds were characterized by $^1$H NMR and MS analyses. $^{13}$C NMR, HRMS and HPLC data were also collected for compounds 10a and 11a.

(3α,5α)-3-hydroxy-3-({4-[3-(trifluoromethyl)benzyl]piperazin-1-yl}methyl)androstan-17-one (10a)

(31 mg, 97%); $^1$H NMR (CDCl$_3$): 0.76 (s, 3H), 0.86 (s, 3H), 0.75-2.10 (m, 22H), 2.27 (s, 2H), 2.44 (broad m, 5H), 2.66 (broad s, 4H), 3.54 (s, 2H), 7.42 (t, J=7.6 Hz, 1H), 7.50 (broad d, J=7.5 Hz, 2H), 7.58 (s, 1H); $^{13}$C NMR (CDCl$_3$): 11.2, 13.8, 20.2, 21.8, 28.3, 30.8, 31.5, 32.7, 33.8, 35.1, 35.8, 35.9, 39.6, 40.7, 47.8, 51.4, 54.2, 55.7 (4×), 62.3, 69.0, 70.1, 124.0 (q, $J_{C-C-C-F}$=3.6 Hz), 124.2 (q, $J_{C-F}$=272 Hz), 125.6 (q, $J_{C-C-C-F}$=3.8 Hz), 128.7, 130.6 (q, $J_{C-C-F}$=32 Hz), 132.4, 139.2, 221.5; LRMS for $C_{32}H_{46}F_3N_2O_2$ [M+H]$^+$ 547.3; HRMS calcd for $C_{32}H_{46}F_3N_2O_2$ [M+H]$^+$ 547.3506. found 547.3510; HPLC purity: 97.2% (RT=5.5 min; 96:4 MeOH/H$_2$O; isocratic).

(3α,5α)-3-hydroxy-3-({4-[2-(trifluoromethyl)benzyl]piperazin-1-yl}methyl)androstan-17-one (10b)

(33 mg, 45%); $^1$H NMR (CDCl$_3$): 0.76 (s, 3H), 0.86 (s, 3H), 0.80-2.10 (m, 22H), 2.27 (s, 2H), 2.43 (dd, $J_1$=8.7 Hz, $J_2$=19.2 Hz, 1H), 2.50 (broad s, 4H), 2.66 (broad, s, 4H), 3.65 (s, 2H), 7.33 (t, J=7.7 Hz, 1H), 7.51 (d, J=6.7 Hz, 1H), 7.62 (d, J=7.8 Hz, 1H), 7.77 (d, J=7.7 Hz, 1H); LRMS for $C_{32}H_{46}F_3N_2O_2$ [M+H]$^+$ 547.1.

(3α,5α)-3-hydroxy-3-({4-[4-(trifluoromethyl)benzyl]piperazin-1-yl}methyl)androstan-17-one (10c)

(32 mg, 97%); $^1$H NMR (CDCl$_3$): 0.76 (s, 3H), 0.86 (s, 3H), 0.80-2.10 (m, 22H), 2.27 (s, 2H), 2.45 (broad m, 5H), 2.65 (broad s, 4H), 3.54 (s, 2H); 7.44 (d, J=8.0 Hz, 2H), 7.57 (d, J=8.0 Hz, 2H); LRMS for $C_{32}H_{46}F_3N_2O_2$ [M+H]+ 547.2.

(3α,5α)-3-hydroxy-3-[(4-{3-[(trifluoromethyl)sulfanyl]benzyl}piperazin-1-yl)methyl]androstan-17-one (10d)

(25 mg, 71%); 1H NMR (CDCl3): 0.76 (s, 3H), 0.86 (s, 3H), 0.78-2.10 (m, 22H), 2.27 (s, 2H), 2.45 (broad m, 5H), 2.65 (broad s, 4H), 3.52 (s, 2H), 7.37 (t, J=7.6 Hz, 1H), 7.43 (d, J=7.7 Hz, 1H), 7.54 (d, J=7.7 Hz, 1H), 7.62 (s, 1H); LRMS for $C_{32}H_{46}F_3N_2O_2S$ [M+H]+ 579.3.

(3α,5α)-3-{[4-(3-chlorobenzyl)piperazin-1-yl]methyl}-3-hydroxyandrostan-17-one (10e)

(31 mg, 94%); 1H NMR (CDCl3): 0.76 (s, 3H), 0.86 (s, 3H), 0.80-2.10 (m, 22H), 2.27 (s, 2H), 2.43 (broad m, 5H), 2.65 (broad s, 4H), 3.46 (s, 2H); 7.19 (m, 1H), 7.23 (s, 2H), 7.33 (s, 1H); LRMS for $C_{31}H_{46}ClN_2O_2$ [M+H]+ 513.3.

(3α,5α)-3-hydroxy-3-{[4-(3-methoxybenzyl)piperazin-1-yl]methyl}androstan-17-one (10f)

(21 mg, 64%); 1H NMR (CDCl3): 0.76 (s, 3H), 0.85 (s, 3H), 0.78-2.10 (m, 22H), 2.26 (s, 2H), 2.43 (broad m, 5H), 2.65 (broad s, 4H), 3.48 (s, 2H), 3.81 (s, 3H), 6.80 (d, J=7.5 Hz, 1H), 6.88 (s, 1H), 6.89 (d, J=7.8 Hz, 1H), 7.23 (t, J=8.0 Hz, 1H); LRMS for $C_{32}H_{49}N_2O_3$ [M+H]+ 509.3.

(3α,5α)-3-hydroxy-3-{[4-(pyridin-3-ylmethyl)piperazin-1-yl]methyl}androstan-17-one (10g)

(20 mg, 65%); 1H NMR (CDCl3): 0.76 (s, 3H), 0.85 (s, 3H), 0.78-2.10 (m, 22H), 2.27 (s, 2H), 2.43 (broad m, 5H), 2.65 (broad s, 4H), 3.51 (s, 2H), 7.24 (t, J=4.9 Hz, 1H), 7.65 (d, J=7.8 Hz, 1H), 8.51 (dd, J=1.3 Hz, J2=4.8 Hz, 1H), 8.54 (d, J=1.4 Hz, 1H); LRMS for $C_{30}H_{46}N_3O_2$ [M+H]+ 480.2.

(3α,5α)-3-({4-[2,5-bis(trifluoromethyl)benzyl]piperazin-1-yl}methyl)-3-hydroxyandrostan-17-one (10h)

(27 mg, 73%); 1H NMR (CDCl3): 0.77 (s, 3H), 0.86 (s, 3H), 0.78-2.10 (m, 22H), 2.29 (s, 2H), 2.43 (dd, J1=8.7 Hz, J2=19.3 Hz, 1H), 2.51 (broad s, 4H), 2.68 (broad s, 4H), 3.69 (s, 2H), 7.59 (d, J=8.1 Hz, 1H), 7.75 (d, J=8.2 Hz, 1H), 8.12 (s, 1H); LRMS for $C_{33}H_{45}F_6N_2O_2$ [M+H]+ 615.5.

(3α,5α)-3-({4-[2,4-bis(trifluoromethyl)benzyl]piperazin-1-yl}methyl)-3-hydroxyandrostan-17-one (10i)

(27 mg, 73%); 1H NMR (CDCl3): 0.77 (s, 3H), 0.86 (s, 3H), 0.83-2.10 (m, 22H), 2.28 (s, 2H), 2.43 (dd, J1=8.5 Hz, J2=19.1 Hz, 1H), 2.51 (broad s, 4H), 2.67 (broad s, 4H), 3.70 (s, 2H), 7.77 (d, J=8.3 Hz, 1H), 7.88 (s, 1H), 7.98 (d, J=8.2 Hz, 1H); LRMS for $C_{33}H_{45}F_6N_2O_2$ [M+H]+ 615.2.

(3α,5α)-3-({4-[3,5-bis(trifluoromethyl)benzyl]piperazin-1-yl}methyl)-3-hydroxyandrostan-17-one (10j)

(29 mg, 78%); 1H NMR (CDCl3): 0.77 (s, 3H), 0.86 (s, 3H), 0.80-2.10 (m, 22H), 2.28 (s, 2H), 2.43 (broad m, 5H), 2.67 (broad s, 4H), 3.59 (s, 2H), 7.77 (s, 1H), 7.79 (s, 2H); LRMS for $C_{33}H_{45}F_6N_2O_2$ [M+H]+ 615.5.

(3α,5α)-3-({[(2ξ,5ξ)-2,5-dimethyl-4-[3-(trifluoromethyl)benzyl]piperazin-1-yl}methyl)-3-hydroxyandrostan-17-one (11a)

(25 mg, 71%); 1H NMR (CDCl3): 0.77 (s, 3H), 0.86 (s, 3H), 0.92 (d, J=6.2 Hz, 3H), 1.10 (d, J=6.0 Hz, 3H), 0.80-2.10 (m, 23H), 2.32 (m, 6H), 2.91 (d, J=11.1 Hz, 1H), 3.11 (d, J=13.7 Hz, 1H), 3.22 (d, J=16.1 Hz, 1H), 4.07 (d, J=13.7 Hz, 1H), 7.43 (m, 1H), 7.51 (d, J=7.8 Hz, 2H), 7.58 (s, 1H); 13C NMR (CDCl3): 11.3, 13.8 (3×), 20.2, 21.8, 28.3, 30.8, 31.6, 32.7, 33.9, 35.1, 35.9 (2×), 39.4, 40.8, 47.8, 51.4, 54.3, 55.8, 56.3, 57.5, 63.8, 69.4, 123.7 (q, $J_{C-C-C-F}$=3.6 Hz), 125.0 (q, $J_{C-F}$=273 Hz), 125.4 (q, $J_{C-C-C-F}$=3.6 Hz), 128.6, 130.5 (q, $J_{C-C-F}$=32 Hz), 132.1, 140.3, 221.6; LRMS for $C_{34}H_{50}F_3N_2O_2$ [M+H]+ 575.2; HRMS calcd for $C_{34}H_{50}F_3N_2O_2$ [M+H]+ 575.3819. found 575.3826; HPLC purity: 99.0% (RT=6.6 min; 75:25 to 5:95 MeOH/H2O isocratic gradient).

(3α,5α)-3-({[(2ξ,5ξ)-2,5-dimethyl-4-[2-(trifluoromethyl)benzyl]piperazin-1-yl}methyl)-3-hydroxyandrostan-17-one (11b)

(17 mg, 49%); 1H NMR (CDCl3): 0.78 (s, 3H), 0.86 (s, 3H), 0.93 (d, J=6.2 Hz, 3H), 1.05 (d, J=6.0 Hz, 3H), 0.75-2.10 (m, 23H), 2.33-2.60 (m, 6H), 2.93 (d, J=11.1 Hz, 1H), 3.23 (broad s, 1H), 3.31 (d, J=15.1 Hz, 1H), 4.07 (d, J=14.8 Hz, 1H), 7.31 (t, J=7.7 Hz, 1H), 7.51 (t, J=7.4 Hz, 1H), 7.61 (d, J=7.9 Hz, 1H), 7.87 (d, J=7.8 Hz, 1H); LRMS calcd for $C_{34}H_{50}F_3N_2O_2$ [M+H]+ 575.3.

(3α,5α)-3-({[(2ξ,5ξ)-2,5-dimethyl-4-[4-(trifluoromethyl)benzyl]piperazin-1-yl}methyl)-3-hydroxyandrostan-17-one (11c)

(22 mg, 63%); 1H NMR (CDCl3): 0.77 (s, 3H), 0.86 (s, 3H), 0.92 (d, J=6.2 Hz, 3H), 1.10 (d, J=6.0 Hz, 3H), 0.75-2.15 (m, 24H), 2.30-2.60 (m, 6H), 2.91 (d, J=11.5 Hz, 1H), 3.11 (d, J=13.6 Hz, 1H), 3.20 (broad s, 1H), 4.07 (d, 1H, J=13.9 Hz, 1H), 7.37 (d, J=7.7 Hz, 1H), 7.43 (d, J=8.0 Hz, 1H), 7.57 (d, J=8.1 Hz, 1H); LRMS for $C_{34}H_{50}F_3N_2O_2$ [M+H]+ 575.2.

(3α,5α)-3-{[(2ξ,5ξ)-2,5-dimethyl-4-{3-[(trifluoromethyl)sulfanyl]benzyl}piperazin-1-yl]methyl}-3-hydroxyandrostan-17-one (11d)

(15 mg, 41%); 1H NMR (CDCl3): 0.77 (s, 3H), 0.86 (s, 3H), 0.92 (d, J=6.2 Hz, 3H), 1.10 (d, J=6.0 Hz, 3H), 0.75-2.10 (m, 23H), 2.30-2.60 (m, 6H), 2.91 (d, J=10.5 Hz, 1H), 3.10 (d, J=13.2 Hz, 1H), 3.21 (d, J=16.2 Hz, 1H), 4.04 (d, J=13.1 Hz, 1H), 7.36 (t, J=7.7 Hz, 1H), 7.43 (d, J=7.7 Hz, 1H), 7.53 (d, J=8.5 Hz, 1H), 7.62 (s, 1H); LRMS for $C_{34}H_{50}F_3N_2O_2S$ [M+H]+ 607.2.

(3α,5α)-3-{[(2ξ,5ξ)-4-(3-chlorobenzyl)-2,5-dimethylpiperazin-1-yl]methyl}-3-hydroxyandrostan-17-one (11e)

(12 mg, 37%); 1H NMR (CDCl3): 0.77 (s, 3H), 0.86 (s, 3H), 0.93 (d, J=6.2 Hz, 3H), 1.09 (d, J=6.0 Hz, 3H), 0.75-2.10 (m, 23H), 2.30-2.62 (m, 6H), 2.89 (d, J=11.2 Hz, 1H), 3.03 (d, J=13.4 Hz, 1H), 3.22 (broad s, 1H), 4.00 (d, J=13.3 Hz, 1H), 7.18 (t, J=7.2 Hz, 1H), 7.23 (s, 2H), 7.33 (s, 1H); LRMS for $C_{33}H_{50}{}^{35}ClN_2O_2$ [M+H]$^+$ 541.3.

(3α,5α)-3-hydroxy-3-{[(2ξ,5ξ)-4-(3-methoxybenzyl)-2,5-dimethylpiperazin-1-yl]methyl}androstan-17-one (11f)

(14 mg, 44%); $^1$H NMR (CDCl$_3$): 0.77 (s, 3H), 0.86 (s, 3H), 0.92 (d, J=6.0 Hz, 3H), 1.11 (d, J=5.3 Hz, 3H), 0.75-2.10 (m, 24H), 2.30-2.80 (m, 6H), 2.89 (d, J=10.2 Hz, 1H), 3.07 (d J=13.2 Hz, 1H), 3.81 (s, 3H), 4.01 (d, J=12.8 Hz, 1H), 6.79 (m, 1H), 6.89 (m, 2H), 7.22 (m, 1H); LRMS for $C_{34}H_{53}N_2O_3$ [M+H]$^+$ 537.4.

(3α,5α)-3-{[(2ξ,5ξ)-2,5-dimethyl-4-(pyridin-3-ylmethyl)piperazin-1-yl]methyl}-3-hydroxyandrostan-17-one (11g)

(10 mg, 33%); $^1$H NMR (CDCl$_3$): 0.77 (s, 3H), 0.86 (s, 3H), 0.92 (d, J=6.0 Hz, 3H), 1.12 (d, J=5.4 Hz, 3H), 0.75-2.10 (m, 22H), 2.30-2.68 (m, 7H), 2.90 (d, J=11.0 Hz, 1H), 3.10 (m, 2H), 4.02 (d, J=13.2 Hz, 1H), 7.25 (s, 1H), 7.64 (m, 1H), 8.52 (m, 2H); LRMS for $C_{32}H_{50}N_3O_2$ [M+H]$^+$ 508.3.

(3α,5α)-3-({(2ξ,5ξ)-4-[2,5-bis(trifluoromethyl)benzyl]-2,5-dimethylpiperazin-1-yl}methyl)-3-hydroxyandrostan-17-one (11h)

(46 mg, 98%); $^1$H NMR (CDCl$_3$): 0.78 (s, 3H), 0.86 (s, 3H), 0.95 (d, J=6.1 Hz, 3H), 1.03 (d, J=6.0 Hz, 3H), 0.75-2.10 (m, 23H), 2.35-2.60 (m, 6H), 2.95 (d, J=11.6 Hz, 1H), 3.18 (broad s, 1H), 3.40 (d, J=15.8 Hz, 1H), 4.06 (d, J=15.8 Hz, 1H), 7.58 (d, J=8.1 Hz, 1H), 7.74 (d, J=8.2 Hz, 1H), 8.22 (s, 1H); LRMS for $C_{35}H_{49}F_6N_2O_2$ [M+H]$^+$ 643.3.

(3α,5α)-3-({(2ξ,5ξ)-4-[2,4-bis(trifluoromethyl)benzyl]-2,5-dimethylpiperazin-1-yl}methyl)-3-hydroxyandrostan-17-one (11i)

(46 mg, 98%); $^1$H NMR (CDCl$_3$): 0.78 (s, 3H), 0.86 (s, 3H), 0.94 (d, J=6.1 Hz, 3H), 1.03 (d, J=6.1 Hz, 3H), 0.75-2.10 (m, 23H), 2.32-2.60 (m, 6H), 2.94 (d, J=11.0 Hz, 1H), 3.13 (broad s, 1H), 3.39 (d, J=15.8 Hz, 1H), 4.08 (d, J=15.4 Hz, 1H), 7.76 (d, J=8.2 Hz, 1H), 7.86 (s, 1H), 8.08 (d, J=8.2 Hz, 1H); LRMS for $C_{35}H_{49}F_6N_2O_2$ [M+H]$^+$ 643.3.

(3α,5α)-3-({(2ξ,5ξ)-4-[3,5-bis(trifluoromethyl)benzyl]-2,5-dimethylpiperazin-1-yl}methyl)-3-hydroxyandrostan-17-one (11j)

(20 mg, 43%); $^1$H NMR (CDCl$_3$): 0.78 (s, 3H), 0.86 (s, 3H), 0.94 (d, J=6.1 Hz, 3H), 1.09 (d, J=6.1 Hz, 3H), 0.75-2.12 (m, 24H), 2.35-2.57 (m, 6H), 2.93 (d, J=11.4 Hz, 1H), 3.18 (d, J=11.4 Hz, 1H), 4.09 (d, J=13.3 Hz, 1H), 7.76 (s, 1H), 7.80 (s, 2H); LRMS for $C_{35}H_{49}F_6N_2O_2$ [M+H]$^+$ 643.4.

General Procedure for Synthesis of Amides 12a-e and 13a-d

To a solution of compound 8 (40 mg, 0.1 mmol) or compound 9 (25 mg, 0.06 mmol) in anhydrous DCM (3 mL) was added triethylamine (4.0 eq) and the appropriate acyl chloride (2.0 eq). The solution was then stirred over a period of 3 h at room temperature. The resulting solution was concentrated and purified by flash chromatography using EtOAc/hexanes (7:3 to 9:1) as to eluant system to provide the corresponding amides 12a-e and 13a-d. All compounds were characterized by $^1$H NMR and MS analyses. $^{13}$C NMR, HRMS and HPLC data were also collected for compounds 12a, 12c and 13a.

(3α,5α)-3-hydroxy-3-{[4-(phenylcarbonyl)piperazin-1-yl]methyl}androstan-17-one (12a)

(33 mg, 64%); $^1$H NMR (CDCl$_3$): 0.77 (s, 3H), 0.86 (s, 3H), 0.80-2.12 (m, 22H), 2.31 (s, 2H), 2.43 (dd, J$_1$=8.7 Hz, J$_2$=19.2 Hz, 1H), 2.57 and 2.70 (broad 2s, 4H), 3.43 (broad s, 2H), 3.79 (broad s, 2H), 7.40 (m, 5H); $^{13}$C NMR (CDCl$_3$) δ 11.2, 13.8, 20.2, 21.7, 28.3, 30.8, 31.5, 32.4, 33.6, 35.0, 35.8, 35.9, 39.3, 40.6, 47.8, 51.4, 54.1, 55.4 (2×), 55.7 (2×), 69.1, 70.5, 127.0 (2×), 128.5 (2×), 129.8, 135.5, 170.3, 221.5; LRMS for $C_{31}H_{45}N_2O_3$ [M+H]$^+$ 493.0; HRMS calcd for $C_{31}H_{45}N_2O_3$ [M+H]$^+$ 493.3425. found 493.3433; HPLC purity: 94.8% (RT=10.2 min; 75:25 to 5:95 MeOH/H$_2$O isocratic).

(3α,5α)-3-{[4-(cyclohexylcarbonyl)piperazin-1-yl]methyl}-3-hydroxyandrostan-17-one (12b)

(30 mg, 56%); $^1$H NMR (CDCl$_3$): 0.77 (s, 3H), 0.86 (s, 3H), 0.80-2.12 (m, 21H), 2.29 (s, 2H), 2.43 (m, 2H), 2.60 (m, 4H), 2.92 (broad s, 1H), 3.49 (broad s, 2H), 3.61 (broad s, 2H); LRMS for $C_{31}H_{51}N_2O_3$ [M+H]$^+$ 499.3.

(3α,5α)-3-hydroxy-3-[(4-{[2-(trifluoromethyl)phenyl]carbonyl}-piperazin-1-yl)methyl]androstan-17-one (12c)

(30 mg, 54%); $^1$H NMR (CDCl$_3$): 0.76 (s, 3H), 0.86 (s, 3H), 0.80-2.12 (m, 22H), 2.30 (s, 2H), 2.43 (dd, J$_1$=8.7 Hz, J$_2$=19.1 Hz, 1H), 2.53 (m, 2H), 2.70 (broad s, 2H), 3.18 (t, J=5.0 Hz, 2H), 3.82 (broad m, 2H), 7.32 (d, J=7.4 Hz, 1H), 7.52 (t, J=7.6 Hz, 1H), 7.60 (t, J=7.5 Hz, 1H), 7.71 (d, J=7.8 Hz, 1H); $^{13}$C NMR (CDCl$_3$): 11.2, 13.8, 20.2, 21.7, 28.3, 30.8, 31.5, 32.3, 33.6, 35.1, 35.8, 35.9, 39.3, 40.6, 41.9, 47.3, 47.8, 51.4, 54.1, 55.1, 55.2, 69.0, 70.6, 123.6 (q, J$_{C-F}$=274 Hz), 126.6 (q, J$_{C-C-C-F}$=4.4 Hz), 126.7 (q, J$_{C-C-F}$=32 Hz), 127.2, 129.2, 132.2, 134.7, 167.3, 221.4; LRMS for $C_{32}H_{44}F_3N_2O_3$[M+H]$^+$ 561.1; HRMS calcd for $C_{32}H_{44}F_3N_2O_3$[M+H]$^+$ 561.3299. found 561.3304; HPLC purity: 96.7% (RT=10.7 min; 75:25 to 5:95 MeOH/H$_2$O isocratic).

(3α,5α)-3-hydroxy-3-[(4-{[3-(trifluoromethyl)phenyl]carbonyl}piperazin-1-yl)methyl]androstan-17-one (12d)

(42 mg, 69%); $^1$H NMR (CDCl$_3$): 0.77 (s, 3H), 0.86 (s, 3H), 0.80-2.12 (m, 22H), 2.32 (s, 2H), 2.43 (dd, J$_1$=8.7 Hz, J$_2$=19.3 Hz, 1H), 2.59 (broad s, 2H), 2.72 (broad s, 2H), 3.41 (broad s, 2H), 3.80 (broad s, 2H), 7.55 (m, 2H), 7.67 (s, 2H); LRMS for $C_{32}H_{44}F_3N_2O_3$[M+H]$^+$ 561.4.

(3α,5α)-3-hydroxy-3-[(4-{[4-(trifluoromethyl)phenyl]carbonyl}piperazin-1-yl)methyl]androstan-17-one (12e)

(44 mg, 72%); $^1$H NMR (CDCl$_3$): 0.77 (s, 3H), 0.86 (s, 3H), 0.80-2.10 (m, 22H), 2.32 (s, 2H), 2.43 (dd, J=8.7 Hz, J$_2$=19.3 Hz, 1H), 2.57 (broad s, 2H), 2.73 (broad s, 2H), 3.39 (broad s, 2H), 3.80 (broad s, 2H), 7.51 (d, J=8.0 Hz, 2H), 7.68 (d, J=8.1 Hz, 2H); LRMS for $C_{32}H_{44}F_3N_2O_3$[M+H]$^+$ 561.2.

(3α,5α)-3-{[(2ξ,5ξ)-2,5-dimethyl-4-(phenylcarbonyl)piperazin-1-yl]methyl}-3-hydroxyandrostan-17-one (13a)

(25 mg, 31%); $^1$H NMR (CDCl$_3$): 0.77 (s, 3H), 0.86 (s, 3H), 1.27 (m, 3H), 1.41 (d, J=6.8 Hz, 3H), 0.75-2.00 (m,

23H), 2.05-2.17 (m, 2H), 2.34-2.47 (m, 3H), 2.90 (broad s, 1H), 3.06 (d, J=8.8 Hz, 1H), 3.50 (broad s, 1H), 7.30-7.42 (m, 5H); $^{13}$C NMR (CDCl$_3$) δ 8.6, 11.2, 13.8 (2×), 20.2, 21.7, 28.3, 30.8, 31.5, 32.5, 33.8, 35.0, 35.8, 35.9, 39.4, 40.7, 47.8, 51.4, 51.7, 54.0, 54.2, 55.1 (2×), 65.8, 70.9, 126.5, 128.5 (2×), 129.3 (2×), 136.4, 171.2, 221.5; LRMS for C$_{33}$H$_{49}$N$_2$O$_3$ [M+H]$^+$ 521.4; HRMS calcd for C$_{33}$H$_{49}$N$_2$O$_3$ [M+H]$^+$ 521.3738, found 521.3745; HPLC purity: 96.4% (RT=12.1 min; 75:25 to 5:95 MeOH/H$_2$O isocratic).

(3α,5α)-3-{[(2ξ,5ξ)-4-(cyclohexylcarbonyl)-2,5-dimethylpiperazin-1-yl]methyl}-3-hydroxyandrostan-17-one (13b)

(14 mg, 44%); $^1$H NMR (CDCl$_3$): 0.77 (s, 3H), 0.86 (s, 3H), 1.27 (m, 6H), 0.80-2.00 (m, 22H), 2.02-2.18 (m, 2H), 2.34-2.47 (m, 3H), 2.90-3.15 (broad m, 3H), 3.46 and 3.60 (2d, J=11.8 Hz, 1H), 4.02, 4.28 and 4.70 (3m, 1H); LRMS for C$_{33}$H$_{55}$N$_2$O$_3$ [M+H]$^+$ 527.3.

(3α,5α)-3-{[(2ξ,5ξ)-2,5-dimethyl-4-{[3-(trifluoromethyl)phenyl]carbonyl}piperazin-1-yl]methyl}-3-hydroxyandrostan-17-one (13c)

(27 mg, 77%); $^1$H NMR (CDCl$_3$): 0.77 (s, 3H), 0.86 (s, 3H), 1.26 (m, 3H), 1.43 (d, J=6.4 Hz, 3H), 0.78-2.00 (m, 22H), 2.02-2.20 (m, 2H), 2.35-2.47 (m, 3H), 2.95 (broad s, 2H), 3.07 (d, J=10.4 Hz, 1H), 3.55 (broad s, 1H), 7.55 (d, J=4.5 Hz, 2H), 7.61 (s, 1H), 7.68 (broad s, 1H); LRMS for C$_{34}$H$_{48}$F$_3$N$_2$O$_3$[M+H]$^+$ 589.3.

(3α,5α)-3-{[(2,5)-2,5-dimethyl-4-{[4-(trifluoromethyl)phenyl]carbonyl}piperazin-1-yl]methyl}-3-hydroxyandrostan-17-one (13d)

(31 mg, 89%); $^1$H NMR (CDCl$_3$): 0.77 (s, 3H), 0.86 (s, 3H), 1.27 (m, 3H), 1.42 (m, 3H), 0.80-1.98 (m, 22H), 2.03-2.09 (m, 2H), 2.35-2.47 (m, 3H), 2.95 (broad s, 2H), 3.05 (broad s, 1H), 3.58 (broad s, 1H), 7.46 (d, J=7.9 Hz, 2H), 7.68 (d, J=8.0 Hz, 2H); LRMS for C$_{34}$H$_{48}$F$_3$N$_2$O$_3$[M+H]$^+$ 589.2.

General Procedure for Synthesis of Sulfonamides 14a-c and 15a-c

To a solution of compound 8 (30 mg, 0.08 mmol) or compound 9 (30 mg, 0.07 mmol) in anhydrous dichloromethane (3 mL) was added triethylamine (33 mL, 24 mg, 0.24 mmol) and the appropriate sulfonyl chloride (0.12 mmol). The solution was then stirred over a period of 3 h at room temperature. The resulting solution was concentrated and purified by flash chromatography using EtOAc/hexanes (3:7 to 1:1) as to eluant system to provide the corresponding sulfonamides 14a-c and 15a-c. All compounds were characterized by $^1$H NMR and MS analyses. $^{13}$C NMR, HRMS and HPLC data were also collected for compounds 14a, 15b and 15c.

(3α,5α)-3-hydroxy-3-[(4-{[3-(trifluoromethyl)phenyl]sulfonyl}piperazin-1-yl)methyl]androstan-17-one (14a)

(29 mg, 63%); $^1$H NMR (CDCl$_3$): 0.74 (s, 3H), 0.84 (s, 3H), 0.75-2.10 (m, 21H), 2.28 (s, 2H), 2.43 (dd, J$_1$=8.7 Hz, J$_2$=19.3 Hz, 1H), 2.50 (s, 1H), 2.72 (t, J=4.7 Hz, 4H), 3.05 (broad s, 4H), 7.73 (t, J=7.8 Hz, 1H), 7.90 (d, J=7.8 Hz, 1H), 7.95 (d, J=7.9 Hz, 1H), 8.01 (s, 1H); $^{13}$C NMR (CDCl$_3$): 11.2, 13.8, 20.2, 21.7, 28.2, 30.7, 31.5, 32.2, 33.6, 35.0, 35.8, 35.9, 39.1, 40.5, 46.3 (2×), 47.8, 51.4, 54.1, 54.7 (2×), 68.8, 70.6, 123.2 (q, J$_{C-F}$=273 Hz), 124.7 (q, J$_{C-C-C-F}$=3.7 Hz), 129.6, 130.0, 130.9, 131.9 (q, J$_{C-C-F}$=33 Hz), 137.0, 221.4; LRMS for C$_{31}$H$_{43}$F$_3$N$_2$O$_4$SNa [M+Na]$^+$ 619.5; HRMS calcd for C$_{31}$H$_{44}$F$_3$N$_2$O$_4$S [M+H]$^+$ 597.2968. found 597.2974; HPLC purity: 98.4% (RT=15.4 min; 70:30 to 5:95 MeOH/H$_2$O isocratic).

(3α,5α)-3-hydroxy-3-[(4-{[2-(trifluoromethyl)phenyl]sulfonyl}piperazin-1-yl)methyl]androstan-17-one (14b)

(33 mg, 72%); $^1$H NMR (CDCl$_3$): 0.75 (s, 3H), 0.85 (s, 3H), 0.75-2.12 (m, 21H), 2.29 (s, 2H), 2.43 (dd, J$_1$=8.6 Hz, J$_2$=19.2 Hz, 1H), 2.69 (m, 5H), 3.26 (broad s, 4H), 7.72 (m, 2H), 7.92 (d, J=9.1 Hz, 1H), 8.10 (d, J=9.1 Hz, 1H); LRMS for C$_{31}$H$_{43}$F$_3$N$_2$O$_4$SNa [M+Na]$^+$ 619.2.

(3α,5α)-3-hydroxy-3-[(4-{[4-(trifluoromethyl)phenyl]sulfonyl}-piperazin-1-yl)methyl]androstan-17-one (14c)

(26 mg, 56%); $^1$H NMR (CDCl$_3$): 0.74 (s, 3H), 0.84 (s, 3H), 0.75-2.10 (m, 23H), 2.27 (s, 2H), 2.43 (dd, J$_1$=8.6 Hz, J$_2$=19.2 Hz, 1H), 2.50 (s, 1H), 2.72 (broad t, J=4.7 Hz, 4H), 3.06 (broad s, 4H), 7.83 (d, J=8.4 Hz, 1H), 7.89 (t, J=8.3 Hz, 1H); LRMS for C$_{31}$H$_{43}$F$_3$N$_2$O$_4$SNa [M+Na]$^+$ 619.3.

(3α,5α)-3-{[(2ξ,5ξ)-2,5-dimethyl-4-{[3-(trifluoromethyl)phenyl]sulfonyl}piperazin-1-yl]methyl}-3-hydroxyandrostan-17-one (15a)

(30 mg, 72%); $^1$H NMR (CDCl$_3$): 0.75 (s, 3H), 0.85 (s, 3H), 1.00 (d, J=6.4 Hz, 3H), 1.14 (d, J=6.8 Hz, 3H), 0.75-2.18 (m, 22H), 2.30-2.46 (m, 3H), 2.69 (s, 1H), 2.95 (m, 1H), 3.07 (dd, J$_1$=3.5 Hz, J$_2$=11.9 Hz, 1H), 3.39 (s, 2H), 4.10 (m, 1H), 7.66 (t, J=7.8 Hz, 1H), 7.82 (d, J=7.9 Hz, 1H), 7.99 (d, J=7.8 Hz, 1H), 8.06 (s, 1H); LRMS for C$_{33}$H$_{47}$F$_3$N$_2$O$_4$SNa [M+Na]$^+$ 647.4.

(3α,5α)-3-{[(2ξ,5ξ)-2,5-dimethyl-4-{[2-(trifluoromethyl)phenyl]sulfonyl}piperazin-1-yl]methyl}-3-hydroxyandrostan-17-one (15b)

(29 mg, 63%); $^1$H NMR (CDCl$_3$): 0.75 (s, 3H), 0.85 (s, 3H), 0.89 (m, 3H), 1.19 (m, 3H), 0.75-1.98 (m, 19H), 2.00-2.17 (m, 2H), 2.33 (t$_{app}$, J=13.2 Hz, 2H), 2.43 (dd, J$_1$=8.8 Hz, J$_2$=19.2 Hz, 1H), 2.82 (s, 1H), 2.90 (m, 1H), 3.09 (d, J=11.6 Hz, 1H), 3.35 (m, 2H), 3.52 (d, J=13.0 Hz, 1H), 4.05 (broad s, 1H), 7.69 (d, J=4.5 Hz, 2H), 7.89 (d, J=9.1 Hz, 1H), 8.18 (d, J=9.1 Hz, 1H); $^{13}$C NMR (CDCl$_3$): 8.6, 11.2, 13.8, 15.6, 20.2, 21.7, 28.3, 30.7, 31.5, 32.4, 33.8, 35.0, 35.8, 35.9, 39.3, 40.7, 46.0, 47.8, 49.5, 51.4, 52.4, 54.2, 54.7, 65.7, 70.9, 122.6 (q, J$_{C-F}$=274 Hz), 127.5 (q, J$_{C-C-F}$=33 Hz), 128.5 (q, J$_{C-C-C-F}$=6.4 Hz), 131.9, 132.1, 132.5, 139.3, 221.5; LRMS for C$_{33}$H$_{47}$F$_3$N$_2$O$_4$SNa [M+Na]$^+$ 647.2; HRMS calcd for C$_{33}$H$_{45}$F$_3$N$_2$O$_4$S [M+H]$^+$ 625.3281. found 625.3291; HPLC purity: 98.9% (RT=16.1 min; 70:30 to 5:95 MeOH/H$_2$O isocratic gradient).

(3α,5α)-3-{[(2ξ,5ξ)-2,5-dimethyl-4-{[2-trifluoromethyl)phenyl]sulfonyl}piperazin-1-yl]methyl}-3-hydroxyandrostan-17-one (15c)

(35 mg, 70%); $^1$H NMR (CDCl$_3$): 0.75 (s, 3H), 0.85 (s, 3H), 1.01 (d, J=5.9 Hz, 3H), 1.14 (d, J=6.7 Hz, 3H), 0.75-1.98 (m, 20H), 2.00-2.18 (m, 2H), 2.30-2.45 (m, 3H), 2.68 (s, 1H), 2.95 (d, J=6.6 Hz, 1H), 3.07 (dd, J$_1$=3.6 Hz, $J_2$=11.8 Hz, 1H), 3.40 (s, 2H), 4.05 (broad s, 1H), 7.77 (d, J=8.3 Hz, 2H), 7.93 (d, J=8.3 Hz, 2H); $^{13}$C NMR (CDCl$_3$): 9.1, 11.2, 13.8, 14.9, 20.2, 21.7, 28.3, 30.7, 31.5, 32.4, 33.7, 35.0, 35.8, 35.9, 39.3, 40.7, 46.1, 47.8, 49.9, 51.4, 53.0, 54.2, 54.6, 65.6, 71.0, 123.2 (q, $J_{C-F}$=273 Hz), 126.1, 126.2 (q, $J_{C-C-C-F}$=3.6 Hz), 127.4 (2×), 134.1 (q, $J_{C-C-F}$=33 Hz), 144.2, 221.5; LRMS for C$_{33}$H$_{47}$F$_3$N$_2$O$_4$SNa [M+Na]$^+$ 647.4; HRMS calcd for C$_{33}$H$_{48}$F$_3$N$_2$O$_4$S [M+H]$^+$ 625.3281. found 625.3287; HPLC purity: 98.7% (RT=17.0 min; 70:30 to 5:95 MeOH/H$_2$O isocratic).

General Procedure for Synthesis of 3-Carbamate-androsterone derivatives 17a-17i

To a solution of oxirane 6$^{50}$ (75 mg, 0.25 mmol) in anhydrous ethanol (5 mL) was added the appropriate primary amine (0.75 mmol). The solution was subsequently stirred overnight at 70° C. The resulting solution was subsequently concentrated and purified by flash chromatography using EtOAc/hexanes (7:3 to 9:1) as the eluent system to provide the corresponding secondary amine product 16 in good yields (70-90%).

To a solution of compound 16 (0.22 mmol) in anhydrous DCM (7 mL), at 0° C. and under an argon atmosphere, was added diisopropylamine (0.66 mmol) and triphosgene (0.11 mmol). The solution was subsequently stirred overnight at room temperature. The reaction mixture was then poured into water, extracted with DCM, filtered using a phase separator (Biotage, Uppsala, Sweden) and concentrated. The crude compounds were purified by flash chromatography using EtOAc/hexanes (1:9 to 3:7) as the eluent system to provide the corresponding carbamates 17a-i. All compounds were characterized by $^1$H NMR and MS analyses. $^{13}$C NMR, HRMS and HPLC data were also collected for compound 17a.

(3R,5S,8R,9S,10S,13S,14S)-3'-benzyl-10,13-dimethyltetradecahydro-2'H spiro[cyclopenta[α]phenanthrene-3,5'-[1,3]oxazolidine]-2',17(2H)-dione (17a)

(20 mg, 18%); $^1$H NMR (Acetone-d$_6$): 0.84 (s, 3H), 0.86 (s, 3H), 0.80-2.10 (m, 22H), 2.37 (dd, $J_1$=8.2 Hz, $J_2$=17.7 Hz, 1H), 3.16 (s, 2H), 4.39 (s, 2H), 7.31 (m, 3H), 7.38 (t, J=7.6 Hz, 1H); $^{13}$C NMR (CDCl$_3$): 11.4, 13.8, 20.2, 21.7, 27.8, 30.6, 31.5, 32.8, 33.8, 35.0, 35.4, 35.8, 39.4, 40.8, 47.7, 48.1, 51.3, 53.8, 55.6, 78.9, 127.9, 128.0, 128.8 (2×), 129.7, 135.9, 157.6, 221.3; LRMS for C$_{28}$H$_{37}$NO$_3$Na [M+Na]$^+$ 458.3; HRMS calcd for C$_{28}$H$_{38}$NO$_3$ [M+H]$^+$ 436.2846. found 436.2854; HPLC purity: 98.7% (RT=13.9 min; 70:30 to 5:95 MeOH/H$_2$O isocratic gradient).

(3R,5S,8R,9S,10S,13S,14S)-10,13-dimethyl-3'-(4-methylbenzyl)tetrahydrodecahydro-2'H-spiro[cyclopenta[α]phenanthrene-3,5'-[1,3]oxazolidine]-2',17(2H)-dione (17b)

(134 mg, 38%); $^1$H NMR (Acetone-d$_6$): 0.84 (s, 3H), 0.86 (s, 3H), 0.80-2.10 (m, 21H), 2.32 (s, 3H), 2.37 (dd, $J_1$=8.7 Hz, $J_2$=18.2 Hz, 1H), 3.13 (s, 2H), 4.34 (s, 2H), 7.19 (s, 4H); LRMS for C$_{29}$H$_{39}$NO$_3$Na [M+Na]$^+$ 472.2.

(3R,5S,8R,9S,10S,13S,14S)-3'-(4-methoxybenzyl)-10,13-dimethyltetradecahydro-2'H-spiro[cyclopenta[α]phenanthrene-3,5'-[1,3]oxazolidine]-2',17(2H)-dione (17c)

(18 mg, 16%); $^1$H NMR (Acetone-d$_6$): 0.84 (s, 3H), 0.86 (s, 3H), 0.80-2.10 (m, 22H), 2.37 (dd, J=8.7 Hz, $J_2$=18.2 Hz, 1H), 3.12 (s, 2H), 3.79 (s, 3H), 4.31 (s, 2H), 6.93 (d, J=8.7 Hz, 2H), 7.23 (d, J=8.7 Hz, 2H); LRMS for C$_{29}$H$_{40}$NO$_4$Na [M+Na]$^+$ 488.3.

(3R,5S,8R,9S,10S,13S,14S)-10,13-dimethyl-3'-[4-(trifluoromethyl)benzyl]tetradecahydro-2'H-spiro[cyclopenta[α]phenanthrene-3,5'-[1,3]oxazolidine]-2',17(2H)-dione (17d)

(55 mg, 33%); $^1$H NMR (Acetone-d$_6$): 0.84 (s, 3H), 0.87 (s, 3H), 0.80-2.10 (m, 21H), 2.38 (dd, $J_1$=8.8 Hz, $J_2$=18.2 Hz, 1H), 3.23 (s, 2H), 4.51 (s, 2H), 7.56 (d, J=8.0 Hz, 2H), 7.74 (d, J=8.1 Hz, 2H); LRMS for C$_{29}$H$_{36}$F$_3$NO$_3$Na [M+Na]$^+$ 526.1.

(3R,5S,8R,9S,10S,13S,14S)-10,13-dimethyl-3'-{[6-trifluoromethyl)pyridine-3-yl]methyl}tetrahydrodecahydro-2'H-spiro[cyclopenta[α]phenanthrene-3,5'-[1,3]oxazolidine]-2',17(2H)-dione (17e)

(18 mg, 24%); $^1$H NMR (Acetone-d$_6$): 0.84 (s, 3H), 0.87 (s, 3H), 0.80-2.10 (m, 21H), 2.38 (dd, $J_1$=8.8 Hz, $J_2$=18.2 Hz, 1H), 3.30 (s, 2H), 4.58 (s, 2H), 7.87 (d, J=8.0 Hz, 1H), 8.03 (d, J=8.0 Hz, 1H), 8.73 (s, 1H); LRMS for C$_{28}$H$_{35}$F$_3$N$_2$O$_3$Na [M+Na]$^+$ 527.4.

(3R,5S,8R,9S,10S,13S,14S)-10,13-dimethyl-3'-[2-(trifluoromethyl)benzyl]tetradecahydro-2'H-spiro[cyclopenta[α]phenanthrene-3,5'-[1,3]oxazolidine]-2',17(2H)-dione (17f)

(62 mg, 37%); $^1$H NMR (Acetone-d$_6$): 0.84 (s, 3H), 0.88 (s, 3H), 0.82-2.10 (m, 21H), 2.38 (dd, $J_1$=8.7 Hz, $J_2$=18.3 Hz, 1H), 3.23 (s, 2H), 4.61 (s, 2H), 7.57 (m, 2H), 7.74 (m, 2H); LRMS for C$_{29}$H$_{36}$F$_3$NO$_3$Na [M+Na]$^+$ 526.4.

(3R,5S,8R,9S,10S,13S,14S)-10,13-dimethyl-3'-[3-(trifluoromethyl)benzyl]tetradecahydro-2'H-spiro[cyclopenta[α]phenanthrene-3,5'-[1,3]oxazolidine]-2',17(2H)-dione (17g)

(30 mg, 18%); $^1$H NMR (Acetone-d$_6$): 0.84 (s, 3H), 0.87 (s, 3H), 0.82-2.10 (m, 21H), 2.38 (dd, $J_{1=8.7}$ Hz, $J_2$=18.2 Hz, 1H), 3.23 (s, 2H), 4.52 (s, 2H), 7.65 (m, 4H); LRMS for C$_{29}$H$_{36}$F$_3$NO$_3$Na [M+Na]$^+$ 526.0.

(3R,5S,8R,9S,10S,13S,14)-3'-[3,5-bis(trifluoromethyl)benzyl]-10,13-dimethyltetradecahydro-2'H-spiro[cyclopenta[α]phenanthrene-3,5'-[1,3]oxazolidine]-2',17(2H)-dione (17h)

(28 mg, 15%); $^1$H NMR (Acetone-d$_6$): 0.84 (s, 3H), 0.87 (s, 3H), 0.81-2.10 (m, 21H), 2.38 (dd, $J_1$=8.7 Hz, $J_2$=17.7 Hz, 1H), 3.31 (s, 2H), 4.64 (s, 2H), 8.00 (s, 3H); LRMS calcd for C$_{30}$H$_{35}$F$_6$NO$_3$Na [M+Na]$^+$ 594.2.

(3R,5S,8R,9S,10S,13S,14S)-3'-cyclohexyl-10,13-dimethyltetradecahydro-2'H-spiro[cyclopenta[α]phenanthrene-3,5'-[1,3]oxazolidine]-2',17(2H)-dione (17i)

(19 mg, 18%); $^1$H NMR (Acetone-d$_6$): 0.84 (s, 3H), 0.88 (s, 3H), 0.80-2.08 (m, 31H), 2.38 (dd, J=8.8 Hz, $J_2$=18.3 Hz, 1H), 3.23 (s, 2H), 3.53 (m, 1H); LRMS for C$_{27}$H$_{41}$NO$_3$Na [M+Na]$^+$ 450.4.

Synthesis of (3R,5S,8R,9S,10S,13S,14S)-10,13,16,16-tetramethyl-3'-(4-methylbenzyl)tetrahydrodecahydro-2'H-spiro[cyclopenta[α]phenanthrene-3,5'-[1,3]oxazolidine]-2',17(2H)-dione (18)

To a solution of compound 17b (100 mg, 0.22 mmol) in anhydrous THF (15 mL), under an argon atmosphere, was added NaH (60% in oil; 89 mg, 2.2 mmol). The resulting solution was stirred at room temperature over a period of 1 h. Methyl iodide (110 μL, 250 mg, 1.76 mmol) was then added and the solution refluxed overnight. The reaction mixture was subsequently poured into water and extracted three times with EtOAc. The combined organic layers were washed with brine and dried with MgSO$_4$. The crude compound was purified by flash chromatography using EtOAc/hexanes (2:8) as the eluant system to provide compound 18 (32 mg, 30%). $^1$H NMR (CDCl$_3$): 0.77 (s, 3H), 0.87 (s, 3H), 1.03 (s, 3H), 1.16 (s, 3H), 0.80-1.85 (m, 20H), 2.34 (s, 3H), 3.03 (s, 2H), 4.37 (s, 2H), 7.15 (s, 4H); LRMS for C$_{31}$H$_{43}$NO$_3$Na [M+Na]$^+$ 500.2.

Synthesis of (3α,5α)-3-{[(2{[tert-butyl(dimethyl)silyl]oxy}ethyl)amino]methyl}-3-hydroxyandrostan-17-one (19)

To a solution of oxirane 6$^{50}$ in anhydrous ethanol (50 mL) was added 2-{[tert-butyl(dimethyl)silyl]oxy}ethanolamine (1.75 g, 10.0 mmol) and the solution refluxed over a period of 5 h. The resulting solution was subsequently concentrated and purified by flash chromatography using EtOAc/hexanes (2:8) as the eluent system to provide compound 19 (1.0 g, 66%). $^1$H NMR (Acetone-d$_6$): 0.08 (s, 6H), 0.81 (s, 6H), 0.91 (s, 9H), 0.80-2.10 (m, 20H), 2.22 and 2.38 (2m, 2H), 2.48 (s, 2H), 2.72 (t, J=5.5 Hz, 2H), 3.25 (m, 1H), 3.72 (t, J=5.5 Hz, 2H), 3.80 (t, J=6.0 Hz, 1H); LRMS calcd for C$_{28}$H$_{52}$NO$_3$Si [M+H]$^+$ 478.2.

Synthesis of (3R,5S,8R,9S,10S,13S,14S)-3'-(2-{[tert-butyl(dimethyl)silyl]oxy}ethyl)-10,13-dimethyltetrahydrodecahydro-2'H-spiro[cyclopenta[α]phenanthrene-3,5'-[1,3]oxazolidine]-2',17(2H)-dione (20)

To a solution of compound 19 (1.0 g, 2.2 mmol) in anhydrous DCM (100 mL), at 0° C. and under an argon atmosphere, was added diisopropylamine (760 μL, 564 mg, 4.4 mmol) and triphosgene (325 mg, 1.1 mmol). The solution was subsequently stirred over a period of 8 h while at room temperature. The reaction mixture was then poured into water, extracted twice with DCM, filtered using a phase separator (Biotage, Uppsala, Sweden) and concentrated. The crude compound was purified by flash chromatography using EtOAc/hexanes (2:8) as the eluant system to provide compound 20 (370 mg, 36%). $^1$H NMR (Acetone-d$_6$): 0.09 (s, 6H), 0.85 (s, 3H), 0.89 (s, 3H), 0.91 (s, 9H), 0.80-2.07 (m, 22H), 2.38 (dd, J$_1$=8.6 Hz, J$_2$=18.3 Hz, 1H), 3.30 (t, J=5.3 Hz, 2H), 3.40 (s, 1H), 3.78 (t, J=5.4 Hz, 2H); LRMS for C$_{29}$H$_{49}$NO$_4$SiNa [M+Na]$^+$ 526.5.

Synthesis of (3R,5S,8R,9S,10S,13S,14S)-3'-(2-hydroxyethyl)-10,13-dimethyltetrahydrodecahydro-2'H-spiro[cyclopenta[α]phenanthrene-3,5'-[1,3]oxazolidine]-2',17(2H)-dione (21)

To a solution of compound 20 (360 mg, 0.76 mmol) in anhydrous THF (70 mL), at room temperature and under an argon atmosphere, was added a solution of tetrabutylammonium fluoride (TBAF) in THF (1.0 M; 1.05 mL, 1.5 mmol). The solution was stirred at room temperature over a period of 1 h. The resulting reaction mixture was then poured into water and extracted twice with EtOAc. The combined organic layers were dried with Na$_2$SO$_4$, filtered and evaporated under reduced pressure to provide crude 21. The crude compound was purified by flash chromatography using EtOAc to provide pure 21 (225 mg, 76%). $^1$H NMR (Acetone-d$_6$): 0.85 (s, 3H), 0.89 (s, 3H), 0.80-2.08 (m, 23H), 2.37 (dd, J$_1$=8.6 Hz, J$_2$=18.3 Hz, 1H), 3.29 (t, J=5.3 Hz, 2H), 3.40 (s, 1H), 3.67 (t, J=5.6 Hz, 2H); LRMS for C$_{23}$H$_{35}$NO$_4$Na [M+Na]$^+$ 412.2.

Synthesis of (3R,5S,8R,9S,10S,13S,14S)-3'-(2-bromoethyl)-10,13-dimethyltetrahydrodecahydro-2'H-spiro[cyclopenta[α]phenanthrene-3,5'-[1,3]oxazolidine]-2',17(2H)-dione (22)

To a solution of compound 21 (225 mg, 0.58 mmol) in anhydrous DCM (50 mL), at 0° C. and under an argon atmosphere, was added triphenylphosphine (303 mg, 1.16 mmol) and carbon tetrabromide (383 mg, 1.16 mmol). The solution was stirred at room temperature over a period of 1 h. The resulting reaction mixture was then washed with water and the organic phase dried using a phase separator syringe (Biotage). The crude compound was purified by flash chromatography using EtOAc/hexanes (4:6) as the eluant system to provide compound 22 (235 mg, 90%). $^1$H NMR (Acetone-d$_6$): 0.85 (s, 3H), 0.89 (s, 3H), 0.82-2.08 (m, H, residual CH and CH$_2$), 2.38 (dd, J$_1$=8.6 Hz, J$_2$=18.3 Hz, 1H), 3.41 (s, 2H), 3.63 (s, 4H); LRMS for C$_{23}$H$_{34}$$^{79}$BrNO$_3$Na [M+Na]$^+$ 474.1.

Synthesis of (3R,5S,8R,9S,10S,13S,14S)-10,13-dimethyl-3'-[2-(3-methylphenoxy)ethyl]tetrahydrodecahydro-2'H-spiro[cyclopenta[α]phenanthrene-3,5'-[1,3]oxazolidine]-2',17(2H)-dione (23a)

To a solution 3-methylphenol (22 μL, 22 mg, 0.200 mmol) and K$_2$CO$_3$ (28 mg, 0.200 mmol) in anhydrous DMF (2 mL), stirred over a period of 10 min at 70° C., was subsequently added compound 22 (30 mg, 0.067 mmol). The reaction mixture was stirred overnight under an argon atmosphere at 70° C. The reaction mixture was then poured into an aqueous NaOH solution (1.0 N) and extracted three times with diethylether. The combined organic layers were successively washed with brine, dried over Na$_2$SO$_4$, filtered, and concentrated. The crude product was purified by flash chromatography using EtOAc/hexanes (2:8) as the eluant system to provide compound 23a (11 mg, 34%). $^1$H NMR (Acetone-d$_6$): 0.84 (s, 3H), 0.88 (s, 3H), 0.80-2.07 (m, H, residual CH and CH$_2$), 2.29 (s, 3H), 2.37 (dd, J$_1$=8.7 Hz, J$_2$=18.8 Hz, 1H), 3.45 (s, 2H), 3.59 (m, 2H), 4.15 (t, J=5.3 Hz, 2H), 6.77 (m, 3H), 7.16 (t, J=7.8 Hz, 1H); LRMS for C$_{30}$H$_{41}$NO$_4$Na [M+Na]$^+$ 502.4.

Synthesis of (3R,5S,8R,9S,10S,13S,14S)-10,13-dimethyl-3'-{2-(3-methylphenyl)sulfonyl]ethyl}tetrahydrodecahydro-2'H-spiro[cyclopenta[α]phenanthrene-3,5'-[1,3]oxazolidine]-2',17(2H)-dione (23b)

To a solution 3-methylbenzenthiol (41 mg, 0.33 mmol) and K$_2$CO$_3$ (46 mg, 0.33 mmol) in anhydrous DMF (3 mL), stirred over a period of 10 min at 70° C., was subsequently added compound 22 (50 mg, 0.11 mmol). The reaction mixture was stirred over a period of 3 h under an argon atmosphere at 70° C. The reaction mixture was then poured into water and extracted three times with diethylether. The combined organic layers were successively washed with brine, dried over $Na_2SO_4$, filtered, and concentrated to provide the corresponding crude thioether derivative. The crude thioether product (45 mg) was subsequently diluted in a methanol/water mixture (1:1) followed by the addition of oxone (112 mg). The resulting reaction mixture was then stirred overnight while at room temperature. The crude reaction mixture was subsequently poured into water and extracted three times with EtOAc. The combined organic layers were then washed with brine, dried over $Na_2SO_4$, filtered, and concentrated. The crude product was purified by flash chromatography using EtOAc/hexanes (1:1) as the eluant system to provide compound 23b (9 mg, 16% for the combined two-step reaction). $^1$H NMR (Acetone-$d_6$): 0.84 (s, 3H), 0.86 (s, 3H), 0.80-2.07 (m, 21H), 2.38 (dd, J=8.7 Hz, $J_2$=8.3 Hz, 1H), 2.46 (s, 3H), 3.30 (s, 2H), 3.50 (t, J=6.6 Hz, 2H), 3.61 (m, 2H), 7.57 (m, 2H), 7.77 (m, 2H); LRMS for $C_{30}H_{41}NO_5SNa$ [M+Na]$^+$ 550.2.

General Procedure for the Synthesis of 3-Carbamate-androsterone derivatives 23c-23f To a solution of compound 22 (30 mg, 0.067 mmol) in anhydrous DMF (2 mL) was added the appropriate secondary amine (0.20 mmol) and sodium carbonate (21 mg, 0.20 mmol). The reaction mixture was stirred over a period of 3 h at 70° C. The reaction mixture was then poured into water and extracted three times with diethylether. The combined organic layers were successively washed with brine, dried over $Na_2SO_4$, filtered, and concentrated. The crude product was purified by flash chromatography using either dichloromethane/methanol/triethylamine (90:9:1) as the eluant system to provide pure 23c, 23e and 23f or EtOAc/hexanes (1:1) as the eluant system to provide 23d.

(3R,5S,8R,9S,10S,13S,14S)-10,13-dimethyl-3'-[2-(piperidin-1-yl)ethyl]tetrahydrodecahydro-2'H-spiro[cyclopenta[α]phenanthrene-3,5'-[1,3]oxazolidine]-2',17(2H)-dione (23c)

(7 mg, 22%); $^1$H NMR (Acetone-$d_6$): 0.84 (s, 3H), 0.89 (s, 3H), 0.80-2.08 (m, 24H), 2.26 (m, 2H), 2.38 (dd, $J_1$=8.8 Hz, $J_2$=18.3 Hz, 1H), 3.05-3.30 (m, 4H), 3.42 (s, 2H), 3.46 (t, J=6.5 Hz, 2H), 3.80 (t, J=6.5 Hz, 2H); LRMS for $C_{28}H_{47}N_3O_3$ [M+NH$_3$]$^+$ 473.3.

(3R,5S,8R,9S,10S,13S,14S)-3'-{2-[ethyl(phenyl)amino]ethyl}-10,13-dimethyltetrahydrodecahydro-2'H-spiro[cyclopenta[α]phenanthrene-3,5'-[1,3]oxazolidine]-2',17(2H)-dione (23d)

(16 mg, 42%); $^1$H NMR (Acetone-$d_6$): 0.85 (s, 3H), 0.88 (s, 3H), 0.82-2.07 (m, 24H), 1.03 (t, J=7.1 Hz, 3H), 2.38 (dd, $J_1$=8.7 Hz, $J_2$=18.3 Hz, 1H), 2.53 (q, J=7.1 Hz, 1H), 2.60 (t, J=6.1 Hz, 2H), 3.28 (s, 2H), 3.32 (m, 2H), 3.59 (s, 2H), 7.23 (t, J=7.2 Hz, 1H), 7.30 (t, J=7.3 Hz, 2H), 7.36 (t, J=7.3 Hz, 2H); LRMS for $C_{32}H_{46}N_2O_3Na$ [M+Na]$^+$ 529.4.

(3R,5S,8R,9S,10S,13S,14S)-3'-{2-[cyclohexyl(ethyl)amino]ethyl}-10,13-dimethyltetradecahydro-2'H-spiro[cyclopenta[α]phenanthrene-3,5'-[1,3]oxazolidine]-2',17(2H)-dione (23e)

(13 mg, 39%); $^1$H NMR (CDCl$_3$): 0.81 (s, 3H), 0.86 (s, 3H), 1.41 (t, J=7.2 Hz, 3H), 2.00 (s, 2H), 0.80-2.40 (m, 30H), 2.43 (dd, J=8.6 Hz, $J_2$=19.3 Hz, 1H), 3.45 (m, 4H), 3.63 (m, 1H), 3.72 (m, 1H), 3.85 (m, 2H); LRMS calcd for $C_{31}H_{53}N_3O_3$ [M+NH$_3$]$^+$ 515.2.

(3R,5S,8R,9S,10S,13S,14S)-3'-[2-(dipropylamino)ethyl]-10,13-dimethyltetradecahydro-2'H-spiro[cyclopenta[α]phenanthrene-3,5'-[1,3]oxazolidine]-2',17(2H)-dione (23f)

(13 mg, 40%); $^1$H NMR (Acetone-$d_6$): 0.84 (s, 3H), 0.89 (s, 3H), 0.78-2.10 (m, 28H), 0.94 (t, J=7.4 Hz, 3H), 2.38 (dd, $J_1$=8.7 Hz, $J_2$=18.2 Hz, 1H), 3.23 (m, 4H), 3.42 (s, 2H), 3.48 (t, J=6.6 Hz, 2H), 3.74 (t, J=6.9 Hz, 2H); LRMS calcd for $C_{29}H_{51}N_3O_3$ [M+NH$_3$]$^+$ 489.3.

Synthesis of N-{(3R,5S,8R,9S,10S,13S,14S)-10,13-dimethyl-2',17-dioxohexadecahydro-3'H-spiro[cyclopenta[α]phenanthrene-3,5'-[1,3]oxazolidine-3'-yl]ethyl}-N-propylpropanamide (23g)

To a solution of compound 22 (30 mg, 0.067 mmol) in anhydrous DMF (3 mL) was added $K_2CO_3$ (21 mg, 0.20 mmol) and N-propylamine (16 μL, 12 mg, 0.20 mmol). The reaction mixture was stirred over a period of 5 h at 80° C. The reaction mixture was then poured into water and extracted three times with diethylether. The combined organic layers were successively washed with brine, dried over $Na_2SO_4$, filtered, and concentrated. The crude secondary amine product was used in the next step without further purification.

To a solution of the crude secondary amine product (30 mg) in anhydrous dichloromethane (50 mL), were successively added triethylamine (27 μL, 21 mg) and propionyl chloride (13 μL, 13 mg). The solution was stirred at room temperature over a period of 4 h while under an argon atmosphere. The reaction mixture was then diluted with dichloromethane (15 mL), washed with water, dried using a phase separator syringe (Biotage), and concentrated. The resulting crude product was purified by flash chromatography using EtOAc/hexanes (1:1) as the eluant system to provide pure 23g (11 mg, 34%). $^1$H NMR (Acetone-$d_6$): 0.84 (s, 3H), 0.88 (s, 3H), 0.91 (t, J=7.4 Hz, 3H), 1.04 (t, J=7.4 Hz, 3H), 0.82-2.07 (m, 23H), 2.34 (m, 3H), 3.25-3.40 (m, 6H), 3.53 (m, 2H); LRMS for $C_{29}H_{46}N_2O_4Na$ [M+Na]$^+$ 509.1.

Biological Assays

Inhibition of 17β-HSD3 in Homogenated Cells

The inhibitory activity of the compounds was determined following a known literature.[48,53] Briefly, HEK-293 cells overexpressing 17β-HSD3 were homogenated and used for the enzymatic assay. The transformation of 50 nM of [4-$^{14}$C]-4-androstene-3,17-dione ([$^{14}$C]-Δ$^4$-dione) into [$^{14}$C]-testosterone ([$^{14}$C]-T) in presence of excess NADPH (5 mM) and ethanol (control) or an inhibitor dissolved in ethanol was measured and used to determine the percentage of inhibition at a given concentration.

Inhibition of 17β-HSD-3 in Intact Cells

HEK-293 cells were seeded at 200000 cells/well in a 12-well plate (BD Falcon) at 37° C. under a 95% air, 5% $CO_2$ humidified atmosphere in minimum essential medium (MEM) containing non-essential amino acids (0.1 mM), glutamine (2 mM), sodium pyruvate (1 mM), 10% foetal bovine serum, penicillin (100 IU/mL) and streptomycin (100 μg/mL). The expression vector encoding for 17β-HSD3 was transfected following the Exgen 500 procedure (Fermentas, Burlington, ON, Canada) with 2 μg of recombinant plasmid per well. For the inhibitory activity assay, a final concentration of 50 nM of [4-$^{14}$C]-4-androstene-3,17-dione in ethanol (53.6 mCi/mmol, Perkin Elmer Life Sciences Inc., Boston, Mass., USA) and an ethanolic solution of inhibitor (0.5% v/v) were added to freshly culture medium and incubated over a period of 1 h. Each inhibitor was assessed in triplicate at tested concentrations. After incubation, the culture medium was removed and the radiolabeled steroids extracted and quantified as described for the enzymatic assay in homogenated cells.[48] Percentage transformation and the $IC_{50}$ values were calculated as previously reported.[48]

Proliferative Activity on Androgen-Sensitive (AR⁺) Shionogi Cells

The proliferative (androgenic) activity was determined using androgen-sensitive Shionogi cells following a known literature procedure.[54] Inhibitors and reference compounds were tested at two concentrations (0.1 and 1.0 µM). The androgenicity was reported as % cell proliferation (versus the control). The basal cell proliferation (control) was fixed at 100%.

General Procedure for the Synthesis of 3A-3D (Scheme 19)

In a Schlenk tube, oxirane 2 (1.7 mmol) was dissolved in dry MeOH (15 mL), followed by the addition of the appropriate amino acid methyl ester (17.2 mmol). The Schlenk tube was then hermetically closed and heated at 90° C. with stirring over a period of 21 h. The MeOH was then evaporated and the crude reaction mixture dissolved in DCM. The solution was then pre-adsorbed on silica gel and purified by flash column chromatography (Hexanes/EtOAc/TEA (89:10:1).

3β-Methyl-N-[(17,17-diethylendioxy-3α-hydroxy-5α-androstane)]-methyl-L-Leucinate (3A)

Yield: 99%; Rf=0.6 (hexanes/EtOAc, 1:1); IR (film): 3479 and 3333 (OH and NH), 1736 (C=O); ¹H NMR (Acetone-d₆): 0.74 (m, 1H), 0.78 (s, $CH_3$-19), 0.82 (s, 3H, $CH_3$-18), 0.91 and 0.92 (2d, J=6.9 Hz, $(CH_3)_2$— from iPr), 1.10-1.95 (unassigned CH and $CH_2$), 2.21 and 2.57 (2d of AB system, J=11.6 Hz, $CH_2$N), 3.14 (s, OH), 3.23 (dd, J=6.4 Hz, J=8.2 Hz, CHC=O) 3.67 (s, $OCH_3$), 3.83 (m, $OCH_2$—$CH_2$O); ¹³C NMR ($CDCl_3$): 11.20, 14.38, 20.33, 21.92, 22.64, 22.87, 24.82, 28.51, 30.72, 31.23, 31.67, 33.77, 34.18, 35.79, 35.96, 38.58, 40.58, 42.75, 45.96, 50.29, 51.67, 53.87, 59.32, 60.87, 64.52, 65.12, 69.90, 119.48, 176.32.

3β-Methyl-N-[(17,17-diethylendioxy-3α-hydroxy-5α-androstane)]-methyl-D-Leucinate (3B)

Yield: 99%; Rf=0.3 (hexanes/EtOAc, 1:1); IR (film): 3479 and 3333 (OH and NH), 1736 (C=O); ¹H NMR ($CDCl_3$): 0.73 (s, $CH_3$-19), 0.83 (s, $CH_3$-18), 0.90 and 0.93 (2d, J=6.6 Hz, $(CH_3)_2$— from iPr), 0.96-1.97 (unassigned CH and $CH_2$), 2.17 and 2.62 (2d of AB system, J=11.9 Hz, $CH_2$N), 3.04 (s, OH), 3.21-3.25 ($t_{app}$, J=6.7 Hz, CHC=O), 3.72 (s, $OCH_3$), 3.87 (m, $OCH_2$—$CH_2$O); ¹³C NMR ($CDCl_3$): 11.16, 14.35, 20.33, 21.91, 22.61, 22.84, 24.78, 28.44, 30.68, 31.16, 31.54, 33.63, 34.13, 35.76, 35.93, 38.56, 40.56, 42.70, 45.90, 50.25, 51.61, 53.82, 59.31, 60.83, 64.47, 65.07, 69.91, 119.41, 176.28.

3β-Methyl-N-[(17,17-diethylendioxy-3α-hydroxy-5α-androstane)]-methyl-L-phenylalaninate (3C)

Yield: 77%; Rf=0.5 (hexanes/EtOAc, 1:1); IR (film): 3472-3340 (NH and OH), 3024 (CH, Ph), 1736 (C=O); ¹H NMR (Acetone-d₆): 0.75 (s, $CH_3$-19), 0.82 (s, $CH_3$-18), 0.95 (m, 1H), 1.01-1.97 (unassigned CH and $CH_2$), 2.24-2.56 (2d of AB system, J=11.6 Hz, $CH_2$N), 2.92 (m, $CH_2$-Ph), 3.04 (s, OH), 3.43-3.45 ($t_{app}$, J=6.6 Hz, CHC=O), 3.62 (s, $OCH_3$), 3.84 (m, $OCH_2$—$CH_2$O); 7.25 (m, Ph); ¹³C NMR ($CDCl_3$): 11.19, 14.39, 20.33, 22.65, 28.49, 30.71, 31.22, 31.53, 33.67, 34.18, 35.78, 35.93, 38.50, 39.81, 40.49, 45.95, 50.27, 51.72, 53.81, 59.34, 63.92, 64.51, 65.11, 69.97, 70.03, 119.45, 126.74, 128.42, 129.10, 137.28, 175.02.

3β-Methyl-N-[(17,17-diethylendioxy-3α-hydroxy-5α-androstane)]-methyl-D-phenylalaninate (3D)

Yield: 87%; Rf=0.43 (hexanes/EtOAc, 1:1); IR (film): 3472-3340 (NH and OH), 3024 (CH, Ph), 1736 (C=O); ¹H NMR (Acetone-d₆): 0.75 (s, $CH_3$-19), 0.82 (s, $CH_3$-18), 0.95 (m, 1H), 1.50-1.97 (unassigned CH and $CH_2$), 2.24-2.56 (2d of AB system, J=11.6 Hz, $CH_2$N), 2.92 (m, $CH_2$-Ph), 3.04 (s, OH), 3.43-3.45 ($t_{app}$, J=6.6 Hz, CHC=O), 3.62 (s, $OCH_3$), 3.84 (m, $OCH_2$—$CH_2$O); 7.25 (m, Ph); ¹³C NMR ($CDCl_3$): 11.17, 14.39, 20.35, 22.65, 28.43, 30.71, 31.18, 31.49, 33.61, 34.17, 35.77, 35.93, 38.41, 39.79, 40.47, 45.93, 50.26, 51.70, 53.80, 59.33, 63.96, 64.50, 65.10, 69.97, 70.02, 119.43, 126.72, 128.40, 129.10, 137.31, 175.03.

Synthesis of 3β-Methyl-N-[(17,17-diethylendioxy-3α-hydroxy-5α-androstane)]-methyl glycinate (3E)

Anhydrous methanol (20 mL) was added to a mixture of glycine methyl ester hydrochloride (1.1 g, 8.8 mmol) and DIPEA (2.2 g, 17.5 mmol) placed in a Schlenk tube. The resulting solution was subsequently stirred over a period of 30 minutes while at room temperature. Oxirane 2 (0.3 g, 0.9 mmol) was then added and the resulting solution heated at 95° C. over a period of 22 h. The solution was then cooled to room temperature and filtered. The resulting filtrate was then concentrated and the residue (1.8 g) dissolved in DCM. The solution was then pre-adsorbed on silica gel and purified by flash column chromatography (hexanes/EtOAc (7:3); 1% TEA). The title compound was isolated as a yellowish product (3E). Yield: 53%; Rf=0.17 (hexanes/EtOAc, 1:1); IR (film): 3464-3348 (NH and OH), 1736 (C=O); ¹H NMR ($CDCl_3$): 0.74 (s, $CH_3$-19), 0.83 (s, $CH_3$-18), 0.85-1.97 (unassigned CH and $CH_2$), 2.50 (s, $CH_2$N), 3.45 (s, $NCH_2$C=O), 3.73 (s, $OCH_3$), 3.83-3.95 (m, $OCH_2$—$CH_2$O); ¹³C NMR (Acetone-d₆): 10.75, 13.91, 20.26, 22.44, 30.65, 31.38, 31.46, 33.34, 33.71, 33.91, 35.79, 35.90, 38.48, 40.45, 45.77, 50.32, 50.73, 51.18, 54.43, 61.09, 64.23, 64.83, 69.95, 118.87, 172.74.

General Procedure for the Synthesis of Azaspirolactones 4A-4E (Scheme 19)

To a solution of MeONa (0.37 mmol) in anhydrous THF (24 mL) at 0° C. was added, under argon atmosphere, a solution of the appropriate amino alcohol (3A-3E) (0.61 mmol) in anhydrous THF (28 mL). The resulting solution was stirred over a period of 2 h at room temperature. The reaction was subsequently quenched with a saturated ammonium chloride solution. The crude product was extracted with EtOAc (4×50 mL), the combined organic layers dried with anhydrous $MgSO_4$ and concentrated. The residue was dissolved in DCM and the solution pre-adsorbed on silica gel and purified by flash column chromatography (hexanes/EtOAc (8:2); 1% TEA).

Azaspirolactone 4A:

Yield: 89%; Rf=0.49 (hexanes/ethyl acetate 1:1); ¹H NMR (Acetone-d₆): 0.79 (m, 1H), 0.83 (s, $CH_3$-19 and $CH_3$-18), 0.89 and 0.92 (2d, J=6.6 Hz, $(CH_3)_2$— from iPr), 0.95-1.98 (unassigned CH and CH$_2$), 2.83 and 2.93 (2d of AB system, J=13.5 Hz, CH$_2$N), 3.43 (m, NCHC=O), 3.85 (m, OCH$_2$—CH$_2$O).

Azaspirolactone 4B:

Yield: 84%; Rf=0.49 (hexanes/ethyl acetate 1:1); $^1$H NMR (CDCl$_3$): 0.76 (s, 3H, CH$_3$-19), 0.83 (s, 3H, CH$_3$-18), 0.91-0.97 (2d, J=6.3 Hz, 3H, (CH$_3$)$_2$— from iPr), 2.78-2.89 (dd, J=13.5 Hz, 2H, CH$_2$N), 3.41-3.50 (m, 1H, NCHC=O), 3.83-3.94 (m, 4H, OCH$_2$—CH$_2$O); $^{13}$C NMR (CDCl$_3$): 11.33, 14.38, 20.34, 20.94, 22.66, 23.40, 24.46, 28.24, 30.64, 31.49, 32.63, 34.18, 35.74, 36.03, 38.31, 39.25, 39.65, 41.46, 45.93, 50.13, 52.55, 53.38, 55.54, 64.54, 65.14, 82.29, 119.39, 171.91.

Azaspirolactone 4C:

Yield: 62%; Rf=0.3 (hexanes/ethyl acetate 1:1); $^1$H NMR (Acetone-d$_6$): 0.78 (s, 3H, CH$_3$-19), 0.82 (s, 3H, CH$_3$-18), 2.86-2.99 (m, 2H, CH$_2$N), 3.01-3.20 (m, 2H, CH$_2$Ph), 3.70-3.74 (m, 1H, NCHC=O), 3.79-3.89 (m, 4H, OCH$_2$—CH$_2$O), 7.22-7.30 (2m, 5H, Ph).

Azaspirolactone 4D:

Yield: 65%; Rf=0.25 (hexanes/ethyl acetate 1:1); $^1$H NMR (Acetone-d$_6$): 0.77 (s, 3H, CH$_3$-19), 0.82 (s, 3H, CH$_3$-18), 2.76-2.90 (m, 2H, CH$_2$N), 3.02-3.16 (m, 2H, CH$_2$Ph), 3.72-3.75 (m, 1H, NCHC=O), 3.78-3.89 (m, 4H, OCH$_2$—CH$_2$O), 7.22-7.32 (2m, 5H, Ph).

Azaspirolactone 4E:

Yield: 52%; Rf=0.27 (hexanes/ethyl acetate 1:1); $^1$H NMR (CDCl$_3$): 0.78 (s, 3H, CH$_3$-19), 0.83 (s, 3H, CH$_3$-18), 2.82 (s, 2H, CH$_2$N), 3.63 (s, 2H, NCH$_2$C=O), 3.85-3.95 (m, 4H, OCH$_2$—CH$_2$O); $^{13}$C NMR (CDCl$_3$): 11.34, 14.39, 20.36, 22.65, 28.14, 30.63, 30.97, 31.25, 32.69, 34.18, 35.74, 36.00, 37.96, 39.39, 45.93, 47.55, 50.13, 53.05, 53.38, 64.55, 65.15, 82.52, 119.39, 168.78.

General Procedure for the Synthesis of N-benzylated Azaspirolactones 6A-6E (Scheme 20)

In a Schlenk tube, the appropriate azaspirolactone (4A-4E) (0.1 mmol) was dissolved in dry DCM (5 mL), followed by the drop-wise addition of diisopropylethylamine (0.17 mmol). The Schlenk tube was then hermetically closed and heated at 75° C. with stirring over a period of 10 min. The Schlenk tube was then cooled to room temperature followed by the addition of benzyl bromide (1.7 mmol). The reaction mixture was subsequently stirred and heated at 75° C. for an additional 48 h. After cooling the Schlenk tube, silica gel was added and the mixture concentrated. The residue was purified by flash column chromatography (hexanes/EtOAc (8:2); 1% TEA).

N-Benzylated Azaspirolactone 6A:

Yield: 63%; Rf=0.83 (hexanes/ethyl acetate 1:1); $^1$H NMR (Acetone-d$_6$): 0.74 (s, 3H, CH$_3$-19), 0.81 (s, 3H, CH$_3$-18), 0.92-0.99 (2d, J=6.7 Hz, 6H, (CH$_3$)$_2$— from iPr), 2.22-2.76 (dd, J=12.5 Hz, 2H, CH$_2$N), 3.19-4.10 (dd, J=13.7 Hz, 2H, CH$_2$-Ph), 3.15-3.18 (m, 1H, NCHC=O), 3.78-3.88 (m, 4H, OCH$_2$—CH$_2$O), 7.28-7.40 (m, 5H, Ph).

N-Benzylated Azaspirolactone 6B:

Yield: 49%; Rf=0.83 (hexanes/ethyl acetate 1:1); $^1$H NMR (CDCl$_3$): 0.68 (s, 3H, CH$_3$-19), 0.82 (s, 3H, CH$_3$-18), 0.94-0.99 (2d, J=6.7 Hz, 3H, (CH$_3$)$_2$— from iPr), 2.16-2.65 (dd, J=12.4 Hz, 2H, CH$_2$N), 3.11-4.04 (dd, J=13.5 Hz, 2H, CH$_2$-Ph), 3.15-3.20 (m, 1H, NCHC=O), 3.83-3.94 (m, 4H, OCH$_2$—CH$_2$O), 7.29-7.38 (m, 5H, Ph). $^{13}$C NMR (CDCl$_3$): 11.37, 14.37, 20.31, 22.09, 22.10, 22.67, 23.93, 25.02, 26.17, 28.34, 30.65, 31.06, 31.95, 32.69, 34.19, 35.72, 36.02, 38.33, 38.59, 39.24, 39.78, 45.95, 50.14, 53.39, 57.84, 58.15, 63.04, 64.56, 65.14, 81.33, 119.41, 127.37, 128.50, 128.53, 137.78, 171.37.

N-Benzylated Azaspirolactone 6C:

Yield: 70%; Rf=0.75 (hexanes/ethyl acetate 1:1); $^1$H NMR (Acetone-d$_6$): 0.62 (s, 3H, CH$_3$-19), 0.79 (s, 3H, CH$_3$-18), 2.20-2.59 (dd, J=12.5 Hz, 2H, CH$_2$N), 2.81-4.41 (dd, J=13.6 Hz, 2H, NCH$_2$-Ph), 3.25-3.47 (m, 2H, CH$_2$Ph); 3.50-3.52 (m, 1H, NCHC=O), 3.80-3.89 (m, 4H, OCH$_2$—CH$_2$O), 7.29-7.38 (m, 10H, Ph). $^{13}$C NMR (Acetone-d$_6$): 10.73, 13.88, 20.16, 22.38, 27.86, 28.36, 29.52, 30.56, 30.64, 31.16, 33.10, 33.88, 35.24, 35.65, 35.72, 37.91, 39.53, 45.74, 50.17, 54.04, 57.45, 57.72, 60.95, 64.24, 64.83, 65.89, 80.54, 118.82, 126.42, 127.11, 127.79, 128.34, 128.53, 130.39, 137.98, 138.09, 169.53.

N-Benzylated Azaspirolactone 6D:

Yield: 61%; Rf=0.75 (hexanes/ethyl acetate 1:1); $^1$H NMR (Acetone-d$_6$): 0.62 (s, 3H, CH$_3$-19), 0.78 (s, 3H, CH$_3$-18), 2.19-2.60 (dd, J=12.4 Hz, 2H, CH$_2$N), 2.81-4.43 (dd, J=13.8 Hz, 2H, NCH$_2$-Ph), 3.27-3.49 (m, 2H, CH$_2$Ph); 3.49-3.51 (m, 1H, NCHC=O), 3.77-3.88 (m, 4H, OCH$_2$—CH$_2$O), 7.25-7.34 (m, 10H, Ph). $^{13}$C NMR (Acetone-d$_6$): 10.76, 13.87, 20.18, 22.42, 27.58, 28.36, 29.52, 30.57, 31.14, 31.19, 32.69, 33.91, 35.04, 35.65, 37.26, 39.94, 45.73, 50.19, 54.10, 57.48, 57.83, 64.24, 64.81, 65.83, 80.46, 118.82, 126.54, 127.12, 127.77, 128.35, 128.59, 130.50, 137.88, 138.07, 169.43.

N-Benzylated Azaspirolactone 6E:

Yield: 70%; Rf=0.83 (hexanes/ethyl acetate 1:1); $^1$H NMR (CDCl$_3$): 0.72 (s, 3H, CH$_3$-19), 0.82 (s, 3H, CH$_3$-18), 2.41 (s-broad, 2H, CH$_2$N); 3.26 (s, 2H, NCH$_2$C=O), 3.83-3.94 (m, 4H, OCH$_2$—CH$_2$O), 7.26-7.36 (m, 5H, Ph). $^{13}$C NMR (CDCl$_3$): 11.4, 14.39, 20.33, 22.66, 28.12, 30.65, 31.01, 31.84, 32.90, 34.19, 35.74, 36.03, 38.43, 39.57, 45.94, 50.14, 53.40, 55.42, 59.79, 60.99, 61.36, 64.55, 65.15, 82.49, 119.40, 127.60, 128.53, 128.71, 136.69, 168.28.

General Procedure for the Synthesis of Azaspirolactones 5A-5E and N-benzylated Azaspirolactones 7A-7E (Scheme 20)

To a solution of the appropriate azaspirolactone (4A-4E) or N-benzylated azaspirolactone (6A-6E) (30 mg to 60 mg) in dioxane (2 mL) was added an aqueous sulfuric acid solution (5%; 2 mL) and the resulting reaction mixture stirred at room temperature over a period ranging from 2-5 h. The progress of the reaction was monitored by TLC. An aqueous saturated solution of sodium bicarbonate (12 mL) was then added to the reaction mixture which was subsequently extracted four times with ethyl acetate (4×12 mL). The combined organic layers were dried with anhydrous MgSO$_4$ and concentrated. The crude compound was purified by flash chromatography using either hexanes/EtOAc (9:1)+ 1% TEA (compounds 5A-5E) or hexanes/EtOAc (95:5)+1% TEA (compounds 7A-7E) as the eluant system.

Azaspirolactone 5A:

Yield: 71%; IR (film) v 3448-3333 (NH), 1736 (C=O), 1458 (C—O) cm$^{-1}$; $^1$H NMR (Acetone-d$_6$): 0.84 (s, 3H, CH$_3$-19), 0.85 (s, 3H, CH$_3$-18), 0.89-0.93 (2d, J=6.6 Hz, 6H, (CH$_3$)$_2$— from iPr), 2.80-2.96 (dd, J=13.5 Hz, 2H, CH$_2$N), 3.41-3.44 (2d, J=4.1 Hz, 1H, NCHC=O); $^{13}$C NMR (Acetone-d$_6$) 10.73, 13.16, 20.13, 20.62, 21.44, 22.86, 24.15, 27.88, 30.66, 31.16, 31.70, 33.16, 34.97, 35.10, 36.05, 37.91, 39.81, 41.29, 47.28, 51.25, 51.94, 54.28, 55.45, 60.95, 80.81, 170.77.

Azaspirolactone 5B:

Yield: 92%; IR (film): 3448-3340 (NH), 1736 (C=O), 1458 (C—O); $^1$H NMR (CDCl$_3$): 0.80 (s, 3H, CH$_3$-19), 0.86 (s, 3H, CH$_3$-18), 0.92-0.997 (2d, J=6.4 Hz, 6H, (CH$_3$)$_2$— from iPr), 2.80-2.90 (dd, J=13.5 Hz, 2H, CH$_2$N), 3.41-3.44 (2d, J=3.70 Hz and J=3.43, 1H, NCHC=O); $^{13}$C NMR (CDCl$_3$): 11.35, 13.82, 20.22, 20.95, 21.75, 23.40, 24.47, 28.02, 30.53, 31.44, 31.51, 32.60, 35.00, 35.83, 36.12, 38.24, 39.66, 41.39, 47.76, 51.37, 52.48, 53.78, 55.58, 82.23, 171.81, 221.23.

Azaspirolactone 5C:

Yield: 97%; IR (film): 3333 (NH), 3032 (CH, Ph), 1736 (C=O), 1450 (C—O); $^1$H NMR (Acetone-$d_6$): 0.81 (s, 3H, $CH_3$-19), 0.84 (s, 3H, $CH_3$-18), 2.77-2.91 (dd, J=13.3 Hz, 2H, $CH_2$N), 2.99-3.19 (m, 2H, $CH_2$Ph), 3.72-3.75 (2d, J=4.0 Hz, 1H, NCHC=O), 7.22-7.30 (m, 5H, Ph); $^{13}$C NMR ($CDCl_3$): 11.30, 13.82, 20.22, 21.74, 27.82, 30.51, 30.99, 31.50, 32.83, 35.01, 35.83, 36.02, 37.98, 39.20, 47.76, 51.38, 52.62, 53.73, 53.76, 58.59, 58.73, 82.72, 127.08, 128.77, 129.52, 137.17, 170.77, 221.27.

Azaspirolactone 5D:

Yield: 56%; IR (film): 3448-3325 (NH), 3024 (CH, Ph), 1728 (C=O), 1450 (C—O); $^1$H NMR (Acetone-$d_6$): 0.80 (s, 3H, $CH_3$-19), 0.83 (s, 3H, $CH_3$-18), 2.77-2.89 (dd, J=13.3 Hz, 2H, $CH_2$N), 3.03-3.16 (m, 2H, $CH_2$Ph), 3.73-3.76 (2d, J=4.1 Hz, 1H, NCHC=O), 7.23-7.30 (m, 5H, Ph); $^{13}$C NMR ($CDCl_3$): 11.31, 13.81, 20.21, 21.75, 27.78, 30.54, 31.27, 31.51, 32.51, 34.99, 35.84, 36.03, 37.95, 39.59, 47.75, 51.38, 52.66, 53.76, 58.75, 60.82, 82.66, 127.09, 128.77, 129.59, 130.48, 137.23, 170.70, 221.22.

Azaspirolactone 5E:

Yield: 54%; Rf=0.29 (hexanes/ethyl acetate 1:1); IR (film): 3448-3333 (NH), 1736 (C=O), 1450 (C—O); $^1$H NMR ($CDCl_3$): 0.80 (s, 3H, $CH_3$-19), 0.86 (s, 3H, $CH_3$-18), 2.83 (s, 2H, $CH_2$N), 3.63 (s, 2H, $NCH_2$C=O); $^{13}$C NMR ($CDCl_3$): 11.36, 13.83, 20.23, 21.75, 27.90, 30.53, 31.19, 31.49, 32.66, 35.00, 35.83, 36.08, 37.88, 39.40, 47.55, 47.6, 51.35, 52.93, 53.78, 82.45, 168.69, 221.27.

N-Benzylated Azaspirolactone 7A:

Yield: 81%; Rf=0.77 (hexanes/ethyl acetate 1:1); IR (film): 3448 (NH), 1736 (C=O), 1450 (C—O); $^1$H NMR (Acetone-$d_6$): 0.77 (s, 3H, $CH_3$-19), 0.83 (s, 3H, $CH_3$-18), 0.92-0.99 (2d, J=6.3 Hz and J=6.5 Hz, 6H, $(CH_3)_2$— from iPr), 2.26-2.77 (dd, J=12.5 Hz, 2H, $CH_2$N), 3.15-3.18 (2d, J=2.6 and J=2.7, 1H, NCHC=O), 3.19-4.10 (dd, J=13.6 Hz, 2H, $CH_2$-Ph), 7.28-7.40 (m, 5H, Ph); $^{13}$C NMR (Acetone-$d_6$): 10.81, 13.19, 20.13, 21.44, 21.64, 23.44, 24.85, 27.77, 30.64, 31.52, 31.69, 33.25, 34.94, 35.11, 36.03, 38.15, 38.33, 39.74, 47.29, 51.25, 54.26, 57.63, 57.72, 63.07, 80.48, 127.18, 128.38, 128.57, 128.62, 138.20, 205.18, 205.24, 218.67.

N-Benzylated Azaspirolactone 7B:

Yield: 92%; Rf=0.85 (hexanes/ethyl acetate 1:1); IR (film): 3448 (NH), 3032 (CH, Ph), 1736 (C=O), 1450 (C—O); $^1$H NMR ($CDCl_3$): 0.71 (s, 3H, $CH_3$-19), 0.84 (s, 3H, $CH_3$-18), 0.92-0.99 (2d, J=6.5 Hz and J=6.7 Hz, 6H, $(CH_3)_2$— from iPr), 2.17-2.66 (dd, J=12.4 Hz, 2H, $CH_2$N), 3.11-4.04 (dd, J=13.5 Hz, 2H, $CH_2$-Ph), 3.15-3.18 (2d, J=2.8 Hz and J=3.0 Hz, 1H, NCHC=O), 7.29-7.36 (m, 5H, Ph); $^{13}$C NMR ($CDCl_3$): 11.39, 13.82, 20.19, 21.76, 22.08, 23.95, 25.01, 28.11, 30.63, 31.51, 31.89, 32.65, 34.98, 35.84, 36.10, 38.22, 38.47, 39.80, 47.76, 50.14, 51.40, 53.81, 57.73, 58.13, 63.05, 64.56, 65.14, 127.40, 128.52, 128.55, 137.74, 171.30, 221.25.

N-Benzylated Azaspirolactone 7C:

Yield: 70%; Rf=0.23 (hexanes/ethyl acetate 1:1); IR (film): 3441 (NH), 3032 (CH, Ph), 1728 (C=O), 1450 (C—O); $^1$H NMR (Acetone-$d_6$): 0.65 (s, 3H, $CH_3$-19), 0.80 (s, 3H, $CH_3$-18), 2.20-2.60 (dd, J=12.5 Hz, 2H, $CH_2$N), 3.26-4.42 (dd, J=13.9 Hz, 2H, $NCH_2$-Ph), 3.31-3.43 (m, 2H, $CH_2$Ph); 3.47-3.53 (m, 1H, NCHC=O), 7.26-7.36 (m, 10H, Ph); $^{13}$C NMR (Acetone-$d_6$): 10.68, 13.14, 20.03, 21.41, 27.71, 30.60, 30.62, 31.64, 33.02, 34.91, 35.09, 35.19, 35.82, 37.85, 39.55, 47.27, 51.21, 54.13, 57.42, 57.72, 65.88, 80.50, 126.45, 127.11, 127.79, 128.35, 128.53, 130.39, 137.96, 138.06, 169.50, 205.17, 205.25, 218.69.

N-Benzylated Azaspirolactone 7D:

Yield: 81%; IR (film): 3448 (NH), 3032 (CH, Ph), 1728 (C=O), 1450 (C—O); $^1$H NMR (Acetone-$d_6$): 0.65 (s, 3H, $CH_3$-19), 0.80 (s, 3H, $CH_3$-18), 2.20-2.61 (dd, J=12.4 Hz, 2H, $CH_2$N), 3.27-4.44 (dd, J=13.8 Hz, 2H, $NCH_2$-Ph), 3.38-3.43 (m, 2H, $CH_2$Ph); 3.49-3.51 (m, 1H, NCHC=O), 7.26-7.34 (m, 10H, Ph); $^{13}$C NMR (Acetone-$d_6$): 10.74, 13.15, 20.06, 21.44, 27.42, 30.57, 31.15, 31.67, 32.62, 34.90, 35.04, 35.12, 35.75, 37.18, 39.96, 47.27, 51.23, 54.22, 57.41, 57.84, 60.95, 65.84, 80.45, 126.55, 127.14, 127.77, 128.37, 128.60, 130.54, 137.88, 138.08, 169.42, 205.28, 218.72.

N-Benzylated Azaspirolactone 7E:

Yield: 71%; Rf=0.7 (DCM/MeOH 39:1); IR (film): 3448 (NH), 1720 (C=O), 1450 (C—O); $^1$H NMR ($CDCl_3$): 0.75 (s, 3H, $CH_3$-19), 0.85 (s, 3H, $CH_3$-18), 2.42 (s-broad, 2H, $CH_2$N); 3.27 (s, 2H, $NCH_2$C=O), 3.52-3.53 (d, J=4.4 Hz, 2H, $CH_2$-Ph), 7.29-7.37 (m, 5H, Ph); $^{13}$C NMR ($CDCl_3$): 11.41, 13.82, 20.21, 21.75, 27.90, 30.57, 31.51, 31.77, 32.86, 35.01, 35.84, 36.12, 38.34, 39.59, 47.76, 51.38, 53.81, 55.42, 59.69, 61.36, 82.38, 127.62, 128.54, 128.72, 136.65, 168.19, 221.26.

General Procedure for the Synthesis of Carbamates 9A-9E (Scheme 21)

To a solution of the appropriate amino alcohol 3 (0.12 mmol) in DCM (3 mL) at 0° C. and under an argon atmosphere, was added diisopropylethylamine (0.24 mmol). The reaction mixture was then stirred over a period of 10 min followed by the addition of triphosgene (0.06 mmol). The resulting reaction mixture was then stirred over a period of 5 h while at room temperature. An acidic solution composed of HCl/MeOH (10:90) (2 mL) was then added and the resulting reaction mixture stirred overnight. The reaction was subsequently quenched by the addition of a saturated aqueous solution of $NaHCO_3$ (10 mL). The desired product was subsequently extracted with dichloromethane (4×10 mL). The combined organic layers were dried using anhydrous $Na_2SO_4$ and concentrated. The crude compound was purified by flash chromatography using hexanes/EtOAc (95:5)+1% TEA as the eluant system.

Carbamate 9A:

Yield: 73%; Rf=0.71 (hexanes/ethyl acetate 1:1); IR (film): 3464 (NH), 1744 (C=O), 1435 (C—O); $^1$H NMR ($CDCl_3$): 0.82 (s, 3H, $CH_3$-19), 0.85 (s, 3H, $CH_3$-18), 0.96-0.98 (2d, J=1.8 Hz and J=2.0 Hz, 6H, $(CH_3)_2$— from iPr), 3.12-3.44 (dd, J=8.1 Hz, 2H, $CH_2$N), 3.72 (s, 3H, $OCH_3$), 4.56-4.60 (2d, J=4.8 Hz, 1H, NCHCO); $^{13}$C NMR ($CDCl_3$): 11.39, 13.82, 20.23, 21.08, 21.75, 23.15, 24.94, 27.88, 30.59, 31.47, 32.73, 33.81, 35.01, 35.41, 35.83, 37.71, 39.47, 40.77, 40.84, 47.74, 51.31, 52.22, 52.88, 53.58, 53.88, 79.64, 157.58, 171.99, 221.17.

Carbamate 9B:

Yield: 67%; Rf=0.57 (hexanes/ethyl acetate 1:1); IR (film): 3464 (NH), 1736 (C=O), 1443 (C—O); $^1$H NMR ($CDCl_3$): 0.83 (s, 3H, $CH_3$-19), 0.86 (s, 3H, $CH_3$-18), 0.96-0.98 (d, J=6.5 Hz, 6H, $(CH_3)_2$— from iPr), 3.13-3.45 (dd, J=8.1 Hz, 2H, $CH_2$N), 3.72 (s, 3H, $OCH_3$), 4.58-4.62 (2d, J=4.8 Hz, 1H, NCHCO); $^{13}$C NMR ($CDCl_3$): 11.40, 13.80, 20.22, 21.07, 21.72, 23.11, 24.93, 27.81, 30.56, 31.47, 32.88, 33.86, 35.00, 35.37, 35.81, 37.69, 39.28, 40.77, 40.83, 47.71, 51.30, 52.18, 52.83, 53.56, 53.86, 79.64, 157.53, 171.97, 221.13.

Carbamate 9C:

Yield: 61%; Rf=0.40 (hexanes/ethyl acetate 1:1); IR (film): 3464 (NH), 3032 (CH, Ph) 1744 (C=O), 1435

(C—O); ¹H NMR (CDCl₃): 0.76 (s, 3H, CH₃-19), 0.84 (s, 3H, CH₃-18), 2.92-3.38 (2m, 2H, CH₂Ph), 3.08-3.32 (dd, J=8.0 Hz, 2H, CH₂N), 3.76 (s, 3H, OCH₃), 4.86-4.90 (2d, J=5.5 Hz, 1H, NCHCO); ¹³C NMR (CDCl₃): 11.33, 13.80, 20.19, 21.72, 27.71, 27.79, 30.50, 31.45, 32.44, 33.80, 34.96, 35.07, 35.29, 35.81, 38.80, 40.56, 47.71, 51.28, 52.42, 53.20, 53.83, 55.81, 79.71, 127.07, 128.52, 128.58, 128.71, 136.02, 157.31, 171.00, 221.16.

Carbamate 9D:

Yield: 75%; Rf=0.50 (hexanes/ethyl acetate 1:1); IR (film): 3456 (NH), 1736 (C=O), 1435 (C—O); ¹H NMR (CDCl₃): 0.77 (s, 3H, CH₃-19), 0.84 (s, 3H, CH₃-18), 2.92-3.41 (2m, 2H, CH₂Ph), 3.09-3.32 (dd, J=8.0 Hz, 2H, CH₂N), 3.76 (s, 3H, OCH₃), 4.84-4.89 (2d, J=5.5 Hz, 1H, NCHCO); ¹³C NMR (CDCl₃): 11.35, 13.80, 20.19, 21.72, 27.71, 27.79, 30.54, 31.46, 32.35, 33.72, 34.98, 35.07, 35.30, 35.82, 39.14, 40.78, 47.71, 51.29, 52.41, 53.32, 53.83, 55.91, 79.67, 127.09, 128.52, 128.59, 128.71, 136.02, 157.29, 171.02, 221.16.

Carbamate 9E:

Yield: 32%; Rf=0.48 (hexanes/ethyl acetate 1:1); IR (film): 3464 (NH), 1744 (C=O), 1443 (C—O); ¹H NMR (CDCl₃): 0.82 (s, 3H, CH₃-19), 0.85 (s, 3H, CH₃-18), 3.33 (s, 2H, CH₂N), 3.75 (s, 3H, OCH₃), 4.01-4.02 (d, J=4.33 Hz, 1H, NCHCO); ¹³C NMR (CDCl₃): 11.42, 13.82, 20.23, 21.74, 27.83, 30.58, 31.48, 32.69, 33.84, 35.01, 35.37, 35.83, 39.27, 40.82, 45.01, 47.73, 51.31, 52.26, 53.89, 56.52, 79.61, 157.57, 169.02, 221.17.

17β-estradiol (17β-E2); 17α-estradiol (17α-E2); 18-epi-17β-E2; and 18-epi-17α-E2;

Two E2 isomers with the 18-methyl group inversed (18-epi), compounds 3 and 4 (Scheme 22A), were prepared and their estrogenic activity tested in representative in vitro and in vivo assays.⁵⁵

Scheme 22A

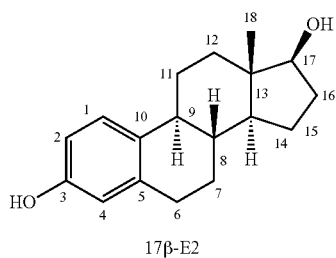

17β-E2
(1)

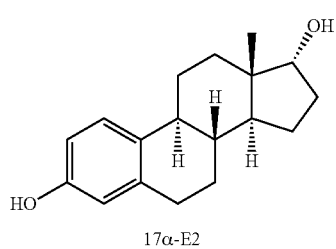

17α-E2
(2)

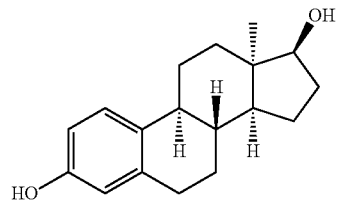

18-epi-17β-E2
(3)

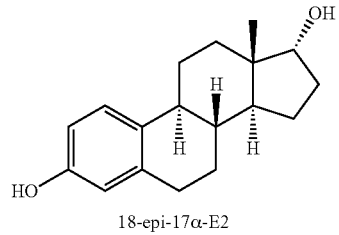

18-epi-17α-E2
(4)

[2,4,6,7 ³H]-17β-estradiol was obtained from American Radiolabeled Chemicals (St. Louis, Mo., USA). Natural estradiol (17β-E2; 1) and the corresponding 17α-isomer (17α-E2; 2) were purchased from Sigma-Aldrich Canada Ltd (Oakville, ON, Canada). 18-Epi-17β-E2 (3) and 18-epi-17α-E2 (4) were prepared from (13α)-3-hydroxyestra-1 (10),2,4-trien-17-one (18-epi-estrone). The purity of compounds 1-4 was determined by high performance liquid chromatography (HPLC) using a Waters' apparatus (Waters Associates Milford, Mass., USA) having a Waters 996 Photodiode array detector (207 nm), a Phenyl/hexyl-RP column (75×4.6 mm id, 3 µm) from Phenomenex (Torrance, Calif., USA) and a linear solvent gradient from 60:40 to 95:5 of methanol/water.

Synthesis of 18-epi-17β-E2 and 18-epi-17α-E2

To a solution of 18-epi-estrone (125 mg, 0.46 mmol) in anhydrous THF (5 mL) was added LiAlH₄ (2.3 mL of a 1.0 M solution in THF) at room temperature. The solution was stirred over a period of 90 min while under an argon atmosphere. The resulting solution was then poured into a saturated Rochelle salt solution (50 mL) and then extracted twice with EtOAc. The combined organic layers were washed with brine, dried with Na₂SO₄, filtered and concentrated to provide 120 mg of a mixture of alcohols. Purification with a Biotage flash chromatography system (Uppsala, Sweden) using a solvent gradient from EtOAc/Hexanes 1:9 to 3:7 and a silica gel column (KP-Sil, 60A) provided two fractions. The first fraction was shown to contain 18-epi-17β-E2 (3) (35 mg, 28% yield) with an HPLC purity of 99.7%. The other fraction (33 mg, 27% yield) was shown to contain 18-epi-17α-E2 (4) with an HPLC purity of 96.5% in addition to 2.8% of undesired 17β-E2 (1). To ensure the absence of 17β-E2, this fraction was recrystallized from acetonitrile (1% w/v) to provide 17 mg of compound 4 with an HPLC purity of 99.7%.

(13α,17β)-estra-1(10),2,4-triene-3,17-diol (3)

HPLC purity: 99.7%; RT=9.2 min (Gradient from 60:40 to 95:5 of methanol/water, Phenyl/hexyl-RP column (75×4.6 mm id, 3 µm; Phenomenex); LRMS for C₁₈H₂₆O₂Na [M+Na]⁺: 295.4 m/z or for C₁₈H₂₅O₂ (M−H)⁻: 271.4 m/z;

$^1$H NMR (CD$_3$OD): 0.96 (s, 18-CH$_3$), 1.10-2.15 (residual CH and CH$_2$), 2.28 (m, 6-CH$_2$), 2.72 (m, 2H), 3.76 (dd, J$_1$=4.0 Hz and J$_2$=6.0 Hz, 17α-H), 6.46 (d, J=2.3 Hz, 4-CH), 6.55 (dd, J$_1$=2.4 Hz and J$_2$=8.4 Hz, 2-CH), 7.07 (d, J=8.5 Hz, 1-CH); $^{13}$C NMR (CD$_3$OD): 26.1 (C15), 28.7 (C11), 28.9 (C7), 29.0 (C18), 30.1 (C6), 30.9 (C12), 31.9 (C16), 40.0 (C9), 42.0 (C8), 44.0 (C13), 51.5 (C14), 82.6 (C17), 112.6 (C2), 114.2 (C4), 127.0 (C1), 132.2 (C10), 137.7 (C5), 154.2 (C3); NOESY showed correlations between 14α-CH and 18-CH$_3$ as well as 18-CH$_3$ and 17β-CH, thus demonstrating the 18-epi-CH$_3$ and 17α-CH configurations of 3 (18-epi-17β-E2).

(13α,17α)-estra-1(10),2,4-triene-3,17-diol (4)

HPLC purity: 99.7%; RT=7.9 min (Gradient from 60:40 to 95:5 of methanol/water, Phenyl/hexyl-RP column (75×4.6 mm id, 3 μm; Phenomenex); LRMS for C$_{18}$H$_{26}$O$_2$Na [M+Na]$^+$: 295.4 m/z or for C$_{18}$H$_{25}$O$_2$ [M−H]$^-$: 271.3 m/z; $^1$H NMR (CD$_3$OD): 0.92 (s, 18-CH$_3$), 0.95-2.30 (residual CH and CH$_2$), 2.72 (m, 6-CH$_2$), 4.19 (t, J=8.5 Hz, 17β-H), 6.50 (d, J=2.6 Hz, 4-CH), 6.57 (dd, J$_1$=2.6 Hz, J$_2$=8.4 Hz, 2-CH), 7.12 (d, J=8.5 Hz, 1-CH); $^{13}$C NMR (CD$_3$OD): 22.0 (C18), 23.5 (C15), 26.5 (C11), 28.5 (C7), 28.7 (C16), 30.1 (C6), 32.8 (C12), 42.3 (C9), 42.7 (C8), 43.2 (C13), 50.3 (C14), 73.1 (C17), 112.5 (C2), 114.5 (C4), 126.4 (C1), 131.1 (C10), 137.8 (C5), 154.5 (C3); NOESY showed a correlation between 14α-CH and 18-CH$_3$, but no correlation between 18-CH$_3$ and 17β-CH, thus demonstrating the 18-epi-CH$_3$ and 17β-CH configurations of 4 (18-epi-17α-E2).

In Vitro Estrogenic Activity
Cell Culture Maintenance

Human breast cancer cell lines (T-47D, MCF-7 and BT-20) were obtained from the American Type Culture Collection (ATCC) and maintained in culture flasks (75 cm$^3$ growth area) at 37° C. under a 5% CO$_2$ humidified atmosphere. The T-47D cells were grown in RPMI medium supplemented with 10% (v/v) fetal bovine serum (FBS), L-glutamine (2 nM), penicillin (100 IU/mL), streptomycin (100 g/mL) and 17β-E2 (1 nM). The MCF-7 cells were propagated in Dubelcco's Modified Eagle's Medium nutrient mixture F-12 Ham (DMEM-F12) medium supplemented with 5% FBS, glutamine (2 nM), penicillin (100 IU/mL), streptomycin (100 μg/mL) and 17β-E2 (1 nM). BT-20 cells were grown in minimal essential medium (MEM) supplemented with 10% (v/v) FBS, glutamine (2 nM), penicillin (100 UI/mL) and streptomycin (100 μg/mL).

Cell Culture Assay

The cells from each breast cancer cell line were seeded into 96-well plates (3000 cells per well). The cells were suspended in the appropriate culture medium reported above, except that FBS was replaced by 5% (v/v) FBS treated with dextran-coated charcoal to remove the endogenous steroids and the medium was supplemented with insulin (50 ng/mL). After 48 h of deprivation, the cells were incubated for 7 days at 37° C. in presence of 17β-E2 (1), 17α-E2 (2), 18-epi-17β-E2 (3) and 18-epi-17α-E2 (4) at different concentrations in freshly changed medium. The effects of the drugs on the growth of three different cell lines (MCF-7, T47-D and BT-20) were determined by using 20 μL of 3-(4,5-dimethylthiazol-2-yl)-5-(3-carboxymethoxyphenyl)-2-(4-sulfophenyl)-2H-tetrazolium (MTS) reagent (Owen's reagent, Cell Titer 96®, Aqueous One Solution, Promega, USA). MTS was added to each well and the reaction was stopped after 4 h. The reagent is converted to water-soluble colored formazan by dehydrogenase enzymes present in metabolically active cells. The ability of cells to cleave MTS is indicative of the degree of mitochondrial/cellular respiration within those cells. Subsequently, the absorbance was recorded at 490 nm with a 96 well plate reader (Molecular Devices, Sunnyvale, Calif., USA). The conversion of MTS by untreated cells at the end of the cultured period was set at 100%. The results shown are representative of two separate experiments run in triplicate.

Estrogen Receptor (ER) Binding
Tissue Preparation of ER

Female Sprague-Dawley rats, weighing 200-300 g were obtained from Charles-River (St. Constant, QC, Canada). The rats were gonadectomised under general anaesthesia (Isoflurane) and killed by cervical dislocation 24 h later. The uteri were rapidly removed, dissected free from adhering tissue and frozen on dry-ice and kept at −80° C. before their use. All subsequent steps needed for the ER preparation were performed at −4° C. Uteri were homogenized in 10 volume (w/v) of buffer A (25 mM Tris-HCl, 1.5 mM EDTA disodium salt, 10 mM α-monothioglycerol, 10% glycerol, and 10 mM sodium molybdate, pH 7.4), using a Polytron PT-10 homogenizer (Brinkman Instruments, Canada) at a setting of 5 for three periods of 10 s, with intervals of 10 s for cooling. The homogenate was then centrifuged at 105 000×g over a period of 60 min in a Beckman L5-65 ultracentrifuge (Fullerton, USA).

ER Binding Assay

Estrogen binding was measured using the dextran-coated charcoal adsorption technique. Radioactive 17β-E2 ([$^3$H]-17β-E2) solubilised in ethanol was diluted into buffer A. Aliquots of uterine cytosol preparation (0.1 mL) were incubated with 5 nM of [$^3$H]-17β-E2 (approximately 200 000 cpm, 0.1 mL) in the presence or absence of the indicated concentrations of compounds 1-4 (0.1 mL, prepared in buffer A containing 10% of ethanol) for 3 h at room temperature. Unbound steroids were then separated by incubation for 15 min at room temperature with 0.3 mL 0.5% Norit-A and 0.005% Dextran T-70 in buffer B (1.5 mM EDTA disodium salt, 10 mM α-monothioglycerol, and 10 mM Tris-HCL, pH 7.4) and centrifuged at 3000×g for 15 min. Aliquots of the supernatant (0.3 mL) were removed for radioactivity measurement. After the addition of 10 mL of Formula-989 scintillation liquid (New England Nuclear-DuPont), the radioactivity was measured in a Beckman counter at a counting efficiency of 62%. The relative binding affinity (RBA) of the tested compounds was calculated as IC$_{50([^3H]-17\beta-E2)}$/IC$_{50\ (tested\ compound)}$×100.

In Vivo Estrogenic Activity (Uterotrophic Assay)

Female BALB/c mice (42-53 days) weighing 18 g were obtained from Charles River (St. Constant, QC, Canada) and housed four to five per cage in temperature (22±3° C.) and light (12 h/day, light on at 7 h15) controlled environment. The mice were fed rodent chow and tap water ad libitum. The animals were ovariectomized (OVX) under isoflurane-anaesthesia via bilateral flank incisions and randomly assigned to groups (5 animals by group). Mice in the OVX control group received the vehicle alone (8% ethanol-0.4% methylcellulose) during the 7-day period. The possible estrogenic activity of tested compounds was evaluated after their administration by subcutaneous (s.c.) injection [1, 10 and 100 μg/kg, s.c., twice daily (BID)] as suspension in 8% ethanol-0.4% methylcellulose to OVX female mice for 7 days. On day 8, the mice were sacrificed by cervical dislocation. The uteri and vagina were rapidly removed, freed from fat and connective tissue and weighed. Results are the means±SEM of 5 mice per group.

Statistical Analysis

Data are expressed as the means±SEM, and statistical significance was determined according to the multiple range test of Duncan-Kramer. P values which were less than 0.05 were considered as statistically significant.

Cell Proliferation Assay

ER+ Cell Lines

Figure 14A:
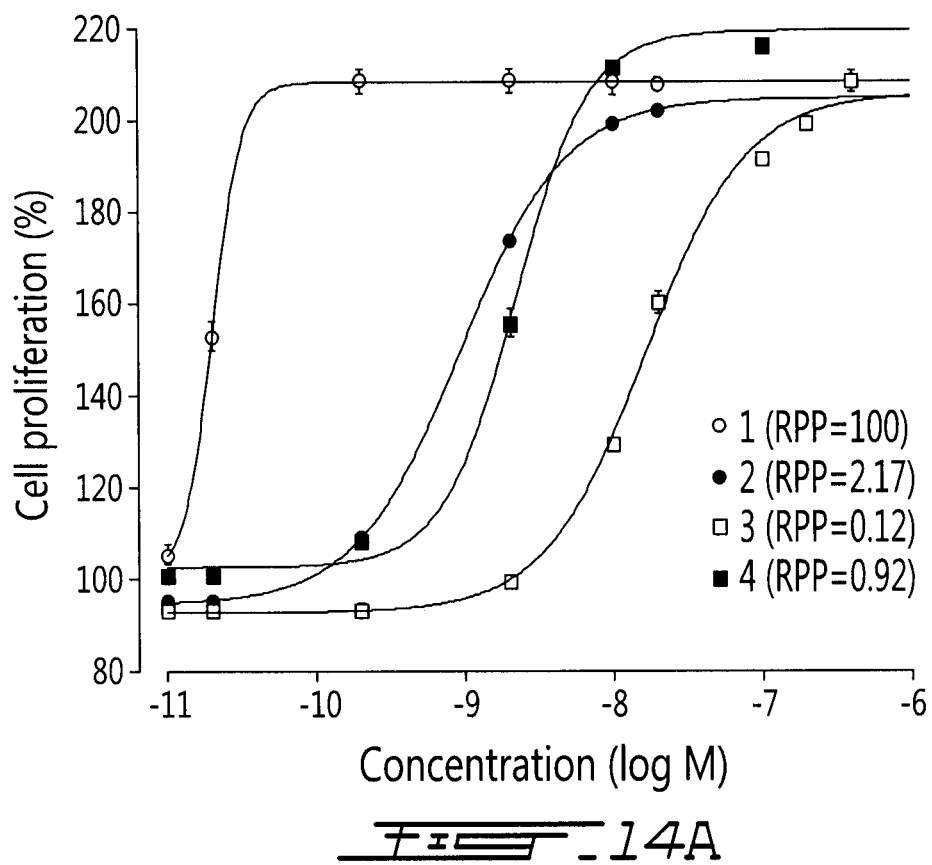
FIG. 14A is an illustration of the proliferative (estrogenic) effect of compounds (1-4) on MCF-7 (ER$^+$) cells growth at different concentrations (<1 μM). (B) Cytotoxic effect of compounds (1-4) on MCF-7 (ER$^+$) cells at high concentrations (>1 μM). The cell proliferation without product was fixed as 100%. The relative proliferative potency (RPP) or relative cytotoxic potency (RCP) were calculated as IC$_{50(17β-E2)}$/IC$_{50\ (compound\ 1,\ 2,\ 3\ or\ 4)}$×100
Figure 14B:
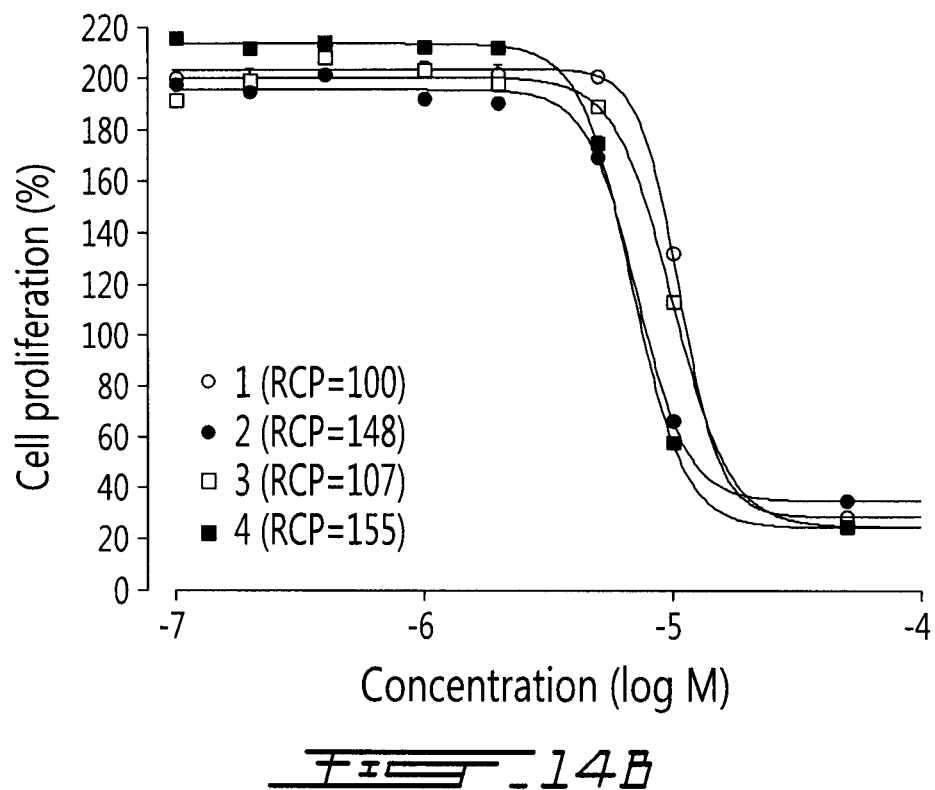
Figure 15A:
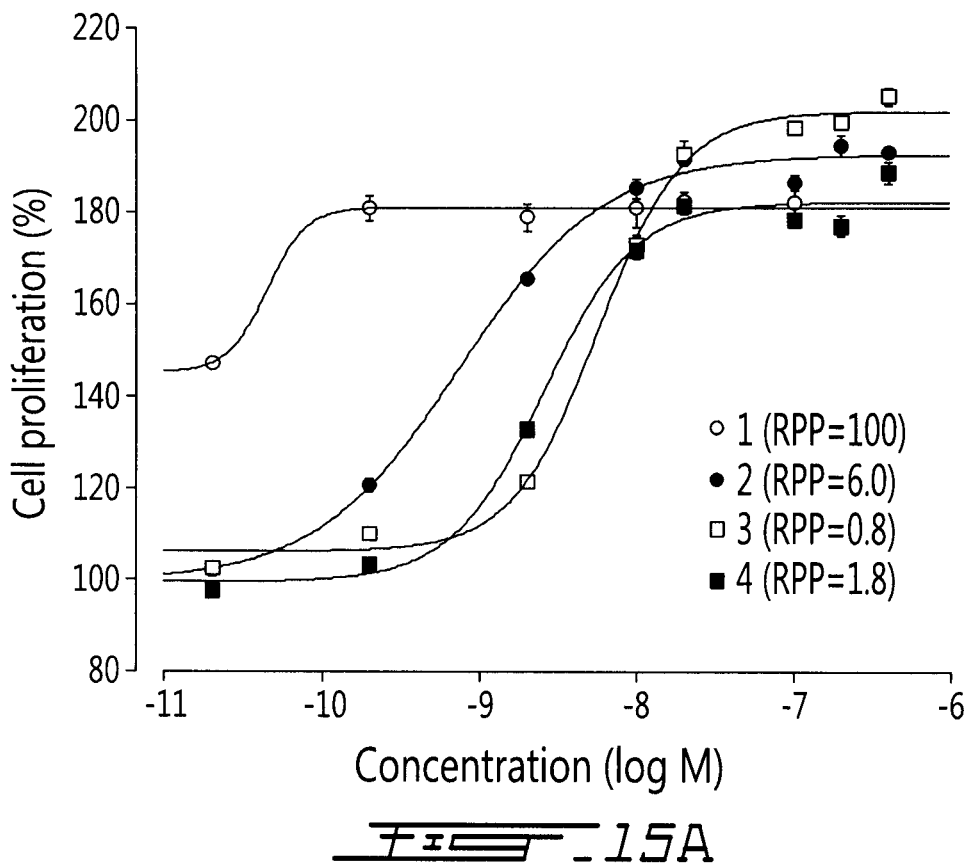
FIG. 15A is an illustration of the proliferative (estrogenic) effect of compounds 1-4 on T-47D (ER$^+$) cells at different concentrations (<1 μM). (B) Cytotoxic effect of compounds 1-4 on T-47D (ER$^+$) cells at high concentrations (>1 μM). The cell proliferation without product was fixed as 100%. The relative proliferative potency (RPP) or relative cytotoxic potency (RCP) was calculated as IC$_{50\ (17β-E2)}$/IC$_{50\ (compound\ 1,\ 2,\ 3\ or\ 4)}$×100.
Figure 15B:
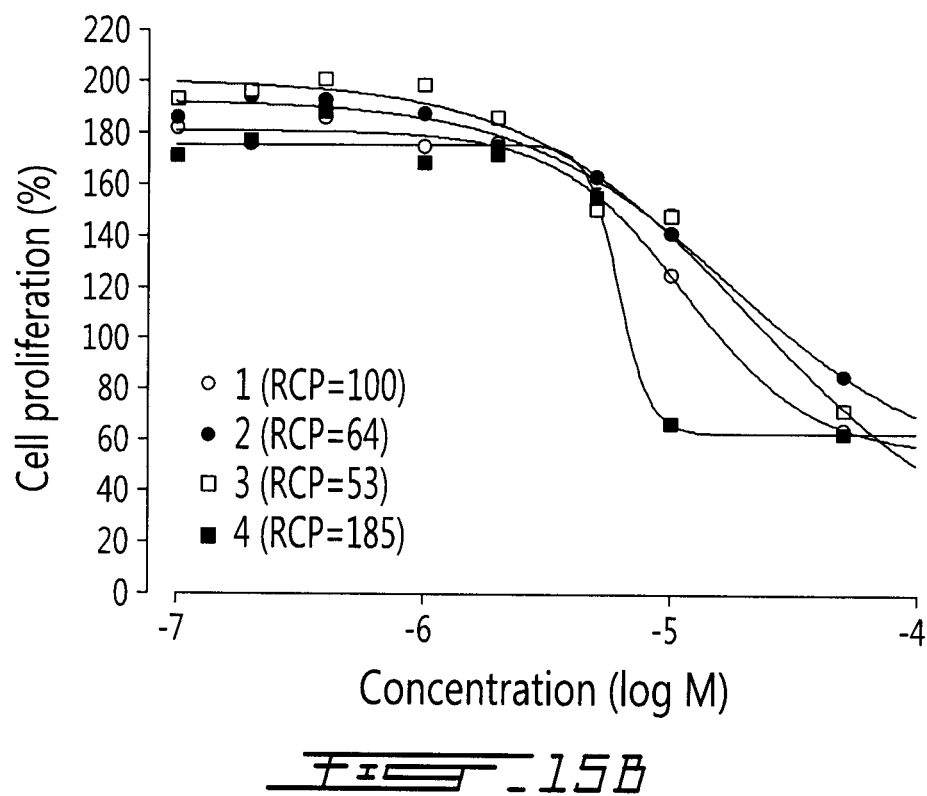

The proliferative activity of the four isomeric compounds 1-4 was evaluated on the human breast cancer (ER+) cell lines MCF-7 and T-47D. These cell lines were chosen because they express the ER, predominantly ERα, and they proliferate in presence of estrogenic compounds. They are therefore good in vitro models to evaluate the effect of the structural modifications of the E2 nucleus on the ER. The assay was performed at concentrations ranging from 0.02 nM to 50 µM for each compound and the results were expressed as the percentage of cell proliferation (FIGS. 14A and 15A). The cell proliferation without compounds was fixed as 100%. The four E2 isomers clearly modulated the proliferation of MCF-7 and T-47D cells, which are both sensitive to ER. However, they are some differences in the pattern of activity according to the range of concentrations and two kinds of proliferation effects, estrogenic and cytotoxic, were observed at low and high concentrations, respectively. At lower concentrations (0.01-5 µM), all tested compounds induced cell growth in different degrees until to reach a plateau (approximately at 200% of cellular proliferation). As expected, 17β-E2 (1) was the most estrogenic compound of the four E2-isomers in MCF-7 cells. Compound 2, with the OH in position 17a, was 45 fold less potent than natural 17β-E2 (1). Compound 3, with an inversion of 18-methyl in position 13 of 17β-E2, was 1000 folds less estrogenic than 17β-E2 (1). Finally, with two changes in the structure of 17β-E2 nucleus, an inversion of both 17-OH and 18-methyl groups, compound 4 was surprisingly only 111 folds weaker estrogenic than 17β-E2 (1). The same tendency was observed in T-47D cells, compounds 2, 3 and 4 were 16, 125 and 55-folds less estrogenic than compound 1, respectively. In summary, the four E2 isomers induced cell proliferation on ER+ cells in the following order: 1 (17β-E2)>2 (17α-E2)>4 (18-epi-17α-E2)>3 (18-epi-17β-E2). After exposure of ER+ cells at high concentrations (over 5 µM) of compounds 1-4, an important cytotoxic effect in terms of cell growth inhibition was observed in both cell lines. Thus, compounds 2 and 4 seem to be more cytotoxic than 1 and 3 in MCF-7 cells (FIG. 14B) whereas compound 4 is more cytotoxic in T-47D cells (FIG. 15B). The results obtained from these cell proliferation experiments assessed the role of 18-methyl group orientation (β or α) on the estrogenic activity and cytotoxicity of natural potent estrogens 17β-E2 (1) and 17α-E2 (2).

ER− Cell Lines

Figure 16:
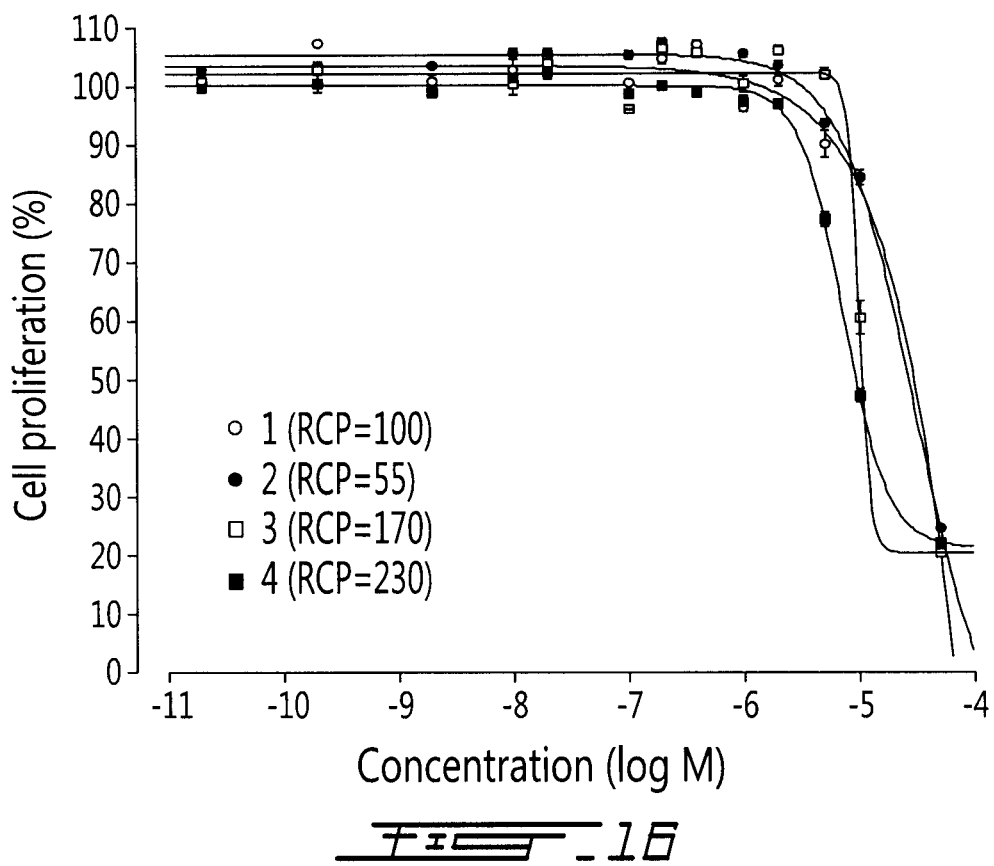
FIG. 16 is an illustration of the effect of compounds 1-4 on BT-20 (ER$^-$) cells growth at different concentrations.

The BT-20 cells are negative for estrogen receptor (ER−), but do express an estrogen receptor mRNA that has deletion of exon 5. It was decided to test compounds 1-4 in this cell line to demonstrate that the effect observed in ER+ cell lines was due to the action on the estrogen receptor. When compounds 1-4 were tested on BT-20 (ER−) cells, no proliferative effect was observed at all tested concentrations (FIG. 16). At high concentrations (>1 µM), cytotoxic effects were observed in BT-20 cells. This effect on ER− cells was observed in the same range of concentrations than for ER+ cell lines (FIG. 16). The present data demonstrate that the cytotoxic activity at high concentrations is working by a non ER-dependent mechanism.

ER-Binding Affinity

Figure 17:
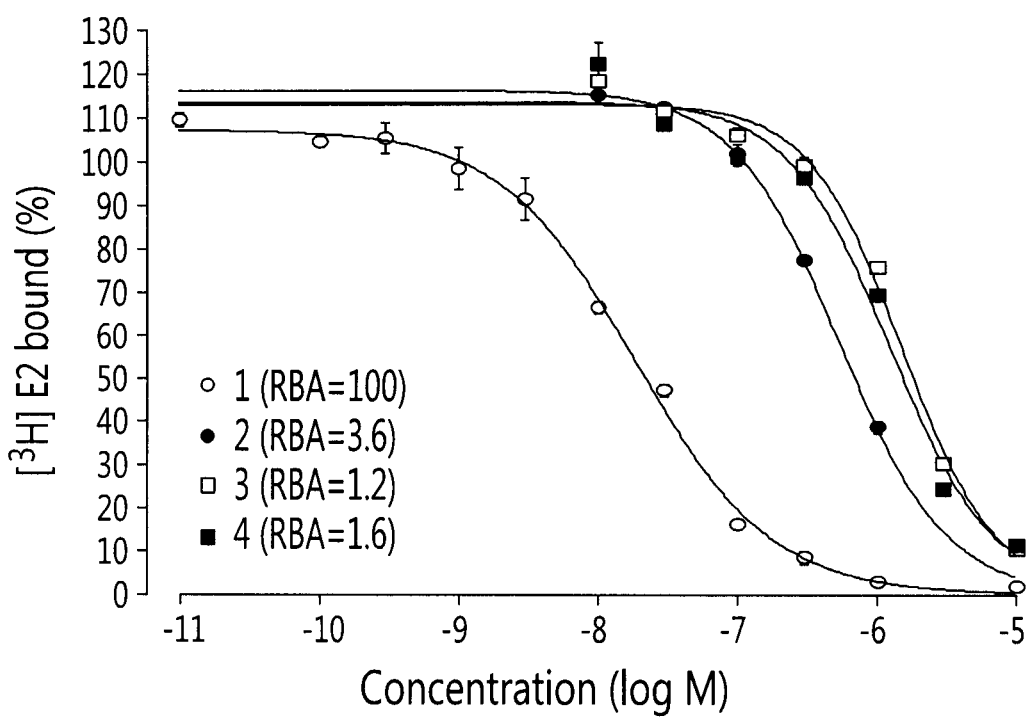
FIG. 17 is an illustration of the effect of increasing concentrations of 17β-E2 (1), 17α-E2 (2), 18-epi-17β-E2 (3) and 18-epi-17α-E2 (4) in displacing [$^3$H]-17β-E2 binding to the rat uterine estrogen receptor alpha (ERα). RBA: relative binding affinity.

Having assessed the in vitro estrogenic activity for the four E2 isomers, the affinity of compounds 1-4 for ER was assessed next. A binding assay using ER obtained from uteri of gonadectomised rats was performed. Since the predominant isoform in the mature uterus is ERα, as in the MCF-7 cells, the results were expressed as a function of the affinity for the ERα. The concentration at which the unlabeled ligand displaces half the specific binding of [$^3$H]-17β-E2 to ER (IC$_{50}$) was determined by computer fitting of the data using non-linear regression analysis. Compounds 1-4 bound to the ER in different degree as represented by the dose response curves (FIG. 17). The relative binding affinity (RBA) of natural 17β-E2 (1) for the ER was established as 100%, because it had the highest ER-binding affinity for ER of the four E2 isomers. Compound 2 (17α-E2) had a RBA of 3.6% indicating that the inversion of 17β-OH to 17α-OH decreases the affinity for ER of 28 folds. The RBA of compounds 3 and 4 were 1.2% and 1.6%, respectively, thus showing a weak ER binding affinity. These two compounds share an important modification of the structure of natural estrogen 17β-E2 (1), the inversion of 18-methyl in position 13, which is apparently responsible for the major lost, 81 and 66 folds, of binding affinity for the ER. The ranking order is thus 17β-E2 (1)>17α-E2 (2)>18-epi-17α-E2 (4)>18-epi-17β-E2 (3) (Table 5). These results are in good agreement with the findings generated from the in vitro proliferation tests with ER+ cells.

TABLE 5

Structural characteristic of compounds 1-4 and radiolabeled ligand assay for ER

| Compound | 18-CH$_3$ orientation | 17-OH orientation | Δ (17-OHs)$^a$ (Å) | IC$_{50}$$^b$ (nM) | ERα-RBA$^c$ (%) |
|---|---|---|---|---|---|
| 17β-E2 (1) | β | β | 0 | 19 | 100 |
| 17α-E2 (2) | β | α | 2.4 | 542 | 3.5 |
| 18-epi-17β-E2 (3) | α | β | 2.9 | 1534 | 1.2 |
| 18-epi-17α-E2 (4) | α | α | 1.2 | 1257 | 1.5 |

$^a$Δ (17-OHs): Distance between the 17-OH of a given compound and the optimal OH positioning of 17β-E2 (1).
$^b$The concentration of tested compound inhibiting 50% of the binding of labelled 17β-E2 (IC$_{50}$) was obtained from dose response curves.
$^c$RBA: Relative Binding Affinity.

Uterotrophic Activity (In Vivo)

Figure 18A:
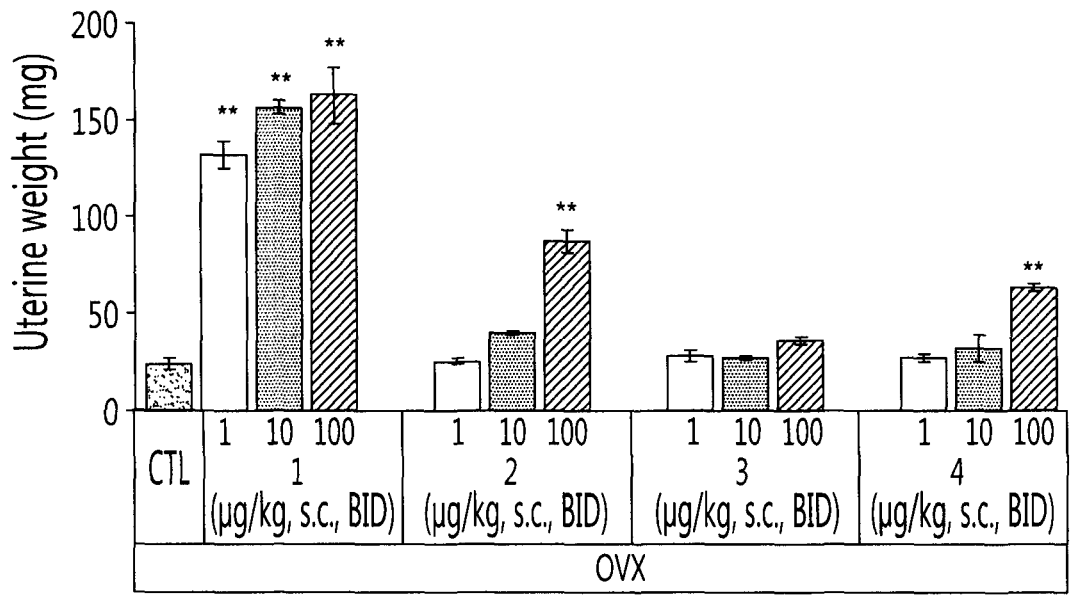
FIG. 18 is an illustration of Uterine (A) and Vagina (B) weight of mice treated 7 days with 1, 10 and 100 μg/kg (s.c. BID) of compound 1, 2, 3 or 4. *P≤0.05 vs control, **P≤0.01 versus control.
Figure 18B:
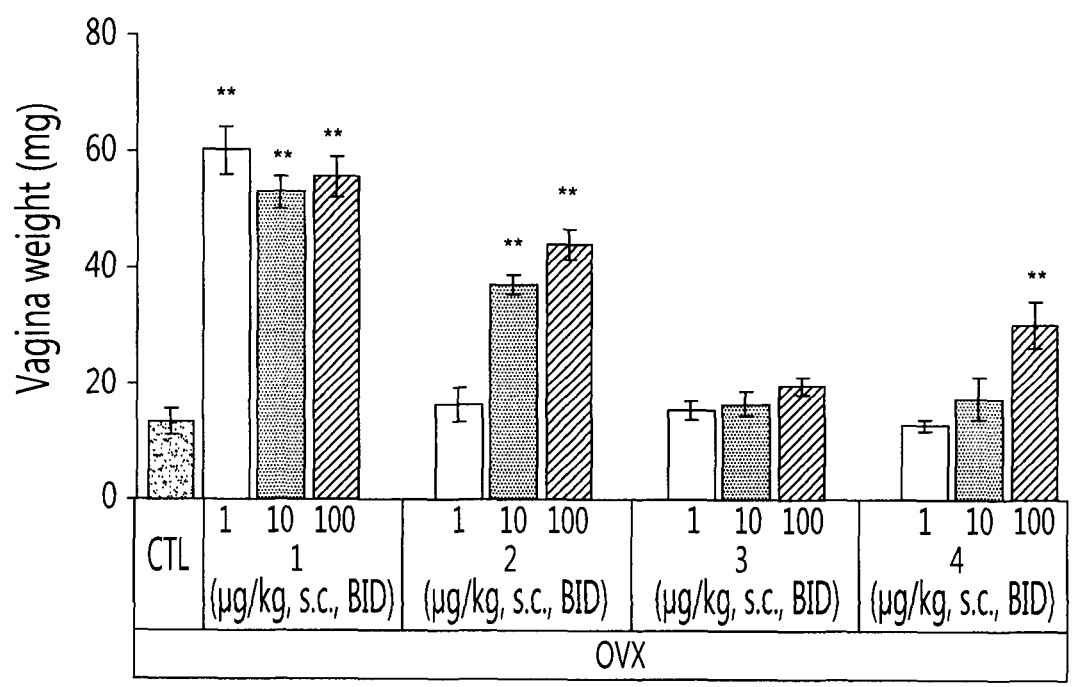

Another approach to evaluate the estrogenic activity of compounds 1-4 was to use the ovariectomized (OVX) mouse model by measuring the weight of the uterus (FIG. 18A) and the vagina (FIG. 18B), two estrogen-sensitive (ER+) tissues. When 17β-E2 (1) was administrated subcutaneously (s.c.) to OVX mice, an increase of the uterine weight from 24 mg (control) to 125, 155 and 160 mg, depending on the dose (1, 10 and 100 µg/kg, respectively), was observed. For 17α-E2 (2) and 18-epi-17α-E2 (4), the increase in uterine weight was only significantly different (P≤0.01) to control group (3.6 and 2.6-folds, respectively) at a dose of 100 µg/kg suggesting an estrogenic effect. This was not in the same way for the 18-epi-17β-E2 (3) which presented a weakly and not significant uterotrophic activity (1.5-folds vs. control group) at this high dose. Doses of 1 and 10 µg/kg reflect the same pattern of response. Measuring the weight of vagina demonstrated the same tendency as observed with the uterus. Thus, like for the uterus, the order of estrogenic potencies in vagina was 17β-E2 (1)>17α-E2 (2)>18-epi-17α-E2 (4), whereas no significant uterotrophic activity was obtained with 18-epi-17β-E2 (3). Such results are in agreement with the ER binding affinity data.

Structural Analysis

Figure 19:
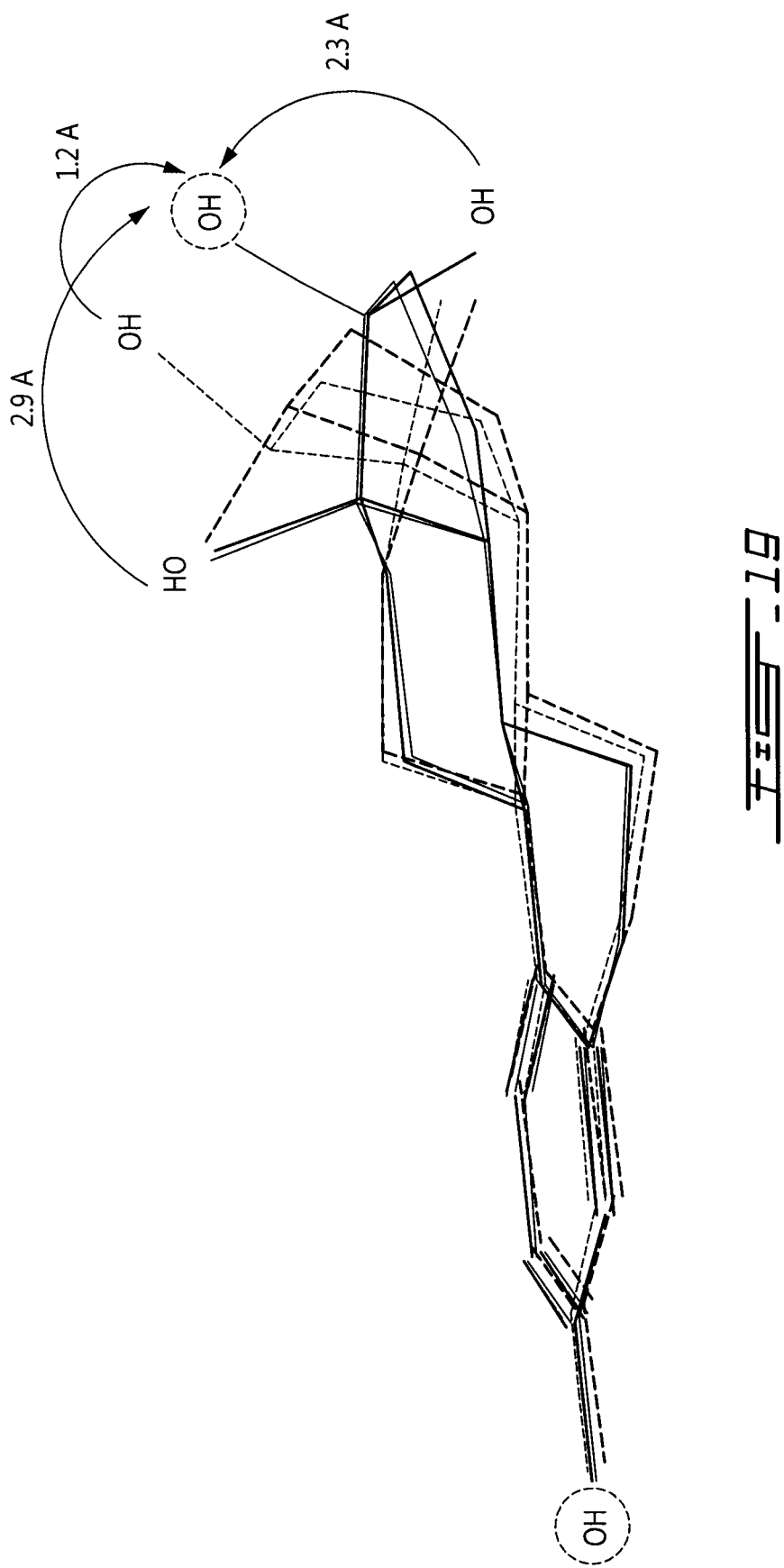
FIG. 19 represents an illustration of the Overlapping of the four E2 isomers (compounds 1-4) showing the positioning of the key 17β-OH group. 17β-E2 (1) in red, 17α-E2 (2) in blue, 18-epi-17β-E2 (3) in green and 18-epi-17α-E2 (4) in pink. The structure energy minimization as well as overlaying were performed using Chem3D (Pro Version 5.0) software. The energy minimization were obtained with the MM2 minization method (RMS gradient=0.100).

An examination of the three dimensional structures of compounds 1-4 was done using Chem3D software (FIG. 19). A superposition of the phenolic A ring of the four E2 isomers suggests that the variability in D-ring orientation and shape is compatible with receptor binding affinity and some degree of activity. In fact, it is known that subtle modifications of the E2 nucleus can modulate the response pattern within a cell. From the data it appears that changes in functional groups, and in D-ring conformation, like those produced by modifying the orientation of 17-OH and 18-methyl group, can explain the variable ER-binding affinity and estrogenic activity of compounds 1-4. As expected, the ideal position of 17-OH to get an optimal interaction with key amino acids of the ER, which resulted in the best ER binding and estrogenic potency, is that of the natural ligand of ER (17β-E2: compound 1). Thus, changing the 17β-OH orientation of 1 to a 17α-OH orientation (compound 2) clearly reduced both the RBA and estrogenicity. The same results were also obtained for compounds 3 and 4 having an 18-methyl orientation inversed from the beta face (natural R configuration) to the alpha face (unnatural S configuration). Such modification greatly changes the shape of the 17β-E2 and 17α-E2 nuclei and consequently the 17-OH positioning. In fact, it was observed that the distance between the optimal positioning of 17β-OH (as in compound 1) and the positioning of OH in 18-epi-17β-E2 (3) and 18-epi-17α-E2 (4) correlates with the biological activity. Thus, the further removed the 17-OH of 3 and 4 is from its positioning in compound 1 (2.9 and 1.2 Å for compounds 3 and 4, respectively), the less estrogenic they are and the weaker they bind to ER (Table 5) However, to explain the difference between 2 and 4, which have roughly the same distance between their 17-OH and that of 1 (2.4 and 2.9 Å, respectively), the consideration of a further parameter (i.e. steric hindrance) is required. Ring D of both C18 epimers 3 and 4 has a less planar shape than ring D of 1 and 2 limiting the access to the ER. In other words, the interference between the ER and the ring D of compounds with unnatural configuration (18-epi-methyl) is harmful to hydrogen bond formation between key amino acids and 17-OH. In summary, the 17-OH group positioning and steric hindrance of 18-epi-E2 nuclei can be used to explain the great reduction of estrogenic activity.

Additional Isomer of E2

The synthesis of a further E2 isomer is illustrated hereinbelow in Scheme 22B.

Scheme 22B: Reagents and conditions: (a) 1,2-phenylendiamine, acetic acid, reflux, 5 h; (b) 3-carboxamide-benzaldehyde, KOH, EtOH, rx; (c), H$_2$, Pd/C (10%), MeOH, rt; (d) NaBH$_4$, MeOH/DM (5:2), rt.

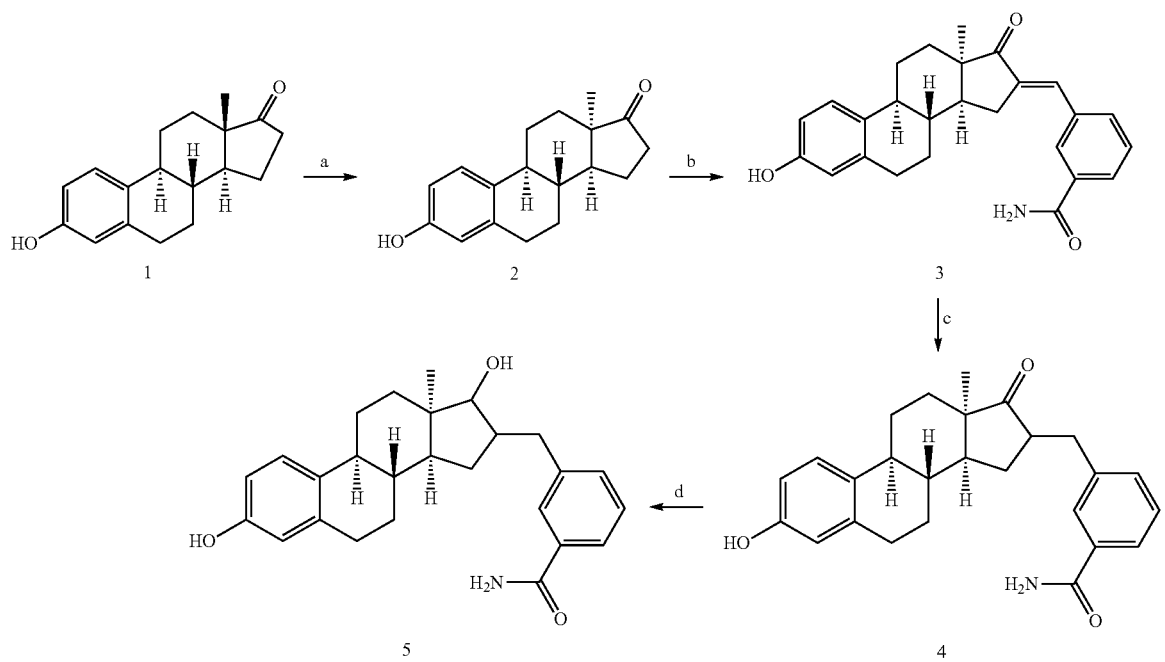

3-{(E)-[(13α,16E)-3-hydroxy-17-oxoestra-1(10),2,4-trien-16-ylidene]methyl}benzamide (3)

To a solution of compound 2 (750 mg, 2.8 mmol) in EtOH (100 mL) was added 3-formyl-benzamide (825 mg, 5.5 mmol) and an aqueous KOH solution (10%; 10 mL). The solution was then heated at reflux over a period of 30 min. The resulting solution was then diluted with water (500 mL), neutralized with aqueous HCl 10%, and extracted with EtOAc (3×150 mL). The combined organic layers were washed with brine, dried with MgSO$_4$ and concentrated. The crude compound was purified by flash chromatography using EtOAc/Hexanes (7:3) as the eluent system providing 598 mg (54% yield) of compound 3. $^1$H NMR (CD$_3$OD): 1.15 (s, 18-CH$_3$), 0.65-2.69 (unassigned CH and CH$_2$), 2.98 and 3.29 (m, 15-CH$_2$), 6.42 (d, J=2.4 Hz, 4-CH), 6.54 (dd, J$_{2=2.6}$ Hz, J$_1$=8.5 Hz, 2-CH), 7.09 (d, J=8.6 Hz, 1-CH), 7.51

(s, 1'-CH), 7.59 (t, J=7.8 Hz, 5"-CH), 7.82 (d, J=7.8 Hz, 6"-CH), 7.91 (d, J=7.8 Hz, 4"-CH), 8.14 (s, 2"-CH).

3-{[(13α)-3-hydroxy-17-oxoestra-1(10),2,4-trien-16-yl]methyl}benzamide (4)

To a solution of compound 3 (100 mg, 0.25 mmol) in MeOH (10 mL) under an argon atmosphere was added Pd on charcoal (10%) (20 mg). The reaction vessel was flushed three times with H₂ and stirred over a period of 48 h, then filtered on celite and evaporated under reduce pressure to provide 100 mg (mixture of two diastereoisomers 16α and 16β-methyl-m-benzamide-estrone). ¹H NMR (DMSO-d₆): 0.79 (s, 18-CH₃), 1.07 (s, 18-CH₃), 0.60-3.16 (unassigned CH and CH₂), 6.39 (m, 1H), 6.48 (m, 1H), 7.02 (d, 1H), 7.34 (m, 4H), 7.67 (m, 2H), 7.91 (s, 1H), 9.1 (broad s, 1H, 3-OH).

3-{[(13α)-3,17-dihydroxyestra-1(10),2,4-trien-16-yl]methyl}benzamide (5)

To a solution of compounds 4 (100 mg, 0.25 mmol) in MeOH (5 mL) was added NaBH₄ (50 mg, 1.31 mmol). The solution was stirred overnight. The resulting solution was concentrated under vacuo, diluted with EtOAc (50 mL), washed with water (100 mL) and brine, dried with MgSO₄ and evaporated under reduce pressure to give 100 mg of the crude 17β-alcohols (mixture of four diastereoisomers) to be separated by LCMS-prep.

Azalactone Inhibitors of 17β-HSD1 and 17β-HSD3

The present disclosure also includes inhibitors of both 17β-HSD1 and 17β-HSD3, which are azalactone derivatives of pregnenolone having the formula Xa or Xb:

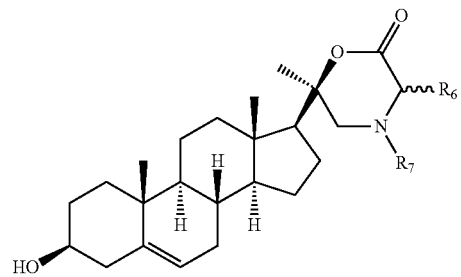

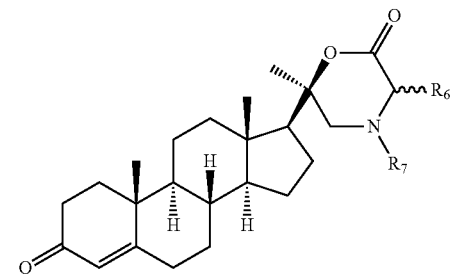

wherein:

$R^6$ and $R^7$ are independently or simultaneously H, alkyl, cycloalkyl, aryl, aralkyl, or heterocyclyl.

The synthesis of such compounds of the formula Xa or Xb is shown in Scheme 23:

Scheme 23

Scheme 23: Reagents and conditions: (a) Phenylalanine methyl ester (L or D); MeOH; 90° C.; (b) CH₂ONa; THF; rt; (c) Benzyl bromide; DIPEA; DCM; 75° C, (Schlenk tube); (d) MeOH/HCl (95/5); THF; rt.

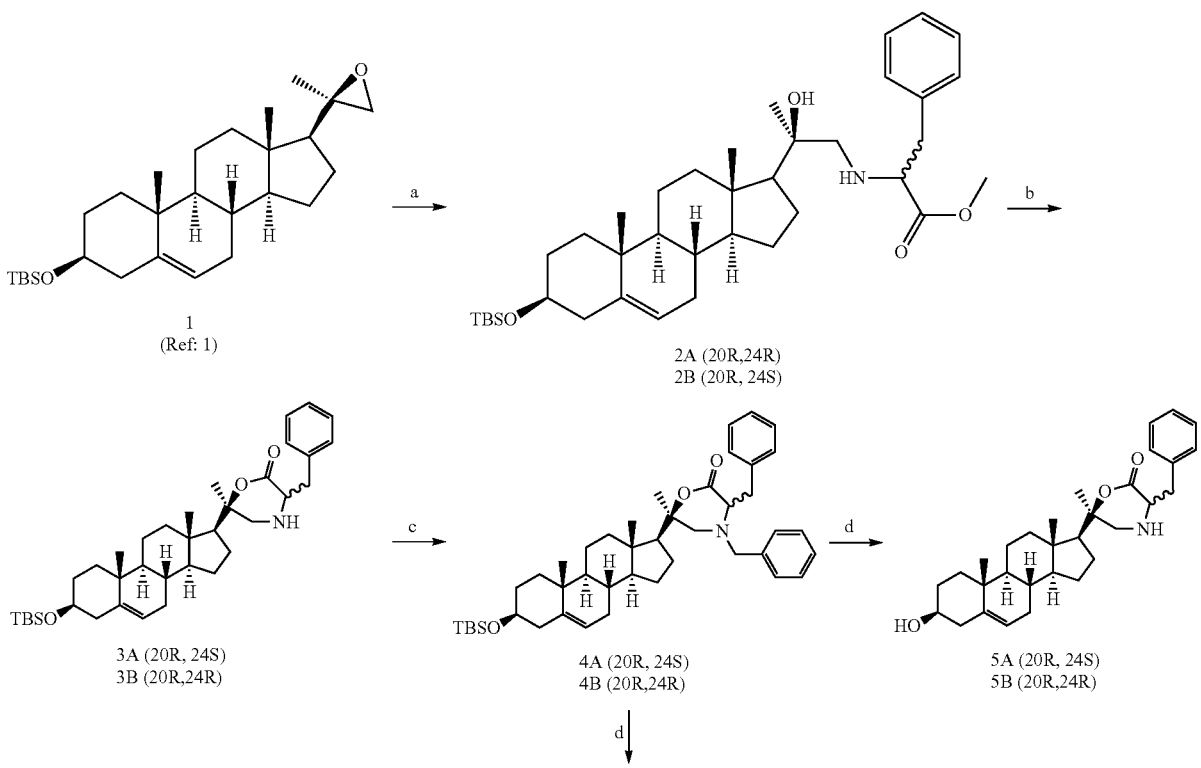

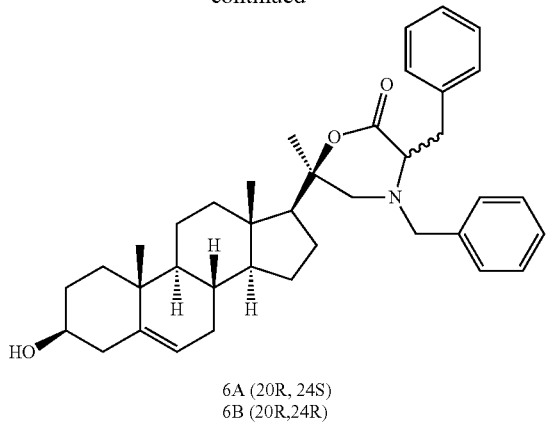

6A (20R, 24S)
6B (20R, 24R)

EXPERIMENTAL

General Remarks

Pregnenolone was purchased from Steraloids (Wilton, N.H.). (L)-phenylalanine methyl ester hydrochlorides and chemical reagents of highest purity were obtained from Sigma-Aldrich Canada Ltd. (Oakville, ON, Canada), solvents were obtained from Fisher Scientific (Montréal, QC, Canada). Reactions were run under an inert (argon) atmosphere in oven-dried glassware. Analytical thin-layer chromatography (TLC) was performed on 0.20-mm silica gel 60 F254 plates (Fisher Scientific), and compounds were visualized by using ammonium molybdate/sulfuric acid/water (with heating). Flash column chromatography was performed with Silicycle R10030B 230-400 mesh silica gel (Québec, QC, Canada). Infrared spectra (IR) were obtained from a thin film of compound usually solubilised in $CH_2Cl_2$ and deposited upon a NaCl pellet. They were recorded with a Horizon MB 3000 ABB FTIR spectrometer (ABB, Canada) and only characteristic bands are reported. Nuclear magnetic resonance (NMR) spectra were recorded with a Bruker Avance 400 digital spectrometer (Billerica, Mass., USA) and reported in ppm; The $CDCl_3$ $^1H$ and $^{13}C$ NMR signals (7.26 and 77.00 ppm respectively) and Acetone-$d_6$ $^1H$ and $^{13}C$ NMR signals (2.05 and 28.94 ppm respectively) were used as internal references.

General Procedure for the Synthesis of Amino Alcohols 2A and 2B

The oxirane[56] 1 (0.5 g, 1.1 mmol) was dissolved in dry MeOH (13 ml) and L-phenylalanine methyl ester (2.0 g, 11.2 mmol) was added in a Schlenk tube. The solution was stirred and heated at 90° C. during 4 days. The reaction mixture was then dissolved in DCM, filtered and evaporated under reduced pressure. The crude reaction mixture was dissolved in DCM and pre-adsorbed on silica gel to be purified by flash column chromatography using hexanes/EtOAc (85:15 to 1:1) as eluent to give compound 2B (330 mg; 47%) as major product and compound 2A as minor product (130 mg; 19%). The starting epoxide 1 (40 mg) was also recuperated.

Methyl (2R)-2-({(2R)-2-[(3S,8S,9S,10R,13S,14S)-3-{[tert-butyl(dimethyl)silyl]oxy}-10,13-dimethyl-2,3,4,7,8,9,10,11,12,13,14,15,16,17-tetradecahydro-1H-cyclopenta[α]phenanthren-17-yl]-2-hydroxypropyl}amino)-3-phenylpropanoate (2A)

Rf=0.4 (hexanes/EtOAc, 7:3); IR (film): 3560 and 3333 (OH and NH), 1732 (C=O of ester). $^1H$ NMR ($CDCl_3$): 0.06 (s, 6H, $(CH_3)_2Si$), 0.81 (s, 3H, $CH_3$-18), 0.89 (s, 9H, $(CH_3)_3CSi$), 0.99 (s, 3H, $CH_3$-19), 1.15 (s, 3H, $CH_3$-21), 1.25-2.16 (unassigned CH and $CH_2$), 2.23 and 2.57 (2d of AB system, J=11.8 Hz, 2H, $CH_2N$), 2.95 (m, 2H, $CH_2$-Ph), 3.44-3.46 ($t_{app}$, J=6.0 Hz, 1H, CHC=O), 3.47, (m, 1H, CH-3), 3.68 (s, 3H, $OCH_3$), 5.31 (d, J=5.7 Hz, 1H, CH-6), 7.23 (m, 5H, Ph). $^{13}C$ NMR ($CDCl_3$): −4.59 ($Si(CH_3)_2$), 13.42, 18.26 ($SiC(CH_3)_3$), 19.41, 20.92, 22.31, 23.84, 24.98, 25.93, 31.37, 31.79, 32.07, 36.56, 37.36, 39.96, 42.59, 42.79, 50.09, 51.75, 56.95, 57.22, 57.84, 63.84, 72.61, 72.98, 121.06, 126.79, 128.46, 129.12, 137.18, 141.55, 175.03.

Methyl (2S)-2-({(2R)-2-[(3S,8S,9S,10R,13S,14S)-3-{[tert-butyl(dimethyl)silyl]oxy}-10,13-dimethyl-2,3,4,7,8,9,10,11,12,13,14,15,16,17-tetradecahydro-1H-cyclopenta[α]phenanthren-17-yl]-2-hydroxypropyl}amino)-3-phenylpropanoate (2B)

Rf=0.3 (hexanes/EtOAc, 7:3); IR (film): 3607 and 3313 (OH and NH), 1736 (C=O of ester). $^1H$ NMR ($CDCl_3$): 0.06 (s, 6H, $(CH_3)_2Si$), 0.78 (s, 3H, $CH_3$-18), 0.89 (s, 9H, $(CH_3)_3CSi$), 0.99 (s, 3H, $CH_3$-19), 1.13 (s, 3H, $CH_3$-21), 1.14-2.15 (unassigned CH and $CH_2$), 2.18 and 2.67 (2d of AB system, J=12.3 Hz, 2H, $CH_2N$), 2.94 (m, 2H, $CH_2$-Ph), 3.44-3.46 ($t_{app}$, J=6.1 Hz, 1H, CHC=O), 3.47, (m, 1H, CH-3), 3.68 (s, 3H, $OCH_3$), 5.32 (d, J=5.1 Hz, 1H, CH-6), 7.23 (m, 5H, Ph). $^{13}C$ NMR ($CDCl_3$): −4.59 ($Si(CH_3)_2$), 13.46, 18.25 ($SiC(CH_3)_3$), 19.41, 20.92, 22.52, 23.86, 24.83, 25.93, 31.38, 31.81, 32.06, 36.57, 37.37, 39.76, 39.83, 42.45, 42.79, 50.13, 51.75, 56.82, 57.27, 58.08, 64.12, 72.60, 73.23, 121.05, 126.76, 128.44, 129.15, 137.33, 141.57, 174.97.

General Procedure for the Synthesis of Azalactones 3A and 3B

To a solution of sodium methoxyde (969 mg, 19 mmol) in anhydrous THF (100 mL) was added a solution of the amino alcohol 2A (590 mg, 0.95 mmol) in dry THF (30 mL) under argon atmosphere. The solution was stirred during 1.5 h at room temperature, and the reaction mixture quenched with water and extracted 4 times with 130 mL of ethyl acetate. The organic layer was dried with anhydrous $Na_2SO_4$, filtered and dried under reduced pressure. The residue was adsorbed on silica gel and purified by flash chromatography using hexanes/ethyl acetate (85:15) as eluent to give compound 3B as the major product (350 mg, 63%) and 3A as minor product (157 mg, 28%).

(3S,6R)-3-benzyl-6-[(3β)-3-{[tert-butyl(dimethyl)silyl]oxy}androst-5-en-17-yl]-6-methylmorpholin-2-one (3A)

Rf=0.6 (hexanes/EtOAc, 3:1); IR (film): 3441-3340 (NH), 1728 (C=O of ester). $^1$H NMR (CDCl$_3$): 0.05 (s, 6H, (CH$_3$)$_2$Si), 0.86 (s, 3H, CH$_3$-18), 0.89 (s, 9H, (CH$_3$)$_3$CSi), 1.00 (s, 3H, CH$_3$-19), 1.31 (s, 3H, CH$_3$-21), 1.36-2.50 (unassigned CH and CH$_2$), 2.65 and 2.96 (2d of AB system, J=13.2 Hz, 2H, CH$_2$N), 3.19 (m, 2H, CH$_2$-Ph), 3.46 (m, 1H, CH-3), 3.62 (m, 1H, CHC=O), 5.31 (d, J=4.8 Hz, 1H, CH-6), 7.30 (m, 5H, Ph). $^{13}$C NMR (CDCl$_3$): −4.60 (Si(CH$_3$)$_2$), 13.62, 18.25 (SiC(CH$_3$)$_3$), 19.42, 20.83, 22.83, 23.70, 23.81, 25.92, 31.28, 31.70, 32.03, 36.54, 37.35, 38.06, 39.90, 42.76, 42.82, 50.07, 51.44, 56.82, 57.67, 58.93, 72.56, 86.90, 120.88, 126.98, 128.75, 129.49, 137.36, 141.58, 170.72.

(3R,6R)-3-benzyl-6-[(3β)-3-{[tert-butyl(dimethyl)silyl]oxy}androst-5-en-17-yl]-6-methylmorpholin-2-one (3B)

Rf=0.4 (hexanes/EtOAc, 3:1); IR (film): 3367-3028 (NH), 1713 (C=O of ester). $^1$H NMR (CDCl$_3$): 0.07 (s, 6H, (CH$_3$)$_2$Si), 0.7 (s, 3H, CH$_3$-18), 0.90 (s, 9H, (CH$_3$)$_3$CSi), 0.98 (s, 3H, CH$_3$-19), 1.35 (s, 3H, CH$_3$-21), 1.36-2.50 (unassigned CH and CH$_2$), 2.72 and 3.07 (2d of AB system, J=14.0 Hz, 2H, CH$_2$N), 3.20 (m, 2H, CH$_2$-Ph), 3.50 (m, 1H, CH-3), 3.80 (m, 1H, CHC=O), 5.32 (d, J=5.1 Hz, 1H, CH-6), 7.30 (m, 5H, Ph). $^{13}$C NMR (CDCl$_3$): −4.58 (Si(CH$_3$)$_2$), 13.66, 18.25 (SiC(CH$_3$)$_3$), 19.37, 20.75, 22.62, 23.25, 23.36, 25.92, 31.31, 31.70, 32.02, 36.54, 37.30, 37.38, 39.21, 42.07, 42.74, 49.82, 50.03, 55.97, 56.04, 57.48, 72.51, 87.16, 120.90, 127.25, 128.80, 129.83, 137.27, 141.55, 171.11.

Synthesis of the N-benzylated Azalactones 4A and 4B

To a solution of azalactones 3A (60 mg, 0.1 mmol) or 3B (150 mg, 0.25 mmol), in dry DCM (3A: 5 mL; 3B: 13 mL) was added dropwise diisopropylethylamine (1.7 eq) in a Schlenk tube. The solution was stirred and heated at 75° C. during 10 min and then allowed to return at room temperature. Benzyl bromide (1.7 eq) was then added to the solution and the reaction mixture was stirred and heated at 75° C. during 48 h. After cooling the Schlenk tube, silica gel was added to the crude mixture and the solvent was evaporated under reduce pressure. The crude compound was purified by flash chromatography using hexanes/ethyl acetate (98:2) as eluent to give corresponding compound 4A (48 mg, 70%) or compound 4B (134 mg, 79%).

(3S,6R)-3,4-dibenzyl-6-[(3β)-3-{[tert-butyl(dimethyl)silyl]oxy}androst-5-en-17-yl]-6-methylmorpholin-2-one (4A)

Yield: 70%; Rf=0.80 (hexanes/ethyl acetate 3:1); IR (film): 1728 (C=O of ester). $^1$H NMR (CDCl$_3$): 0.04 (s, 6H, (CH$_3$)$_2$Si), 0.77 (s, 3H, CH$_3$-18), 0.88 (s, 9H, (CH$_3$)$_3$CSi), 0.96 (s, 3H, CH$_3$-19), 0.98-1.53 (unassigned CH and CH$_2$), 1.55 (s, 3H, CH$_3$-21), 1.56-2.16 (unassigned CH and CH$_2$), 2.24 and 2.40 (2d of AB system, J=12.34 Hz, 2H, CH$_2$N), 3.11 and 4.35 (2d of AB system, J=13.56 Hz, 2H, PhCH$_2$N), 3.27 and 3.56 (m, 2H, CH$_2$Ph), 3.41 (m, 1H, CHC=O), 3.42 (m, 1H, CH-3), 5.30 (m, 1H, CH-6), 7.27 (m, 10H, Ph). $^{13}$C NMR (CDCl$_3$): −4.60 (Si(CH$_3$)$_2$), 13.42, 18.24 (SiC(CH$_3$)$_3$), 19.40, 20.78, 22.76, 23.51, 23.66, 25.91, 29.69, 31.20, 31.66, 32.01, 35.69, 36.49, 37.31, 39.79, 42.74, 42.79, 50.02, 56.40, 56.76, 57.50, 58.23, 66.15, 72.57, 84.96, 120.87, 126.62, 127.35, 127.96, 128.08, 128.47, 128.51, 130.36, 137.40, 137.51, 141.55, 170.94.

(3R,6R)-3,4-dibenzyl-6-[(3β)-3-{[tert-butyl(dimethyl)silyl]oxy}androst-5-en-17-yl]-6-methylmorpholin-2-one (4B)

Yield: 79%; Rf=0.78 (hexanes/ethyl acetate 3:1); IR (film): 1720 (C=O of ester). $^1$H NMR (CDCl$_3$): 0.08 (s, 6H, (CH$_3$)$_2$Si), 0.77 (s, 3H, CH$_3$-18), 0.89 (s, 9H, (CH$_3$)$_3$CSi), 0.90 (s, 3H, CH$_3$-19), 0.91-1.50 (unassigned CH and CH$_2$), 1.54 (s, 3H, CH$_3$-21), 1.56-2.16 (unassigned CH and CH$_2$), 2.23 and 2.90 (2d of AB system, J=12.68 Hz, 2H, CH$_2$N), 3.23 and 3.46 (m, 2H, CH$_2$Ph), 3.59 and 3.98 (2d of AB system, J=13.12 Hz, 2H, PhCH$_2$N), 3.58 (m, 1H, CHC=O), 3.52 (m, 1H, CH-3), 5.32 (d, J=5.0 Hz, 1H, CH-6), 7.29 (m, 10H, Ph). $^{13}$C NMR (CDCl$_3$): −4.54 (Si(CH$_3$)$_2$), 13.91, 18.28 (SiC(CH$_3$)$_3$), 19.37, 20.55, 22.51, 23.03, 23.35, 25.97, 31.26, 31.66, 32.07, 34.50, 36.50, 37.37, 38.52, 41.69, 42.79, 50.09, 54.76, 55.32, 55.40, 58.38, 63.83, 72.56, 85.71, 121.03, 126.75, 127.77, 128.26, 128.29, 130.15, 130.48, 135.47, 137.96, 141.52, 170.52.

Synthesis of Azalactones 5A, 5B, 6A and 6B: General Procedure for the TBS Deprotection To a solution of compounds 3A, 3B, 4A or 4B in THF (4 mL) was added a methanolic solution of hydrochloric acid (5%) (3 mL). The mixture was stirred at room temperature during 90 min. A saturated solution of aqueous sodium bicarbonate was added and the aqueous phase extracted four times with ethyl acetate. The organic phase was dried with anhydrous Na$_2$SO$_4$ and evaporated under reduced pressure. The crude compound was purified by flash chromatography using hexane/ethyl acetate/triethylamine (79:20:1) as eluent for compounds 5A, 5B and hexane/ethyl acetate (3:1) for compounds 6A and 6B respectively.

(3S,6R)-3-benzyl-6-[(3β)-3-hydroxyandrost-5-en-17-yl]-6-methylmorpholin-2-one (5A)

Yield: 15 mg, 98%; Rf=0.2 (hexanes/EtOAc, 1:1); IR (film): 3086-3600 (OH and NH), 1720 (C=O of ester). $^1$H NMR (CDCl$_3$): 0.87 (s, 3H, CH$_3$-18), 1.00 (s, 3H, CH$_3$-19), 1.31 (s, 3H, CH$_3$-21), 1.34-2.60 (unassigned CH and CH$_2$), 2.65 and 2.96 (2d of AB system, J=13.2 Hz, 2H, CH$_2$N), 3.19 (m, 2H, CH$_2$-Ph), 3.51 (m, 1H, CH-3), 3.62 (m, 1H, CHC=O), 5.34 (d, J=5.0 Hz, 1H, CH-6), 7.26 (m, 5H, Ph). $^{13}$C NMR (CDCl$_3$): 13.62, 19.38, 20.84, 22.83, 23.69, 23.82, 29.69, 31.26, 31.60, 31.66, 36.45, 37.20, 38.04, 39.87, 42.24, 42.82, 49.97, 51.41, 56.77, 57.65, 58.92, 71.73, 86.88, 121.42, 126.99, 128.75, 129.50, 137.34, 140.77, 170.72.

(3R,6R)-3-benzyl-6-[(3β)-3-hydroxyandrost-5-en-17-yl]-6-methylmorpholin-2-one (5B)

Yield: 79 mg, 65%; Rf=0.15 (hexanes/EtOAc, 1:1); IR (film): 3086-3600 (OH and NH), 1713 (C=O of ester). $^1$H NMR (CDCl$_3$): 0.71 (s, 3H, CH$_3$-18), 0.99 (s, 3H, CH$_3$-19), 1.36 (s, 3H, CH$_3$-21), 1.39-2.33 (unassigned CH and CH$_2$), 2.72 and 3.06 (2d of AB system, J=13.8 Hz, 2H, CH$_2$N), 3.20 (m, 2H, CH$_2$-Ph), 3.55 (m, 1H, CH-3), 3.79 and 3.80 (2d of AB system, J=4.4 Hz, 1H, CHC=O), 5.36 (d, J=5.1

Hz, 1H, CH-6), 7.30 (m, 5H, Ph). $^{13}$C NMR (CDCl$_3$): 13.65, 19.34, 20.76, 22.61, 23.27, 23.35, 31.28, 31.56, 31.67, 36.45, 37.26, 37.29, 39.18, 42.06, 42.22, 49.75, 49.95, 55.94, 56.05, 57.42, 71.60, 87.14, 121.39, 127.24, 128.80, 129.82, 137.22, 140.80, 171.13.

(3S,6R)-3,4-dibenzyl-6-[(3β)-3-hydroxyandrost-5-en-17-yl]-6-methylmorpholin-2-one (6A)

Yield: 22 mg, 53%; Rf=0.2 (hexanes/ethyl acetate 3:1); IR (film): 3398 (OH), 1720 (C═O), 1454 (C—O). $^1$H NMR (CDCl$_3$): 0.78 (s, 3H, CH$_3$-18), 0.96 (s, 3H, CH$_3$-19), 0.97 (s, 3H, CH$_3$-21), 0.99-2.17 (unassigned CH and CH$_2$), 2.24 and 2.40 (2d of AB system, J=12.3 Hz, 2H, CH$_2$N), 3.10 and 4.35 (2d of AB system, J=13.6 Hz, 2H, PhCH$_2$N), 3.28 and 3.56 (m, 2H, CH$_2$Ph), 3.41 (m, J=3.0 Hz, 1H, CHC═O), 3.49 (m, 1H, CH-3), 5.31 (m, 1H, HC-6), 7.36 (m, 10H, Ph). $^{13}$C NMR (CDCl$_3$): 13.43, 19.35, 20.79, 22.77, 23.53, 23.66, 31.18, 31.59, 31.62, 35.69, 36.41, 37.18, 39.76, 42.23, 42.79, 49.92, 56.39, 56.72, 57.48, 58.22, 66.14, 71.69, 71.72, 84.95, 121.41, 126.62, 127.35, 127.95, 128.08, 128.22, 128.46, 128.51, 130.36, 137.40, 137.51, 140.74, 170.95.

(3R,6R)-3,4-dibenzyl-6-[(3β)-3-hydroxyandrost-5-en-17-yl]-6-methylmorpholin-2-one (6B)

Yield: 90 mg, 83%; Rf=0.15 (hexanes/ethyl acetate 3:1); IR (film): 3402 (OH), 1720 (C═O), 1454 (C—O). $^1$H NMR (CDCl$_3$): 0.57 (s, 3H, CH$_3$-18), 0.95 (s, 3H, CH$_3$-19), 1.24 (s, 3H, CH$_3$-21), 1.26-2.19 (unassigned CH and CH$_2$), 2.24 and 2.91 (2d of AB system, J=12.7 Hz, 2H, CH$_2$N), 3.58 and 3.97 (2d of AB system, J=13.2 Hz, 2H, PhCH$_2$N), 3.23 and 3.46 (m, 2H, CH$_2$Ph), 3.55 (m, 1H, CHC═O), 3.59 (m, 1H, CH-3), 5.36 (d, J=5.1 Hz, 1H, CH-6), 7.29 (m, 10H, Ph). $^{13}$C NMR (CDCl$_3$): 13.89, 19.32, 20.56, 22.51, 23.03, 23.38, 31.24, 31.59, 31.62, 34.46, 36.42, 37.23, 38.53, 41.71, 42.26, 50.01, 54.81, 55.23, 55.39, 58.35, 63.80, 71.69, 85.74, 121.53, 126.74, 127.75, 128.26, 128.29, 130.11, 130.45, 135.49, 137.97, 140.78, 170.58.

17β-HSD10

17β-hydroxysteroid dehydrogenase type 10 (17β-HSD10) is a mitochondrial enzyme involved in estrogen inactivation, androgen activation, β-oxidation of fatty acids and isomerisation of bile acids. Since this enzyme uses estradiol (E2) as a substrate, there is evidence that the enzyme contributes to Alzheimer's disease pathogenesis by reducing neuroprotective estrogen levels. Moreover, this enzyme plays a significant role in a non-classical androgen synthesis pathway and its expression is up-regulated in certain prostate cancer cells, thus conferring an advantage upon these cells for surviving androgen ablation therapy. Consequently, the inhibition of 17β-HSD10 may provide a new approach to the treatment of these diseases. From the screening study of available molecules in our laboratory, we identified a series of steroid derivatives, showing more than 50% of inhibition for the transformation of estradiol (E2) (1 μM) into estrone (E1) by 17β-HSD10 when tested at 1 μM in intact cells. An IC$_{50}$ value of 0.55 μM was obtained for RM-532-46, the 3β-androsterone steroid core with the best enzyme inhibition. This inhibitory activity is a good starting point considering that the Km of the enzyme for E2 as a substrate is 43 μM. The obtaining of 17β-HSD10 inhibitors could be useful tools to further elucidate the role of 17β-HSD10 in normal cellular function as well as in regulating steroid hormone levels.

The human 17β-hydroxysteroid dehydrogenase type 10 (17β-HSD10) is known for its multiple functions. 17β-HSD10 is a homotetrameric mitochondrial protein and is essentially expressed in the liver and several other tissues including brain and gonads.[6,35,36] It plays an important role in the metabolism of sex steroid hormones through its 17β-HSD as well as 3α-HSD activities (FIG. 19).[37] This enzyme can inactivate E2, the most potent sex steroid responsible for estrogenic activity in women. A strong link has been established between the development of Alzheimer's disease (AD) and the accumulation of amyloid β-peptide (Aβ) in the brain.[57,58] Based on the finding that 17β-HSD10 uses E2 as a substrate, it has been suggested that the enzyme could contribute to AD pathogenesis by reducing neuroprotective E2 levels in the brain.[6] The estrogen-deficient state in AD brain likely promotes neuronal and synaptic loss and impairs hippocampal-dependent learning and memory. He et al[59] have observed higher levels of 17β-HSD10 in brain regions such as the hippocampus, hypothalamus and amygdale, which are more susceptible to AD. Moreover, E2 exerts neuroprotective effects by its regulation of β-amyloid protein precursor trafficking and metabolism. It was reported that E2 treatment reduces the formation of Aβ in both in vivo and in vitro experiments.[60] Additionally, this enzyme can catalyze the intracellular oxidation of allopregnanolone, a positive allosteric modulator of GABA$_A$ receptors, into 5α-dihydroprogesterone (5α-DHP) in astrocytes. Allopregnanolone rapidly modulates neuronal excitability and has pronounced anxiolytic and anticonvulsant effects in man.[61] He et al[62] reported that the expression of 17β-HSD10 has been greatly up-regulated in the activated astrocytes of AD patients. Taken together, these observations provide evidence that 17β-HSD10 may exacerbate the progress of AD.

17β-HSD10 also plays a significant role in a non-classical androgen synthesis pathway because it enables prostate cancer cells to generate dihydrotestosterone (DHT) in the absence of testosterone.[63] In fact, this mitochondrial enzyme catalyzes the transformation of 5α-androstane-3α,17β-diol (3α-diol), an almost inactive androgen, into DHT, a potent androgen, by a regioselective oxidation of the 3α-hydroxyl group rather than the 17β-hydroxyl group (FIG. 19). DHT stimulates prostate growth and is implicated in baldness, acne and hirsutism. A higher expression of this dehydrogenase has been demonstrated in certain prostate cancer cells and there is evidence that these high levels of 17β-HSD10 might confer an advantage upon these cells for surviving androgen ablation therapy.[37] Thus, inhibition of 17β-HSD10 enzymatic activity provides a new approach to the treatment of AD and prostate cancer in combination with known inhibitors of 5α-reductase. In addition to potential therapeutic applications, 17β-HSD10 inhibitors also delineate the role of this steroidogenic enzyme in normal cellular function and in disease pathogenesis.

In one embodiment of the present disclosure, there are included inhibitors of 17β-HSD10, in which the inhibitor has the structure

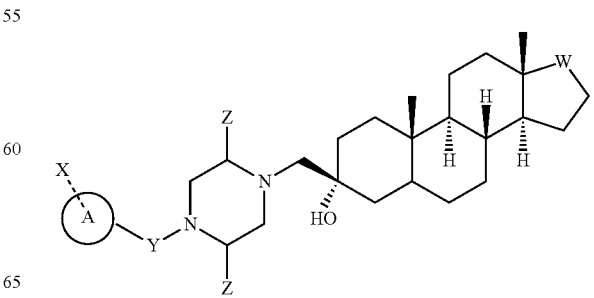

wherein:
A is aryl or heteroaryl;
W is —C(=O)—, —CH(—OH) or —CH(—COCH$_3$);
X is H, alkyl, thioalkyl, halo or alkoxy;
Y is —CH$_2$—, —C(=O)— or —S(=O)$_2$;
Z is H or alkyl.

The 17β-HSD10 inhibitors of the disclosure include compounds such as those shown in Table 6:

TABLE 6

Inhibition of 17β-HSD10 ([$^{14}$C]-E2 into [$^{14}$C]-E1)

| Entry | Compound | X | Y | Z | W | Inhibition (%) at 1 μM |
|---|---|---|---|---|---|---|
| 1 | 15a | 2-CF$_3$ | SO$_2$ | CH$_3$ | C=O | 42 |
| 2 | — | 2-CF$_3$ | SO$_2$ | CH$_3$ | β-OH | 16 |
| 3 | 15b | 3-CF$_3$ | SO$_2$ | CH$_3$ | C=O | 30 |
| 4 | 15c | 4-CF$_3$ | SO$_2$ | CH$_3$ | C=O | 18 |
| 5 | 14b | 2-CF$_3$ | SO$_2$ | H | C=O | 32 |
| 6 | 14a | 3-CF$_3$ | SO$_2$ | H | C=O | 3 |
| 7 | 14c | 4-CF$_3$ | SO$_2$ | H | C=O | 14 |
| 8 | 13d | 4-CF$_3$ | C=O | CH$_3$ | C=O | 22 |
| 9 | 12c | 2-CF$_3$ | C=O | H | C=O | 47 |
| 10 | 11b | 2-CF$_3$ | CH$_2$ | CH$_3$ | C=O | 25 |
| 11 | 11a | 3-CF$_3$ | CH$_2$ | CH$_3$ | C=O | 26 |
| 12 | 11c | 4-CF$_3$ | CH$_2$ | CH$_3$ | C=O | 24 |
| 13 | 11d | 3-CF$_3$S | CH$_2$ | CH$_3$ | C=O | 27 |
| 14 | 11e | 3-Cl | CH$_2$ | CH$_3$ | C=O | 25 |
| 15 | 11f | 3-CH$_3$O | CH$_2$ | CH$_3$ | C=O | 21 |
| 16 | 11g | H (3-Pyr)* | CH$_2$ | CH$_3$ | C=O | 21 |
| 17 | 10b | 2-CF$_3$ | CH$_2$ | H | C=O | 50 |
| 18 | 10a | 3-CF$_3$ | CH$_2$ | H | C=O | 34 |
| 19 | 10d | 3-CF$_3$S | CH$_2$ | H | C=O | 29 |
| 20 | 10e | 3-Cl | CH$_2$ | H | C=O | 21 |
| 21 | 10f | 3-CH$_3$O | CH$_2$ | H | C=O | 59 |
| 22 | 10g | H (3-Pyr)* | CH$_2$ | H | C=O | 37 |
| 23 | — | H | CH$_2$ | H | C=O | 53 |
| 24 | 7j | H | CH$_2$ | H | C=O | 57 |
| 25 | — | H | CH$_2$ | H | β-COCH$_3$ | 11 |
| 26 | — | — | — | — | — | 6 |
| 27 | — | — | — | — | — | 5 |

*A 3-pyridyl group instead of a phenyl derivative.
**4-Androstene instead of 5α-androstane nucleus.

Figure 20:
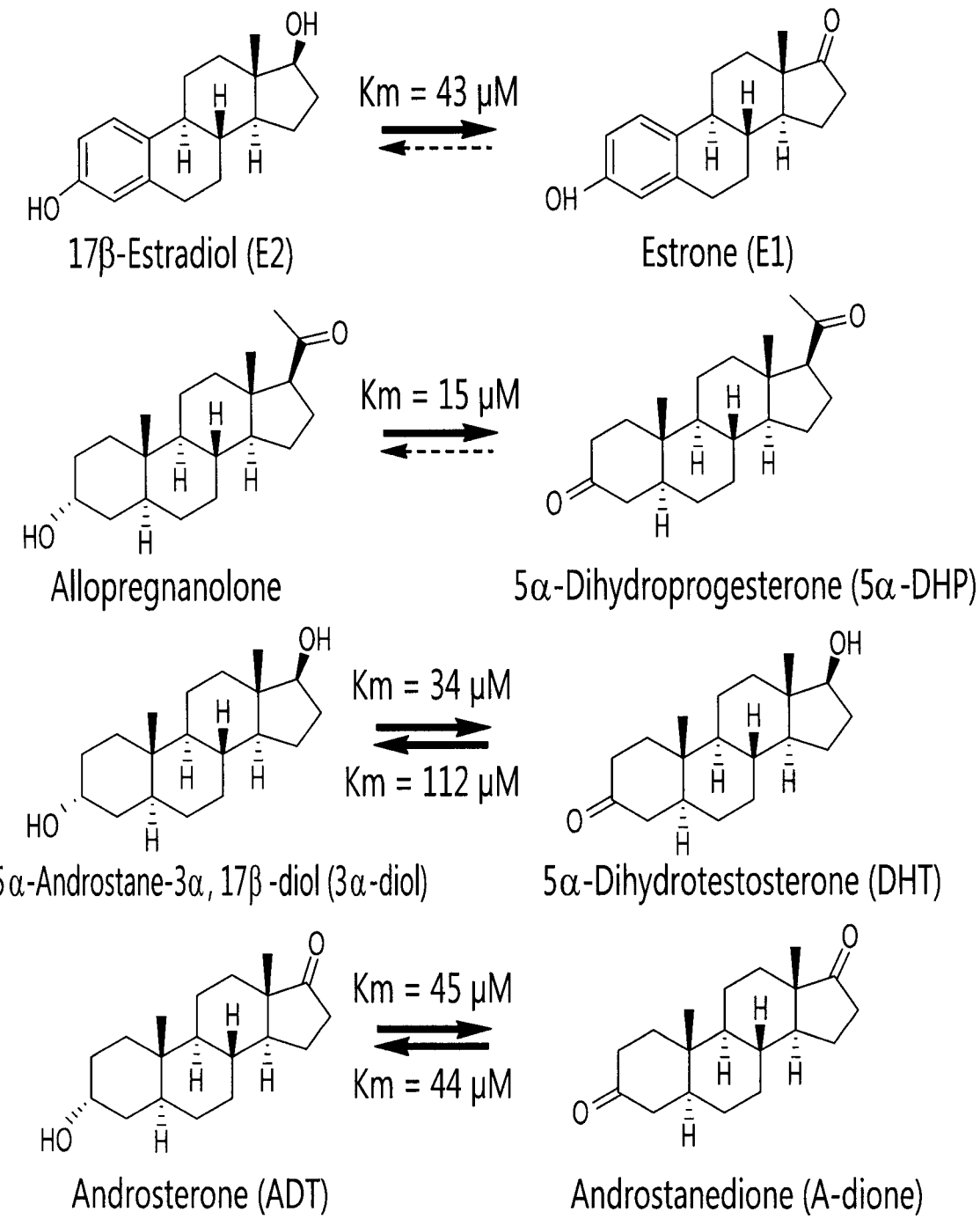
FIG. 20 illustrates the reactions catalyzed by 17β-HSD10 and cofactors NAD+ (oxidation) or NADH (reduction).

The IC$_{50}$ for compound 21 was also determined (the concentration that inhibits 50% of enzymatic activity), and also for the natural substrate of the enzyme E2. As shown in FIG. 20, an IC$_{50}$ value of 0.55 μM was obtained for compound 21, it was not possible to determine the IC$_{50}$ for E2 in the range of concentrations used (0.1-10 μM), suggesting an IC$_{50}$>10 μM.

Figure 21:
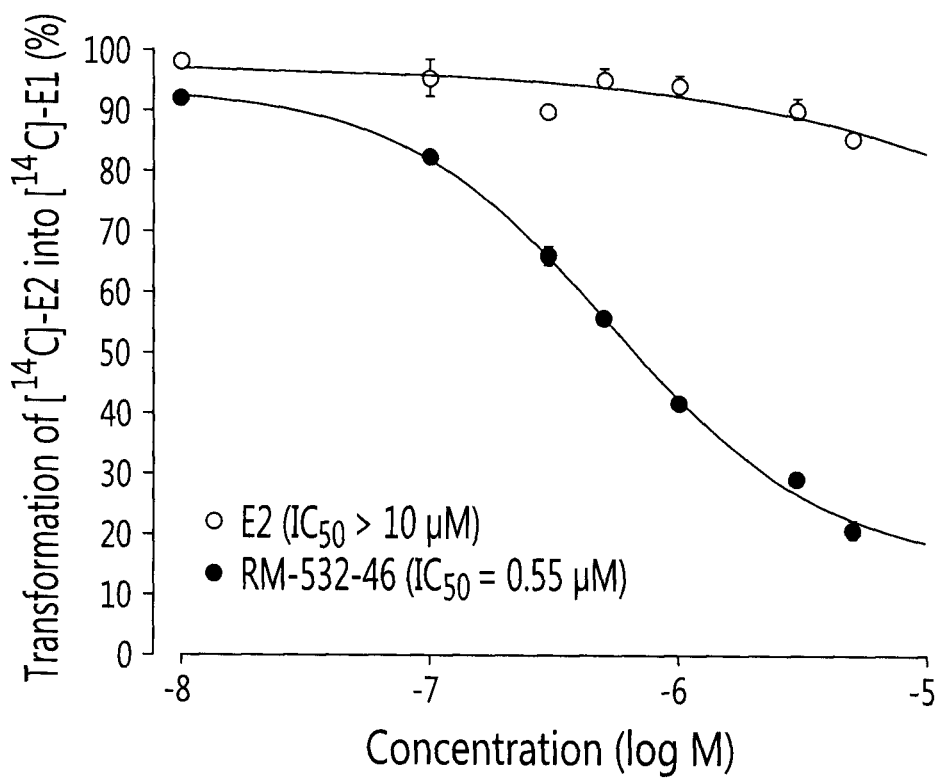
FIG. 21 illustrates the inhibition of transfected 17β-HSD10 in intact HEK-293 cells by compound 21 and E2. Compounds were tested at various concentrations to determine IC$_{50}$ values. When the error bars are not shown, it is because they are smaller than the symbol.

FIG. 21 illustrates the inhibition of transfected 17β-HSD10 in intact HEK-293 cells by compound 21 and E2. Compounds were tested at various concentrations to determine IC$_{50}$ values. When the error bars are not shown, it is because they are smaller than the symbol.

The chemical synthesis of compounds tested as inhibitors of 17β-HSD10 and shown in Table 6 was reported in previous sections reporting inhibitors of 17β-HSD3. The section corresponding to each tested compound was reported in Table 6.

Enzymatic Assay (Inhibition of 17β-HSD10)
Generation of Stably Transfected Human Embryonic Kidney (HEK)-293 Cells Expressing 17β-hydroxysteroid dehydrogenase type 10

Cells were cultured in 6-well falcon flasks to approximately 3×10$^5$ cells/well in Dubelcco's Modified Eagle's Medium (DMEM) (Life Technologies, Burlington, ON, Canada) supplemented with 10% (vol/vol) of foetal bovine serum (FBS) (HyClone Laboratories, Inc., Logan, Utah, USA) at 37° C. under a 95% air-5% CO$_2$ humidified atmosphere. Five (5) micrograms of pCMVneo-h17bHSD10 plasmids were transfected using a lipofectin transfection kit (Life Technologies, Burlington, ON, Canada). After 6 h of incubation at 37° C., the transfection medium was removed, and 2 mL DMEM were added. Cells were further cultured for 48 h and then transferred into 10-cm petri dishes and cultured in DMEM containing 700 μg/mL of Geneticin (G418; Wisent, Montréal, QC, Canada) to inhibit the growth of non-transfected cells. Medium containing G418 was changed every 2 days until resistant colonies were observed.

Cell Culture
Stably transfected HEK-293 cells were cultured in minimum essential medium (MEM) containing non-essential amino acids (0.1 nM), glutamine (2 mM), sodium pyruvate (1 mM), 10% FBS, penicillin (100 IU/mL), streptomycin (100 μg/mL) and G418 (0.7 mg/mL).

Inhibition of 17β-HSD10: In Vitro Activity Esing Whole Cells

HEK-293 cells stably transfected with 17β-HSD10 were seeded at 250 000 cells/well in a 24-well plate at 37° C. under 95% air 5% CO$_2$ humidified atmosphere in 990 μL of culture medium. Inhibitor stock solutions were prepared in ethanol and diluted with culture medium. After 24 h, 5 μL of these solutions were added to the cells to obtain a final concentration of 1 μM for inhibitors. For the most active inhibitors, concentrations of 0.01 μM to 5 μM were tested to determine their IC$_{50}$ value. The final concentration of ethanol in each well was adjusted to 0.5%. Additionally, 5 μL of a solution containing [$^{14}$C]-17β-estradiol (American Radiolabeled Chemicals, Inc., St. Louis, Mo., USA) and 17β-estradiol (Sigma-Aldrich, St. Louis, Mo., USA) (1:9) was added to obtain a final concentration of 1 μM and cells were incubated for 24 h. Each inhibitor was assessed in triplicate. After incubation, the culture medium was removed and labeled steroids (E1 and E2) were extracted with 1 mL of diethylether. The organic phases were separated and evaporated to dryness with nitrogen. Residues were dissolved in dichloromethane and dropped on silica gel thin layer chromatography plates (EMD Chemicals Inc., Gibbstown, N.J., USA) and eluted with toluene/acetone (4:1) solvent system. Substrate [$^{14}$C]-E2 and metabolites [$^{14}$C]-E1 were identified by comparing them with reference steroids (E2 and E1) and quantified using the Storm 860 system (Molecular Dynamics, Sunnyvale, Calif., USA). The percentages of transformation and inhibition were calculated as follow: % transformation=100×[$^{14}$C]-E1/([$^{14}$C]-E2+[$^{14}$C]-E1) and % of inhibition=100×(% transformation without inhibitor–% transformation with inhibitor)/% transformation without inhibitor.

It is to be understood that the specification is not limited in its application to the details of construction and parts as described hereinabove. The specification is capable of other embodiments and of being practiced in various ways. It is also understood that the phraseology or terminology used herein is for the purpose of description and not limitation. Hence, although the present invention has been described hereinabove by way of illustrative embodiments thereof, it can be modified, without departing from the spirit, scope and nature of the subject disclosure as defined in the appended claims.

REFERENCES (1) Luu-The, V.; Zhang, Y.; Poirier. D.; Labrie, F. Characteristics of human types 1, 2 and 3 17 beta-hydroxysteroid dehydrogenase activities: oxidation/reduction and inhibition. *J. Steroid Biochem. Mol. Biol.* 1995, 55, 581-587.
(2) Simard, J.; Vincent, A.; Duchesne, R.; Labrie, F. Full estrogenic activity of C19-delta 5 adrenal steroids in rat pituitary lactotrophs and somatotrophs. *Mol. Cell. Endocrinol.* 1988, 55, 233-242.
(3) Theobald, A. J. Management of advanced breast cancer with endocrine therapy: the role of the primary healthcare team. *Int. J. Clin. Pract.* 2000, 54, 665-669.
(4) Dizerega, G. S.; Barber, D. L.; Hodgen, G. D. Endometriosis: role of ovarian steroids in initiation, maintenance, and suppression. *Fertil. Steril.* 1980, 33, 649-653.
(5) Penning, T. M. 17β-hydroxysteroid dehydrogenase: inhibitors and inhibitor design. *Endocr. Relat. Cancer,* 1996, 3, 41-56.
(6) Poirier, D. Advances in Development of Inhibitors of 17β-Hydroxysteroid Dehydrogenases. *Anticancer Agents Med. Chem.,* 2009, 9, 642-660.
(7) Moeller, G.; Adamski, J. Integrated view on 17β-hydroxysteroid dehydrogenase. *Mol. Cell. Endocrinol.* 2009, 301, 7-19.
(8) Poirier, D. Contribution to the development of inhibitors of 17β-hydroxysteroid dehydrogenase type 1 and 7: Key tools for studying and treating estrogen-dependent diseases. *J. Steroid Biochem. Mol. Biol.,* 2011, 125, 83-94.
(9) Poirier, D. 17β-Hydroxysteroid dehydrogenase inhibitors: a patent review. *Expert. Opin. Ther. Patents,* 2010, 20, 1123-1145.
(10) Poirier, D. Inhibitors of 17β-hydroxysteroid dehydrogenase. *Curr. Med. Chem.,* 2003, 10, 453-477.
(11) Tremblay, M. R.; Poirier, D. Overview of a rational approach to design type I 17 beta-hydroxysteroid dehydrogenase inhibitors without estrogenic activity: chemical synthesis and biological evaluation. *J. Steroid Biochem. Mol. Biol,* 1998, 66, 179-191.
(12) Laplante, Y.; Cadot, C.; Fournier, M. C.; Poirier, D. Estradiol and Estrone C-16 derivatives as inhibitors of type 1 17β-hydroxysteroid dehydrogenase: Blocking of ER+ breast cancer cell proliferation induced by estrone. *Bioorg. Med. Chem.* 2008, 16, 1849-1860.
(13) Mazumdar, M.; Fournier, D.; Zhu, D. W.; Cadot, C.; Poirier, D.; Lin, S. X. Binary and ternary crystal structure analyses of a novel inhibitor with 17β-HSD type 1: a lead compound for breast cancer therapy. *Biochem. J.* 2009, 10, 357-366.
(14) http://www.cancer.org/Cancer-ProstateCancer/DetailedGuide/prostate-cancer-key-statistics.
(15) Group. VACUR. Treatment and survival of patients with cancer of the prostate. *Surg. Gynecol. Obset.* 1967, 124, 1011-1017.
(16) Seidenfeld, J.; Samson, D. J.; Hasselblad, V.; Aronson, N.; Albertsen, P. C.; Bennett, C. L.; Wilt, T. J. Single-therapy androgen suppression in men with advanced prostate cancer: a systematic review and meta-analysis. *Ann. Intern. Med.* 2000, 132, 566-577.
(17) Santen, R. J. Clinical Review 37: Endocrine treatment of prostate cancer. *J. Clin. Endo. Metab.* 1992, 75, 685-689.
(18) Hedlund, P. O, Side effects of endocrine treatment and their mechanisms: castration, antiandrogens and estrogens. *Prostate Suppl* 2000, 10, 32-37.
(19) Wysowski, D. K; Freiman, J. P; Tourtelot, J. B; Horton, M. L. Fatal and nonfatal hepatotoxicity associated with flutamide. *Ann. Intern. Med.* 1993, 118, 860-864.
(20) Shahinian, V. B; Kuo, Y. F; Freeman, J. L.; Goodwin, J. S. Risk of fracture after androgen deprivation for prostate cancer. *N. Engl. J. Med.* 2005, 352, 154-164.
(21) a) Tammela, T. Endocrine treatment of prostate cancer. *J. Steroid Biochem. Mol. Biol.* 2004, 92, 287-295; b) Nakamura et al., *The Prostate,* 2006, 66, 1005-1012.
(22) Laplante, Y.; Poirier, D. Proliferative effect of androst-4-ene-3,17-dione and its metabolites in the androgen-sensitive LNCaP cell line. *Steroids* 2008, 73, 266-271.
(23) Inano, H.; Tamaoki, B. I. Testicular 17β-hydroxysteroid dehydrogenase: molecular properties and reaction mechanism. *Steroids* 1986, 48, 1-26.
(24) Mohler, M. L.; Narayanan, R.; He, Y.; Miller, D. D.; Dalton, J. T. *Recent Patents Endocrine Metabolic Immune Drug Discovery* 2007, 1, 103-118.
(25) Day, J. M.; Tutill, H. J.; Purohit, A.; Reed, M. J. *Endocr.-Relat. Cancer* 2008, 15, 665-692.
(26) Labrie, F. Intracrinology. *Mol. Cell. Endocrinol.* 1991, 78, C113-C118.
(27) Poirier, D. New cancer drugs targeting the biosynthesis of estrogens and androgens. *Drug. Dev. Res.* 2008, 69, 304-318.
(28) Luu-The, V.; Belanger, A.; Labrie, F. Androgen biosynthetic pathways in the human prostate. *Best Pract Res Clin Endocrinol Metab* 2008, 22, 207-221.
(29) Koh, E.; Noda, T.; Kanya, J.; Namiki, M. Differential expression of 17β-hydroxysteroid dehydrogenase isozyme genes in prostate cancer and non-cancer tissues. *The Prostate* 2002, 53, 154-159.
(30) Deqtyar, V. G.; Babkina, T. V.; Kazantseva, I. A.; Morozov, A. P.; Trapeznikova, M. F.; Kushlinski, N. E. Reductase activity of 17beta-hydroxysteroid oxidoreductase in prostatic tumors of different histological structure. *Bull. Exp. Biol. Med.* 2005, 139, 715-717.
(31) Montgomery, R. B.; Mostaghel, E. A.; Vessella, R.; Hess, D.; Kalhorn, T. F.; Higano, C. S.; True, L. D.; Nelson, P. S. Maintenance of intratumoral androgens in metastatic prostate cancer: mechanism for castration-resistant tumor growth. *Cancer Res.* 2008, 68, 4447-4454.
(32) Locke, J. A.; Guns, E.; Lubik, A. A.; Adomat, H. H.; Hendy, S. C.; Wood, C. A.; Ettinger, S. L.; Gleave, M. E.; Nelson, C. C. Androgen levels increase by intratumoral De novo steroidogenesis during progression of castration-resistant prostate cancer. *Cancer Res.* 2008, 68, 6407-6415.
(33) Mostaghel, E. A.; Page, S. T.; Lin, D. W.; Fazli, L.; Coleman, I. M.; True, L. D.; Knudsen, B.; Hess, D. L.; Nelson, C. C.; Matsumoto, A. M.; Bremner, W. J.; Gleave, M. E.; Nelson, P. Intraprostatic androgens and androgen-regulated gene expression persist after testosterone suppression: therapeutic implications for castration-resistant prostate cancer. *Cancer Res.* 2007, 67, 5033-5041.
(34) Page, S. T.; Lin, D. W.; Mostaghel, E. A.; Hess, D. L.; True, L. D.; Amory, J. K.; Nelson, P. S.; Matsumoto, A. M.; Bremner, W. J. Persistent intrapostatic androgen concentration after medical castration in healthy men. *J. Clin. Endocrinol. Metab.* 2006, 91, 3850-3856.
(35) Nordling, E.; Oppermann, U. C.; Jornvall, H.; Persson, B.; Human type 10 17 beta-hydroxysteroid dehydrogenase: molecular modelling and substrate docking. *J. Mol. Graph. Model* 2001, 19, 514-520.

(36) He, H. Y.; Merz, G.; Yang, Y. Z.; Mehta, P.; Schulz, H.; Yang, S. Y. Characterization and localization of human type 10 17beta-hydroxysteroid dehydrogenase. *Eur. J. Biochem.* 2001, 268, 4899-4907.

(37) Yang, S. Y.; He, X. Y.; Schulz, H. Multiple functions of type 10 17beta-hydroxysteroid dehydrogenase. *Trends Endocrinol. Metab.* 2005, 16, 167-175.

(38) Fang, H.; Tong, W.; Branham, W. S.; Moland, C. L.; Dial, S. L.; Hong, H.; Xie, Perkins, R.; Owens, W.; Sheehan, D. M. Study of 202 Natural, Synthetic, and Environmental Chemicals for Binding to the Androgen Receptor. *Chem. Res. Toxicol.* 2001, 14, 280-294.

(39) Maltais, R.; Tremblay, M. R.; Poirier, D. Solid-phase synthesis of hydroxysteroid derivatives using the diethylsilyloxy linker. *J. Comb. Chem.* 2000, 2, 604-614.

(40) Poirier, D.; Chang, H. J.; Azzi, A.; Boivin, R. P.; Lin, S. X. Estrone and estradiol C-16 derivatives as inhibitors of type 1 17β-hydroxysteroid dehydrogenase. *Mol. Cell. Endocrinol.* 2006, 27, 236-238.

(41) Sharifi, A.; Mohsenzadeh, F.; Mojtahedi, M. M.; Saidi, M. R.; Balalaie, S. Microwave-promoted transformation of nitriles to amides with aqueous sodium perborate. *Synth. Comm.* 2001, 31, 431-434.

(42) Skoda-Földes, R.; Kollár, L.; Marinelli, F.; Arcadi, A. Direct and carbonylative vinylation of steroid triflates in the presence of homogeneous palladium catalysts. *Steroids,* 1994, 59, 691-695.

(43) Tian, Y-S.; Joo, J-E.; Kong, B-S.; Pham, V-T.; Lee, K-Y.; Ham, W-H. Asymmetric synthesis of (–) swainsonine. *J. Org. Chem.* 2009, 74, 3962-3965.

(44) Wang, L. G.; Mencher, S. K.; McCarron, J. P.; Ferrari, A. C. The biological basis for the use of an anti-androgen and a 5-alpha-reductase inhibitor in the treatment of recurrent prostate cancer: case report and review. *Oncology Reports* 2004, 11, 1325-1329.

(45) Leibowitz, R. L.; Tucker, S. J. Treatment of localized prostate cancer with intermittent triple androgen blockade: preliminary results in 110 consecutive patients. *Oncologist,* 2001, 6, 177-182.

(46) Maltais, R.; Luu-The, V.; Poirier, D. Synthesis and optimization of a new family of type 3 17 beta-hydroxysteroid dehydrogenase inhibitors by parallel liquid-phase chemistry. *J. Med. Chem.* 2002, 45, 640-653.

(47) Tchedam-Nagtcha, B.; Laplante, Y.; Labrie, F.; Luu-The, V.; Poirier, D. 3-Beta-alkyl-androsterones as inhibitors of type 3 17beta-hydroxysteroid dehydrogenase: inhibitory potency in intact cells, selectivity towards isoforms 1, 2, 5 and 7, binding affinity for steroid receptors, and proliferative/antiproliferative activities on AR$^+$ and ER$^+$ cell lines. *Mol. Cell. Endocrinol.* 2006, 248, 225-232.

(48) Tchedam-Nagtcha, B.; Luu-The, V.; Labrie, F.; Poirier, D. Androsterone 3-alpha-ether-3beta-substituted and androsterone 3beta-substituted derivatives as inhibitors of type 3 17beta-hydroxysteroid dehydrogenase: chemical synthesis and structure-activity relationship. *J. Med. Chem.* 2005 48, 5257-5268.

(49) Maltais, R.; Poirier, D. A Solution-phase combinatorial parallel synthesis of 3β-amido-3α-hydroxy-5α-androstane-17-ones. *Tetrahedron Lett.* 1998, 39, 4151-4154.

(50) Maltais R.; Luu-The, V.; Poirier, D. Parallel solid-phase synthesis of 3beta-peptido-3alpha-hydroxy-5alpha-androstan-17-one derivatives for inhibition of type 3 17beta-hydroxysteroid dehydrogenase. *Bioorg. Med. Chem.* 2001, 9, 3101-3111.

(51) Berube, M.; Laplante, Y.; Poirier, D. Design, synthesis and in vitro evaluation of 4-androstene-3,17-dione/adenosine hybrid compounds as bisubstrate inhibitors of type 3 17β-hydroxysteroid dehydrogenase. *Med. Chem.* 2006, 2, 329-347.

(52) Berube, M.; Poirier, D. Chemical synthesis and in vitro biological evaluation of a phosphorylated bisubstrate inhibitor of type 3 17β-hydroxysteroid dehydrogenase. *J. Enz. Inhib. Med. Chem.* 2007, 22, 201-211.

(53) Maltais, R.; Fournier, M. A., Poirier, D. Development of 3β-substituted androsterone derivatives as potent inhibitors of 17β-hydroxysteroid dehydrogenase type 3. *Bioorg. Med. Chem.* 2011, 19, 4652-4668.

(54) Roy, J.; Breton, R.; Martel, C.; Labrie, F.; Poirier, D. Chemical synthesis and biological activities of 16α-derivatives of 5α-androstane-3α,17β-diol as antiandrogens. *Bioorg. Med. Chem.* 2007, 15, 3003-3018.

(55) Ayan, D.; Roy, J.; Maltais, R.; Poirier, D. Impact of estradiol structural modifications (18-methyl and/or 17-hydroxy inversion of configuration) on the in vitro and in vivo estrogenic activity. *J. Steroid Biochem. Mol. Biol.* 2011, 127, 324-330.

(56) WO2008/089093A2 (2008) to Quatrix Pharmaceuticals Company.

(57) Kissinger, C. R.; Rejto, P. A.; Pelletier, L. A.; Thomson, J. A.; Showalter, R. E.; Abreo, M. A.; Agree, C. S.; Margosiak, S.; Meng, J. J.; Aust, R. M.; Vanderpool, D.; Li, B.; Tempczyk-Russell, A.; Villafranca, J. E. Crystal structure of human ABAD/HSD10 with a bound inhibitor: implications for design of Alzheimer's disease therapeutics. *J. Mol. Biol.* 2004, 342, 943-952.

(58) Ittner, L. M.; Gotz, J. Amyloid-beta and tau—a toxic pas de deux in Alzheimer's disease, *Nat. Rev. Neurosci.* 2011, 12, 65-72.

(59) He, H. Y.; Wen, G. Y.; Merz, G.; Lin, D.; Yang, Y. Z.; Mehta, P.; Schulz, H.; Yang, S. Y. Abundant type 10 17 beta-hydroxysteroid dehydrogenase in the hippocampus of mouse Alzheimer's disease model. *Brain Res. Mol. Brain. Res.* 2002, 99, 46-53.

(60) Xu, H.; Gouras, G. K.; Greenfield, J. P.; Vincent, B.; Naslund, J.; Mazzarelli, L.; Fried, G.; Jovanovic, J. N.; Seeger, M.; Relkin, N. R.; Liao, F.; Checker, F.; Buxbaum, J. D.; Chait, B. T.; Thinakaran, G.; Sisodia, S. S.; Wang, R.; Greengard, P.; Gandy, S. Estrogen reduces neuronal generation of Alzheimer beta-amyloid peptides. *Nat. Med.* 1998, 4, 447-451.

(61) He, X. Y.; Wegiel, J.; Yang, S. Y. Intracellular oxidation of allopregnanolone by human brain type 10 17beta-hydroxysteroid dehydrogenase. *Brain Res.* 2005, 1040, 29-35.

(62) He, X. Y.; Yang, S. Y. Roles of type 10 17beta-hydroxysteroid dehydrogenase in intracrinology and metabolism of isoleucine and fatty acids. *Endocr. Metab Immune Disord. Drug Targets* 2006, 6, 95-102.

(63) He, X. Y.; Yang, Y. Z.; Peehl, D. M.; Lauderdale, A.; Schulz, H.; Yang, S. Y. Oxidative 3alpha-hydroxysteroid dehydrogenase activity of human type 10 17beta-hydroxysteroid dehydrogenase. *J. Steroid Biochem. Mol. Biol.* 2003, 87, 191-198.

What is claimed is:

1. An inhibitor of 17β-HSD1, wherein the inhibitor is of the structure:

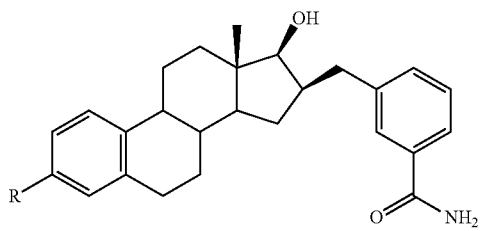

wherein R is halo, —NH$_2$, alkyl, —OCH$_2$CH$_2$Br, aralkyl, carboxy, —CH$_2$-heterocyclyl, heterocyclyloyl, —C(O)N(R')(R") or —B(OH)$_2$, wherein R' and R" are independently or simultaneously H or alkyl, or R' and R" are joined together, along with the nitrogen atom to which they are attached, to form a heterocyclic ring, or a pharmaceutically acceptable salt or tautomer thereof.

2. The inhibitor of claim 1, wherein the inhibitor is of the structure

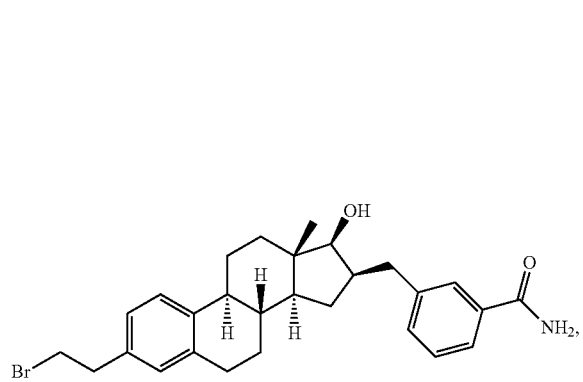

or a pharmaceutically acceptable salt thereof.

3. The inhibitor of claim 2, wherein the inhibitor is of the structure

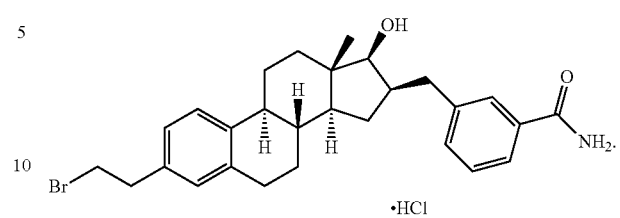

4. An inhibitor of 17β-HSD1, wherein the inhibitor is of the structure:

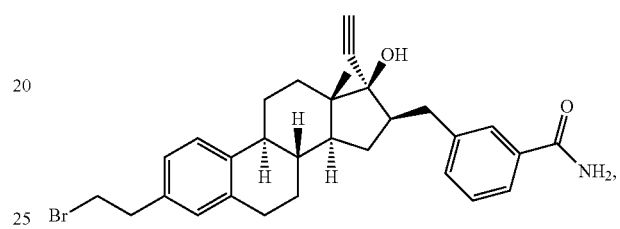

or a pharmaceutically acceptable salt thereof.

5. A radiolabeled compound of the structure

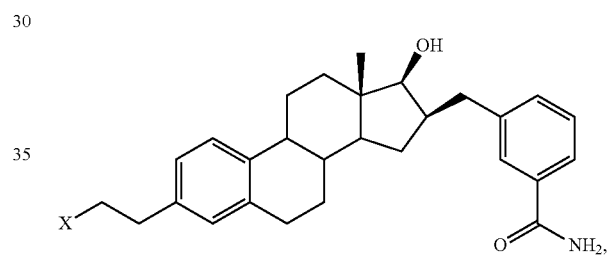

wherein X is I$^{123}$, I$^{125}$, I$^{131}$ or Br$^{76}$, or a pharmaceutically acceptable salt or tautomer thereof.

6. A method of treating breast cancer or prostate cancer in a subject comprising administering to said subject a radiolabeled compound of claim 5.

* * * * *